(12) United States Patent
Chen et al.

(10) Patent No.: US 8,143,282 B2
(45) Date of Patent: Mar. 27, 2012

(54) HETEROCYCLIC COMPOUNDS

(75) Inventors: Dizhong Chen, Singapore (SG); Weiping Deng, Shanghai (CN); Ken C. Lee, Singapore (SG); Pek L. Lye, Singapore (SG); Eric T. Sun, Singapore (SG); Haishan Wang, Singapore (SG); Niefang Yu, Singapore (SG)

(73) Assignee: **S*BIO Pte Ltd.**, Singapore Science Park II (SG)

( * ) Notice: Subject to any disclaimer, the term of this patent is extended or adjusted under 35 U.S.C. 154(b) by 639 days.

(21) Appl. No.: 12/065,989

(22) PCT Filed: Aug. 1, 2006

(86) PCT No.: PCT/SG2006/000217
§ 371 (c)(1),
(2), (4) Date: Jun. 26, 2008

(87) PCT Pub. No.: WO2007/030080
PCT Pub. Date: Mar. 15, 2007

(65) Prior Publication Data
US 2009/0048300 A1    Feb. 19, 2009

Related U.S. Application Data

(60) Provisional application No. 60/783,819, filed on Mar. 21, 2006, provisional application No. 60/714,827, filed on Sep. 8, 2005.

(51) Int. Cl.
*C07D 401/04*     (2006.01)
*C07D 235/14*     (2006.01)
*A61K 31/4184*    (2006.01)
*A61K 31/454*     (2006.01)
*A61P 25/00*      (2006.01)
*A61P 29/00*      (2006.01)
*A61P 35/00*      (2006.01)

(52) U.S. Cl. ..... 514/322; 514/394; 546/199; 548/306.1; 548/309.7

(58) Field of Classification Search .................. 514/322, 514/394; 546/199; 548/306.1, 309.7
See application file for complete search history.

(56) References Cited

U.S. PATENT DOCUMENTS
2005/0137234 A1    6/2005    Bressi et al.

FOREIGN PATENT DOCUMENTS
WO       2005028447       3/2005
WO    WO 2005/028447  *  3/2005

OTHER PUBLICATIONS

Collins, Expert Opinion Investig. Drugs 2007, 16(11), 1743-1751.*
Alzheimer's Disease Treatment Phases, http://www.alzheimerstreatment.org/treatment/disease-treatment.htm.*
Alzheimer's Drugs, Consumer Reports Best Buy Drugs (p. 1-5).*
Cumming et al., 2007, caplus an 2007:705011.*
Alzheimer's disease Treatment Phases, http://www.alzheimerstreatment.org/treatment/disease-treatment.htm (2008).*
Alzheimer's Drugs, Consumer Reports Best Buy Drugs (p. 1-5) 2008.*

* cited by examiner

*Primary Examiner* — Sun Jae Loewe
(74) *Attorney, Agent, or Firm* — Connolly Bove Lodge & Hutz LLP

(57) ABSTRACT

The present invention relates to compounds which are inhibitors of histone deacetylase. More particularly, the present invention relates to heterocyclic compounds and methods for their preparation. These compounds may be useful as medicaments for the treatment of proliferative disorders as well as other diseases involving, relating to or associated with enzymes having histone deacetylase (HDAC) activities.

19 Claims, No Drawings

HETEROCYCLIC COMPOUNDS

CROSS REFERENCE TO RELATED APPLICATIONS

This application is a National Phase filing under 35 U.S.C. §371 of PCT/SG2006/000217 filed Aug. 1, 2006, which claims priority to Provisional Patent Application No. 60/714,827, filed in the United States on Sep. 8, 2005, and Provisional Patent Application No. 60/783,819, filed in the United States on Mar. 21, 2006. The entire contents of each of the above-applications is incorporated herein by reference.

FIELD OF THE INVENTION

The present invention relates to hydroxamate compounds that are inhibitors of histone deacetylase (HDAC). More particularly, the present invention relates to heterocyclic compounds and methods for their preparation. These compounds may be useful as medicaments for the treatment of proliferative disorders as well as other diseases involving, relating to or associated with enzymes having histone deacetylase (HDAC) activities.

BACKGROUND OF THE INVENTION

Local chromatin architecture is generally recognized as an important factor in the regulation of gene expression. The architecture of chromatin, a protein-DNA complex, is strongly influenced by post-translational modifications of the histones which are the protein components. Reversible acetylation of histones is a key component in the regulation of gene expression by altering the accessibility of transcription factors to DNA. In general, increased levels of histone acetylation are associated with increased transcriptional activity, whereas decreased levels of acetylation are associated with repression of gene expression [Wadem P. A. Hum. Mol. Genet. 10, 693-698 (2001), De Ruijter A. J. M. et al, Biochem. J., 370, 737-749 (2003)]. In normal cells, histone deacetylases (HDACs) and histone acetyltransferase together control the level of acetylation of histones to maintain a balance. Inhibition of HDACs results in the accumulation of acetylated histones, which results in a variety of cell type dependent cellular responses, such as apoptosis, necrosis, differentiation, cell survival, inhibition of proliferation and cytostasis.

Inhibitors of HDAC have been studied for their therapeutic effects on cancer cells. For example, suberoylanilide hydroxamic acid (SAHA) is a potent inducer of differentiation and/or apoptosis in murine erythroleukemia, bladder, and myeloma cell lines [Richon V. M. et al, Proc. Natl. Acad. Sci. USA, 93: 5705-5708 (1996), Richon V. M. et al, Proc. Natl. Acad. Sci. USA, 95: 3003-3007 (1998)]. SAHA has been shown to suppress the growth of prostate cancer cells in vitro and in vivo [Butler L. M. et al, Cancer Res. 60, 5165-5170 (2000)]. Other inhibitors of HDAC that have been widely studied for their anti-cancer activities are trichostatin A (TSA) and trapoxin B [Yoshida M. et al, J. Biol. Chem., 265, 17174 (1990), Kijima M. et al, J. Biol. Chem., 268, 22429 (1993)]. Trichostatin A is a reversible inhibitor of mammalian HDAC. Trapoxin B is a cyclic tetrapeptide, which is an irreversible inhibitor of mammalian HDAC. However, due to the in vivo instability of these compounds they are less desirable as anti-cancer drugs. Recently, other small molecule HDAC inhibitors have become available for clinical evaluation [U.S. Pat. No. 6,552,065]. Additional HDAC inhibiting compounds have been reported in the literature [Bouchain G. et al, J. Med. Chem., 46, 820-830 (2003)] and patents [WO 03/066579A2].

The in vivo activity of such inhibitors can be directly monitored by their ability to increase the amount of acetylated histones in the biological sample. HDAC inhibitors have been reported to interfere with neurodegenerative processes, for instance, HDAC inhibitors arrest polyglutamine-dependent neurodegeneration [Nature, 413(6857): 739-43, 18 Oct. 2001]. In addition, HDAC inhibitors have also been known to inhibit production of cytokines such as TNF, IFN, IL-1 which are known to be implicated in inflammatory diseases and/or immune system disorders. [J. Biol. Chem. 1990; 265(18): 10232-10237; Science, 1998; 281: 1001-1005; Dinarello C. A. and Moldawer L. L. Proinflammatory and anti-inflammatory cytokines in rheumatoid arthritis, A primer for clinicians, $3^{rd}$ Edition, Amgen Inc., 2002].

Nevertheless, there is still a need to provide further HDAC inhibitors that would be expected to have useful, improved pharmaceutical properties in the treatment of diseases such as cancer, neurodegenerative diseases, disorders involving angiogenesis and inflammatory and/or immune system disorders. With a view to meeting this need a number of small organic moiety scaffolds have been investigated including a number of heterocyclic systems, especially bicyclic heterocyclic ring systems. One heterocyclic system that has been investigated has been the benzimidazole ring system. We have now found that judicious selection of the substituents on the 5 membered ring of the benzimidazole ring system leads to the production of a family of compounds with improved pharmacokinetic properties when compared with the compounds of the prior art. The compounds within the family exhibit microsomal stability and thereby demonstrate improved half lives in the plasma when compared to the compounds of the prior art. The compounds within the family typically provide a longer duration of action due to the increased in vivo exposure (i.e., area under the curve, $AUC_{0\text{-}last}$) thereby yielding improved tumor growth inhibition profiles in the xenograft models.

SUMMARY OF THE INVENTION

In one aspect the present invention provides a compound of the formula (I):

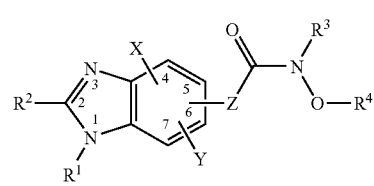

Formula (I)

wherein $R^1$ is an optionally substituted heteroaryl group, an optionally substituted heterocycloalkyl group or a group of formula:

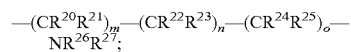

$R^2$ is selected from the group consisting of: H, alkyl, alkenyl, alkynyl, heteroalkyl, cycloalkyl, cycloalkenyl, cycloalkylalkyl, alkoxyalkyl, $R^{11}S(O)R^{13}$—, $R^{11}S(O)_2R^{13}$—, $R^{11}C(O)N(R^{12})R^{13}$—, $R^{11}SO_2N(R^{12})R^{13}$—, $R^{11}N(R^{12})C(O)R^{13}$—, $R^{11}N(R^{12})SO_2R^{13}$—, $R^{11}N(R^{12})C(O)N(R^{12})R^{13}$— and acyl, each of which may be optionally substituted;

$R^3$ is selected from the group consisting of H, $C_1$-$C_6$ alkyl, and acyl, each of which may be optionally substituted;

X and Y are the same or different and are independently selected from the group consisting of: H, halogen, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, -amino, alkylamino, acylamino, aminoalkyl, arylamino, sulfonyl, alkylsulfonyl, arylsulfonyl, aminosulfonyl, aminoalkyl, alkoxyalky, —COOH—C(O)OR$^5$, —COR$^5$, —SH, —SR$^6$, —OR$^6$ acyl and —NR$^7$R$^8$, each of which may be optionally substituted;

R$^4$ is selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each R$^5$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each R$^6$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl; each of which may be optionally substituted;

each R$^7$ and R$^8$ is independently selected from the group consisting of: H, alkyl, alkenyl, alkynyl, haloalkyl, heteroalkyl, cycloalkyl, heterocycloalkyl, aryl, heteroaryl, cycloalkylalkyl, heterocycloalkylalkyl, arylalkyl, heteroarylalkyl and acyl, each of which may be optionally substituted;

each R$^{11}$ and R$^{12}$ is independently selected from the group consisting of H, alkyl, alkenyl, and alkynyl, each of which may be optionally substituted;

each R$^{13}$ is a bond or is independently selected from the group consisting of: alkyl, alkenyl, and alkynyl, each of which may be optionally substituted;

each R$^{20}$, R$^{21}$, R$^{22}$, R$^{23}$, R$^{24}$ and R$^{25}$ is independently selected from the group consisting of: H, halogen, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkoxyheteroaryl, alkenyloxy, alkynyloxy, cycloalkylkoxy, heterocycloalkyloxy, aryloxy, arylalkyloxy, phenoxy, benzyloxy heteroaryloxy, amino, alkylamino, acylamino, aminoalkyl, arylamino, alkoxycarbonyl, alkylaminocarbonyl, sulfonyl, alkylsulfonyl, aminosulfonyl, arylsulfonyl, arylsulfinyl-COOH, —C(O)OR$^5$, —COR$^5$, —SH, —SR$^3$, —OR$^6$ and acyl, each of which may be optionally substituted; or R$^{20}$ and R$^{21}$ when taken together may form a group of formula =O or =S, and/or R$^{22}$ and R$^{23}$ when taken together may form a group of formula =O or =S, and/or R$^{24}$ and R$^{25}$ when taken together may form a group of formula =O or =S;

each R$^{26}$ and R$^{27}$ is independently selected from the group consisting of: H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkylkoxy, heterocycloalkyloxy, aryloxy, arylalkyloxy, heteroaryloxy, amino, alkylamino, aminoalkyl, acylamino, arylamino, phenoxy, benzyloxy, COOH, alkoxycarbonyl, alkylaminocarbonyl, sulfonyl, alkylsulfonyl, alkylsulfinyl, arylsulfonyl, arylsulfinyl, aminosulfonyl, SR$^5$ and acyl, each of which may be optionally substituted, or R$^{26}$ and R$^{27}$ when taken together with the nitrogen atom to which they are attached form an optionally substituted heterocycloalkyl group;

Z is selected from the group consisting of —CH$_2$—, —CH$_2$CH$_2$—, —CH=CH—, C$_3$-C$_6$ alkylene, C$_3$-C$_6$ alkenylene, C$_3$-C$_6$ alkynylene, C$_3$-C$_6$ cycloalkyl, unsubstituted or substituted with one or more substituents independently selected from the group consisting of C$_1$-C$_4$ alkyl;

m, n and o are integers independently selected from the group consisting of 0, 1, 2, 3 and 4;

or a pharmaceutically acceptable salt or prodrug thereof.

In one embodiment of the invention R$^4$ is H and the compounds are those of formula (Ia):

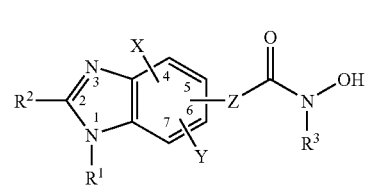

Formula (Ia)

or a pharmaceutically acceptable salt or prodrug thereof.

wherein R$^1$, R$^2$, R$^3$, X, Y and Z are as defined for compounds of formula (I).

In another embodiment R$^3$ and R$^4$ are H and the compounds are of formula (Ib):

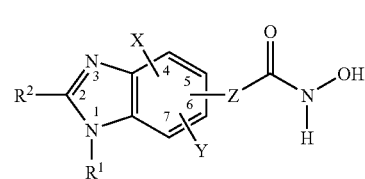

Formula (Ib)

or a pharmaceutically acceptable salt or prodrug thereof wherein R$^1$, R$^2$, X, Y and Z are as defined for compounds of formula (I).

As with any group of structurally related compounds which possess a particular utility, certain groups are preferred for the compounds of the Formula (I), (Ia) and (Ib) in their end use application.

In one embodiment the group R$^1$ is a group of formula

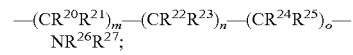

in which m, n and o are integers independently selected from the group consisting of 0, 1, 2, 3 and 4.

Accordingly, in one embodiment the compounds of the invention are compounds of formula (Ic):

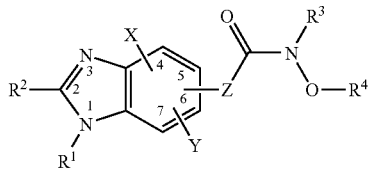

Formula (Ic)

wherein $R^1$ is a group of formula

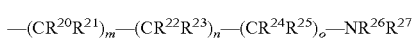

and $R^2 R^3$, $R^4$, X, Y, Z, $R^{20}$, $R^{21}$, $R^{22}$, $R^{23}$, $R^{24}$, $R^{25}$, $R^{26}$, $R^{27}$, m, n and o are as defined for compounds of formula (I).

As the values of m, n and o are integers ranging from 0 to 4 the sum of m+n+o is an integer selected from the group consisting of 0, 1, 2, 3, 4, 5, 6, 7, 8, 9, 10, 11, and 12. In one embodiment the sum of m+n+o is an integer selected from the group consisting of 0, 1, 2, 3, 4, 5, 6, 7 and 8. In another embodiment the sum of m+n+o is an integer selected from the group consisting of 0, 1, 2, 3 and 4. In another embodiment the sum of m+n+o is an integer selected from the group consisting of 2 and 3.

In one specific embodiment the sum of m+n+o is 2. When this occurs $R^1$ is selected from the group consisting of:

—$(CR^{20}R^{21})_2$—$NR^{26}R^{27}$;
—$(CR^{22}R^{23})_2$—$NR^{26}R^{27}$;
—$(CR^{24}R^{25})_2$—$NR^{26}R^{27}$;
—$(CR^{20}R^{21})$—$(CR^{22}R^{23})$—$NR^{26}R^{27}$;
—$(CR^{20}R^{21})$—$(CR^{24}R^{25})$—$NR^{26}R^{27}$;
—$(CR^{22}R^{23})$—$(CR^{24}R^{25})$—$NR^{26}R^{27}$;

In one form of this embodiment $R^1$ is the group:

—$(CR^{20}R^{21})$—$(CR^{22}R^{23})$—$NR^{26}R^{27}$;

This provides compounds of the formula (II):

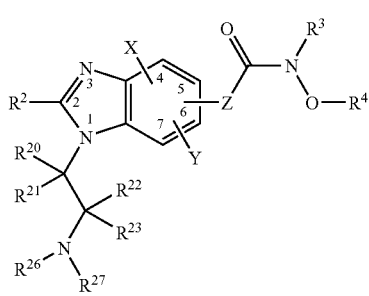

Formula (II)

wherein X, Y, Z, $R^2$, $R^3$, $R^4$, $R^{20}$, $R^{21}$, $R^{22}$, $R^{23}$, $R^{26}$ and $R^{27}$ are as defined in formula (I).

In a specific form of this embodiment $R^4$ is H which provides compounds of formula (IIa):

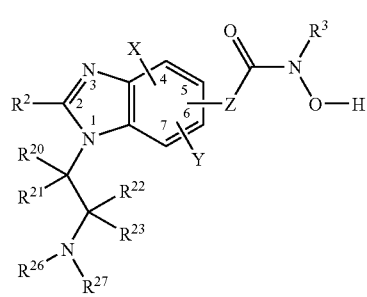

Formula (IIa)

wherein X, Y, Z, $R^2$, $R^3$, $R^{20}$, $R^{21}$, $R^{22}$, $R^{23}$, $R^{26}$ and $R^{27}$ are as defined in formula (I).

In another specific form $R^3$ is H leading to compounds of formula (IIb):

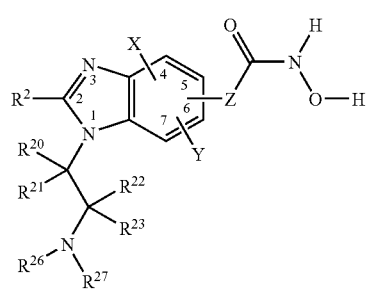

Formula (IIb)

wherein X, Y, Z, $R^2$, $R^{20}R^{21}R^{22}R^{23}R^{26}$ and $R^{27}$ are as defined in formula (I).

In an even more specific form of this embodiment $R^{20}$, $R^{21}$, $R^{22}$ and $R^{23}$ are H providing compounds of formula (IIc):

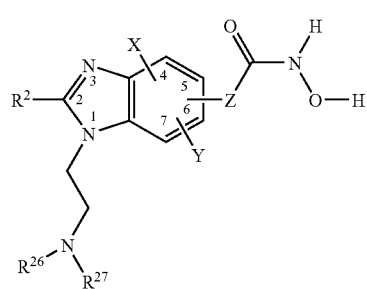

Formula (IIc)

wherein X, Y, Z, $R^2$, $R^{26}$ and $R^{27}$ are as defined in formula (I).

In another embodiment the sum of m+n+o is 3. When this occurs $R^1$ is selected from the group consisting of:

—$(CR^{20}R^{21})_3$—$NR^{26}R^{27}$;
—$(CR^{22}R^{23})_3$—$NR^{26}R^{27}$;
—$(CR^{24}R^{25})_3$—$NR^{26}R^{27}$;
—$(CR^{20}R^{21})_2$—$(CR^{22}R^{23})$—$NR^{26}R^{27}$;
—$(CR^{20}R^{21})_2$—$(CR^{24}R^{25})$—$NR^{26}R^{27}$;
—$(CR^{20}R^{21})$—$(CR^{22}R^{23})_2$—$NR^{26}R^{27}$;
—$(CR^{22}R^{23})_2$—$(CR^{24}R^{25})$—$NR^{26}R^{27}$;
—$(CR^{20}R^{21})$—$(CR^{24}R^{25})_2$—$NR^{26}R^{27}$;
—$(CR^{22}R^{23})$—$(CR^{24}R^{25})_2$—$NR^{26}R^{27}$;
—$(CR^{20}R^{21})$—$(CR^{22}R^{23})$—$(CR^{24}R^{25})$—$NR^{26}R^{27}$;

In one form of this embodiment $R^1$ is a group of the formula:

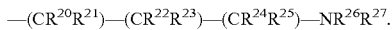
—(CR$^{20}$R$^{21}$)—(CR$^{22}$R$^{23}$)—(CR$^{24}$R$^{25}$)—NR$^{26}$R$^{27}$.

This provides compounds of the formula (III):

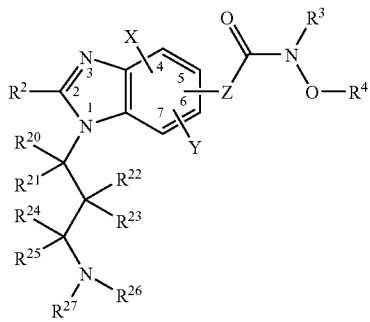

Formula (III)

wherein X, Y, Z, $R^2$, $R^3$, $R^4$, $R^{20}$, $R^{21}$, $R^{22}$, $R^{23}$, $R^{24}$, $R^{25}$, $R^{26}$ and $R^{27}$ are as defined in formula (I).

In a specific form of this embodiment $R^4$ is H which provides compounds of formula (IIIa).

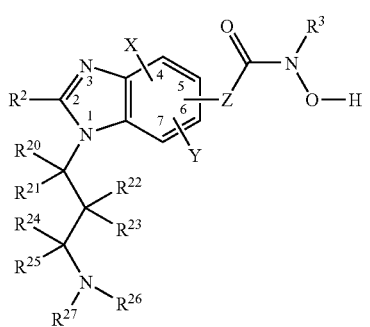

Formula (IIIa)

wherein X, Y, Z, $R^2$, $R^3$, $R^{20}$R$^{21}$, $R^{22}$, $R^{23}$, $R^{24}$, $R^{25}$, $R^{26}$ and $R^{27}$ are as defined in formula (I).

In another specific form $R^3$ is H leading to compounds of formula (IIIb):

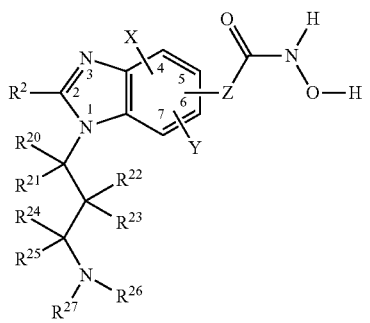

Formula (IIIb)

wherein X, Y, Z, $R^2$, $R^{20}$R$^{21}$, $R^{22}$, $R^{23}$, $R^{24}$, $R^{25}$, $R^{26}$ and $R^{27}$ are as defined in formula (I).

In an even more specific form of this embodiment $R^{20}$, $R^{21}$, $R^{24}$ and $R^{25}$ are H, and $R^{22}$ and $R^{23}$ are methyl providing compounds of formula (IIIc).

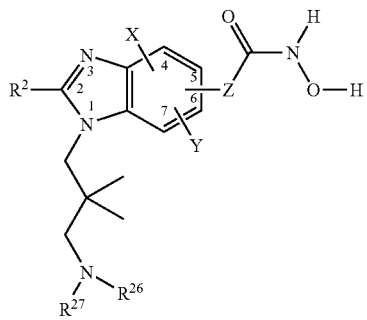

Formula (IIIc)

wherein X, Y, Z, $R^2$, $R^{26}$ and $R^{27}$ are as defined in formula (I).

In each of the above embodiments of the invention $R^{20}$ and $R^{21}$ may represent a number of different variables. In one embodiment $R^{20}$ and $R^{21}$ are independently selected from the group consisting of H, alkyl, alkenyl and alkynyl. In another embodiment $R^{20}$ and $R^{21}$ are independently selected from the group consisting of H and alkyl. In yet another embodiment $R^{20}$ and $R^{21}$ are independently selected from the group consisting of H, methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, pent-4-enyl, hexyl, heptyl and octyl. In a specific embodiment $R^{20}$ and $R^{21}$ are both H.

In each of the above embodiments of the invention $R^{22}$ and $R^{23}$ may represent a number of different variables. In one embodiment $R^{22}$ and $R^{23}$ are independently selected is from the group consisting of H, alkyl, alkenyl and alkynyl. In another embodiment $R^{22}$ and $R^{23}$ are independently selected from the group consisting of H and alkyl. In yet another embodiment $R^{22}$ and $R^{23}$ are independently selected from the group consisting of H, methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, pent-4-enyl, hexyl, heptyl and octyl. In a further embodiment $R^{22}$ and $R^{23}$ are independently selected from the group consisting of alkyl. In a most specific embodiment $R^{22}$ and $R^{23}$ are both methyl.

In each of the above embodiments of the invention $R^{24}$ and $R^{25}$ may represent a number of different variables. In one embodiment $R^{24}$ and $R^{25}$ are preferably independently selected from the group consisting of H, alkyl, alkenyl and alkynyl. In another embodiment $R^{24}$ and $R^{25}$ are independently selected from the group consisting of H and alkyl. In yet another embodiment $R^{24}$ and $R^{25}$ are independently selected from the group consisting of H, methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, pent-4-enyl, hexyl, heptyl and octyl. In a specific embodiment $R^{24}$ and $R^{25}$ are both H.

In each of the above embodiments there are a number of values for $R^{26}$ and $R^{27}$. In one embodiment $R^{26}$ and $R^{27}$ are independently selected from the group consisting of: H, alkyl, alkenyl, alkynyl, alkoxyalkyl, and acyl. In another embodiment $R^{26}$ and $R^{27}$ are independently selected from the group consisting of: H, alkyl and acyl. In a further embodiment $R^{26}$ and $R^{27}$ are independently selected from the group consisting of H, methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, pent-4-enyl, hexyl, heptyl, octyl, acetyl and 2-methoxy-ethyl.

In another embodiment R¹ is a heterocycloalkyl group which may optionally be substituted.

In one form of this embodiment the heterocycloalkyl group is selected from the group consisting of:

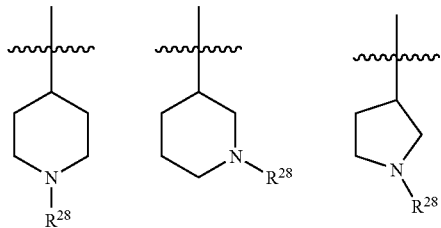

wherein $R^{28}$ is selected from the group consisting of H, halogen, alkyl, alkenyl, alkynyl, haloalkyl, haloalkenyl, heteroalkyl, cycloalkyl, cycloalkenyl, heterocycloalkyl, heterocycloalkenyl, aryl, heteroaryl, cycloalkylalkyl, heterocycloalkylalkyl, arylalkyl, heteroarylalkyl, arylalkenyl, cycloalkylheteroalkyl, heterocycloalkylheteroalkyl, heteroarylheteroalkyl, arylheteroalkyl, hydroxy, hydroxyalkyl, alkoxy, alkoxyalkyl, alkoxyaryl, alkenyloxy, alkynyloxy, cycloalkyloxy, heterocycloalkyloxy, aryloxy, arylalkyloxy, heteroaryloxy, amino, alkylamino, aminoalkyl, acylamino, arylamino, phenoxy, benzyloxy, COOH, alkoxycarbonyl, alkylaminocarbonyl, arylacyl, sulfonyl, alkylsulfonyl, alkylsulfinyl, arylsulfonyl, arylsulfinyl, aminosulfonyl, $SR^5$ and acyl, each of which may be optionally substituted.

In one embodiment $R^{28}$ is selected from the group consisting of H, alkyl, alkenyl, arylalkyl and arylacyl. Specific values of $R^{28}$ are H, methyl; ethyl; propyl; 2-methyl-propyl, 2-2-dimethyl-propyl; isopropyl; 3,3,3-trifluoro-propyl; butyl; isobutyl; 3,3-dimethyl-butyl; pentyl; 2,4,4-trimethyl-pentyl; penten-4-yl, hexyl; heptyl, octyl, nonyl, 2-methoxy nonyl, benzyl, 2-phenyl-ethyl, 2-phenyl-acetyl, 3-phenyl-propyl, In another embodiment the heterocycloalkyl group is pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. In one specific embodiment R¹ is selected from the group consisting of piperidine-3-yl, piperidine-4-yl and pyrollidin-3-y.

In another embodiment R¹ is a heteroaryl group.

In another embodiment R¹ is a group selected from the group consisting of:

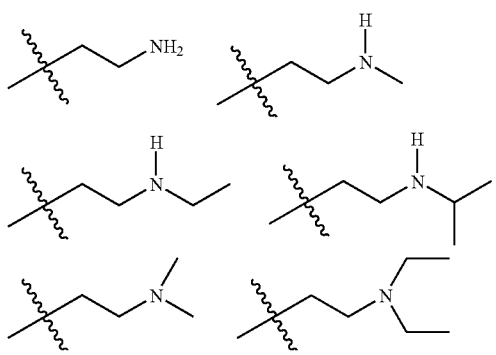

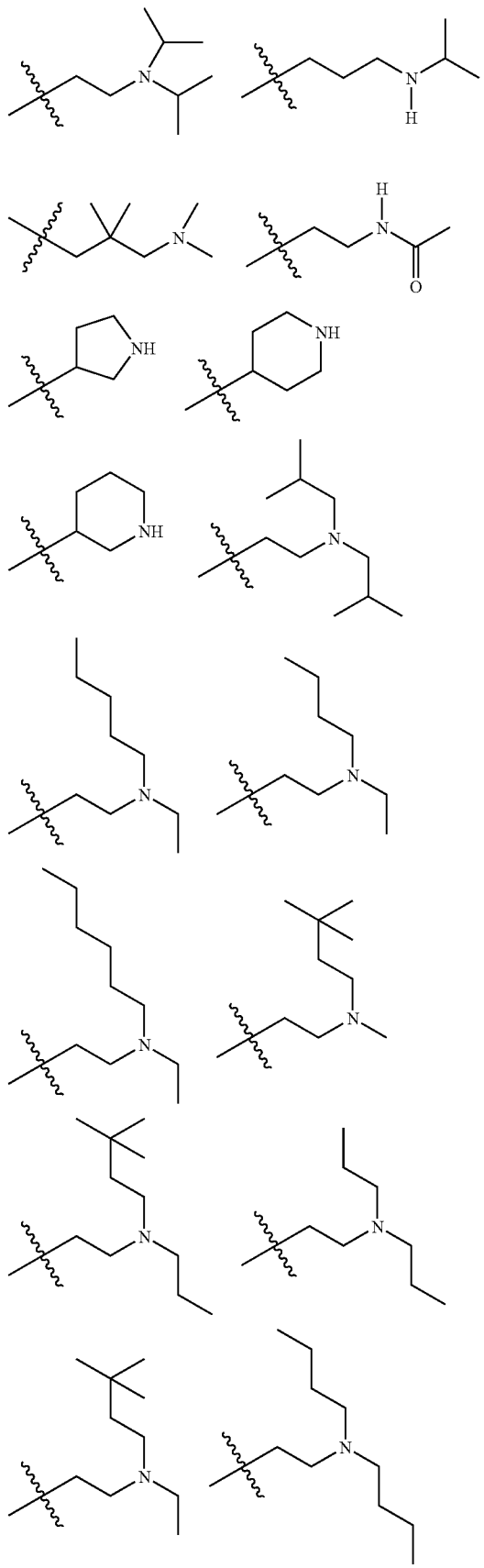

-continued

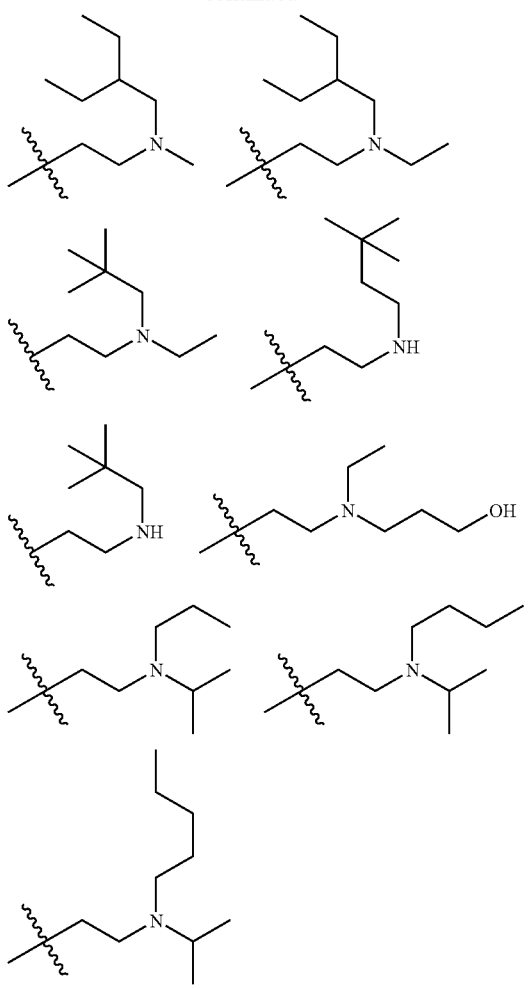

In one specific embodiment $R^1$ is a group of formula:

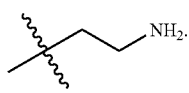

In another specific embodiment $R^1$ is a group of formula:

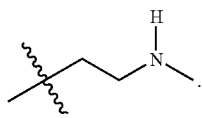

In another specific embodiment $R^1$ is a group of formula:

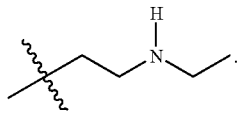

In yet another specific embodiment $R^1$ is a group of formula:

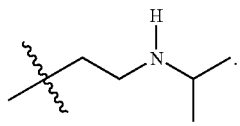

In another specific embodiment $R^1$ is a group of formula:

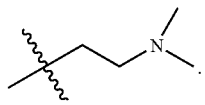

In another specific embodiment $R^1$ is a group of formula:

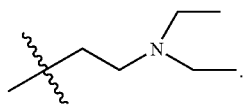

In another specific embodiment $R^1$ is a group of formula:

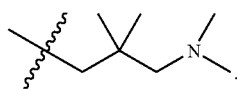

In another specific embodiment $R^1$ is a group of formula:

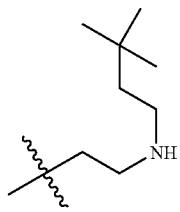

In another specific embodiment $R^1$ is a group of formula:

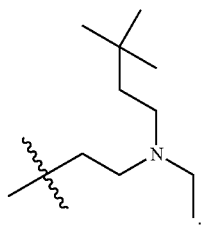

In one embodiment $R^2$ is selected from the group consisting of H, alkyl, cycloalkyl, heteroalkyl, alkenyl, alkynyl, alkoxyalkyl and cycloalkylalkyl, each of which may be optionally substituted.

In one form of this embodiment $R^2$ is alkyl. In one embodiment the alkyl is a $C_1$-$C_{10}$ alkyl. In another form of this embodiment the alkyl is a $C_1$-$C_6$ alkyl group. In another form of this embodiment $R^2$ is selected from the group consisting of: methyl; ethyl; propyl; 2-methyl-propyl, 2-2-dimethyl-propyl; isopropyl; 3,3,3-trifluoro-propyl; butyl; isobutyl; 3,3-dimethyl-butyl; pentyl; 2,4,4-trimethyl-pentyl; hexyl; heptyl, octyl, nonyl, and 2-methoxy nonyl.

In one form of this embodiment $R^2$ is alkenyl. In one form of this embodiment the alkenyl is a $C_1$-$C_{10}$ alkenyl. In another form of this embodiment the alkenyl is a $C_1$-$C_6$ alkenyl group. In another form of this embodiment $R^2$ is selected from the group consisting of: ethenyl, prop-1-enyl, prop-2-enyl, but-1-enyl, but-2-enyl but-3-enyl, pent-1-enyl, pent-2-enyl, pent-3-enyl, pent-4-enyl, hex-1-enyl, hex-2-enyl, hex-3-enyl, hex-4-enyl and hex-5-enyl.

In another embodiment $R^2$ is selected from the group consisting of $R^{11}S(O)R^{13}$—, $R^{11}S(O)_2R^{13}$—, $R^{11}C(O)N(R^{12})R^{13}$—, $R^{11}SO_2N(R^{12})R^{13}$—, $R^{11}N(R^{12})C(O)R^{13}$—, $R^{11}N(R^{12})SO_2R^{13}$—, and $R^{11}N(R^{12})C(O)N(R^{12})R^{13}$—. In one form of this embodiment $R^2$ is a group of the formula $R^{11}C(O)N(R^{12})R^{13}$—. In one form of this embodiment $R^{13}$ is a $C_1$-$C_6$ alkyl. In a specific form of this embodiment $R^{13}$ is methyl or ethyl. In one form of this embodiment $R^{12}$ is H or $C_1$-$C_6$alkyl. A specific value for $R^{12}$ is H. In one form of this embodiment $R^{11}$ is $C_1$-$C_6$ alkyl group. Specific values for $R^{11}$ include t-butyl and propyl. Specific examples of groups of this type include: $(CH_3)_3CCH_2CONH(CH_2)_2$—; $(CH_3)_3CCONH(CH_2)_2$—; $(CH_3)_3CCONH(CH_2)$— and $CH_3(CH_2)_2CONH(CH_2)$—.

Specific values of $R^2$ are selected from the group consisting of: H; methyl; ethoxymethyl; [Bicylco[2.2.1]2-ylmethyl; Adamantan-2-ylmethyl; 2-methansulfanyl-ethyl; 2,2,2-trifluoro-ethyl; propyl; 2-2-dimethyl-propyl; isopropyl; 3,3,3-trifluoro-propyl; butyl; isobutyl; 3,3-dimethyl-butyl; but-3-enyl; but-3-yny; pentyl; 2,4,4-trimethyl-pentyl; Bicyclo[2.2.1]hept-5-en-2-yl; hexyl; hex-3-enyl; octyl; non-3-enyl; non-6-enyl; 2-methoxy-nonyl, 2-phenyl-cyclopropyl; cyclohexyl; $(CH_3)_3CCH_2CONH(CH_2)_2$—; $(CH_3)_3CCONH(CH_2)_2$—; $(CH_3)_3CCONH(CH_2)$— and $CH_3(CH_2)_2CONH(CH_2)$—.

In one embodiment X and Y may be the same or different and are selected from the group consisting of H, halogen, $C_1$-$C_4$ alkyl, —$CF_3$, —$NO_2$, —$C(O)R^5$, —$OR^6$, —$SR^6$, —CN and $NR^7R^8$.

In one embodiment X is H;
In one embodiment Y is H;
In one embodiment X and Y (if present) are at the 4 and 7 positions of the aromatic ring.

In one embodiment $R^3$ is H, $C_1$-$C_6$ alkyl, or acyl. In another embodiment $R^3$ is H or $C_1$-$C_4$ alkyl. A specific value for $R^3$ is H;

In one embodiment $R^4$ is H or $C_1$-$C_4$ alkyl. A specific value for $R^4$ is H;

In one embodiment $R^5$ is $C_1$-$C_4$ alkyl, heteroalkyl, or acyl. A specific value for $R^5$ is methyl;

In one embodiment $R^6$ is $C_1$-$C_4$ alkyl, heteroalkyl or acyl. A specific value for $R^6$ is $C_1$-$C_4$ alkyl;

In one embodiment $R^7$ and $R^8$ are selected from the group consisting of H, $C_1$-$C_6$ alkyl, $C_4$-$C_9$cycloalkyl, $C_4$-$C_9$heterocycloalkyl, aryl, heteroaryl, arylalkyl, and heteroarylalkyl Many if not all of the variables discussed above may be optionally substituted. If the variable is optionally substituted then in one embodiment the optional substituent is selected from the group consisting of: halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkoxy, alkoxyalkyl, alkoxyaryl, alkoxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, -amino, alkylamino, acylamino, aminoalkyl, arylamino, sulfonyl, alkylsulfonyl, arylsulfonyl, aminosulfonyl, aminoalkyl, alkoxyalky, —COOH, —$COR^5$, —$C(O)OR^5$, —SH, —$SR^5$, —$OR^6$ and acyl.

In a further embodiment the optional substituents are selected from the group consisting of: halogen, =O, =S, —CN, —$NO_2$, alkyl, alkenyl, heteroalkyl, haloalkyl, alkynyl, aryl, cycloalkyl, heterocycloalkyl, heteroaryl, hydroxy, hydroxyalkyl, alkoxy, alkylamino, aminoalkyl, acylamino, phenoxy, alkoxyalkyl, benzyloxy, alkylsulfonyl, arylsulfonyl, aminosulfonyl, —$C(O)OR^5$, COOH, SH, and acyl.

In one embodiment the Z moiety is at the 5 or 6 position. In a specific embodiment the Z moiety is at the 5 position. In one embodiment the Z moiety is a group of formula —CH=CH—. If the Z moiety is a group of this type it is preferably in the "E" configuration.

In addition to compounds of Formula (I), the embodiments disclosed are also directed to pharmaceutically acceptable salts, pharmaceutically acceptable prodrugs, and pharmaceutically active metabolites of such compounds, and pharmaceutically acceptable salts of such metabolites. Such compounds, salts, prodrugs and metabolites are at times collectively referred to herein as "HDAC inhibiting agents" or "HDAC inhibitors".

The invention also relates to pharmaceutical compositions including a compound of the invention with a pharmaceutically acceptable carrier, diluent or excipient.

In yet a further aspect the present invention provides a method of treatment of a disorder caused by, associated with or accompanied by disruptions of cell proliferation and/or angiogenesis including administration of a therapeutically effective amount of a compound of formula (I). The embodiments disclosed also relate to pharmaceutical compositions each comprising a therapeutically effective amount of a HDAC inhibiting agent of the embodiments described with a pharmaceutically acceptable carrier or diluent for treating cellular proliferative ailments, e.g., inhibition of proliferation of malignant cancer cells, benign tumor cells or other proliferative cells.

In one embodiment the method includes administration of a compound of formula (Ia) or (Ib) as described herein.

In one embodiment the disorder is selected from the group consisting of but not limited to cancer (e.g. breast cancer, colon cancer, prostate cancer, pancreatic cancer, leukemias, lymphomas, ovarian cancers, neuroblastomas, melanoma, inflammatory diseases/immune system disorders, angiofibroma, cardiovascular diseases (e.g. restenosis, arteriosclerosis), fibrotic diseases (e.g. liver fibrosis), diabetes, autoimmune diseases, chronic and acute neurodegenerative disease like disruptions of nerval tissue, Huntington's disease and infectious diseases like fungal, bacterial and viral infections. In another embodiment the disorder is a proliferative disorder. In one embodiment the proliferative disorder is cancer. The cancer can include solid tumors or hematologic malignancies.

The invention also provides agents for the treatment of a disorder caused by, associated with or accompanied by disruptions of cell proliferation and/or angiogenesis including a compound of formula (I) as disclosed herein. In one embodiment the agent is an anti-cancer agent. In another embodiment the agent is an anti-angiogenesis agent.

In one embodiment the agent contains a compound of formula (Ia) or (Ib).

The invention also relates to the use of compounds of formula (I) in the preparation of a medicament for the treatment of a disorder caused by, associated with or accompanied by disruptions of cell proliferation and/or angiogenesis. In one embodiment the disorder is a proliferative disorder. In a specific embodiment the disorder is a cancer.

The compounds of the present invention surprisingly show low toxicity, together with a potent anti-proliferative activity.

In yet a further embodiment the invention provides a method of treatment of a disorder, disease or condition that can be treated by the inhibition of histone deacetylase including administration of a therapeutically effective amount of a compound of formula (I).

In one embodiment the method includes administration of a compound of formula (Ia) or (Ib) as described herein.

In one embodiment the disorder is selected from the group consisting of but not limited to Proliferative disorders (e.g. cancer); Neurodegenerative diseases including Huntington's Disease, Polyglutamine diseases, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Pick's disease, Intracerebral haemorrhage Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, macular myopic degeneration, Rubeotic glaucoma, Interstitial keratitis, Diabetic retinopathy, Peter's anomaly retinal degeneration, Cellophane Retinopathy; Cogan's Dystrophy; Corneal Dystrophy; Iris Neovascularization (Rubeosis); Neovascularization of the Cornea; Retinopathy of Prematurity; Macular Edema; Macular Hole; Macular Pucker; Marginal Blepharitis, Myopia, nonmalignant growth of the conjunctiva; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, Crohn's Disease, inflammatory bowel disease, Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus, allergic contact dermatitis; Disease involving angiogenesis including cancer, psoriasis, rheumatoid arthritis; Psychological disorders including bipolar disease, schizophrenia, depression and dementia; Cardiovascular Diseases including Heart failure, restenosis, cardiac hypertrophy and arteriosclerosis; Fibrotic diseases including liver fibrosis, lung fibrosis, cystic fibrosis and angiofibroma; Infectious diseases including Fungal infections, such as *Candida Albicans*, Bacterial infections, Viral infections, such as Herpes Simplex, Protozoal infections, such as *Malaria, Leishmania* infection, *Trypanosoma brucei* infection, Toxoplasmosis and coccidiosis, and Haematopoietic disorders including thalassemia, anemia and sickle cell anemia.

The invention also provides agents for the treatment of a disorder, disease or condition that can be treated by the inhibition of histone deacetylase including a compound of formula (I) as disclosed herein. In one embodiment the agent is an anti-cancer agent.

The invention also relates to the use of compounds of formula (I) in the preparation of a medicament for the treatment of a disorder, disease or condition that can be treated by the inhibition of histone deacetylase.

The invention also provides a method for inhibiting cell proliferation including administration of an effective amount of a compound according to formula (I).

In yet an even further aspect the invention provides a method of treatment of a neurodegenerative disorder in a patient including administration of a therapeutically effective amount of a compound of formula (I). In one embodiment the method includes administration of a compound of formula (Ia) or (Ib) as described herein. In one embodiment the neurodegenerative disorder is Huntington's Disease.

The invention also provides agents for the treatment of neurodegenerative disorder including a compound of formula (I) as disclosed herein. In one embodiment the agent is preferably anti-Huntington's disease agent.

The invention also relates to the use of compounds of formula (I) in the preparation of a medicament for the treatment of a neurodegenerative disorder. In one embodiment the neurodegenerative disorder is Huntington's Disease.

In yet an even further aspect the invention provides a method of treatment of an inflammatory disease and/or immune system disorder in a patient including administration of a therapeutically effective amount of a compound of formula (I). In one embodiment the method includes administration of a compound of formula (Ia) or (Ib) as described herein.

In one embodiment the inflammatory disease and/or immune system disorder is rheumatoid arthritis. In another embodiment the inflammatory disease and/or immune system disorder is Systemic Lupus Erythematosus.

The invention also provides agents for the treatment of inflammatory disease and/or immune system disorder including a compound of formula (I) as disclosed herein.

The invention also provides agents for the treatment of eye disease mediated by HDAC inhibition including a compound of formula (I) as disclosed herein. In one embodiment, the eye disease is macular degeneration. In another embodiment, the eye disease is glaucoma. In another embodiment, the eye disease is retinal degeneration.

The invention also relates to the use of compounds of formula (I) in the preparation of a medicament for the treatment of inflammatory disease and/or immune system disorder. In one embodiment the inflammatory disease and/or immune system disorder is rheumatoid arthritis. In another embodiment the inflammatory disease and/or immune system disorder is Systemic Lupus Erythematosus.

The invention also provides methods of preparation of the compounds of the invention. In one embodiment the invention provides a method of synthesis of compounds of formula I as defined above the method including:

(a) providing a compound of the formula (A1):

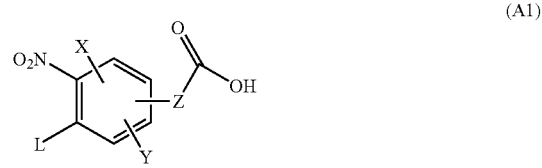

wherein X, Y and Z are as defined above and L is a leaving group;

(b) protecting the carboxyl group to produce a compound of the formula (A2):

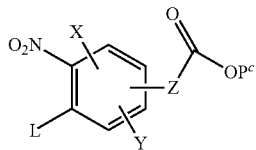
(A2)

wherein X, Y and Z are as defined above L is a leaving group and $P^c$ is a carboxyl protecting group;

(c) displacing the leaving group with an amine of formula $R^1NH_2$ to produce a compound of the formula (A3):

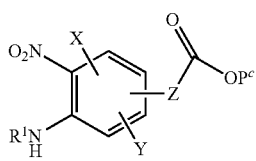
(A3)

wherein X, Y, Z are as defined above, $R^1$ is as defined above or a protected form thereof, and $P^c$ is a carboxyl protecting group;

(d) optionally reacting the compound to further functionalise $R^1$;

(e) reducing the nitro group;

(f) reacting the reduced product with a compound of formula $R^2CO_2H$ or a compound of formula $R^2CHO$ and cyclising the product thus produced to produce a compound of the formula (A4)

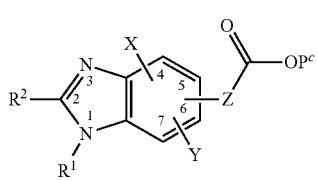
(A4)

wherein X, Y, Z are as defined above, $R^1$ and $R^2$ are as defined above or protected forms thereof, and $P^c$ is a carboxyl protecting group;

(g) converting the compound to a compound of formula I;

wherein (d) can be carried out after any one of (c) (e) or (f) and further wherein (e) and (f) can be carried out sequentially or simultaneously.

In yet an even further aspect the invention provides a method of synthesis of compounds of formula I as defined above

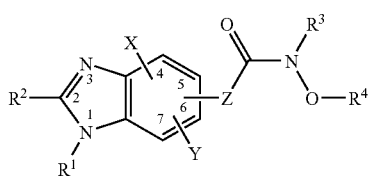
Formula I wherein $R^1$, $R^2$, $R^3$, $R^4$, X, Y and Z are as defined above, the method including:

(a) providing an aldehyde of the formula (B1)

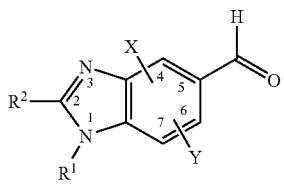
(B1)

wherein $R^1$, $R^2$, X, and Y are as defined above;

(b) subjecting the aldehyde to reaction with an appropriately substituted olefination agent to produce a compound of formula (B2)

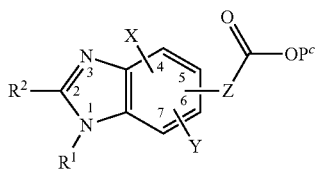
(B2)

wherein $R^1$, $R^2$, X, Y, and Z are as defined above, and $P^c$ is H or a carboxyl protecting group;

(c) converting the compound to a compound of formula I.

In one embodiment of this method (a) includes:

(a1) providing a compound of the formula (B3):

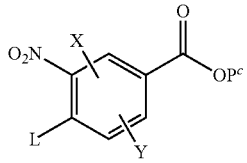
(B3)

wherein X and Y are as defined above, L is a leaving group and $P^c$ is a carboxyl protecting group;

(a2) displacing the leaving group with an amine of formula $R^1NH_2$ to produce a compound of the formula (B4):

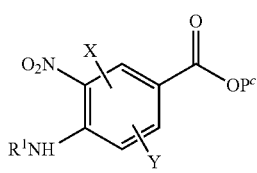
(B4)

wherein X, and Y are as defined above, $R^1$ is as defined above or a protected form thereof, and $P^c$ is a carboxyl protecting group (a3) optionally reacting the compound to further functionalise $R^1$ (a4) reducing the nitro group;

(a5) reacting the reduced product with a compound of formula $R^2CO_2H$ or a compound of formula $R^2CHO$ and cyclising the product thus produced to produce a compound of the formula (B5):

(B5)

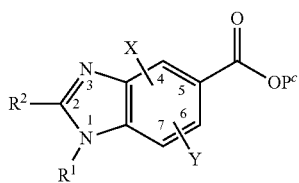

wherein X, and Y are as defined above, $R^1$ and $R^2$ are as defined above or protected forms thereof, and $P^c$ is a carboxyl protecting group (a6) converting the compound of formula (B5) to the corresponding aldehyde wherein (a3) can be carried out after any one of (a2), (a4), (a5) or (a6) and further wherein (a4) and (a5) may be carried out sequentially or simultaneously.

In yet an even further aspect the invention provides a method of synthesis of compounds of formula I as defined above Formula I

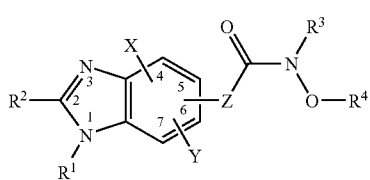

wherein $R^1$, $R^2$, $R^3$, $R^4$, X, Y and Z are as defined above, the method including:

(a) providing a compound of the formula (C1)

(C1)

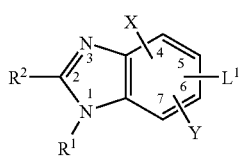

wherein X, and Y are as defined above, $R^1$ and $R^2$ are as defined above or protected forms thereof, and $L^1$ is a leaving group (b) converting the compound (C1) to a compound of formula (C2);

(C2)

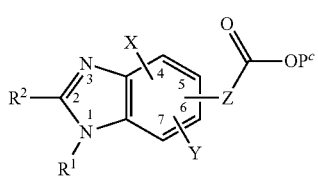

wherein X, Y and Z are as defined above, $R^1$ and $R^2$ are as defined above or protected forms thereof, and $P^c$ is H or a carboxyl protecting group (c) converting the compound to a compound of formula I.

In one form of this embodiment (a) includes:
(a1) providing a compound of the formula (C3):

(C3)

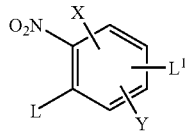

wherein X and Y are as defined above and L and $L^1$ are leaving groups;

(a2) displacing the leaving group (L) with an amine of formula $R^1NH_2$ to produce a compound of the formula (C4):

(C4)

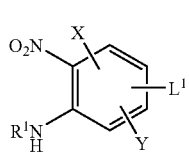

wherein X and Y, are as defined above, $R^1$ is as defined above or a protected form thereof, and $L^1$ is a leaving group;

(a3) optionally reacting the compound to further functionalise $R^1$;

(a4) reducing the nitro group;

(a5) reacting the reduced product with a compound of formula $R^2CO_2H$ or a compound of formula $R^2CHO$ and cyclising the product thus produced to produce a compound of the formula (C1):

(C1)

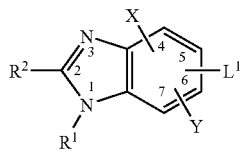

wherein (a3) can be carried out after any one of (a2), (a4) or (a5) and further wherein (a4) and (a5) may be carried out sequentially or simultaneously.

DETAILED DESCRIPTION OF THE INVENTION

In this specification a number of terms are used which are well known to a skilled addressee. Nevertheless for the purposes of clarity a number of terms will be defined.

As used herein, the term unsubstituted means that there is no substituent or that the only substituents are hydrogen.

The term "optionally substituted" as used throughout the specification denotes that the group may or may not be further substituted or fused (so as to form a condensed polycyclic system), with one or more substituent groups. Preferably the substituent groups are one or more groups independently selected from the group consisting of halogen, =O, =S, —ON, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkoxy, alkoxyalkyl, alkoxycycloalkyl, alkoxyheterocycloalkyl, alkoxyaryl, alkoxyheteroaryl, alkoxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, arylalkyl, heteroarylalkyl, cycloalkylalkyl, heterocycloalkylalkyl, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —COOH, —COR$^5$, —C(O)OR$^5$, CONHR$^5$, NHCOR$^5$, NHCOOR$^5$, NHCONHR$^5$, C(=NOH)R$^5$, —SH, —SR$^5$, —OR$^5$ and acyl.

"Alkyl" as a group or part of a group refers to a straight or branched aliphatic hydrocarbon group, preferably a $C_1$-$C_{14}$ alkyl, more preferably $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both monoalkylamino and dialkylamino, unless specified. "Monoalkylamino" means a —NH-Alkyl group, in which alkyl is as defined above. "Dialkylamino" means a —N(alkyl)$_2$ group, in which each alkyl may be the same or different and are each as defined herein for alkyl. The alkyl group is preferably a $C_1$-$C_6$ alkyl group. The group may be a terminal group or a bridging group.

"Arylamino" includes both mono-arylamino and di-arylamino unless specified. Mono-arylamino means a group of formula aryl NH—, in which aryl is as defined herein. di-arylamino means a group of formula (aryl$_2$) N— where each aryl may be the same or different and are each as defined herein for aryl. The group may be a terminal group or a bridging group.

"Acyl" means an alkyl-CO— group in which the alkyl group is as described herein. Examples of acyl include acetyl and benzoyl. The alkyl group is preferably a $C_1$-$C_6$ alkyl group. The group may be a terminal group or a bridging group.

"Alkenyl" as a group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkoxy" refers to an —O-alkyl group in which alkyl is defined herein. Preferably the alkoxy is a $C_1$-$C_6$alkoxy. Examples include, but are not limited to, methoxy and ethoxy. The group may be a terminal group or a bridging group.

"Alkenyloxy" refers to an —O— alkenyl group in which alkenyl is as defined herein. Preferred alkenyloxy groups are $C_1$-$C_6$ alkenyloxy groups. The group may be a terminal group or a bridging group.

"Alkynyloxy" refers to an —O-alkynyl group in which alkynyl is as defined herein. Preferred alkynyloxy groups are $C_1$-$C_6$ alkynyloxy groups. The group may be a terminal group or a bridging group.

"Alkoxycarbonyl" refers to an —C(O)—O-alkyl group in which alkyl is as defined herein. The alkyl group is preferably a $C_1$-$C_6$ alkyl group. Examples include, but are not limited to, methoxycarbonyl and ethoxycarbonyl. The group may be a terminal group or a bridging group.

"Alkylsulfinyl" means a —S(O)-alkyl group in which alkyl is as defined above. The alkyl group is preferably a $C_1$-$C_6$ alkyl group. Exemplary alkylsulfinyl groups include, but not limited to, methylsulfinyl and ethylsulfinyl. The group may be a terminal group or a bridging group.

"Alkylsulfonyl" refers to a —S(O)$_2$-alkyl group in which alkyl is as defined above. The alkyl group is preferably a $C_1$-$C_6$ alkyl group. Examples include, but not limited to methylsulfonyl and ethylsulfonyl. The group may be a terminal group or a bridging group.

"Alkynyl as a group or part of a group means an aliphatic hydrocarbon group containing a carbon-carbon triple bond and which may be straight or branched preferably having from 2-14 carbon atoms, more preferably 2-12 carbon atoms, more preferably 2-6 carbon atoms in the normal chain. Exemplary structures include, but are not limited to, ethynyl and propynyl. The group may be a terminal group or a bridging group.

"Alkylaminocarbonyl" refers to an alkylamino-carbonyl group in which alkylamino is as defined above. The group may be a terminal group or a bridging group.

"Cycloalkyl" refers to a saturated or partially saturated, monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. The group may be a terminal group or a bridging group.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

The above discussion of alkyl and cycloalkyl substituents also applies to the alkyl portions of other substituents, such as without limitation, alkoxy, alkyl amines, alkyl ketones, arylalkyl, heteroarylalkyl, alkylsulfonyl and alkyl ester substituents and the like.

"Cycloalkylalkyl" means a cycloalkyl-alkyl-group in which the cycloalkyl and alkyl moieties are as previously described. Exemplary monocycloalkylalkyl groups include cyclopropylmethyl, cyclopentylmethyl, cyclohexylmethyl and cycloheptylmethyl. The group may be a terminal group or a bridging group.

"Halogen" represents chlorine, fluorine, bromine or iodine.

"Heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazapane, and 1,4-oxathiapane. The group may be a terminal group or a bridging group.

"Heterocycloalkenyl" refers to a heterocycloalkyl as described above but containing at least one double bond. The group may be a terminal group or a bridging group.

"Heterocycloalkylalkyl" refers to a heterocycloalkyl-alkyl group in which the heterocycloalkyl and alkyl moieties are as previously described. Exemplary heterocycloalkylalkyl groups include (2-tetrahydrofuryl)methyl, (2-tetrahydrothiofuranyl)methyl. The group may be a terminal group or a bridging group.

"Heteroalkyl" refers to a straight- or branched-chain alkyl group preferably having from 2 to 14 atoms, more preferably 2 to 10 atoms in the chain, one or more of which is a heteroatom selected from S, O, and N. Exemplary heteroalkyls include alkyl ethers, secondary and tertiary alkyl amines, alkyl sulfides, and the like. The group may be a terminal group or a bridging group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group.

"Arylalkenyl" means an aryl-alkenyl-group in which the aryl and alkenyl are as previously described. Exemplary arylalkenyl groups include phenylallyl. The group may be a terminal group or a bridging group.

"Arylalkyl" means an aryl-alkyl-group in which the aryl and alkyl moieties are as previously described. Preferred arylalkyl groups contain a $C_{1-5}$ alkyl moiety. Exemplary arylalkyl groups include benzyl, phenethyl and naphthelenemethyl. The group may be a terminal group or a bridging group.

"Arylacyl" means an aryl-acyl-group in which the aryl and acyl moieties are as previously described. In general the aryl moiety is attached to the alkyl portion of the acyl moiety, typically to the terminal carbon of the alkyl portion of the acyl moiety. Preferred arylacyl groups contain a $C_{1-5}$ alkyl moiety in the acyl moiety. Exemplary arylacyl groups include 2-phenyl-acetyl. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl1-, 2-, or 3-indolyl, and 2-, or 3-thienyl. The group may be a terminal group or a bridging group.

"Heteroarylalkyl" means a heteroaryl-alkyl group in which the heteroaryl and alkyl moieties are as previously described. Preferred heteroarylalkyl groups contain a lower alkyl moiety. Exemplary heteroarylalkyl groups include pyridylmethyl. The group may be a terminal group or a bridging group.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n-butyl, isobutyl or tertiary-butyl). The group may be a terminal group or a bridging group.

In Formula (I), as well as in Formulae (Ia)-(Ib) defining sub-sets of compounds within Formula (I), there is shown a benzimidazole ring system. Within this ring system, there are substitutable positions at the 4-, 5-, 6-, and 7-ring positions. In each of Formulae (I), (Ia), and (Ib), there is a requirement for attachment of an acidic moiety at one of the ring positions. This acidic moiety may be provided by but is not limited to groups containing, a hydroxamic acid or salt derivatives of such acid which when hydrolysed would provide the acidic moiety. In some embodiments the acidic moiety may be attached to the ring position through an alkylene group such as —$CH_2$— or —$CH_2CH_2$—, or an alkenylene group such as —CH=CH—. Preferred positions for attachment of the acidic moiety are the 5- and 6-ring positions.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof are intended to be within the scope of the subject matter described and claimed.

Additionally, Formula (I) is intended to cover, where applicable, solvated as well as unsolvated forms of the compounds. Thus, each formula includes compounds having the indicated structure, including the hydrated as well as the non-hydrated forms.

In addition to compounds of the Formula (I), the HDAC inhibiting agents of the various embodiments include pharmaceutically acceptable salts, prodrugs, and active metabolites of such compounds, and pharmaceutically acceptable salts of such metabolites.

The term "Pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Suitable pharmaceutically acceptable base addition salts of compounds of Formula (I) include metallic salts made from lithium, sodium, potassium, magnesium, calcium, aluminium, and zinc, and organic salts made from organic bases such as choline, diethanolamine, morpholine. Other examples of organic salts are: ammonium salts, quaternary salts such as tetramethylammonium salt; amino acid addition salts such as salts with glycine and arginine. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound which is convertible in vivo by metabolic means (e.g. by hydrolysis, reduction or oxidation) to a compound of formula (I). For example an ester prodrug of a compound of formula (I) containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987).

Preferred HDAC inhibiting agents include those having an IC$_{50}$ value of 10 μM or less.

Specific compounds of the invention include the following:

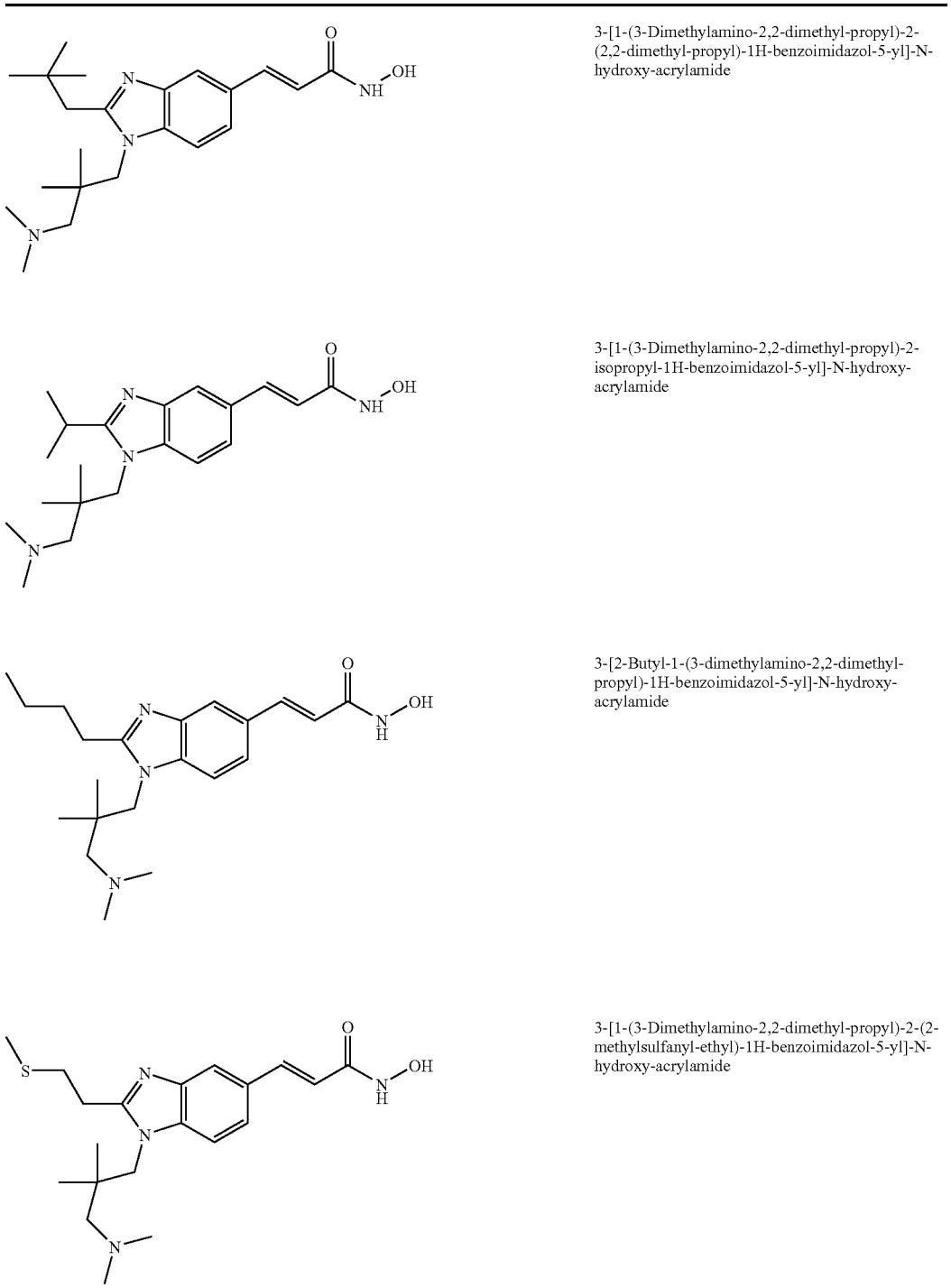

3-[1-(3-Dimethylamino-2,2-dimethyl-propyl)-2-(2,2-dimethyl-propyl)-1H-benzoimidazol-5-yl]-N-hydroxy-acrylamide 3-[1-(3-Dimethylamino-2,2-dimethyl-propyl)-2-isopropyl-1H-benzoimidazol-5-yl]-N-hydroxy-acrylamide 3-[2-Butyl-1-(3-dimethylamino-2,2-dimethyl-propyl)-1H-benzoimidazol-5-yl]-N-hydroxy-acrylamide 3-[1-(3-Dimethylamino-2,2-dimethyl-propyl)-2-(2-methylsulfanyl-ethyl)-1H-benzoimidazol-5-yl]-N-hydroxy-acrylamide

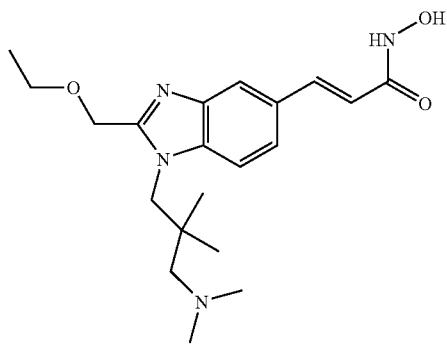

3-[1-(3-Dimethylamino-2,2-dimethyl-propyl)-2-ethoxymethyl-1H-benzoimidazol-5-yl]-N-hydroxy-acrylamide

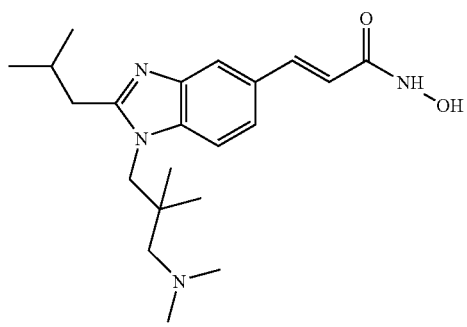

3-[1-(3-Dimethylamino-2,2-dimethyl-propyl)-2-isobutyl-1H-benzoimidazol-5-yl]-N-hydroxy-acrylamide

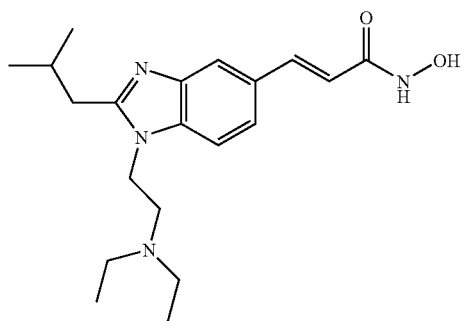

3-[1-(2-Diethylamino-ethyl)-2-isobutyl-1H-benzoimidazol-5-yl]-N-hydroxy-acrylamide

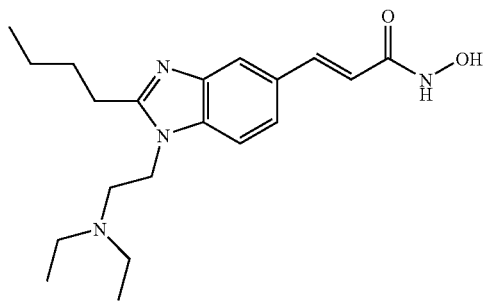

3-[2-Butyl-1-(2-diethylamino-ethyl)-1H-benzoimidazol-5-yl]-N-hydroxy-acrylamide

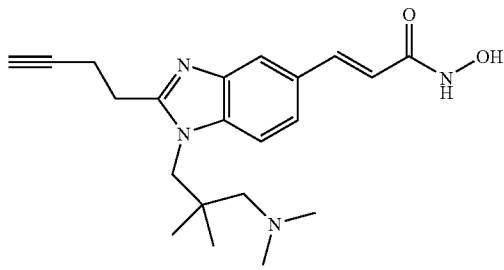

3-[2-But-3-ynyl-1-(3-dimethylamino-2,2-dimethyl-propyl)-1H-benzoimidazol-5-yl]-N-hydroxy-acrylamide -continued

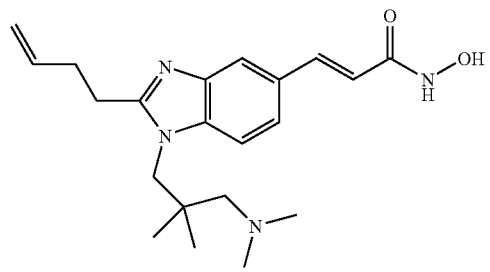

3-[2-But-3-enyl-1-(3-dimethylamino-2,2-dimethyl-propyl)-1H-benzoimidazol-5-yl]-N-hydroxy-acrylamide

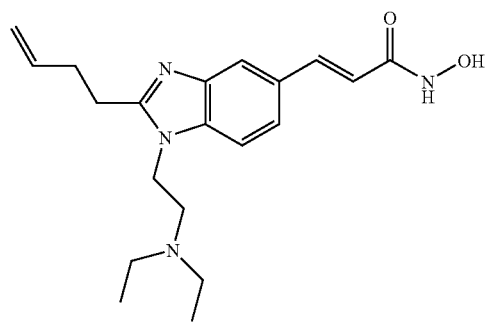

3-[2-But-3-enyl-1-(2-diethylamino-ethyl)-1H-benzoimidazol-5-yl]-N-hydroxy-acrylamide

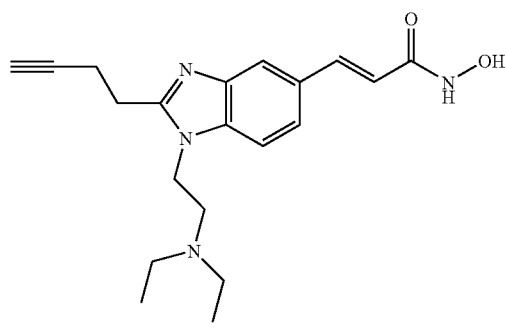

3-[2-But-3-ynyl-1-(2-diethylamino-ethyl)-1H-benzoimidazol-5-yl]-N-hydroxy-acrylamide

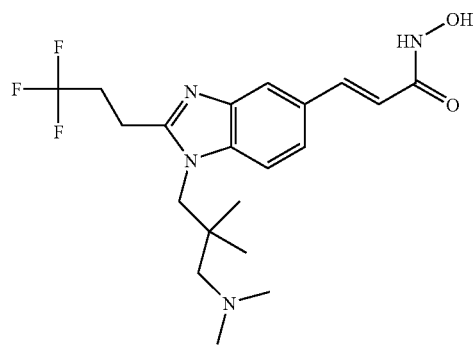

3-[1-(3-Dimethylamino-2,2-dimethyl-propyl)-2-(3,3,3-trifluoro-propyl)-1H-benzoimidazol-5-yl]-N-hydroxy-acrylamide

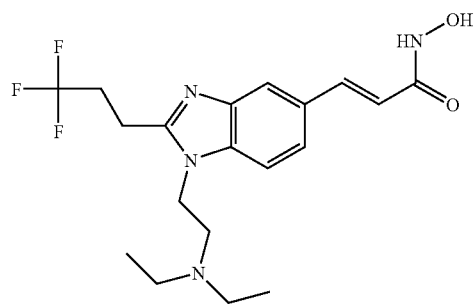

3-[1-(2-Diethylamino-ethyl)-2-(3,3,3-trifluoro-propyl)-1H-benzoimidazol-5-yl]-N-hydroxy-acrylamide

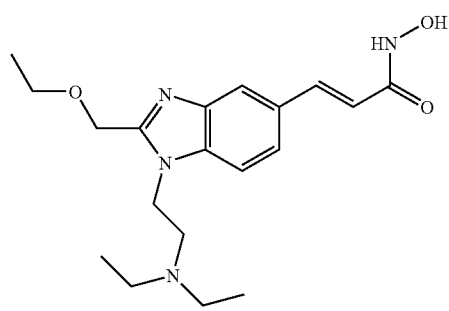 3-[1-(2-Diethylamino-ethyl)-2-ethoxymethyl-1H-benzoimidazol-5-yl]-N-hydroxy-acrylamide
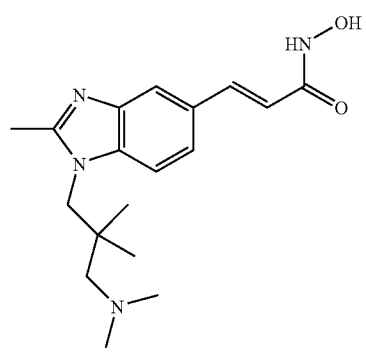 3-[1-(3-Dimethylamino-2,2-dimethyl-propyl)-2-methyl-1H-benzoimidazol-5-yl]-N-hydroxy-acrylamide
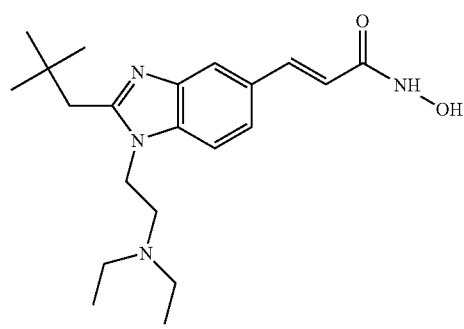 3-[1-(2-Diethylamino-ethyl)-2-(2,2-dimethyl-propyl)-1H-benzoimidazol-5-yl]-N-hydroxy-acrylamide
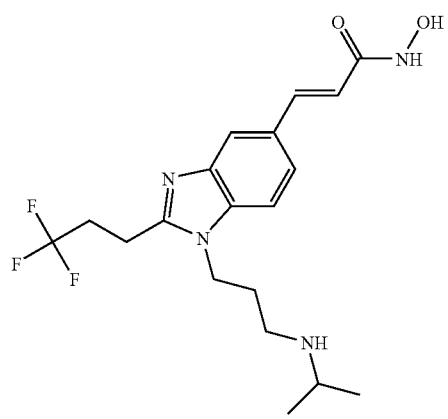 N-Hydroxy-3-[1-(3-isopropylamino-propyl)-2-(3,3,3-trifluoro-propyl)-1H-benzoimidazol-5-yl]-acrylam

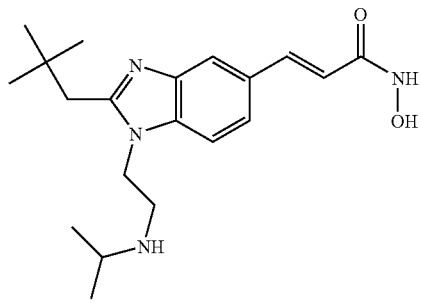

3-[2-(2,2-Dimethyl-propyl)-1-(2-isopropylamino-ethyl)-1H-benzoimidazol-5-yl]-N-hydroxy-acrylamide

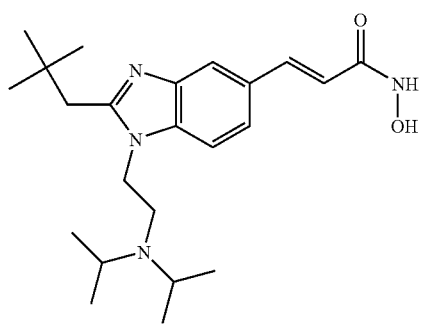

3-[1-(2-Diisopropylamino-ethyl)-2-(2,2-dimethyl-propyl)-1H-benzoimidazol-5-yl]-N-hydroxy-acrylamide

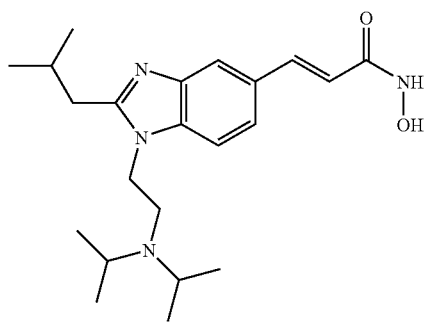

3-[1-(2-Diisopropylamino-ethyl)-2-isobutyl-1H-benzoimidazol-5-yl]-N-hydroxy-acrylamide

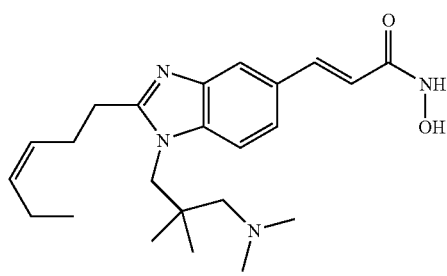

3-[1-(3-Dimethylamino-2,2-dimethyl-propyl)-2-hex-3-enyl-1H-benzoimidazol-5-yl]-N-hydroxy-acrylamide

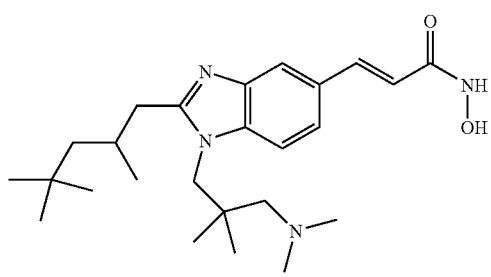

3-[1-(3-Dimethylamino-2,2-dimethyl-propyl)-2-(2,4,4-trimethyl-pentyl)-1H-benzoimidazol-5-yl]-N-hydroxy-acrylamide -continued

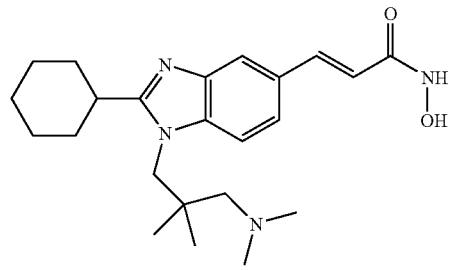

3-[2-Cyclohexyl-1-(3-dimethylamino-2,2-dimethyl-propyl)-1H-benzoimidazol-5-yl]-N-hydroxy-acrylamide

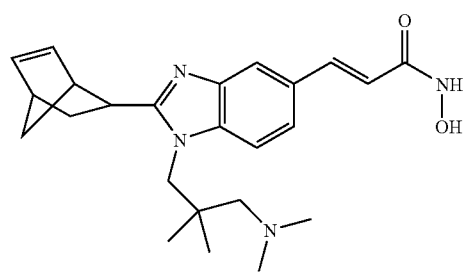

3-[2-Bicyclo[2.2.1]hept-5-en-2-yl-1-(3-dimethylamino-2,2-dimethyl-propyl)-1H-benzoimidazol-5-yl]-N-hydroxy-acrylamide

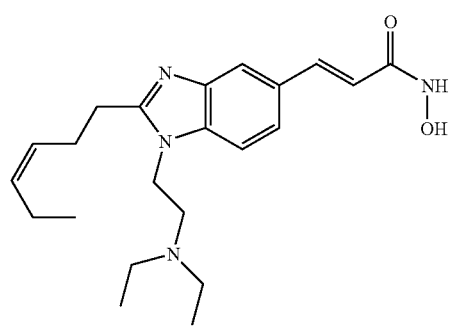

3-[1-(2-Diethylamino-ethyl)-2-hex-3-enyl-1H-benzoimidazol-5-yl]-N-hydroxy-acrylamide

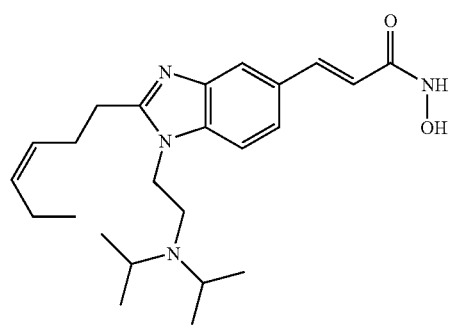

3-[1-(2-Diisopropylamino-ethyl)-2-hex-3-enyl-1H-benzoimidazol-5-yl]-N-hydroxy-acrylamide

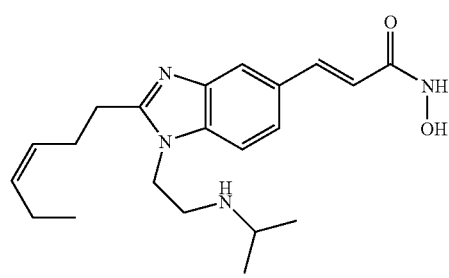

3-[2-Hex-3-enyl-1-(2-isopropylamino-ethyl)-1H-benzoimidazol-5-yl]-N-hydroxy-acrylamide -continued

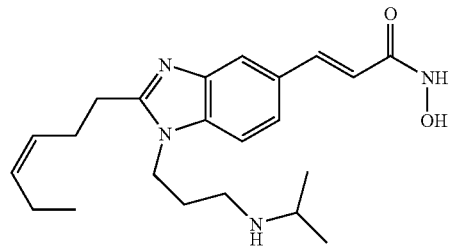

3-[2-Hex-3-enyl-1-(3-isopropylamino-propyl)-1H-benzoimidazol-5-yl]-N-hydroxy-acrylamide

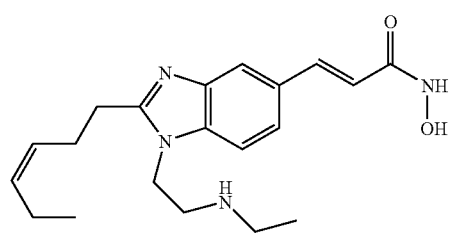

3-[1-(2-Ethylamino-ethyl)-2-hex-3-enyl-1H-benzoimidazol-5-yl]-N-hydroxy-acrylamide

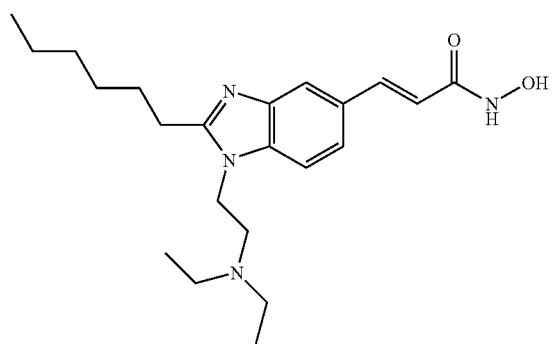

3-[1-(2-Diethylamino-ethyl)-2-hexyl-1H-benzoimidazol-5-yl]-N-hydroxy-acrylamide

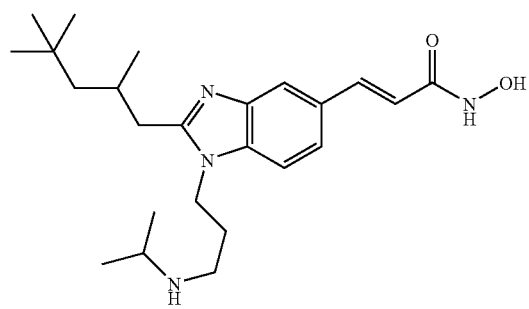

N-Hydroxy-3-[1-(3-isopropylamino-propyl)-2-(2,4,4-trimethyl-pentyl)-1H-benzoimidazol-5-yl]-acrylamide

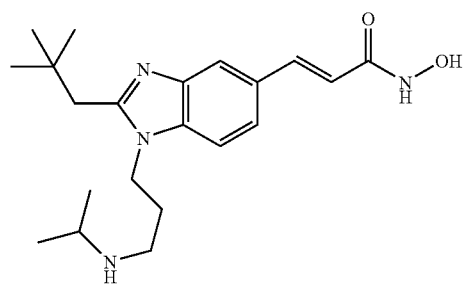

3-[2-(2,2-Dimethyl-propyl)-1-(3-isopropylamino-propyl)-1H-benzoimidazol-5-yl]-N-hydroxy-acrylamide

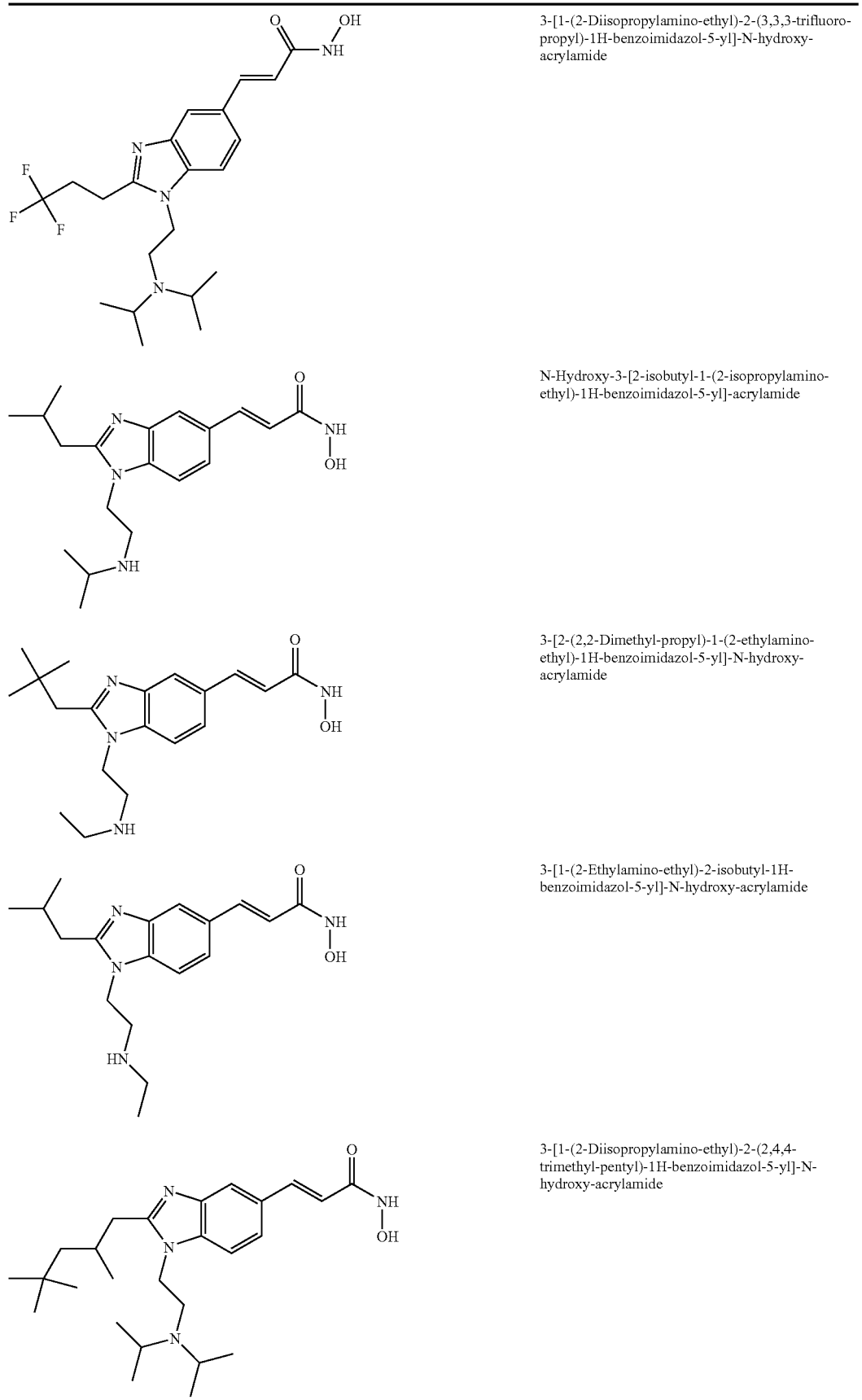

3-[1-(2-Diisopropylamino-ethyl)-2-(3,3,3-trifluoro-propyl)-1H-benzoimidazol-5-yl]-N-hydroxy-acrylamide N-Hydroxy-3-[2-isobutyl-1-(2-isopropylamino-ethyl)-1H-benzoimidazol-5-yl]-acrylamide 3-[2-(2,2-Dimethyl-propyl)-1-(2-ethylamino-ethyl)-1H-benzoimidazol-5-yl]-N-hydroxy-acrylamide 3-[1-(2-Ethylamino-ethyl)-2-isobutyl-1H-benzoimidazol-5-yl]-N-hydroxy-acrylamide 3-[1-(2-Diisopropylamino-ethyl)-2-(2,4,4-trimethyl-pentyl)-1H-benzoimidazol-5-yl]-N-hydroxy-acrylamide -continued

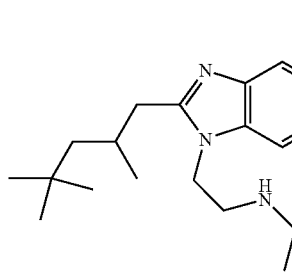

N-Hydroxy-3-[1-(2-isopropylamino-ethyl)-2-(2,4,4-trimethyl-pentyl)-1H-benzoimidazol-5-yl]-acrylamide

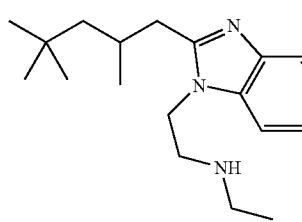

3-[1-(2-Ethylamino-ethyl)-2-(2,4,4-trimethyl-pentyl)-1H-benzoimidazol-5-yl]-N-hydroxy-acrylamide

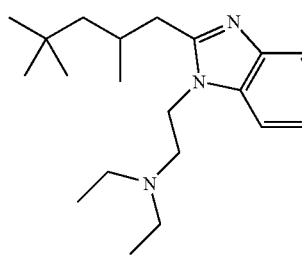

3-[1-(2-Diethylamino-ethyl)-2-(2,4,4-trimethyl-pentyl)-1H-benzoimidazol-5-yl]-N-hydroxy-acrylamide

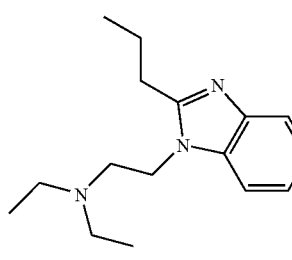

3-[1-(2-Diethylamino-ethyl)-2-propyl-1H-benzoimidazol-5-yl]-N-hydroxy-acrylamide

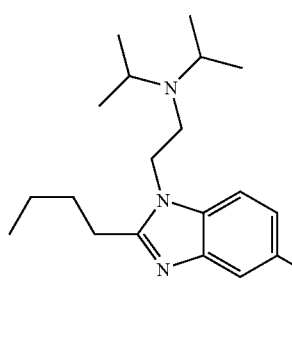

3-[2-Butyl-1-(2-diisopropylamino-ethyl)-1H-benzoimidazol-5-yl]-N-hydroxy-acrylamide -continued

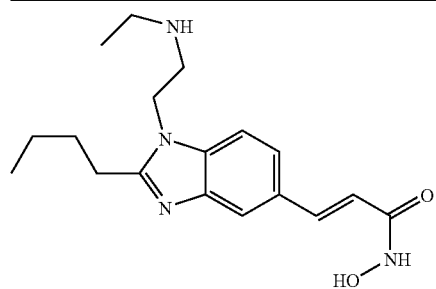

3-[2-Butyl-1-(2-ethylamino-ethyl)-1H-benzoimidazol-5-yl]-N-hydroxy-acrylamide

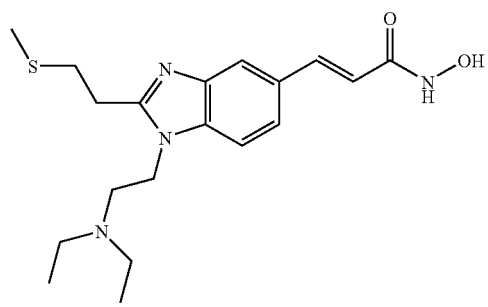

3-[1-(2-Diethylamino-ethyl)-2-(2-methylsulfanyl-ethyl)-1H-benzoimidazol-5-yl]-N-hydroxy-acrylamide

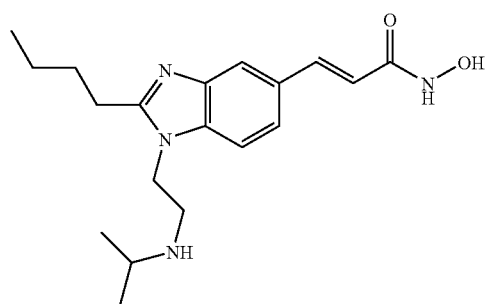

3-[2-Butyl-1-(2-isopropylamino-ethyl)-1H-benzoimidazol-5-yl]-N-hydroxy-acrylamide

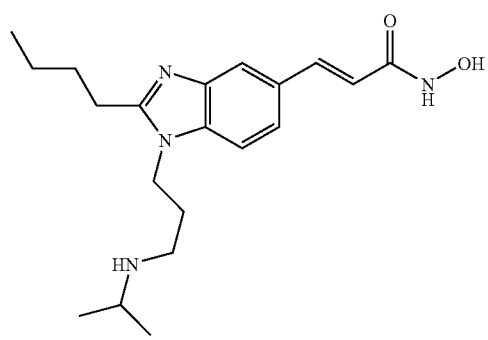

3-[2-Butyl-1-(3-isopropylamino-propyl)-1H-benzoimidazol-5-yl]-N-hydroxy-acrylamide

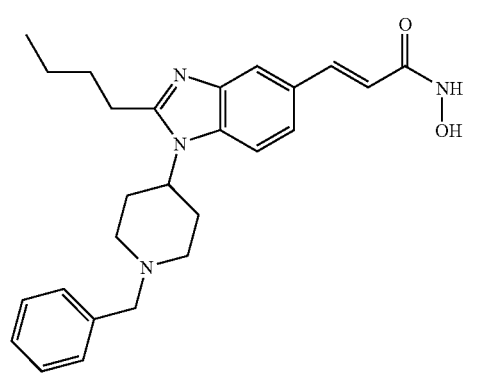

3-[1-(1-Benzyl-piperidin-4-yl)-2-butyl-1H-benzoimidazol-5-yl]-N-hydroxy-acrylamide

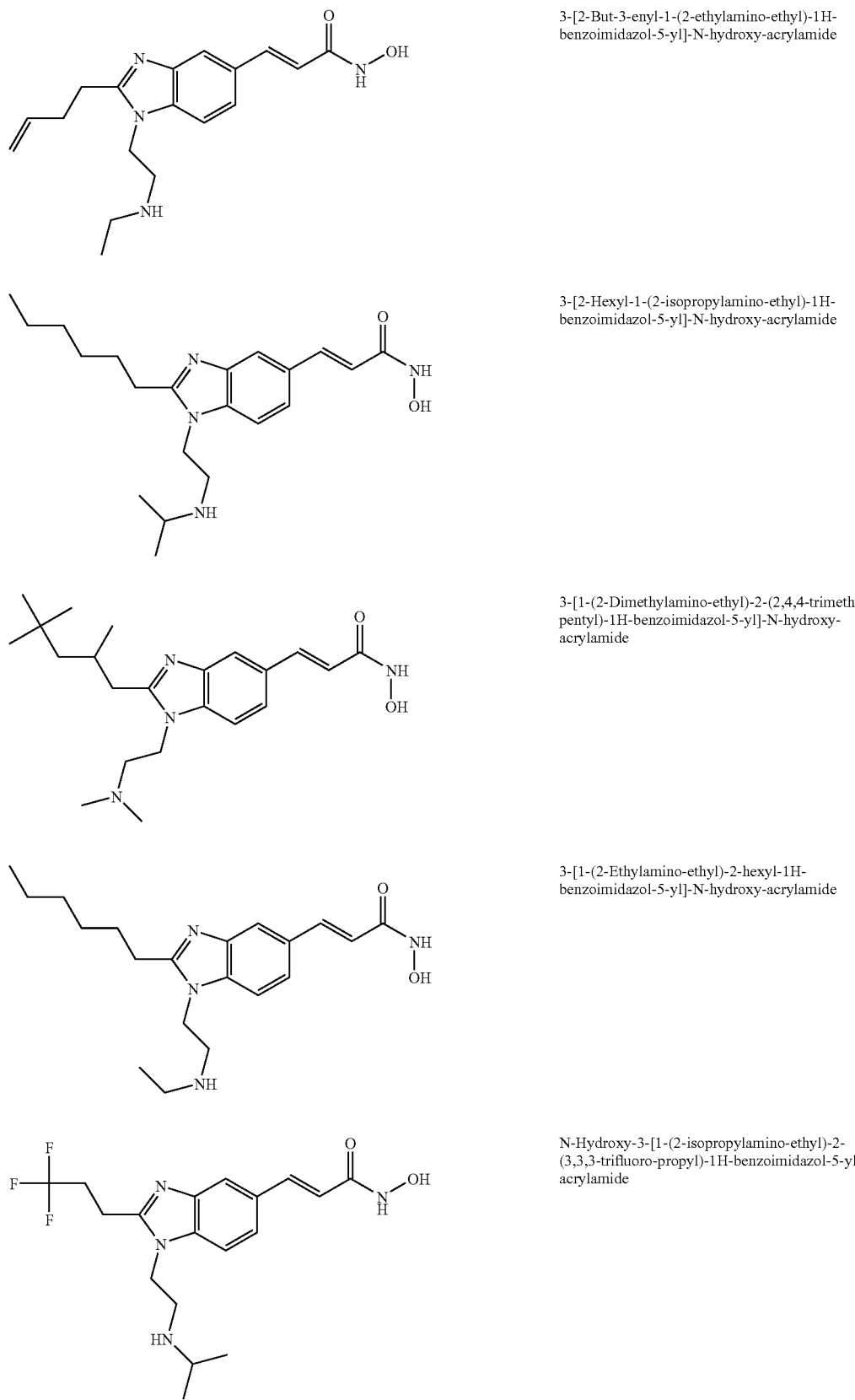

3-[2-But-3-enyl-1-(2-ethylamino-ethyl)-1H-benzoimidazol-5-yl]-N-hydroxy-acrylamide 3-[2-Hexyl-1-(2-isopropylamino-ethyl)-1H-benzoimidazol-5-yl]-N-hydroxy-acrylamide 3-[1-(2-Dimethylamino-ethyl)-2-(2,4,4-trimethyl-pentyl)-1H-benzoimidazol-5-yl]-N-hydroxy-acrylamide 3-[1-(2-Ethylamino-ethyl)-2-hexyl-1H-benzoimidazol-5-yl]-N-hydroxy-acrylamide N-Hydroxy-3-[1-(2-isopropylamino-ethyl)-2-(3,3,3-trifluoro-propyl)-1H-benzoimidazol-5-yl]-acrylamide -continued
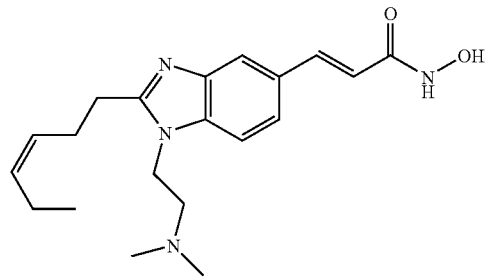
3-[1-(2-Dimethylamino-ethyl)-2-hex-3-enyl-1H-benzoimidazol-5-yl]-N-hydroxy-acrylamide
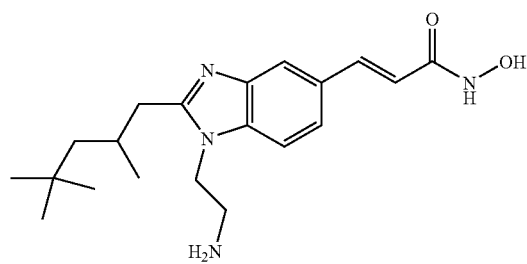
3-[1-(2-Amino-ethyl)-2-(2,4,4-trimethyl-pentyl)-1H-benzoimidazol-5-yl]-N-hydroxy-acrylamide
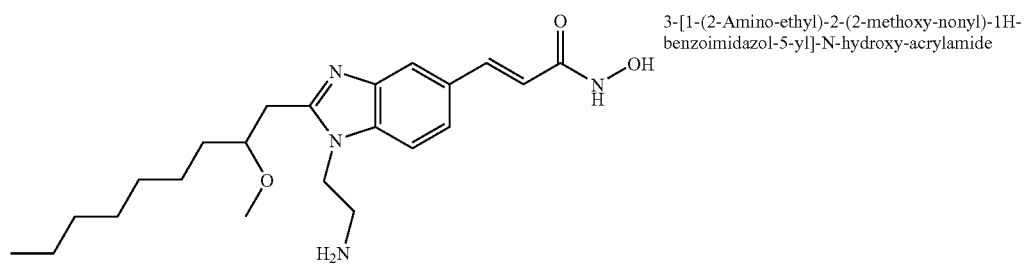
3-[1-(2-Amino-ethyl)-2-(2-methoxy-nonyl)-1H-benzoimidazol-5-yl]-N-hydroxy-acrylamide
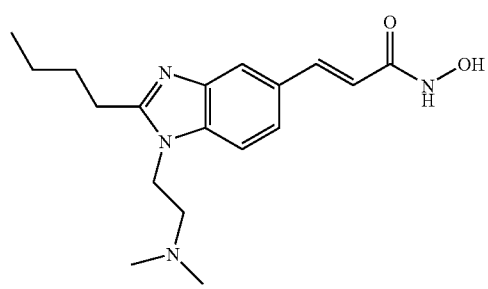
3-[2-Butyl-1-(2-dimethylamino-ethyl)-1H-benzoimidazol-5-yl]-N-hydroxy-acrylamide
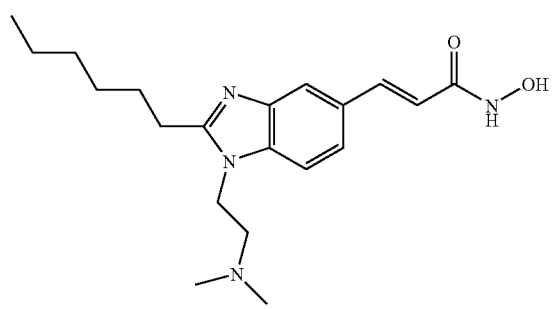
3-[1-(2-Dimethylamino-ethyl)-2-hexyl-1H-benzoimidazol-5-yl]-N-hydroxy-acrylamide -continued

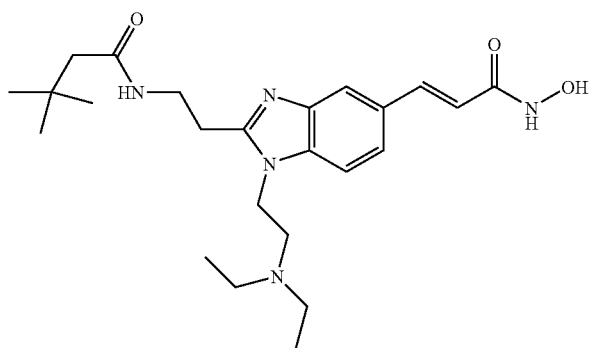

N-{2-[1-(2-Diethylamino-ethyl)-5-(2-hydroxycarbamoyl-vinyl)-1H-benzoimidazol-2-yl]-ethyl}-3,3-dimethyl-butyramide

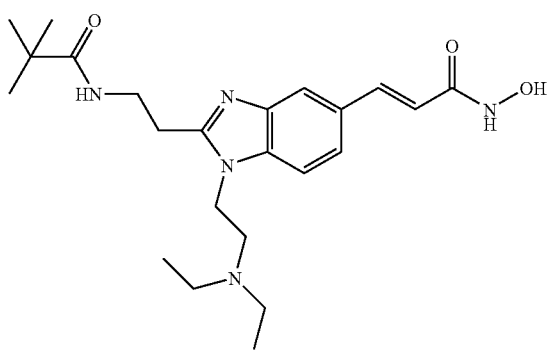

3-{1-(2-Diethylamino-ethyl)-2-[2-(2,2-dimethyl-propionylamino)-ethyl]-1H-benzoimidazol-5-yl}-N-hydroxy-acrylamide

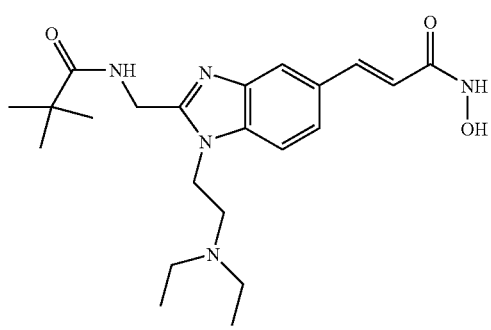

3-{1-(2-Diethylamino-ethyl)-2-[(2,2-dimethyl-propionylamino)-methyl]-1H-benzoimidazol-5-yl}-N-hydroxy-acrylamide

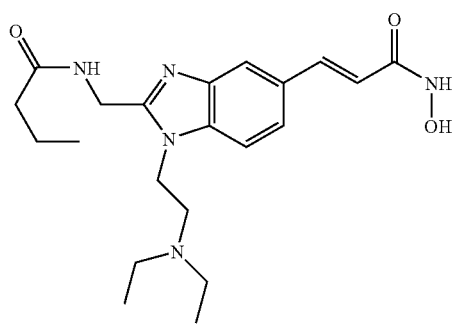

N-[1-(2-Diethylamino-ethyl)-5-(2-hydroxycarbamoyl-vinyl)-1H-benzoimidazol-2-ylmethyl]-butyramide

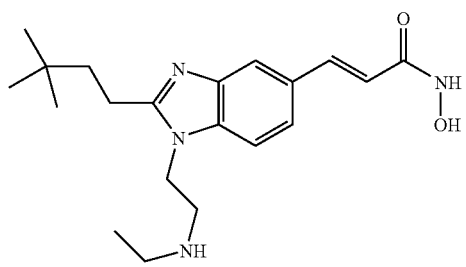

3-[1-(2-ethylamino-ethyl)-2-(3,3-dimethyl-butyl)-1H-benzoimidazol-5-yl]-N-hydroxy-acrylamide

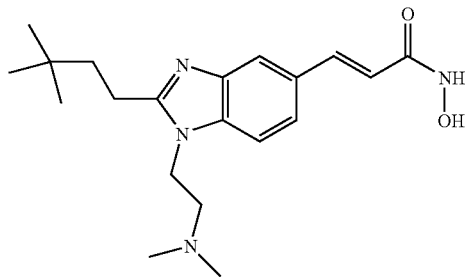

3-[2-(3,3-Dimethyl-butyl)-1-(2-Dimethylamino-ethyl)-1H-benzoimidazol-5-yl]-N-hydroxy-acrylamide

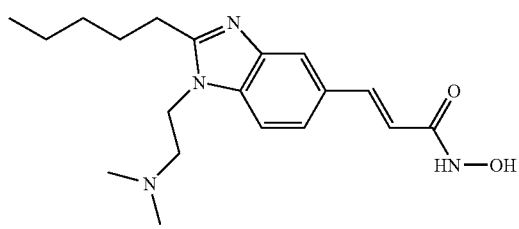

3-[1-(2-Dimethylamino-ethyl)-2-pentyl-1H-benzoimidazol-5-yl]-N-hydroxy-acrylamide

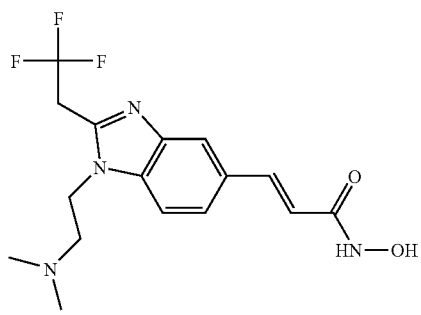

3-[1-(2-Dimethylamino-ethyl)-2-(2,2,2-trifluoro-ethyl)-1H-benzoimidazol-5-yl]-N-hydroxy-acrylamide

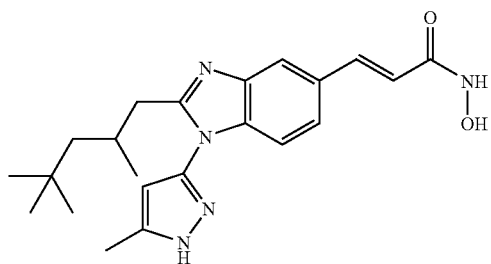

N-Hydroxy-3-[1-(5-methyl-1H-pyrazol-3-yl)-2-(2,4,4-trimethyl-pentyl)-1H-benzoimidazol-5-yl]-acrylamide

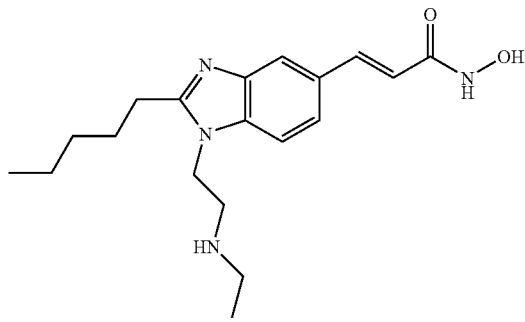

3-[1-(2-Ethylamino-ethyl)-2-pentyl-1H-benzoimidazol-5-yl]-N-hydroxy-acrylamide

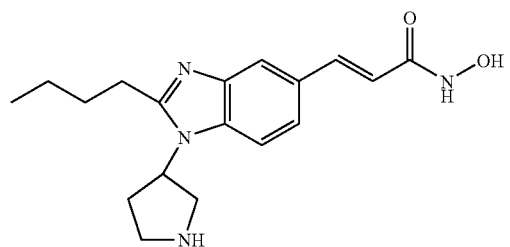
3-(2-Butyl-1-pyrrolidin-3-yl-1H-benzoimidazol-5-yl)-N-hydroxy-acrylamide
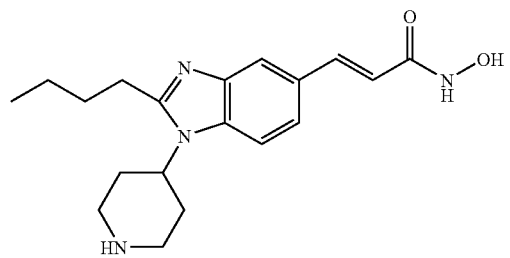
3-(2-Butyl-1-piperidin-4-yl-1H-benzoimidazol-5-yl)-N-hydroxy-acrylamide
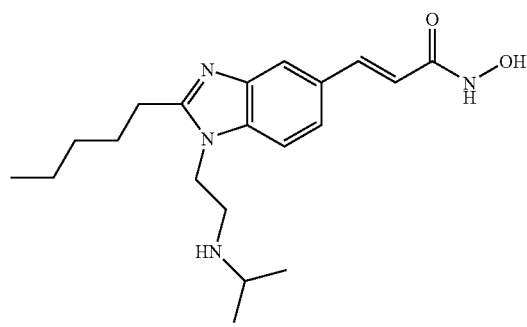
N-Hydroxy-3-[1-(2-isopropylamino-ethyl)-2-pentyl-1H-benzoimidazol-5-yl]-acrylamide
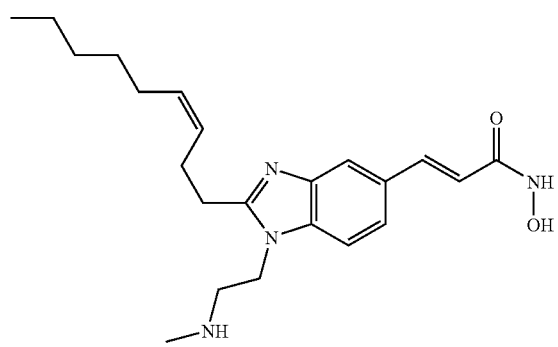
N-Hydroxy-3-[1-(2-methylamino-ethyl)-2-non-3-enyl-1H-benzoimidazol-5-yl]-acrylamide
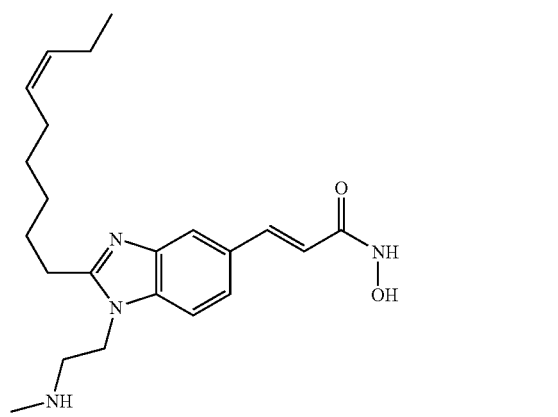
N-Hydroxy-3-[1-(2-methylamino-ethyl)-2-non-6-enyl-1H-benzoimidazol-5-yl]-acrylamide

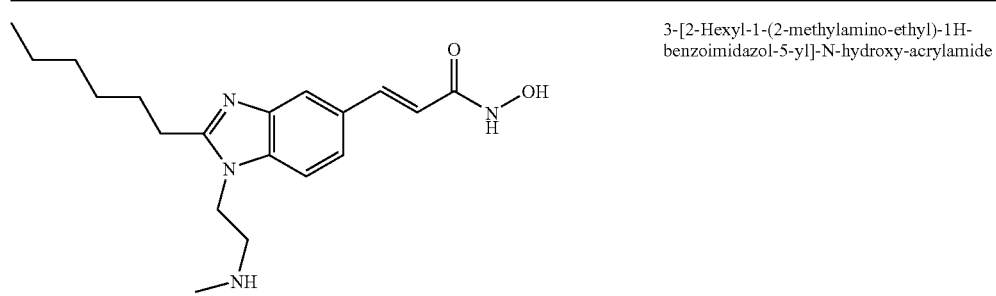
3-[2-Hexyl-1-(2-methylamino-ethyl)-1H-benzoimidazol-5-yl]-N-hydroxy-acrylamide
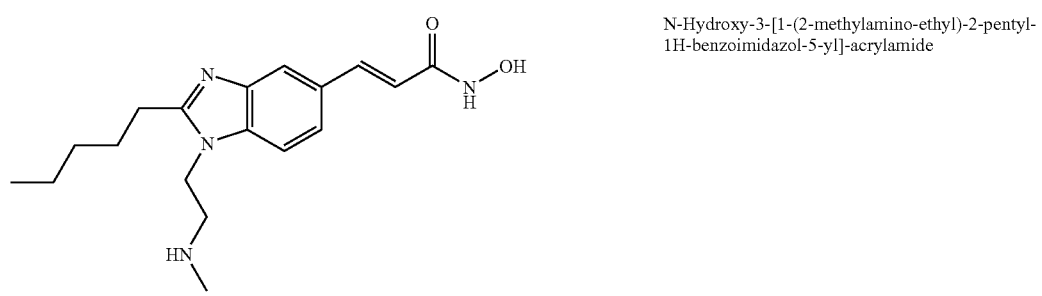
N-Hydroxy-3-[1-(2-methylamino-ethyl)-2-pentyl-1H-benzoimidazol-5-yl]-acrylamide
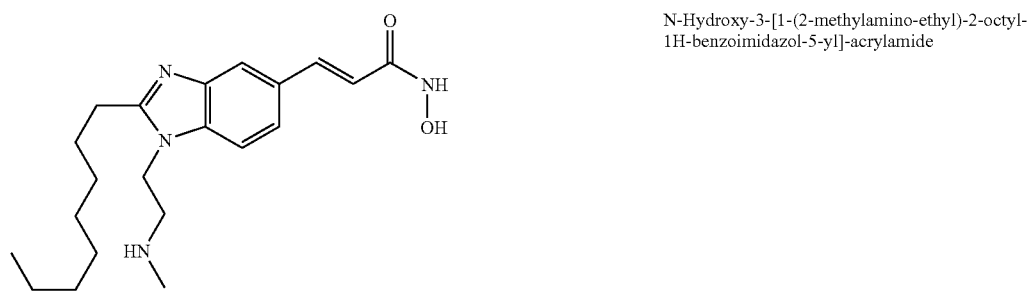
N-Hydroxy-3-[1-(2-methylamino-ethyl)-2-octyl-1H-benzoimidazol-5-yl]-acrylamide
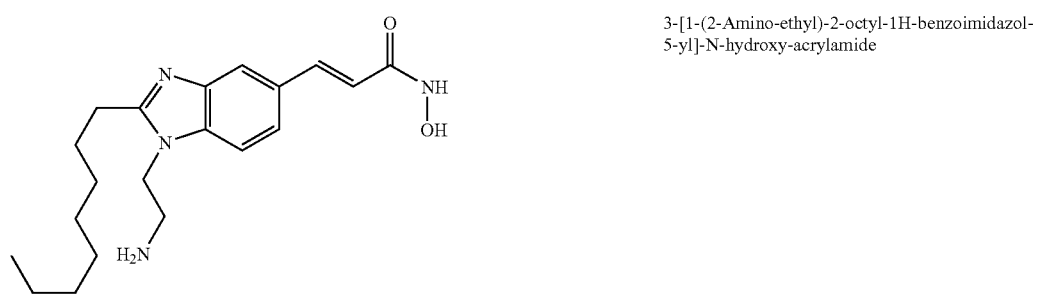
3-[1-(2-Amino-ethyl)-2-octyl-1H-benzoimidazol-5-yl]-N-hydroxy-acrylamide
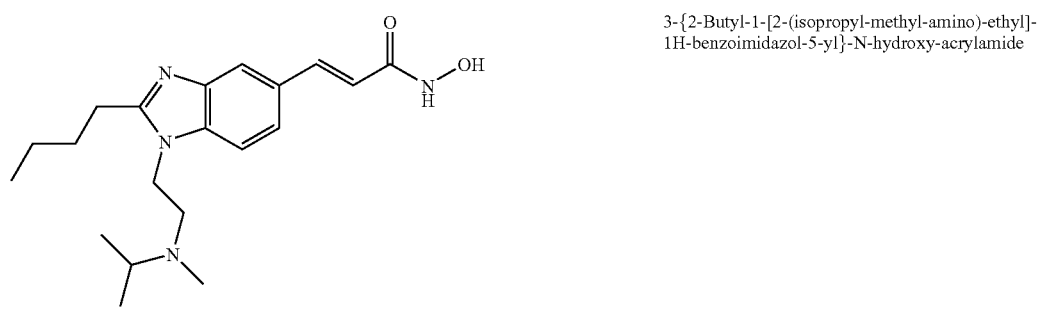
3-{2-Butyl-1-[2-(isopropyl-methyl-amino)-ethyl]-1H-benzoimidazol-5-yl}-N-hydroxy-acrylamide

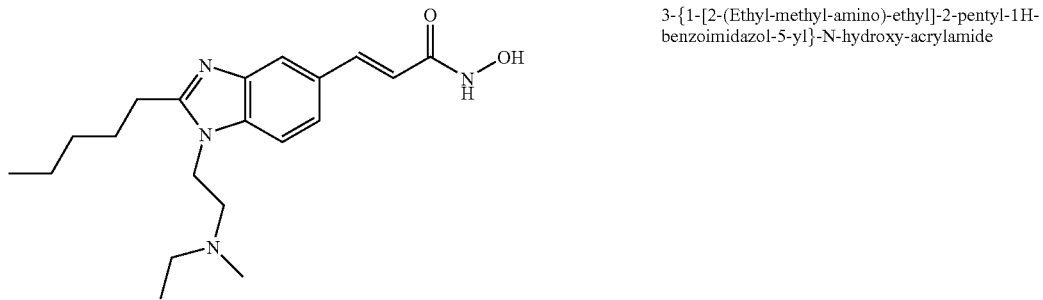
3-{1-[2-(Ethyl-methyl-amino)-ethyl]-2-pentyl-1H-benzoimidazol-5-yl}-N-hydroxy-acrylamide
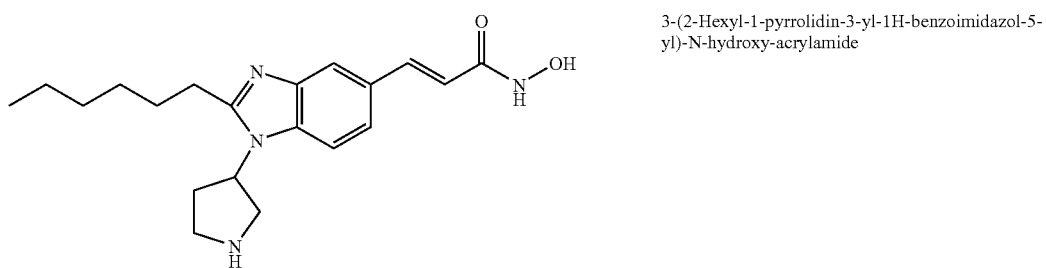
3-(2-Hexyl-1-pyrrolidin-3-yl-1H-benzoimidazol-5-yl)-N-hydroxy-acrylamide
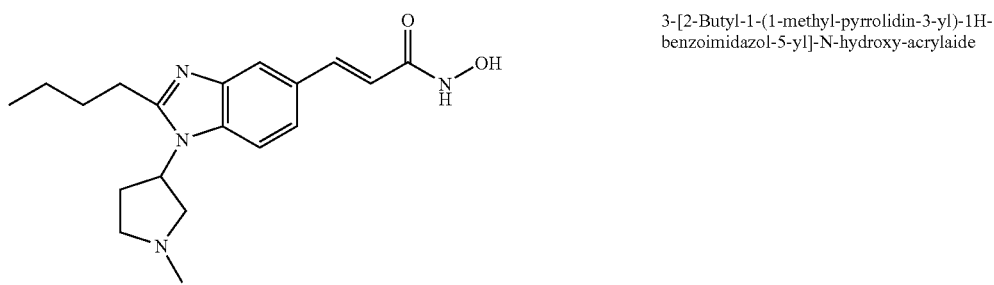
3-[2-Butyl-1-(1-methyl-pyrrolidin-3-yl)-1H-benzoimidazol-5-yl]-N-hydroxy-acrylaide
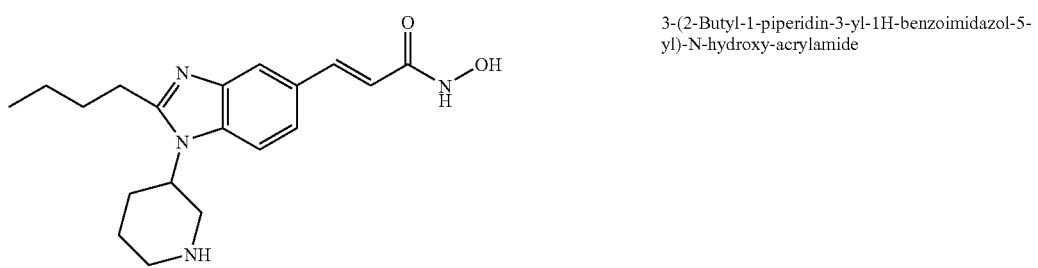
3-(2-Butyl-1-piperidin-3-yl-1H-benzoimidazol-5-yl)-N-hydroxy-acrylamide
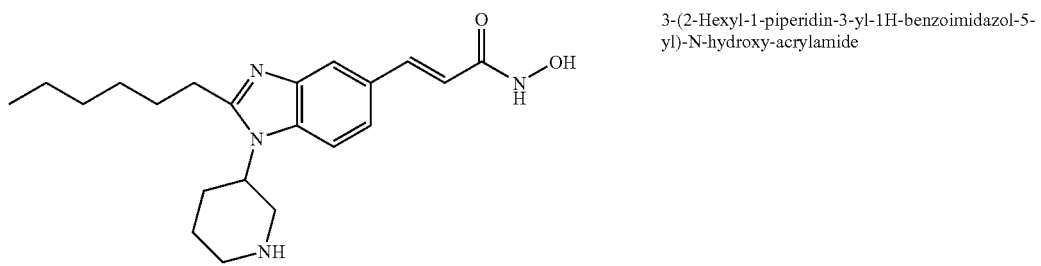
3-(2-Hexyl-1-piperidin-3-yl-1H-benzoimidazol-5-yl)-N-hydroxy-acrylamide

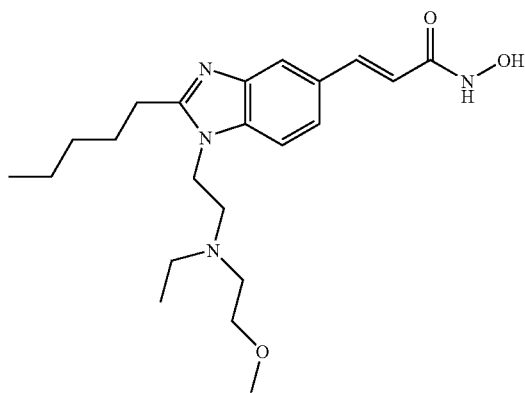
3-(1-{2-[Ethyl-(2-methoxy-ethyl)-amino]-ethyl}-2-pentyl-1H-benzoimidazol-5-yl)-N-hydroxy-acrylamide
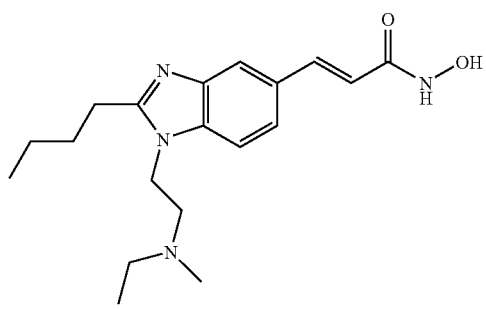
3-{2-Butyl-1-[2-(ethyl-methyl-amino)-ethyl]-1H-benzoimidazol-5-yl}-N-hydroxy-acrylamide
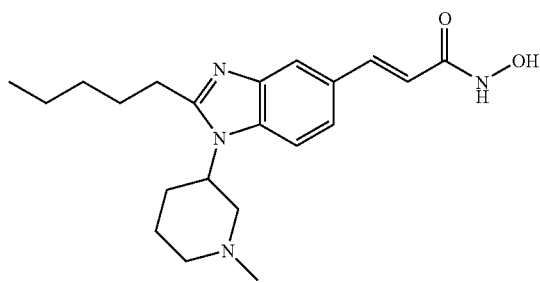
N-Hydroxy-3-[1-(1-methyl-piperidin-3-yl)-2-pentyl-1H-benzoimidazol-5-yl]-acrylaide
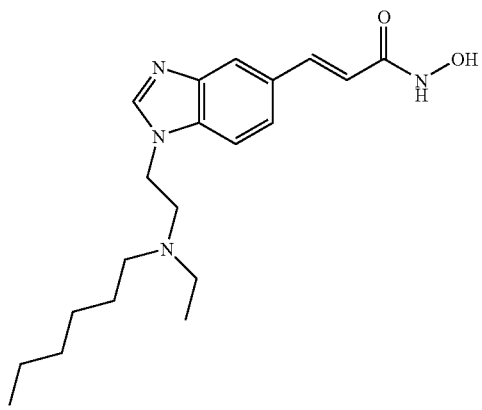
3-{1-[2-(Ethyl-hexyl-amino)-ethyl]-1H-benzoimidazol-5-yl}-N-hydroxy-acrylamide -continued
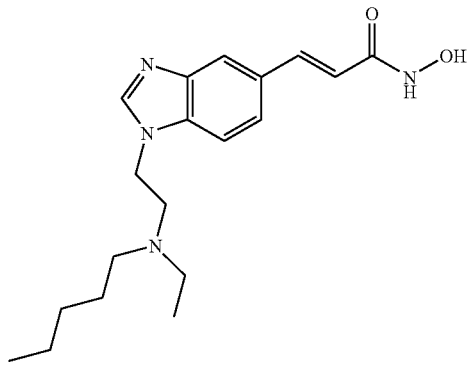
3-{1-[2-(Ethyl-pentyl-amino)-ethyl]-1H-benzoimidazol-5-yl}-N-hydroxy-acrylamide
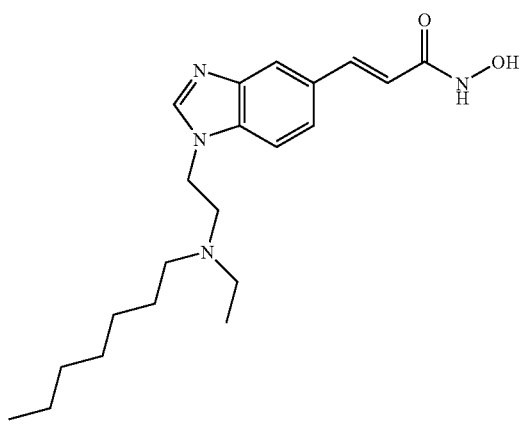
3-{1-[2-(Ethyl-heptyl-amino)-ethyl]-1H-benzoimidazol-5-yl}-N-hydroxy-acrylamide
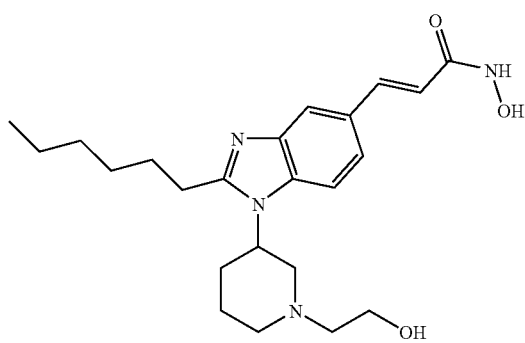
(E)-3-(2-hexyl-1-(1-(2-hydroxyethyl)piperidin-3-yl)-1H-benzo[d]imidazol-5-yl)-N-hydroxyacrylamide
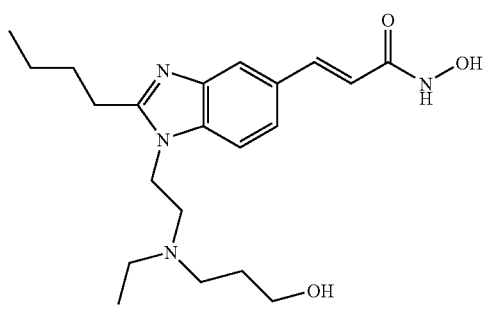
3-(2-Butyl-1-{2-[ethyl-(3-hydroxy-propyl)-amino]-ethyl}-1H-benzoimidazol-5-yl)-N-hydroxy-acrylamide

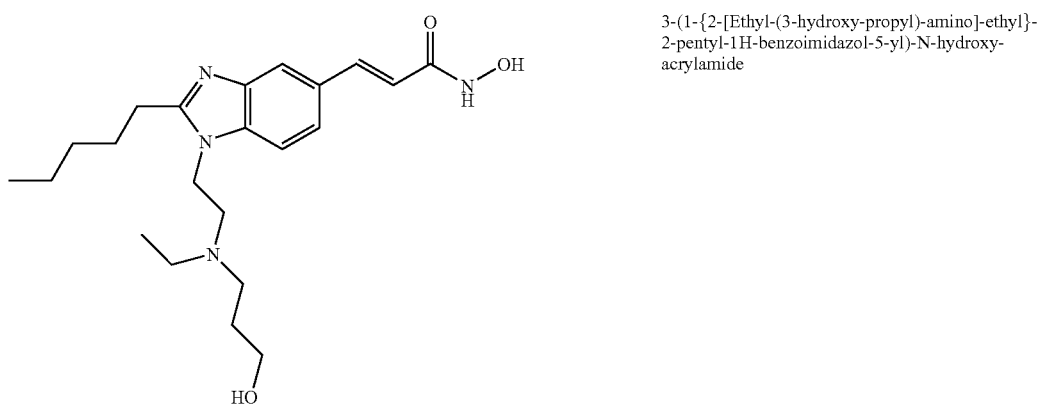
3-(1-{2-[Ethyl-(3-hydroxy-propyl)-amino]-ethyl}-2-pentyl-1H-benzoimidazol-5-yl)-N-hydroxy-acrylamide
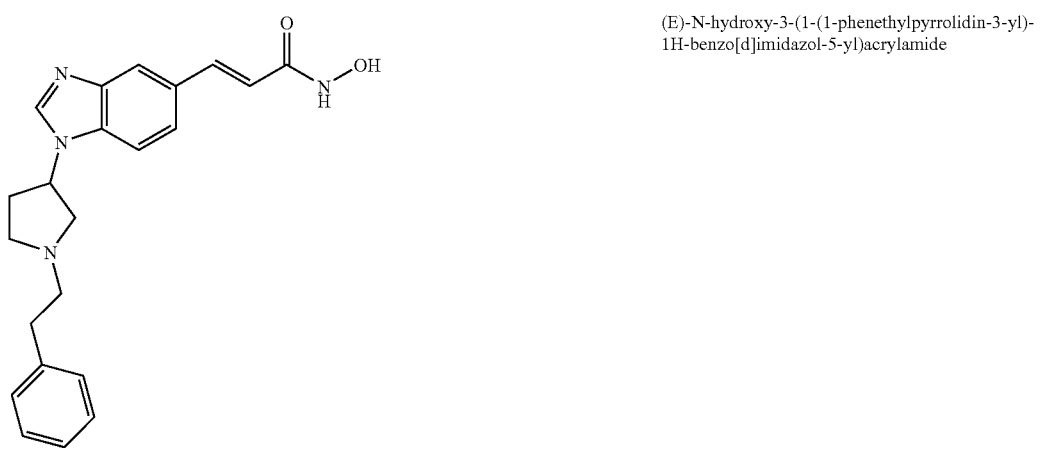
(E)-N-hydroxy-3-(1-(1-phenethylpyrrolidin-3-yl)-1H-benzo[d]imidazol-5-yl)acrylamide
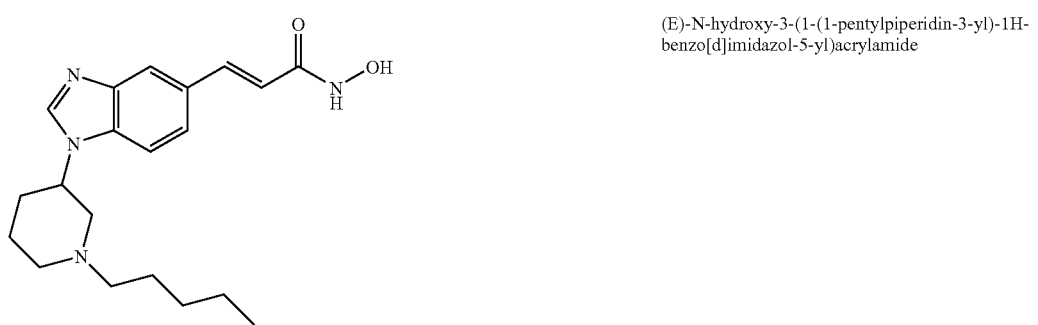
(E)-N-hydroxy-3-(1-(1-pentylpiperidin-3-yl)-1H-benzo[d]imidazol-5-yl)acrylamide
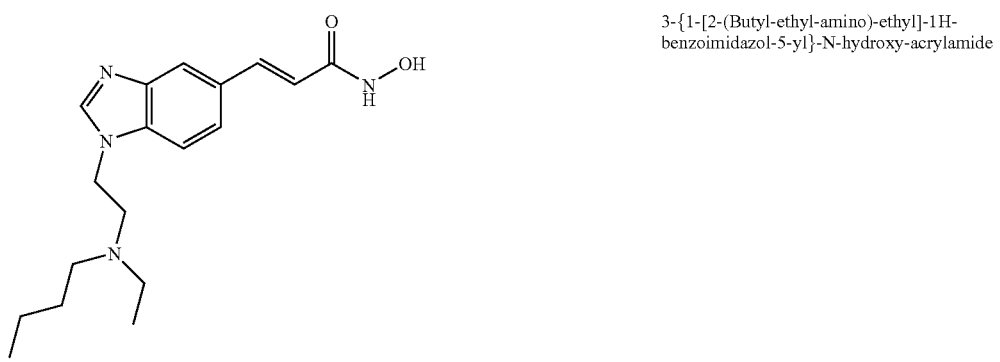
3-{1-[2-(Butyl-ethyl-amino)-ethyl]-1H-benzoimidazol-5-yl}-N-hydroxy-acrylamide

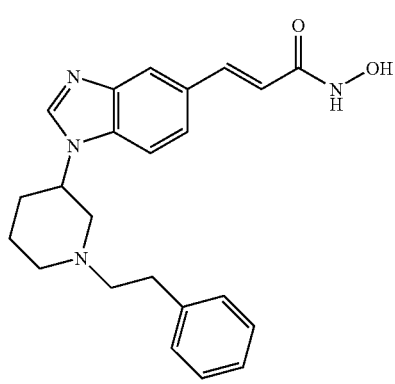
(E)-N-hydroxy-3-(1-(1-phenethylpiperidin-3-yl)-1H-benzo[d]imidazol-5-yl)acrylamide
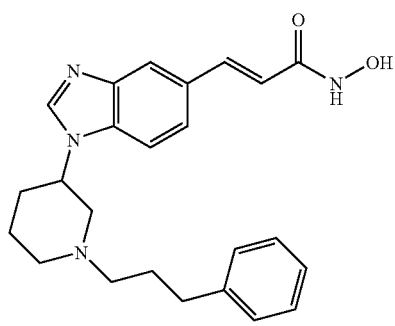
(E)-N-hydroxy-3-(1-(1-(3-phenylpropyl)piperidin-3-yl)-1H-benzo[d]imidazol-5-yl)acrylamide
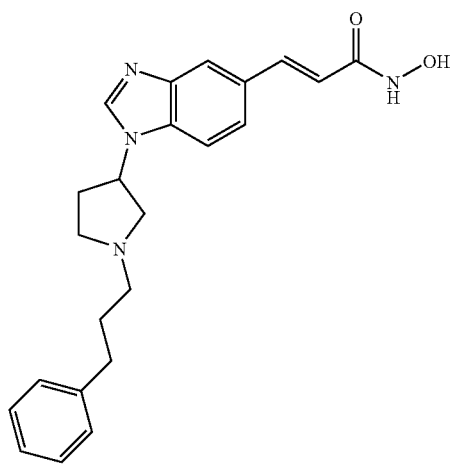
(E)-N-hydroxy-3-(1-(1-(3-phenylpropyl)pyrrolidin-3-yl)-1H-benzo[d]imidazol-5-yl)acrylamide
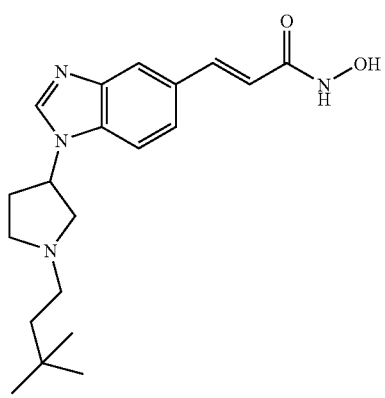
3-{1-[1-(3,3-Dimethyl-butyl)-pyrrolidin-3-yl]-1H-benzoimidazol-5-yl}-N-hydroxy-acrylamide

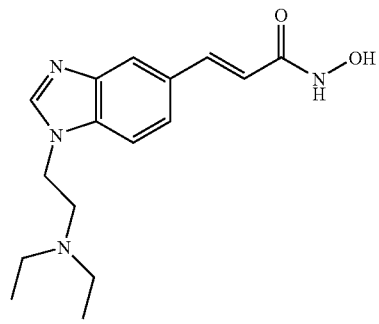
(E)-3-(1-(2-(diethylamino)ethyl)-1H-benzo[d]imidazol-5-yl)-N-hydroxyacrylamide
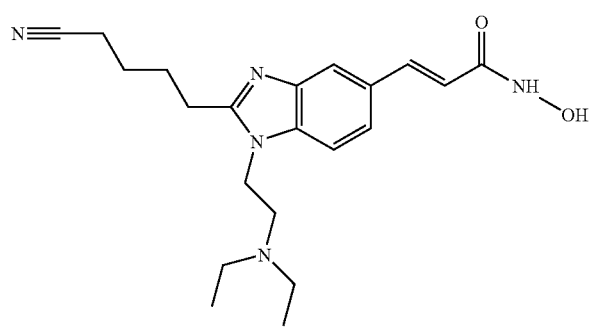
3-[2-(4-Cyano-butyl)-1-(2-diethylamino-ethyl)-1H-benzoimidaozl-5-yl]-N-hydroxy-acrylamide
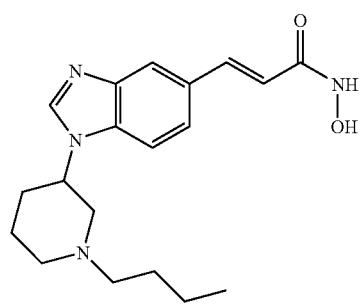
(E)-3-(1-(1-butylpiperidin-3-yl)-1H-benzo[d]imidazol-5-yl)-N-hydroxyacrylamide
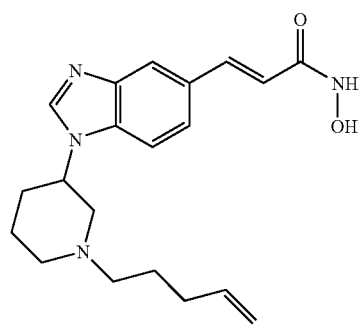
(E)-N-hydroxy-3-(1-(1-(pent-4-enyl)piperidin-3-yl)-1H-benzo[d]imidazol-5-yl)acrylamide

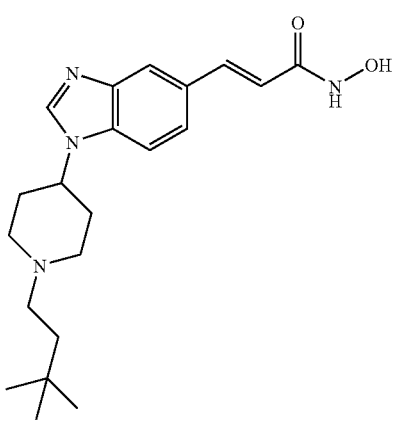
(E)-3-(1-(1-(3,3-dimethylbutyl)piperidin-4-yl)-1H-benzo[d]imidazol-5-yl)-N-hydroxyacrylamide
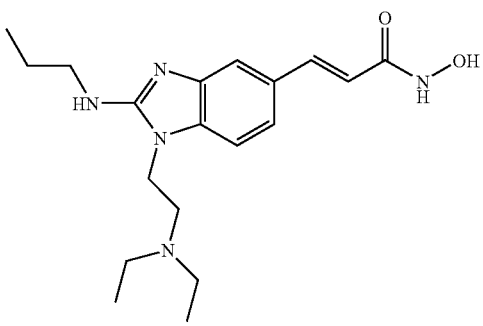
3-[1-(2-Diethylamino-ethyl)-2-propylamino-1H-benzoimidazol-5-yl]-N-hydroxy-acrylamde
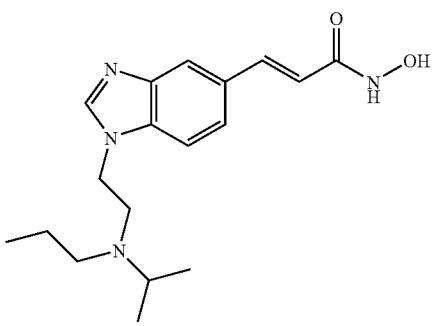
(E)-N-hydroxy-3-(1-(2-(isopropyl(propyl)amino)ethyl)-1H-benzo[d]imidazol-5-yl)acrylamide
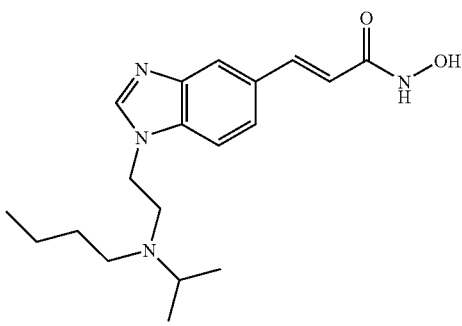
3-{1-[2-(Butyl-isopropyl-amino)-ethyl]-1H-benzoimidazol-5-yl}-N-hydroxy-acrylamide

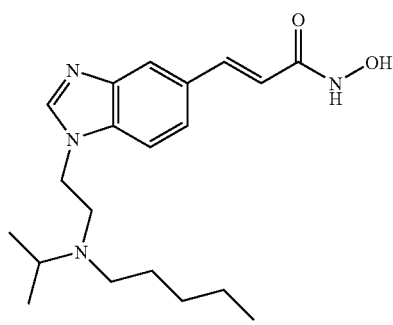
N-Hydroxy-3-{1-[2-(isopropyl-pentyl-amino)-ethyl]-1H-benzoimidazol-5-yl}-acrylamide
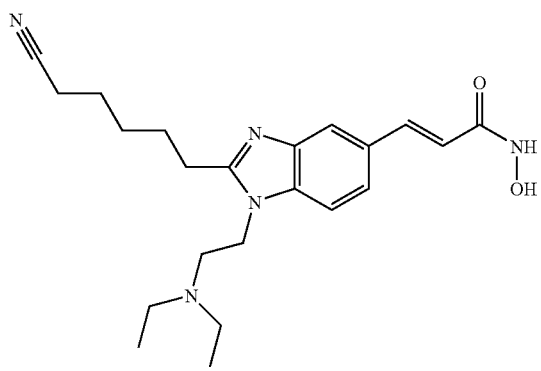
3-[2-(5-Cyano-pentyl)-1-(2-diethylamino-ethyl)-1H-benzoimidazol-5-yl]-N-hydroxy-acrylaide
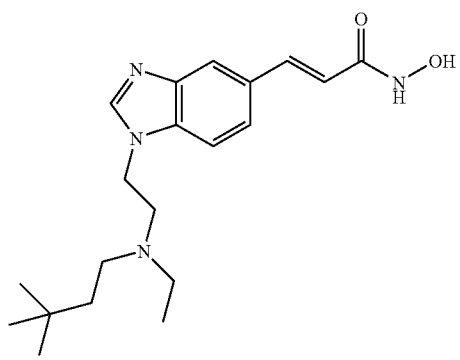
3-(1-{2-[(3,3-Dimethyl-butyl)-ethyl-amino]-ethyl}-1H-benzoimidazol-5-yl)-N-hydroxy-acrylamide
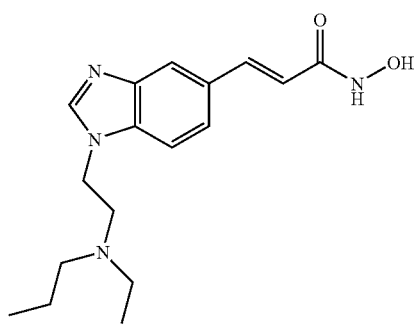
3-{1-[2-(Ethyl-propyl-amino)-ethyl]-1H-benzoimidazol-5-yl}-N-hydroxy-acrylamide

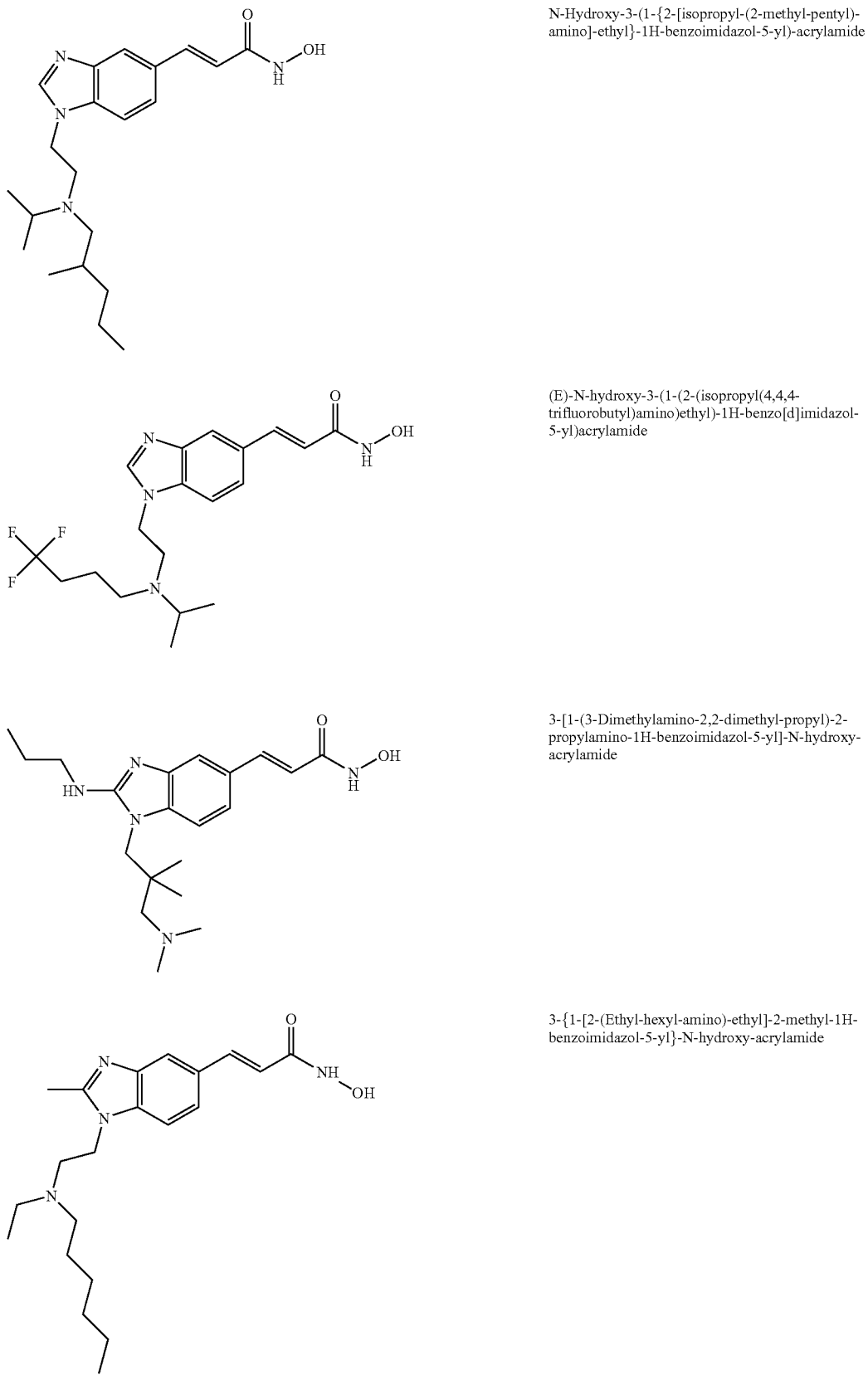
N-Hydroxy-3-(1-{2-[isopropyl-(2-methyl-pentyl)-amino]-ethyl}-1H-benzoimidazol-5-yl)-acrylamide
(E)-N-hydroxy-3-(1-(2-(isopropyl(4,4,4-trifluorobutyl)amino)ethyl)-1H-benzo[d]imidazol-5-yl)acrylamide
3-[1-(3-Dimethylamino-2,2-dimethyl-propyl)-2-propylamino-1H-benzoimidazol-5-yl]-N-hydroxy-acrylamide
3-{1-[2-(Ethyl-hexyl-amino)-ethyl]-2-methyl-1H-benzoimidazol-5-yl}-N-hydroxy-acrylamide

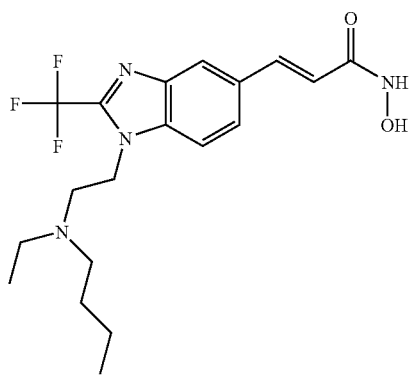 3-{1-[2-(Butyl-ethyl-amino)-ethyl]-2-trifluoromethyl-1H-benzoimidazol-5-yl}-N-hydroxy-acrylamide
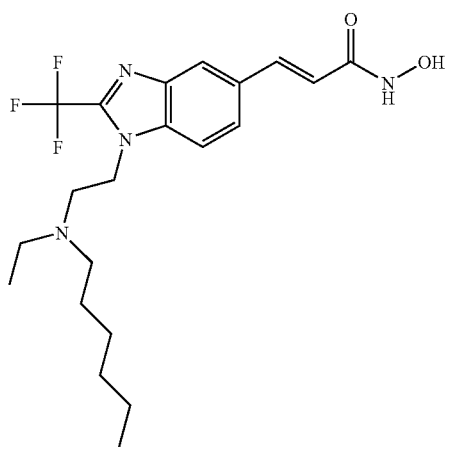 3-{1-[2-(Ethyl-hexyl-amino)-ethyl]-2-trifluoromethyl-1H-benzoimidazol-5-yl}-N-hydroxy-acrylamide
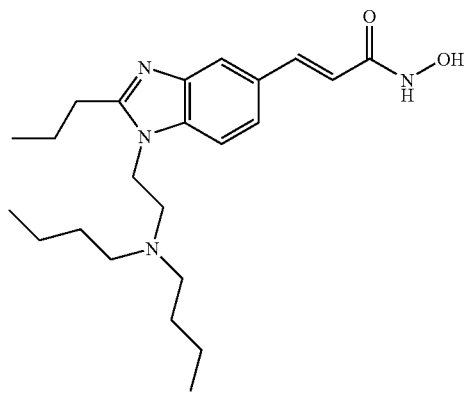 (E)-3-(1-(2-(dibutylamino)ethyl)-2-propyl-1H-benzo[d]imidazol-5-yl)-N-hydroxyacrylamide
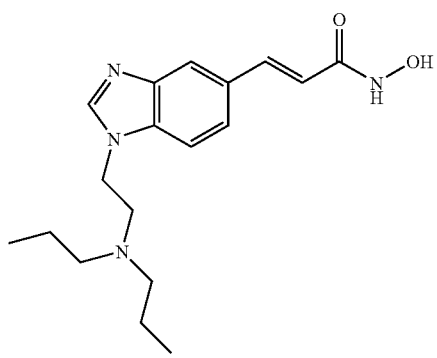 3-[1-(2-Dipropylamino-ethyl)-1H-benzoimidazol-5-yl]-N-hydroxy-acrylamide

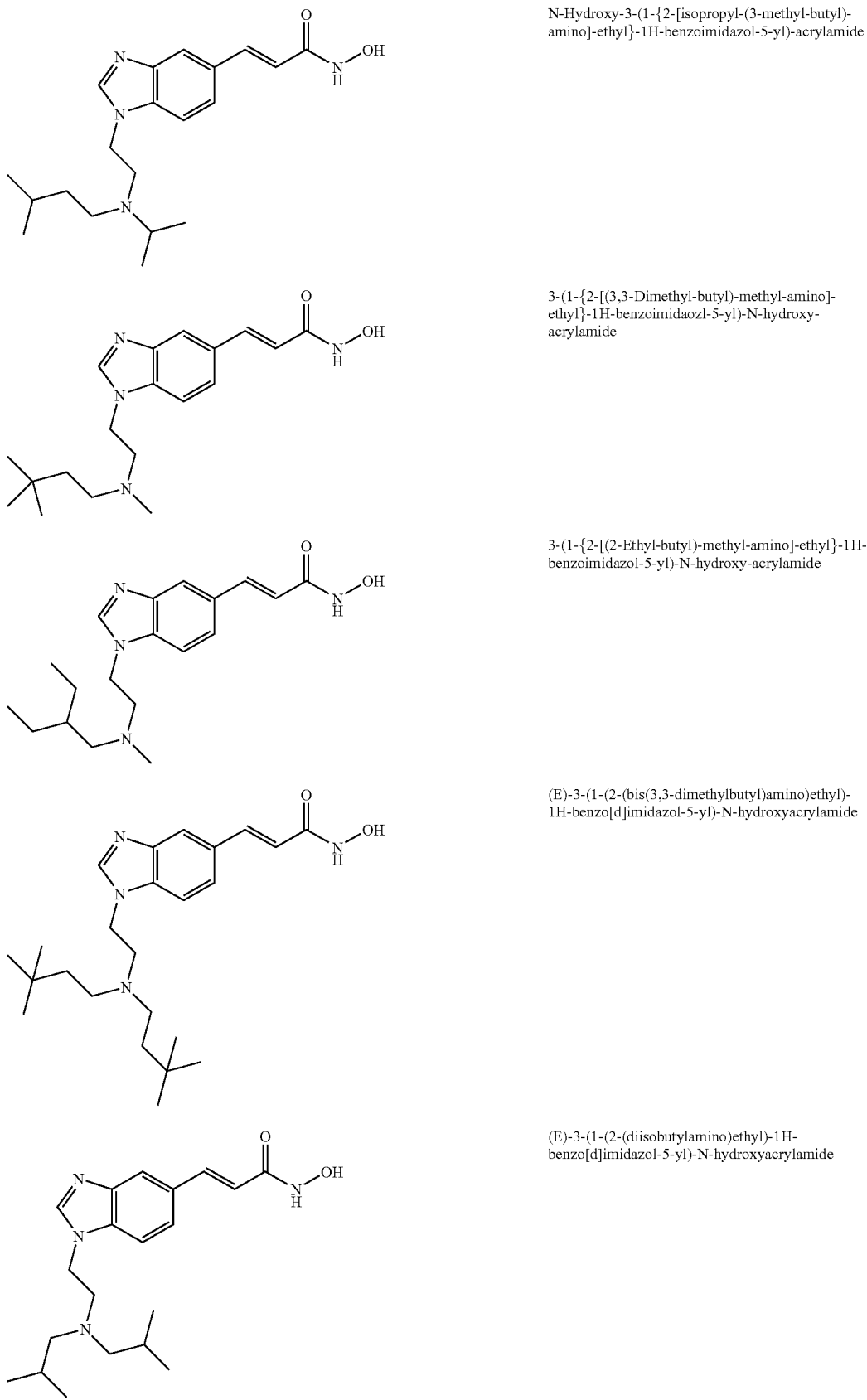

N-Hydroxy-3-(1-{2-[isopropyl-(3-methyl-butyl)-amino]-ethyl}-1H-benzoimidazol-5-yl)-acrylamide 3-(1-{2-[(3,3-Dimethyl-butyl)-methyl-amino]-ethyl}-1H-benzoimidaozl-5-yl)-N-hydroxy-acrylamide 3-(1-{2-[(2-Ethyl-butyl)-methyl-amino]-ethyl}-1H-benzoimidazol-5-yl)-N-hydroxy-acrylamide (E)-3-(1-(2-(bis(3,3-dimethylbutyl)amino)ethyl)-1H-benzo[d]imidazol-5-yl)-N-hydroxyacrylamide (E)-3-(1-(2-(diisobutylamino)ethyl)-1H-benzo[d]imidazol-5-yl)-N-hydroxyacrylamide

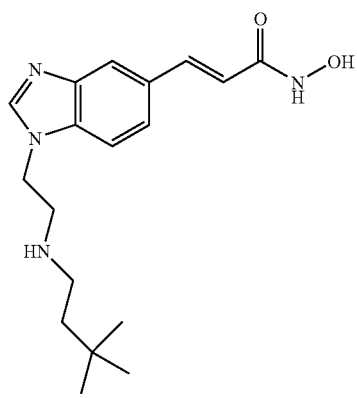
3-{1-[2-(3,3-Dimethyl-butylamino)-ethyl]-1H-benzoimidazol-5-yl}-N-hydroxy-acrylamide
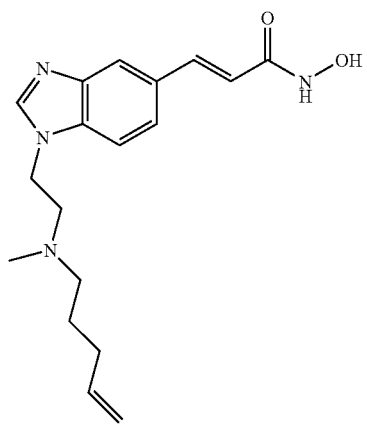
N-Hydroxy-3-{1-[2-(methyl-pent-4-enyl-amino)-ethyl]-1H-benzoimidazol-5-yl}-acrylamide
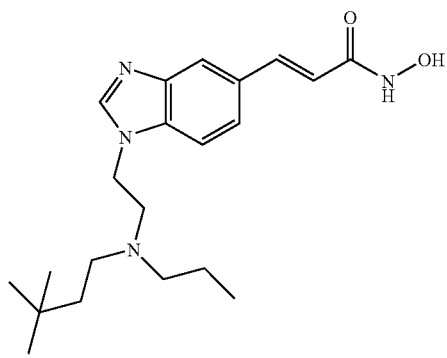
3-(1-{2-[(3,3-Dimethyl-butyl)-propyl-amino]-ethyl}-1H-benzoimidazol-5-yl)-N-hydroxy-acrylamide
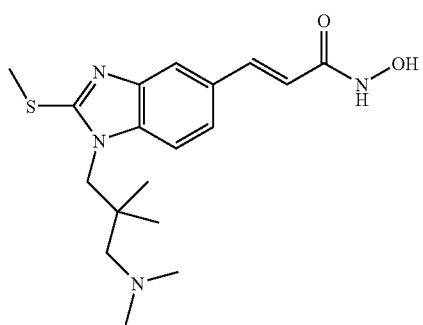
3-[1-(3-Dimethylamino-2,2-dimethyl-propyl)-2-methylsulfanyl-1H-benzoimidazol-5-yl]-N-hydroxy-acrylamide -continued
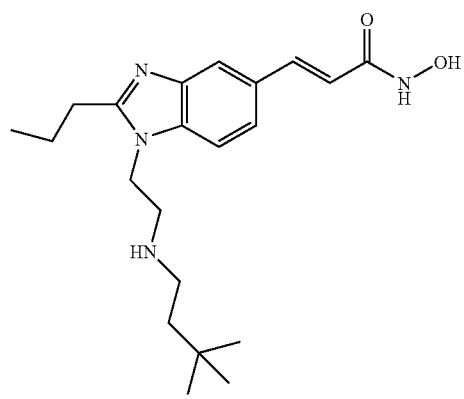
3-{1-[2-(3,3-Dimethyl-butylamino)-ethyl]-2-propyl-1H-benzoimidazol-5-yl}-N-hydroxy-acrylamide
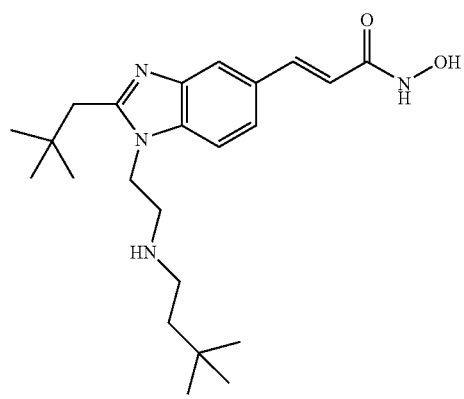
3-[1-[2-(3,3-Dimethyl-butylamino)-ethyl]-2-(2,2-dimethyl-propyl)-1H-benzoimidazol-5-yl]-N-hydroxy-acrylamide
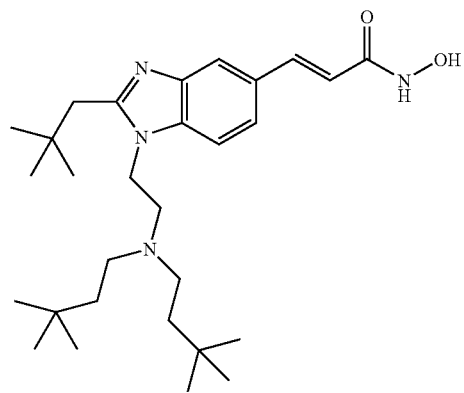
3-[1-{2-[Bis-(3,3-dimethyl-butyl)-amino]-ethyl}-2-(2,2-dimethyl-propyl)-1H-benzoimidazol-5-yl]-N-hydroxy-acrylamide
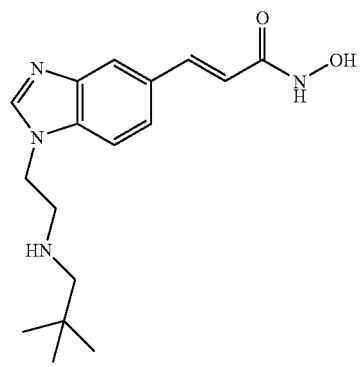
3-{1-[2-(2,2-Dimethyl-propylamino)-ethyl]-1H-benzoimidazol-5-yl}-N-hydroxy-acrylamide

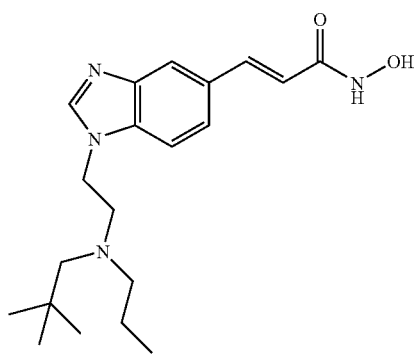
3-(1-{2-[(2,2-Dimethyl-propyl)-propyl-amino]-ethyl}-1H-benzoimidazol-5-yl)-N-hydroxy-acrylamide
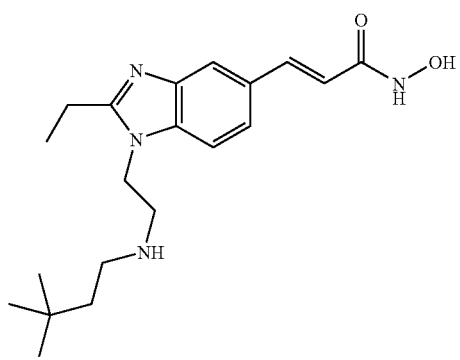
3-{1-[2-(3,3-Dimethyl-butylamino)-ethyl]-2-ethyl-1H-benzoimidazol-5-yl}-N-hydroxy-acrylamide
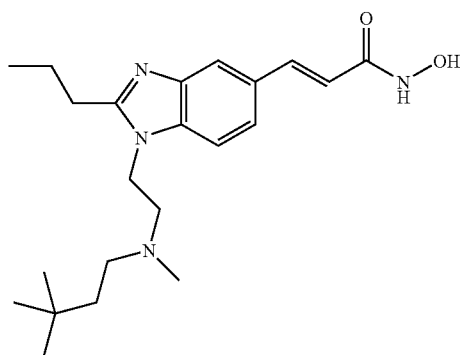
3-(1-{2-[(3,3-Dimethyl-butyl)-methyl-amino]-ethyl}-2-propyl-1H-benzoimidazol-5-yl)-N-hydroxy-acrylamide
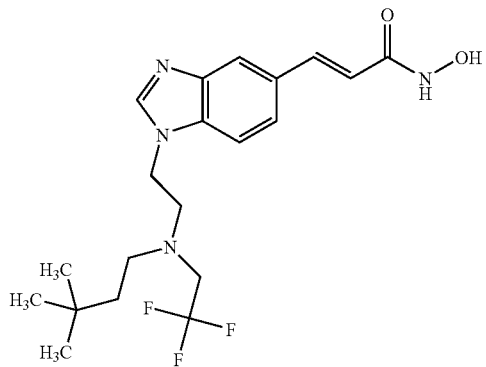
3-(1-{2-[(3,3-Dimethyl-butyl)-(2,2,2-trifluoro-ethyl)-amino]-ethyl}-1H-benzoimidazol-5-yl)-N-hydroxy-acrylamide

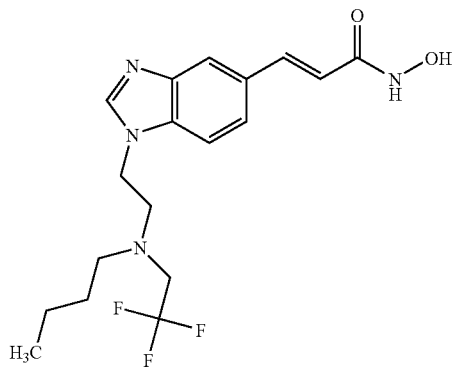

3-(1-{2-[Butyl-(2,2,2-trifluoro-ethyl)-amino]-ethyl}-1H-benzoimidazol-5-yl)-N-hydroxy-acrylamide The compounds disclosed are hydroxamate compounds containing a hydroxamic acid type moiety in one of the substituents that may be inhibitors of deacetylases, including but not limited to inhibitors of histone deacetylases. The hydroxamate compounds may be suitable for prevention or treatment of a disorder caused by, associated with or accompanied by disruptions of cell proliferation and/or angiogenesis when used either alone or together with a pharmaceutically acceptable carrier, diluent or excipient. An example of such a disorder is cancer.

Administration of compounds within Formula (I) to humans can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose. In various embodiments the inhibitor compound may be selectively toxic or more toxic to rapidly proliferating cells, e.g. cancerous tumors, than to normal cells.

As used herein the term 'cancer' is a general term intended to encompass the vast number of conditions that are characterised by uncontrolled abnormal growth of cells.

It is anticipated that the compounds of the invention will be useful in treating various cancers including but not limited to bone cancers including Ewing's sarcoma, osteosarcoma, chondrosarcoma and the like, brain and CNS tumours including acoustic neuroma, neuroblastomas, glioma and other brain tumours, spinal cord tumours, breast cancers including ductal adenocarcinoma, metastatic ductal breast carcinoma, colorectal cancers, advanced colorectal adenocarcinomas, colon cancers, endocrine cancers including adenocortical carcinoma, pancreatic cancer, pituitary cancer, thyroid cancer, parathyroid cancer, thymus cancer, multiple endocrine neoplasma, gastrointestinal cancers including stomach cancer, esophageal cancer, small intestine cancer, liver cancer, extra hepatic bile duct cancer, gastrointestinal carcinoid tumour, gall bladder cancer, genitourinary cancers including testicular cancer, penile cancer, prostate cancer, gynaecological cancers including cervical cancer, ovarian cancer, vaginal cancer, uterus/endometrium cancer, vulva cancer, gestational trophoblastic cancer, fallopian tube cancer, uterine sarcoma, head and neck cancers including oral cavity cancer, lip cancer, salivary gland cancer, larynx cancer, hypopharynx cancer, orthopharynx cancer, nasal cancer, paranasal cancer, nasopharynx cancer, leukemias including childhood leukemia, acute lymphocytic leukemia, acute myeloid leukemia, chronic lymphocytic leukemia, chronic myeloid leukemia, hairy cell leukemia, acute promyelocytic leukemia, plasma cell leukemia, erythroleukemia, myelomas, haematological disorders including myelodysplastic syndromes, myeloproliferative disorders, aplastic anemia, Fanconi anemia, Waldenstroms Macroglobulinemia, lung cancers including small cell lung cancer, non-small cell lung cancer, mesothelioma, lymphomas including Hodgkin's disease, non-Hodgkin's lymphoma, cutaneous T-cell lymphoma, peripheral T-cell lymphoma, AIDS related Lymphoma, B-cell lymphoma, Burkitt's lymphoma, eye cancers including retinoblastoma, intraocular melanoma, skin cancers including melanoma, non-melanoma skin cancer, squamous cell carcinoma, merkel cell cancer, soft tissue sarcomas such as childhood soft tissue sarcoma, adult soft tissue sarcoma, Kaposi's sarcoma, urinary system cancers including kidney cancer, Wilms tumour, bladder cancer, urethral cancer, and transitional cell cancer.

Exemplary cancers that may be treated by the compounds of the present invention are breast cancer, lung cancer, ovarian cancer, prostate cancer, head and neck cancer, renal cancer (e.g. renal cell carcinoma), gastric cancer, colon cancer, colorectal cancer and brain cancer.

Exemplary cancers that may be treated by compounds of the present invention include but are not limited to leukemias such as erythroleukemia, acute promyelocytic leukemia, acute myeloid leukemia, acute lymphocytic leukemia, acute T-cell leukemia and lymphoma such as B-cell lymphoma (e.g. Burkitt's lymphoma), cutaneous T-cell lymphoma (CTCL), and peripheral T-cell lymphoma.

Exemplary cancers that may be treated by compounds of the present invention include solid tumors and hematologic malignancies. In another embodiment, preferred cancers that may be treated with the compounds of the present invention are colon cancer, prostate cancer, hepatoma and ovarian cancer.

In another embodiment, exemplary cancers that may be treated with the compounds of the present invention are non small cell lung cancer, small cell lung cancer and mesothelioma.

In another embodiment, exemplary cancers that may be treated with the compounds of the present invention are clear cell carcinoma/mesonephroma, intestinal cancer and pancreatic cancer.

The compounds may also be used in the treatment of a disorder involving, relating to or, associated with dysregulation of histone deacetylase (HDAC).

There are a number of disorders that have been implicated by or known to be mediated at least in part by HDAC activity, where HDAC activity is known to play a role in triggering disease onset, or whose symptoms are known or have been shown to be alleviated by HDAC inhibitors. Disorders of this type that would be expected to be amenable to treatment with the compounds of the invention include the following but not limited to: Proliferative disorders (e.g. cancer); Neurodegenerative diseases including Huntington's Disease, Polyglutamine diseases, Parkinson's Disease, Alzheimer's Disease, Seizures, Striatonigral degeneration, Progressive supranuclear palsy, Torsion dystonia, Spasmodic torticollis and dyskinesis, Familial tremor, Gilles de la Tourette syndrome, Diffuse Lewy body disease, Pick's disease, Intracerebral haemorrhage Primary lateral sclerosis, Spinal muscular atrophy, Amyotrophic lateral sclerosis, Hypertrophic interstitial polyneuropathy, Retinitis pigmentosa, Hereditary optic atrophy, Hereditary spastic paraplegia, Progressive ataxia and Shy-Drager syndrome; Metabolic diseases including Type 2 diabetes; Degenerative Diseases of the Eye including Glaucoma, Age-related macular degeneration, macular myopic degeneration, Rubeotic glaucoma, Interstitial keratitis, Diabetic retinopathy, Peter's anomaly, retinal degeneration, Cellophane Retinopathy; Cogan's Dystrophy; Corneal Dystrophy; Iris Neovascularization (Rubeosis); Neovascularization of the Cornea; Retinopathy of Prematurity; Macular Edema; Macular Hole; Macular Pucker; Marginal Blepharitis, Myopia, nonmalignant growth of the conjunctiva; Inflammatory diseases and/or Immune system disorders including Rheumatoid Arthritis (RA), Osteoarthritis, Juvenile chronic arthritis, Graft versus Host disease, Psoriasis, Asthma, Spondyloarthropathy, Crohn's Disease, inflammatory bowel disease, Colitis Ulcerosa, Alcoholic hepatitis, Diabetes, Sjoegrens's syndrome, Multiple Sclerosis, Ankylosing spondylitis, Membranous glomerulopathy, Discogenic pain, Systemic Lupus Erythematosus, allergic contact dermatitis; Disease involving angiogenesis including cancer, psoriasis, rheumatoid arthritis; Psychological disorders including bipolar disease, schizophrenia, depression and dementia; Cardiovascular Diseases including Heart failure, restenosis, cardiac hypertrophy and arteriosclerosis; Fibrotic diseases including liver fibrosis, lung fibrosis, cystic fibrosis and angiofibroma; Infectious diseases including Fungal infections, such as *Candida Albicans*, Bacterial infections, Viral infections, such as Herpes Simplex, Protozoal infections, such as Malaria, *Leishmania* infection, *Trypanosoma brucei* infection, Toxoplasmosis and coccidiosis, and Haematopoietic disorders including thalassemia, anemia and sickle cell anemia.

In using the compounds of the invention they can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, 19$^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. As such in a further embodiment the present invention provides a pharmaceutical composition including a compound of Formula (I) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent (s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds of the invention may be used or administered in combination with one or more additional drug (s) that are chemotherapeutic drugs or HDAC inhibitor drugs and/or procedures (e.g. surgery, radiotherapy) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs that include chemotherapeutic drugs or HDAC inhibitor drugs the compounds of the invention may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The term "therapeutically effective amount" or "effective amount" is an amount sufficient to effect beneficial or desired results. An effective amount can be administered in one or more administrations. An effective amount is typically sufficient to palliate, ameliorate, stabilize, reverse, slow or delay the progression of the disease state. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.

As discussed above, the compounds of the embodiments disclosed inhibit histone deacetylases. The enzymatic activity of a histone deacetylase can be measured using known methodologies [Yoshida M. et al, J. Biol. Chem., 265, 17174 (1990), J. Taunton et al, Science 1996 272: 408]. In certain embodiments, the histone deacetylase inhibitor interacts with and/or reduces the activity of more than one known histone deacetylase in the cell, which can either be from the same class of histone deacetylase or different class of histone deacetylase. In some other embodiments, the histone deacetylase inhibitor interacts and reduces the activity of predominantly one histone deacetylase, for example HDAC-1, HDAC-2, HDAC-3 or HDAC-8 which belongs to Class I HDAC enzymes [De Ruijter A. J. M. et al, Biochem. J., 370, 737-749 (2003)]. HDACs can also target non-histone substrates to regulate a variety of biological functions implicated in disease pathogenesis. These non-histone substrates include Hsp90, α-tubulin, p53, NFkb and HIF1a [Drummond et al., Annu. Rev. Pharmacol. Toxicol. 45:495 (2004)]. Certain preferred histone deacetylase inhibitors are those that interact with, and/or reduce the activity of a histone deacetylase which is involved in tumorigenesis, and these compounds may be useful for treating proliferative diseases. Examples of such cell proliferative diseases or conditions include cancer (include any metastases), psoriasis, and smooth muscle cell proliferative disorders such as restenosis. The inventive compounds may be particularly useful for treating tumors such as breast cancer, colon cancer, lung cancer, ovarian cancer, prostate cancer, head and/or neck cancer, or renal, gastric, pancreatic cancer and brain cancer as well as hematologic malignancies such as lymphomas and leukemias. In addition, the inventive compounds may be useful for treating a proliferative disease that is refractory to the treatment with other chemotherapeutics; and for treating hyperproliferative condition such as leukemias, psoriasis and restenosis. In other embodiments, compounds of this invention can be used to treat pre-cancer conditions or hyperplasia including familial adenomatous polyposis, colonic adenomatous polyps, myeloid dysplasia, endometrial dysplasia, endometrial hyperplasia with atypia, cervical dysplasia, vaginal intraepithelial neoplasia, benign prostatic hyperplasia, papillomas of the larynx, actinic and solar keratosis, seborrheic keratosis and keratoacanthoma. In a preferred embodiment, exemplary pre-cancer conditions or hyperplasia that can be treated by compounds of this invention are familial adenomatous polyposis, colonic adenomatous polyps and myeloid dysplasia.

Additionally compounds of the various embodiments disclosed herein may be useful for treating neurodegenerative diseases, and inflammatory diseases and/or immune system disorders.

In one embodiment the disorder is selected from the group consisting of cancer, inflammatory diseases and/or immune system disorders (e.g. rheumatoid arthritis, systemic lupus erythematosus), angiofibroma, cardiovascular diseases, fibrotic diseases, diabetes, autoimmune diseases, chronic and acute neurodegenerative disease like Huntington's disease, Parkinson's disease, disruptions of nerval tissue and infectious diseases like fungal, bacterial and viral infections. In another embodiment the disorder is a proliferative disorder. In yet another embodiment, the proliferative disorder is cancer.

The histone deacetylase inhibitors of the invention have significant anti-proliferative effects and promote differentiation, cell cycle arrest in the G1 or G2 phase, and induce apoptosis.

Synthesis of Deacetylase Inhibitors

The present invention also provides a number of synthetic routes to synthesize the compounds of the invention.

In one embodiment the method of synthesis of compounds of formula I as defined above

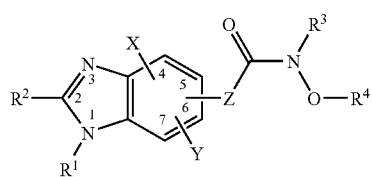

Formula I includes: (a) providing a compound of the formula (A1):

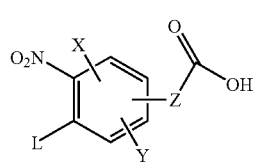

(A1)

(b) protecting the carboxyl group to produce a compound of the formula (A2):

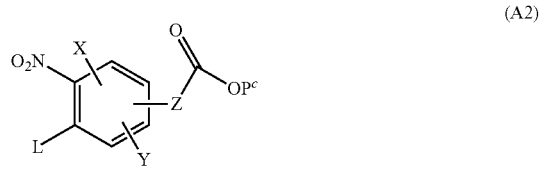

(A2)

(c) displacing the leaving group with an amine of formula $R^1NH_2$ to produce a compound of the formula (A3):

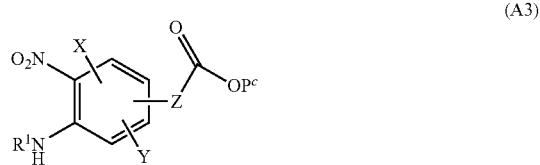

(A3)

(d) optionally reacting the compound to further functionalise $R^1$ (e) reducing the nitro group;

(f) reacting the reduced product with a compound of formula $R^2CO_2H$ or a compound of formula $R^2CHO$ and cyclising the product thus produced to produce a compound of the formula (A4):

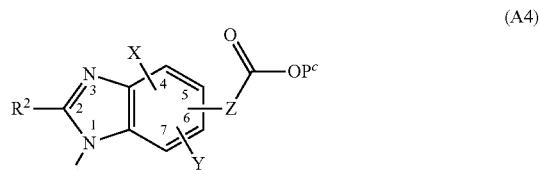

(A4)

(g) converting the compound to a compound of formula I;

wherein (d) can be carried out after any one of (c) (e) or (f) and further wherein (e) and (f) can be carried out sequentially or simultaneously.

The reaction sequence employed above typically utilises a carboxyl protecting group. The term "protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) Protective Groups in Organic Synthesis, 2nd Ed. (John Wiley & Sons, Inc., New York). A number of well known carboxyl protecting groups may be used and the methodology chosen to attach the protecting group will depend upon the choice of protecting group to be used as would be well understood by a skilled addressee in the art. In one embodiment the protecting group is an alkyl protecting group to form the ether. These may be produced in a number of ways however it is typically found that they can be readily accessed via reaction of the free acid with an alcohol under acidic conditions.

An example of a suitable alcohol for this purpose is methanol however other alcohols such as ethanol, propanol, butanol and the like may also be used.

The reaction sequence detailed above also takes advantage of a suitably located leaving group on the starting material to facilitate reaction with the amine in (b). A leaving group is a chemical group that is readily displaced by the desired incoming chemical moiety. Accordingly in any situation the choice of leaving group will depend upon the ability of the particular group to be displaced by the incoming chemical moiety. Suitable leaving groups are well known in the art, see for example "Advanced Organic Chemistry" Jerry March 4$^{th}$ Edn. pp 351-357, Oak Wick and Sons NY (1997). Examples of suitable leaving groups include, but are not limited to, halogen, alkoxy (such as ethoxy, methoxy), sulphonyloxy, optionally substituted arylsulfonyl and the like. Specific examples include chloro, iodo, bromo, fluoro, ethoxy, methoxy, methonsulphonyl, triflate and the like. It is preferred that the leaving group is either chloro or bromo. The displacement of the leaving group typically is carried out by reaction of the compound containing the leaving group with a nucleophile such as an amine which undergoes nucleophilic aromatic substitution to displace the leaving group. This typically involves reaction of the compound containing the leaving group in a non-interfering solvent with an excess of amine. The amine may vary and is typically chosen to provide the appropriate substitution pattern after displacement of the leaving group. The substitution reaction may also be catalysed by any of a number of catalysts well known in the art such as palladium, copper and the like.

In some embodiments it may be desired to then further functionalise the $R^1$ group introduced in the displacement either at this stage or at a later stage in the synthesis. This may be achieved in a number of ways depending upon the exact functionality of the $R^1$ group introduced. For example if the $R^1$ group contains an NH group then it may be further reacted with other agents to add additional functionality. For example it may be reacted with an acid, an acid chloride or an acid anhydride under standard conditions to introduce an amide linkage. Alternatively it may be reacted with an aldehyde under reducing conditions (reductive amination) to form an alkyl amine (via the imine). Alternatively it may be reacted with an alkylating agent such as an alkyl halide to produce the corresponding alkylated amine. The amine may also be reacted with an aryl or alkyl sulphonyl chloride to introduce an aryl or alkyl sulphonyl group onto the amine. It may also be that the amine introduced is in a protected form in which case the amine protecting group may need to be removed under standard conditions prior to the modifications discussed above being carried out. If this is done the protecting group is typically removed under standard conditions (depending upon the exact nature of the protecting group) and then reacted as discussed above.

The reaction sequence also involves a reduction of the nitro group. Reduction of the nitro group may be carried out using any technique well known in the art. For example it may be reduced using strong reducing agents such as LiAlH$_4$ or NaBH$_4$ (typically in an alcoholic solvent). It may also be achieved by reaction with triphenyl phosphine in water or by reaction with SnCl$_2$ or Zn (typically in an alcoholic solvent or acetic acid or a combination thereof). The reduction may be conducted in any suitable solvent although it is typically conducted in a hydroxylic solvent such as methanol or ethanol in the presence of acetic acid.

The process then typically involves reaction of the reduced nitro moiety with a carboxyl group or an aldehyde to produce a product which is then cyclised to produce the cyclised product. This typically involves addition of a stoichiometric amount of the carboxyl group or the aldehyde to a solution of the di-amine under suitable reaction conditions. These conditions typically induce dehydration of the reaction product such as Dean-and-Stark apparatus or the presence of a coupling agent such as DCC.

The reduction of the nitro moiety to produce a reduced product and the reaction of the reduced product with a carbonyl moiety (acid or aldehyde) followed by intramolecular cyclisation may be carried out in a sequential fashion or they may be carried out simultaneously in a one-pot operation.

The synthesis involves conversion of the compounds thus formed into the compounds of the invention. This may be carried out in a number of ways but is most conveniently achieved by reaction with hydroxylamine hydrochloride to produce the free hydroxamic acid. Entry to other hydroxamic acid species within the scope of the invention may be readily achieved through the use of different hydroxylamine derivatives.

In another embodiment the method of synthesis of compounds of formula I as defined above

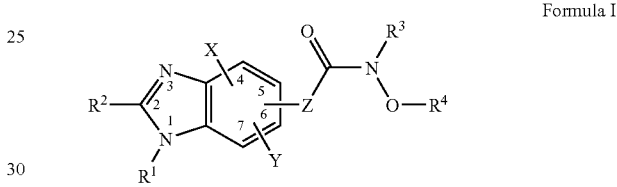

Formula I includes: (a) providing an aldehyde of the formula (B1)

(B1)

(b) subjecting the aldehyde to reaction with an appropriately substituted olefination agent to produce a compound of formula (B2)

(c) converting the compound to a compound of formula I.

This sequence employs an olefination to introduce the desired functionality to the six membered ring. The olefination agent used may be any olefination agent well known in the art. In one embodiment the olefination agent is a Wittig reagent (a phosphorous ylide or phosphorane). Reagents of this type are readily accessible by reaction of a phosphonium salt with a base. In another embodiment the olefination agent is a Horner Emmons or Wadsworth Emmons reagent which is a phosphonate ylide (RO)$_2$P(O)—CH$_2$R which can readily be accessed via the Arbuzov reaction. In each of these instances the reaction is carried out under standard conditions. Judicious selection of the reagent allows for a wide variety of products to be accessed.

As with the earlier sequence the product is then converted to the compounds of the invention using the techniques described above.

The aldehyde used as the starting material in the sequence described above may be provided using any methodology well known in the art. In one embodiment the aldehyde is produced by (1) providing a compound of the formula (B3) as described above

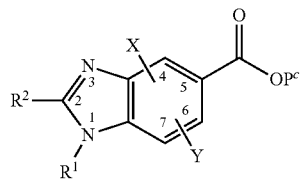

(B5)

(2) converting the compound to the aldehyde.

The compound (B5) may be converted to the aldehyde via a variety of techniques well known in the art. In one embodiment the conversion includes first reducing the protected carboxyl group to the alcohol followed by oxidation of the alcohol. The reduction of the carboxyl group may be carried out using any technique well known in the art. For example it may include treatment of the protected carboxyl group with a strong reducing agent such as DIBAL, $LiAlH_4$, $LiBH_4$, lithium trimethyl borohydride, $BH_3$—$SMe_2$ (in refluxing THF) and triethoxysilane in a non-interfering solvent. Alternatively, rather than reducing the protected carboxyl group all the way to the alcohol it may be selectively reduced directly to the aldehyde using standard conditions.

Once the alcohol has been obtained it may be oxidised to the aldehyde using a number of techniques well known in the art. This may involve reaction of the alcohol with oxidants such as acid dichromate, $KMnO_4$, $Br_2$, $MnO_2$, ruthenium tetroxide and the like. The reaction may also be carried out by the use of Jones reagent. The conversion may also be carried out by catalytic dehydrogenation or by reaction with agents such as N-bromosuccinimide or related compounds. These oxidation conditions are typically carried out under standard conditions.

The compound of formula (B5) may be provided in any way well known in the art. In one embodiment providing the compound of formula (B5) includes (1) providing a compound of formula (B4)

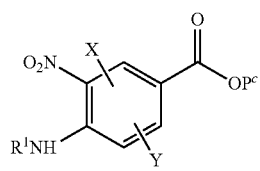

(B4)

(2) reducing the nitro group;
(3) reacting the reduced product with a compound of formula $R^2CO_2H$ or a compound of formula $R^2CHO$ and cyclising the product thus produced to produce (B5).

The reduction of the nitro compound and the reaction of the reduced product thus produced followed by cyclisation are typically carried out using the methodologies as discussed above.

Providing a compound of formula (B4) generally includes (1) providing a compound of the formula (B3):

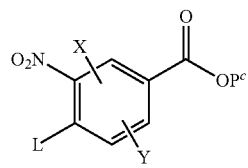

(B3)

(2) displacing the leaving group with an amine of formula $R^1NH_2$ to produce a compound of the formula (B4): The reaction of the amine to displace the leaving group typically occurs in the presence of a base. Any suitable base may be used with examples of suitable bases including hindered tertiary amines, alkali earth metal carbonates and any inorganic base, which is compatible with protected carboxylic group by way of example. Specific bases include sodium carbonate, sodium bicarbonate, potassium carbonate and potassium bicarbonate.

In another embodiment the invention provides a method of synthesis of compounds of formula I as defined above

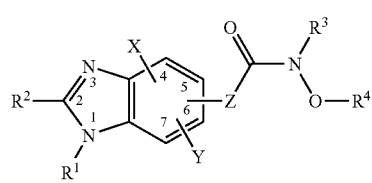

Formula I (a) providing a compound of the formula (C1)

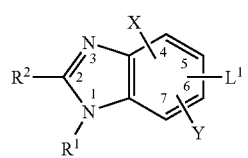

(C1)

(b) converting the compound of formula (C1) to a compound of formula (C2);

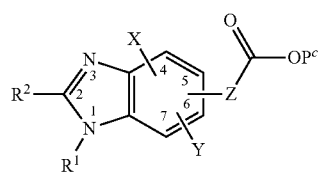

(C2)

(c) converting the compound to a compound of formula I.
Conversion of the compound of formula (C1) to a compound of formula (C2) may be carried out using any of a wide range of conditions well known in the art. In general any electrophilic aromatic substitution reaction may be used to introduce the desired functionality. An example of a suitable reaction is a Heck reaction.

The compound of formula (C1) may be provided by (1) providing a compound of formula (C4) and converting a compound of formula (C4) to a compound of formula (C1). This typically involves (a4) reducing the nitro group to produce a reduced product and reacting the reduced product with a compound of formula $R^2CO_2H$ or a compound of formula $R^2CHO$ followed by intramolecular cyclisation of the product thus produced to produce a compound of the formula (C1). These processes are typically carried out using the methodology as discussed above.

The compound of formula (C4) is typically provided by providing a compound of the formula (C3):

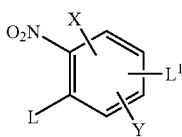

(C3)

and displacing the leaving group (L) with an amine of formula $R^1NH_2$ to produce a compound of the formula (C4):

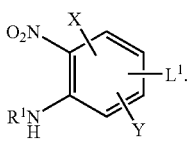

(C4)

The displacement reaction is typically carried out using the methodology as discussed above.

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, $3^{rd}$ Edition, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal bottles and used as received. All solvents were purified by using standard methods in the art, unless otherwise indicated.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried. Analytical thin-layer chromatography was performed on glass-backed silica gel 60 F 254 plates (E Merck (0.25 mm)) and eluted with the appropriate solvent ratios (v/v). The reactions were assayed by TLC and terminated as judged by the consumption of starting material.

The TLC plates were visualized by UV absorption or with a p-anisaldehyde spray reagent or a phosphomolybdic acid reagent (Aldrich Chemical, 20 wt % in ethanol) which was activated with heat, or by staining in iodine chamber. Workups were typically done by doubling the reaction volume with the reaction solvent or extraction solvent and then washing with the indicated aqueous solutions using 25% by volume of the extraction volume (unless otherwise indicated). Product solutions were dried over anhydrous sodium sulfate prior to filtration, and evaporation of the solvents was under reduced pressure on a rotary evaporator and noted as solvents removed in vacuo. Flash column chromatography [Still et al, J. Org. Chem., 43, 2923 (1978)] was conducted using Silica gel 60 (Merck KGaA, 0.040-0.063 mm, 230-400 mesh ASTM) and a silica gel:crude material ratio of about 20:1 to 50:1, unless otherwise stated. Hydrogenolysis was done at the pressure indicated or at ambient pressure.

NMR spectra were recorded on a Bruker AVANCE 400 spectrometer operating at 400 MHz for $^1H$ NMR and 100 MHz for $^{13}C$-NMR. NMR spectra are obtained as $CDCl_3$ solutions (reported in ppm), using chloroform as the reference standard (7.26 ppm and 77.14 ppm) or $CD_3OD$ (3.3 and 49.3 ppm), or DMSO-$d_6$ (2.50 and 39.5 ppm) or an internal tetramethylsilane standard (0.00 ppm) when appropriate. Other NMR solvents were used as needed. When peak multiplicities are reported, the following abbreviations are used: s=singlet, d=doublet, t=triplet, q=quartet, m=multiplet, br=broadened, dd=doublet of doublets, dt=doublet of triplets. Coupling constants, when given, are reported in Hertz.

Mass spectra were obtained using LC/MS either in ESI or APCI. All melting points are uncorrected.

All final products had greater than 90% purity (by HPLC at wavelengths of 254 nm and/or 220 nm). Analytical HPLC conditions for purity check: Xterra® RP18 3.5 µm 4.6×20 mm IS column; 2.0 ml/min, gradient 5-65% B over 4 min, then 65-95% b over 1 min and 95% B for additional 0.1 min; Solvent A: $H_2O$ with 0.1% trifluoroacetic acid (TFA); Solvent B: acetonitrile with 0.1% TFA.

The following examples are intended to illustrate the embodiments disclosed and are not to be construed as being limitations thereto. Additional compounds, other than those described below, may be prepared using the following described reaction scheme or appropriate variations or modifications thereof.

Synthesis

Schemes I and II illustrate the procedures used for preparing compounds of formula Ib, wherein X and Y are hydrogens, compounds (VII) of formula Ia can be prepared by analogous procedure, for example, by the choice of appropriate starting material. For example, in the case of Z is —CH═CH— and attached to $C_5$-position in Formula Ib, such compound(s) can be synthesized by analogous method illustrated in Scheme I and II starting with a substituted cinnamic acid (e.g. trans-3-nitro-4-chloro-cinnamic acid), appropriate amine component ($R^1NH_2$), carboxylic acid component ($R^2CO_2H$, Scheme I) or aldehyde ($R^2CHO$, Scheme II), and appropriate hydroxylamine or N-alkyl hydroxylamine ($NHR^3OH$ where $R^3$ is defined as above in Formula Ia).

carboxylic acid (I) may be esterified to the methyl ester (Ia) and then the chloride was replaced by the appropriate amine component $R^1NH_2$ to give compound (III). The nitro group of (III) can be reduced by appropriate reducing agent (e.g. tin (II) chloride) and the resulting phenylenediamine (IV) was coupled with an acid $R^2CO_2H$ to give amide (V) which was subsequently cyclized in an appropriate solvent (e.g. acetic acid) to give benzimidazole (VI) (J. Med. Chem. 2001, 44, 1516-1529). The hydroxamate compounds (VI) were obtained from methyl ester (VI) by a known synthesis method (J. Med. Chem., 2002, 45, 753-757).

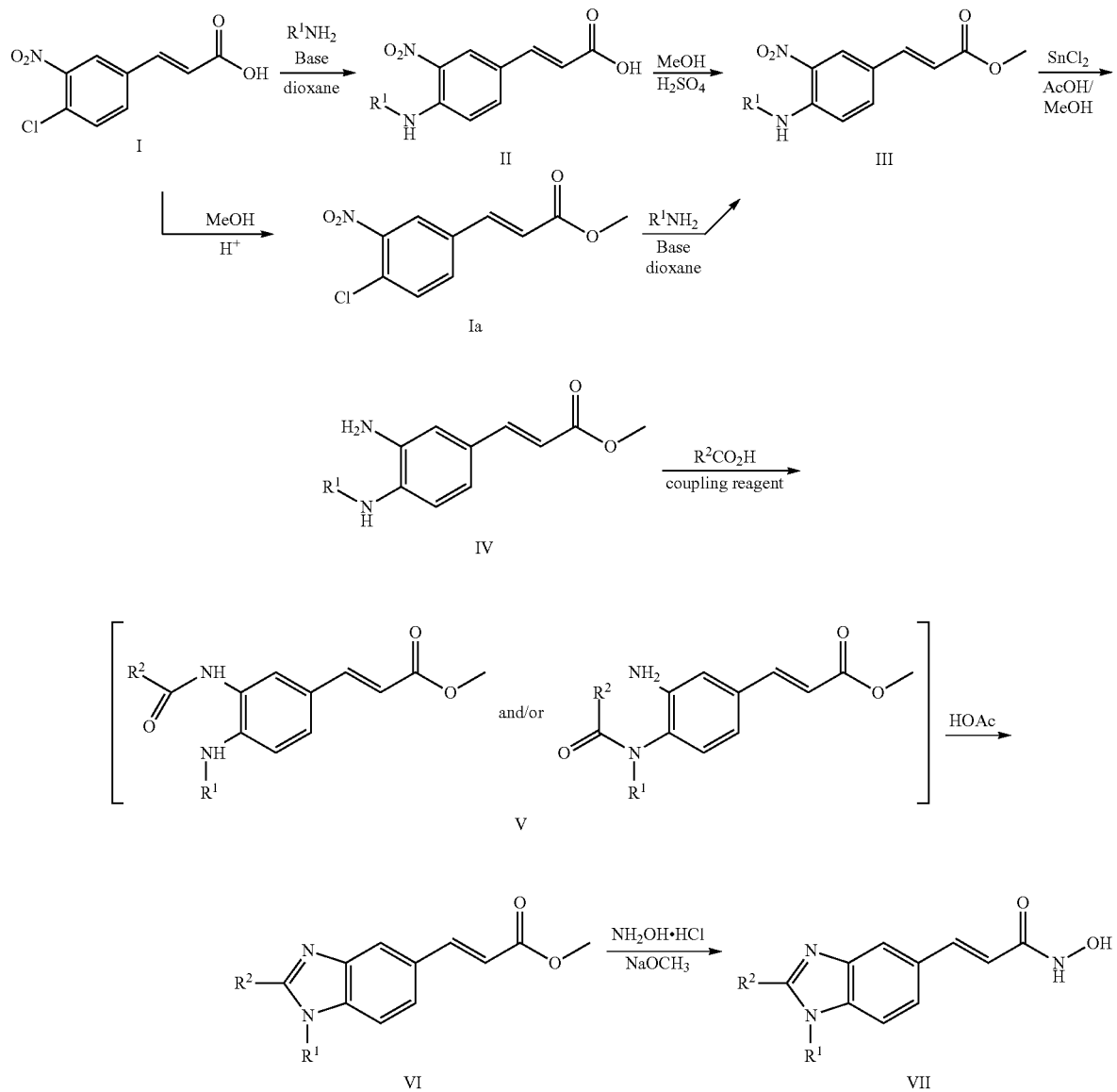

Specifically, the hydroxamate compounds Formula Ib can be synthesized by the synthetic route shown in Scheme I. The reaction of trans-4-chloro-3-nitrocinnamic acid (I) with an amine $R^1NH_2$ in the presence of a base (e.g. triethylamine) in an appropriate solvent (e.g. dioxane) gave (II). Treatment of (II) in methanol under acid catalysis (e.g. sulfuric acid) resulted in esterification providing (III). Alternatively, the Alternatively, as depicted in Scheme II, compound (VI) was prepared by reacting with an appropriate aldehyde component $R^2CHO$ in the presence of a reducing agent of nitro group (e.g. tin (II) chloride, or zinc powder) in one-pot (Tetrahedron Letters, 2000, 41, 9871-9874). Formic acid was used to prepare compound (VI) when $R^2$═H.

Scheme II

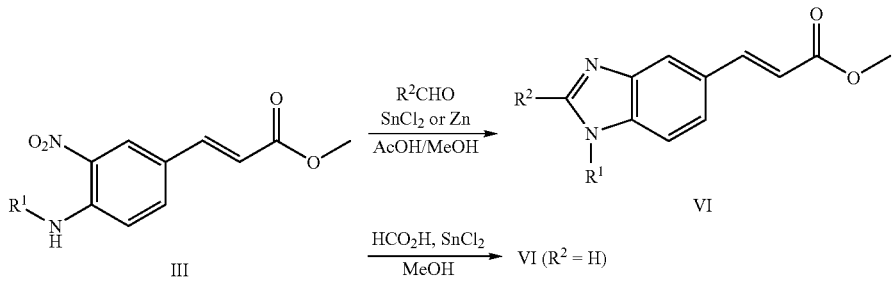

In both Schemes I & II, the benzimidazole ring may be constructed by a cyclization step involving either an aldehyde or a carboxylic acid. The following reaction steps 1-4 refer to the use of carboxylic acid for the cyclization of (IV) via (V) to form benzimidazole derivatives (VI), followed by the conversion of ester (VI) to the hydroxamate (VII). For one-pot cyclization of (III) to (VI), see the procedures under Example 1.

Step 1: Reduction of Nitro Group

To a pre-stirred solution of starting material (III, 1.0 mmol) in 50 mL of co-solvent (glacial acetic acid: methanol=2:8), Tin chloride was added (5.0 mmol). The resulting solution was heated to 55° C. overnight and then cooled to room temperature. The solvent was removed and the mixture was neutralized with sodium bicarbonate to pH 8. The crude product was extracted with dichloromethane (20 mL) for three times. The organic extracts were combined and washed with water (15 mL) twice and brine (15 mL) once and further dried over $Na_2SO_4$ for 1 hour. It was filtered and concentrated; the diamino product (IV) was purified by flash chromatography.

Step 2: Amide Formation

To a pre-stirred solution of carboxylic acid (1.1 mmol), diamino product (IV, 1.0 mmol) and PyBOP (1.1 mmol) in 10 mL of dried dichloromethane, was added DIEA (3.0 mmol) via a syringe. The resulting mixture was stirred at room temperature for 4 hours. The amide product (V) was purified by silica gel column chromatography.

Step 3: Cyclization

The amide product (V), obtained in Step 2, was treated with 5 mL of glacial acetic acid, the resulting solution was heated to 75° C. for 24 hours. After cooling down to rt, the solvent was removed under vacuum to give product (VI) near quantitatively.

Step 4: Hydroxamic Acid Formation

To a stirred solution of ester (VI) and $NH_2OH.HCl$ (10 equiv.) in MeOH (0.5 M) was added NaOMe solution (20 equiv.) at −78° C. The reaction mixture was then allowed to warm up slowly to room temperature. The reaction was monitored by LC/MS and was completed in around 15~60 min. 1N HCl was then added slowly into the reaction mixture at 0° C. The desired product was separated by reverse-phase preparative HPLC and the fractions containing the desired product were freeze-dried. The hydroxamate product (VI) was obtained as TFA salt (isolated yield varies between 40-70%).

Scheme III illustrates another alternative procedure used for preparing compounds of formula Ib, where X and Y are hydrogens and $R^2$ is selected from the group $R^{11}S(O)R^{13}$—, $R^{11}S(O)_2R^{13}$—, $R^{11}C(O)N(R^{12})R^{13}$—, $R^{11}SO_2N(R^{12})R^{13}$—, $R^{11}N(R^{12})C(O)R^{13}$—, $R^{11}N(R^{12})SO_2R^{13}$—, $R^{11}N(R^{12})C(O)N(R^{12})R^{13}$— and heteroalkyl. For example, in the case of Z is —CH=CH— and attached to $C_5$-position in Formula Ib, such compound(s) (XIII) can be synthesized by analogous method illustrated in Schemes I & starting with appropriate (III), appropriate Fmoc protected amino acids, appropriate acid chlorides or aldehydes, and hydroxylamine.

Scheme III

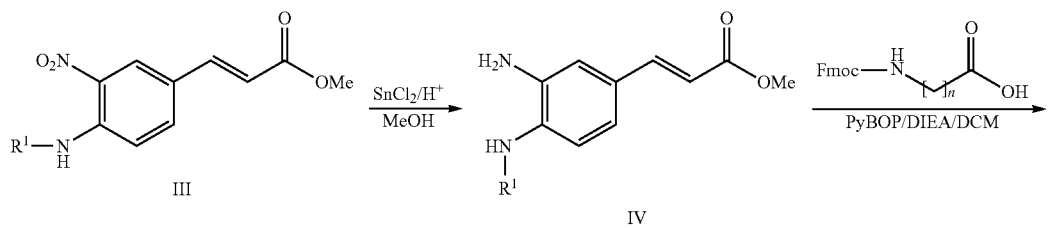

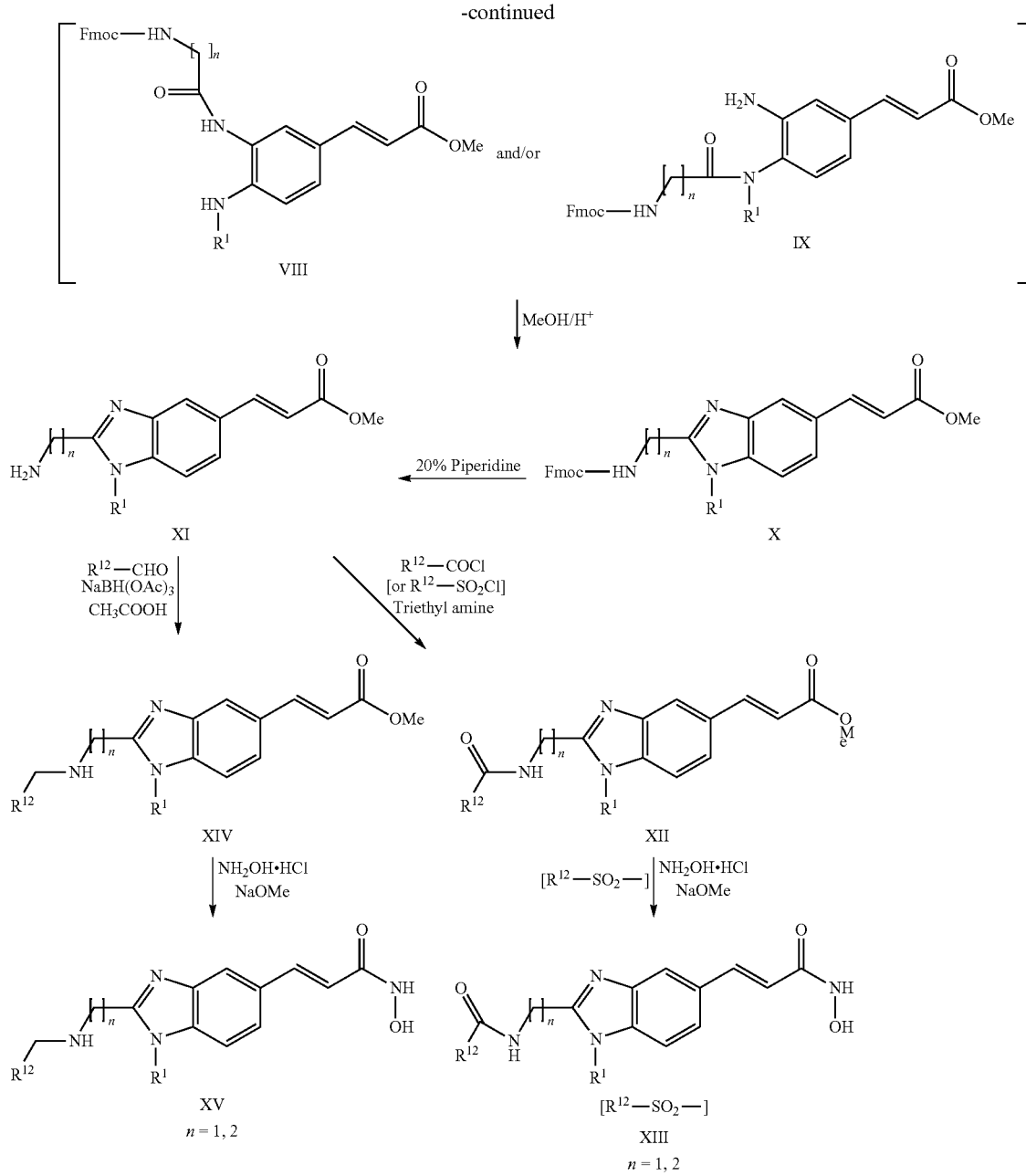

More specifically, for example, the hydroxamate compounds Formula Ib, where X and Y are hydrogens, $R^2$ is selected from the group $R^{11}S(O)R^{13}$—, $R^{11}S(O)_2R^{13}$—, $R^{11}C(O)N(R^{12})R^{13}$—, $R^{11}SO_2N(R^{12})R^{13}$—, $R^{11}N(R^{12})C(O)R^{13}$—, $R^{11}N(R^{12})SO_2R^{13}$—, $R^{11}N(R^{12})C(O)N(R^{12})R^{13}$— and heteroalkyl; and Z is attached to $C_5$-position, can be synthesized by the synthetic route shown in Scheme III. Appropriate intermediate (III) was reduced with tin chloride to the corresponding diamines (IV). The coupling reaction with appropriate Fmoc protected amino acids in the presence of PyBOP gave coupling product(s) (VIII) and/or (IX). Without further separation, (VIII) and/or (IX) were subjected to cyclization under acid conditions and yielded benzimidazole (X). The key intermediate (XI) can be obtained by treating (X) with 20% piperidine. Treatment of (XI) with an appropriate acid chloride or an appropriate sulfonyl chloride gave (XII) and the target compounds (XIII) were obtained by using similar method described in Scheme I.

When (XI) was reacted with an appropriate aldehyde under reduction conditions ($NaBH(OAc)_3/CH_3CO_2H$), (XIV) was obtained and can be transformed to corresponding hydroxamate derivatives (XV) by the same methods described above.

Scheme IV illustrates some reactions to further modify $R^1$ side chain. If the $R^1$ side chain contained a protecting group such as Boc in compound (VIa1), it could be removed before converting to the final hydroxamic acid (VIIa). The intermediate (VIa) could be modified by acylation, reductive alkylation, alkylation or sulfonylation to form new analogs (VIIb, VIIc, VIId and VIIe) through new intermediates (VIb, VIc, VId and VIe). The above described methods were also applied to $R^1$=heterocycles, e.g., $R^1$=N-Boc-piperidin-3-yl, N-Boc-piperidin-4-yl and N-Boc-pyrrolidin-3-yl.

Scheme IV
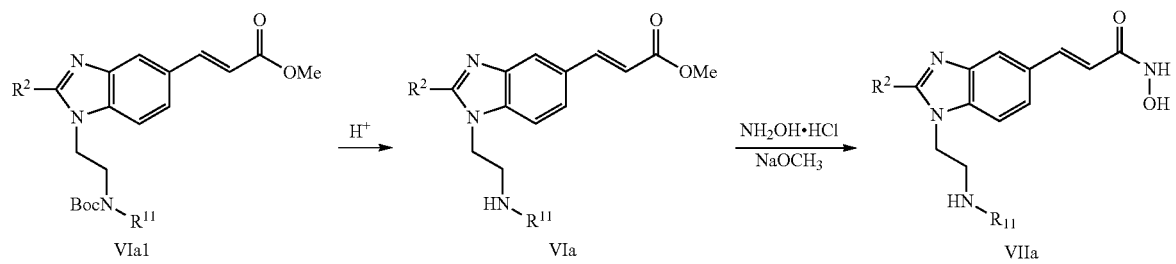
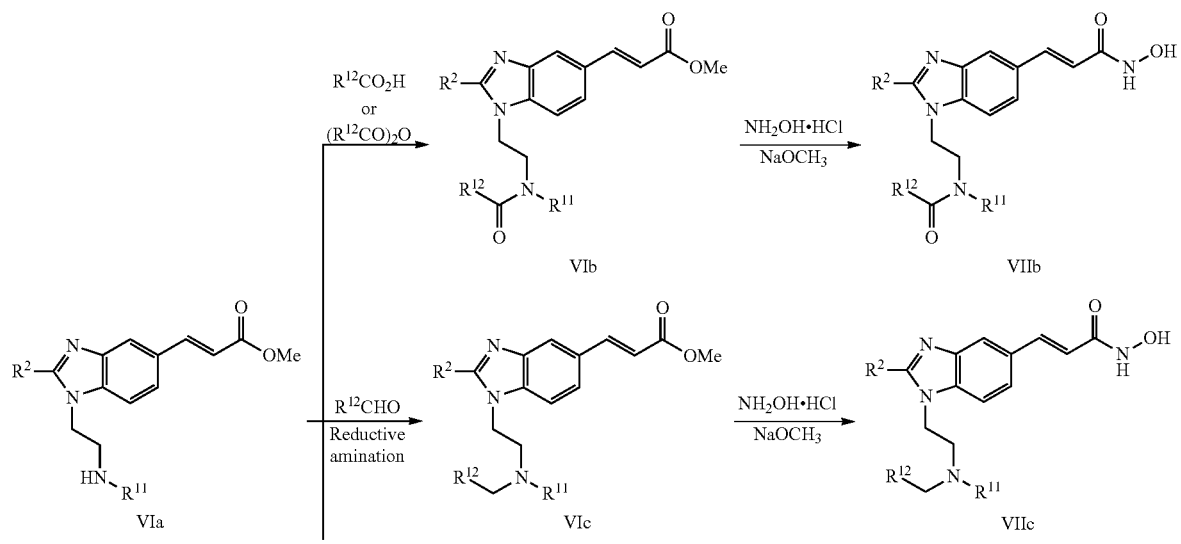
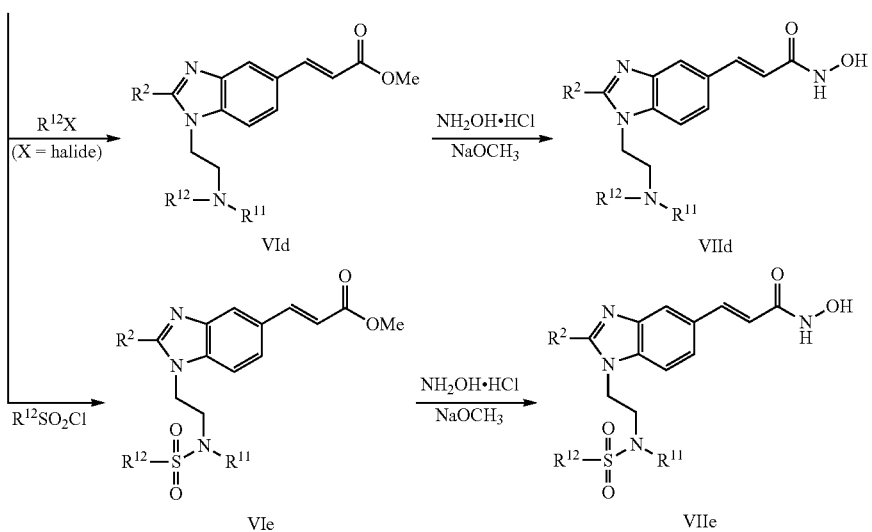
Scheme V illustrates some alternative method to prepare (VIa) and (VIc). The primary amine (IIIa2) was prepared either from (Ia) or via (IIIa1). The derivertization of the amino group (e.g., reductive amination) could be performed either from (IIIa2) or (VIa2). The products, i.e., (IIIa2-1) and (VIa2-1), could be further derivertized (e.g., reductive amination of the secondary amine).

Scheme V

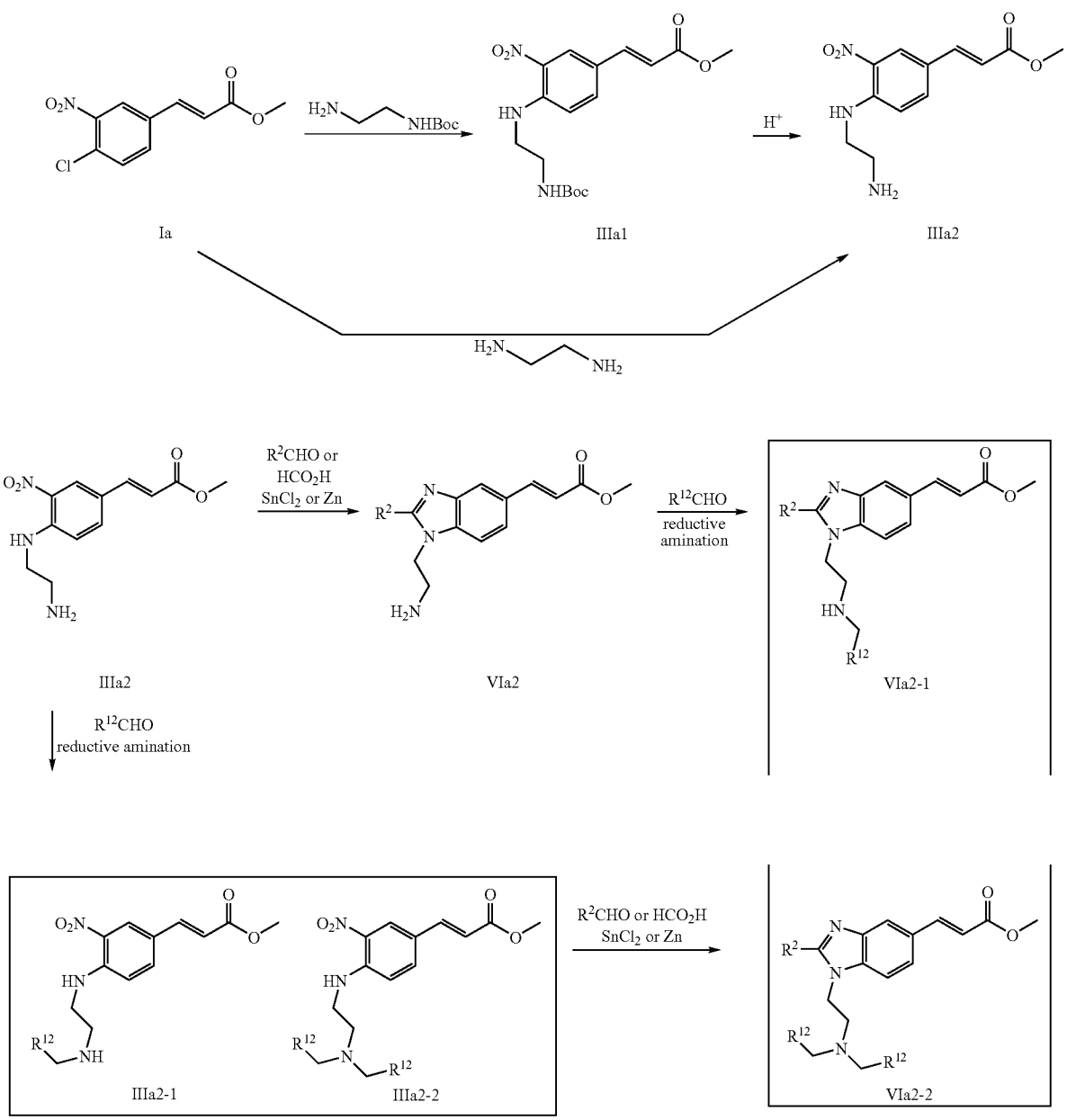

Scheme VI and VII illustrate some alternative methods to prepare (VI) by forming the benzimidazole ring first and introducing the double bond later.

In Scheme VI, compound (XVI) was reacted with an amine $R^1NH_2$ in the presence of a base (e.g. triethylamine) in an appropriate solvent (e.g. dioxane) to give (XVII). Benzimidazole (XVIII) ring was formed by reacting compound (XVII) with aldehyde $R^2CHO$ in the presence of a reducing agent of nitro group (e.g. tin (II) chloride, zinc powder or other appropriate reducing agent) in one-pot. The ester (XVIII) was converted to the aldehyde (XX) via a reduction and oxidation process. Finally, (VI) was obtained by reacting aldehyde (XX) with a Wittig or Wittig-Horner reagent.

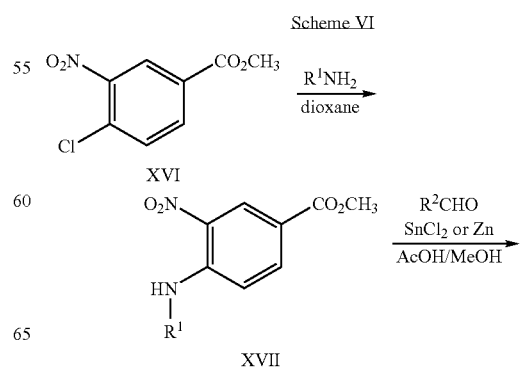

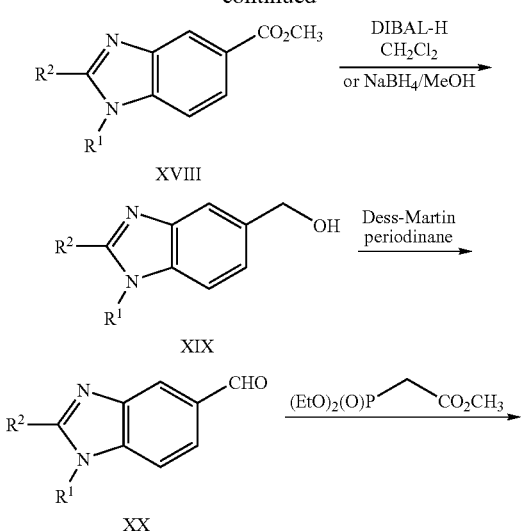

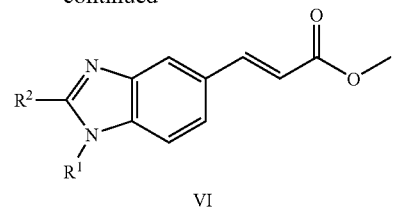

In Scheme VII, compound (XXI) was reacted with an amine R¹NH₂ in the presence of a base (e.g. triethylamine) in an appropriate solvent (e.g. dioxane) to give (XXII). Benzimidazole (XXIII) ring was formed by reacting compound (XXII) with aldehyde R²CHO in the presence of a reducing agent of nitro group (e.g. tin (II) chloride, zinc powder or other appropriate reducing agent) in one-pot. Finally, the bromide (XXIII) was converted to (VI) under Heck reaction condition.

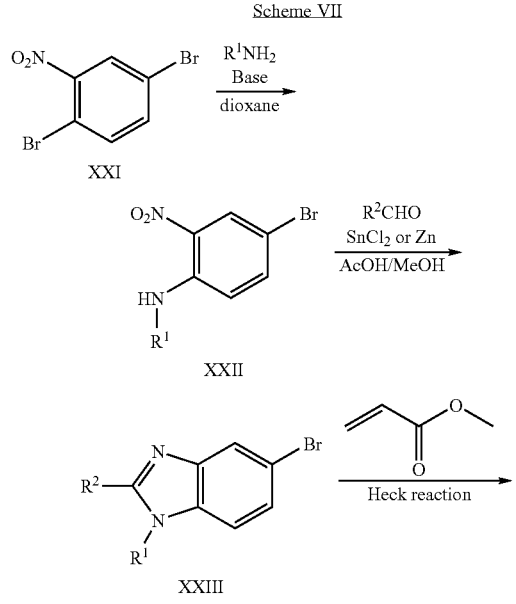

The following preparations and examples are given to enable those skilled in the art to more clearly understand and to practice the subject matter hereof. They should not be considered as limiting the scope of the disclosure, but merely as being illustrative and representative thereof.

Preparation of Intermediates III

Compound (III) was prepared either from (I) via (II) or from (I) via (Ia) (Scheme I and V). The following are examples of (III).

Intermediate 1

3-[4-(2-Dimethylamino-ethylamino)-3-nitro-phenyl]-acrylic acid methyl ester

A mixture of 3-(4-chloro-3-nitro-phenyl)-acrylic acid methyl ester (Ia, 0.658 g, 2.72 mmol), N,N-dimethylethylenediamine (0.90 mL, 8.20 mmol) and triethylamine (1.2 mL, 8.6 mmol) in dioxane (20 mL) was heated at 80° C. for 5 h. The solution was evaporated and the residue was added DCM and aqueous $Na_2CO_3$. The DCM (×3) extracts were concentrated and the residue was added EtOAc-hexane. The resulting red solid was filtered to give the titled compound (0.672 g, 84.2%). HPLC purity at 254 nm: 99.2%, $t_R$=1.59 min. LCMS (ESI) m/z: 294 ([M+H]$^+$). $^1$H NMR (CDCl$_3$+CD$_3$OD) δ 8.21 (1H, d, J=2.1 Hz), 7.56 (1H, dd, J=9.0, 2.1 Hz), 7.48 (1H, d, J=16.0 Hz), 6.81 (1H, d, J=9.0 Hz), 6.20 (1H, d, J=15.9 Hz), 3.70 (3H, s), 3.34 (2H, t, J=6.5 Hz), 2.56 (2H, t, J=6.4 Hz), 2.23 (6H, s); $^{13}$C NMR (CDCl$_3$+CD$_3$OD) δ 167.3, 145.4, 142.6, 134.0, 131.1, 127.1, 121.3, 114.8, 114.0, 56.7, 51.1, 44.6, 40.1.

Intermediate 2

3-[4-(2-Diethylamino-ethylamino)-3-nitro-phenyl]-acrylic acid methyl ester

Yellow solid. LCMS (ESI) m/z: 322 ([M+H]$^+$). $^1$H NMR (CDCl$_3$) δ 8.73 (1H, t-like, J=4.3 Hz), 8.32 (1H, d, J=2.0 Hz), 7.62 (1H, dd, J=9.2, 2.0 Hz), 7.58 (1H, d, J=15.9 Hz), 6.85 (1H, d, J=9.0 Hz), 6.29 (1H, d, J=15.9 Hz), 3.80 (3H, s), 3.35 (2H, td, J=5.4, 6.0 Hz), 2.77 (2H, t, J=6.2 Hz), 2.59 (4H, q, J=7.1 Hz), 1.07 (6H, t, J=7.1 Hz).

Intermediate 3

3-[4-(2-Ethylamino-ethylamino)-3-nitro-phenyl]-acrylic acid methyl ester

Red solid. LCMS (ESI) m/z: 294 ([M+H]$^+$). $^1$H NMR (DMSO-d$_6$) δ 8.49 (1H, t, J=6.1 Hz), 8.35 (1H, d, J=2.0 Hz), 7.96 (1H, dd, J=9.1, 1.9 Hz), 7.62 (1H, d, J=16.0 Hz), 7.20 (1H, d, J=9.1 Hz), 6.52 (1H, d, J=16.0 Hz), 3.75 (2H, td, J=6.5, 6.2 Hz), 3.70 (3H, s), 3.08 (2H, t, J=6.5 Hz), 2.93 (4H, q, J=7.2 Hz), 1.17 (6H, t, J=7.2 Hz).

Intermediate 4

3-[4-(2-Isopropylamino-ethylamino)-3-nitro-phenyl]-acrylic acid methyl ester Red solid. LCMS (ESI) m/z: 308 ([M+H]$^+$). $^1$H NMR (DMSO-d$_6$) δ 8.58 (1H, t, J=5.6 Hz), 8.33 (1H, d, J=2.0 Hz), 7.94 (1H, dd, J=9.1, 1.9 Hz), 7.60 (1H, d, J=16.0 Hz), 7.14 (1H, d, J=9.2 Hz), 6.49 (1H, d, J=16.0 Hz), 3.70 (3H, s), 3.56 (2H, masked by water peak, identified by COSY), 3.10 (1H, septet, J=6.4 Hz), 2.94 (2H, t, J=6.2 Hz), 1.10 (6H, d, J=6.4 Hz).

Intermediate 5

3-[4-(3-Dimethylamino-2,2-dimethyl-propylamino)-3-nitro-phenyl]-acrylic acid methyl ester Red solid. LCMS (ESI) m/z: 336 ([M+H]$^+$). $^1$H NMR (CDCl$_3$) δ 9.73 (1H, br s or t), 8.33 (1H, d, J=2.0 Hz), 7.60 (1H, dd, J=8.9, 2.0 Hz), 7.59 (1H, d, J=16.1 Hz), 6.88 (1H, d, J=9.1 Hz), 6.28 (1H, d, J=15.9 Hz), 3.80 (3H, s), 3.21 (2H, d, J=4.6 Hz), 2.36 (2H, s), 2.34 (6H, s), 1.04 (6H, s).

Intermediate 6

3-[4-(2-Diisopropylamino-ethylamino)-3-nitro-phenyl]-acrylic acid methyl ester Yellow solid. LCMS (ESI) m/z: 350 ([M+H]$^+$). $^1$H NMR (CDCl$_3$) δ 8.76 (1H, t-like, J=4.3 Hz), 8.32 (1H, d, J=2.0 Hz), 7.61 (1H, dd, J=8.3, 2.7 Hz), 7.58 (1H, d, J=15.8 Hz), 6.85 (1H, d, J=9.0 Hz), 6.29 (1H, d, J=15.9 Hz), 3.79 (3H, s), 3.31 (2H, td, J=5.3, 6.1 Hz), 3.08 (2H, septet, J=6.6 Hz), 2.84 (2H, t, J=6.2 Hz), 1.07 (12H, d, J=6.6 Hz).

Intermediate 7

3-[4-(2-Methylamino-ethylamino)-3-nitro-phenyl]-acrylic acid methyl ester

Red solid. LCMS (ESI) m/z: 280 ([M+H]$^+$). $^1$H NMR (CDCl$_3$) δ 8.54 (1H, t-like, J=4.2 Hz), 8.33 (1H, d, J=2.1 Hz), 7.63 (1H, dd, J=9.0, 2.2 Hz). 7.59 (1H, d, J=16.0 Hz), 6.90 (1H, d, J=9.0 Hz), 6.31 (1H, d, J=15.9 Hz), 3.80 (3H, s), 3.45 (2H, td, J=5.8, 5.6 Hz), 2.96 (2H, t, J=6.2 Hz), 2.50 (3H, s).

Intermediate 8

3-[4-(2-tert-Butoxycarbonylamino-ethylamino)-3-nitro-phenyl]-acrylic acid methyl ester (IIIa1)

Step 1:
A suspension of trans-4-chloro-3-nitrocinnamic acid (I, 5.057 g, 22.22 mmol) in MeOH (40 mL) and DCM (20 mL) was stirred and cooled in a dry-ice/acetone bath. SOCl$_2$ (1.0 mL, 13.8 mmol) was added to the above mixture. Dry-ice bath was removed, then the mixture was warmed to room temperature and stirred at 40° C. till the reaction completed. The solution was evaporated to dryness to a pale yellow solid (5.364 g, 99.9%). HPLC purity at 254 nm: 99.5%; t$_R$=2.96 min. LCMS (ESI) m/z: 210 and 212 (very weak signal, [M+H-MeOH]$^+$).

Step 2:
A mixture of 3-(4-chloro-3-nitro-phenyl)-acrylic acid methyl ester (Ia, 0.243 g, 1.00 mmol), N-Boc-ethylenediamine (0.316 mL, 2.0 mmol) and triethylamine (0.50 mL, 3.59 mmoL) in dioxane (7 mL) was heated at 80° C. for about 80 h. The solution was evaporated and the residue was added MeOH. The resulting solid was filtered and washed with MeOH. 3-[4-(2-tert-Butoxycarbonylamino-ethylamino)-3-nitro-phenyl]-acrylic acid methyl ester (IIIa1) was obtained as bright yellow solid (0.193 g, 52.6%). HPLC purity at 254 nm: 96.0~98.1%; t$_R$=3.27 min. LCMS (ESI) m/z: 366 ([M+H]$^+$), 310 (M+H-56), 266 (M+H-Boc). $^1$H NMR (CDCl$_3$) δ 8.41 (1H, br t like, NHAr), 8.31 (1H, d, J=1.8 Hz), 7.63 (1H, dd, J=9.0, 1.7 Hz), 7.57 (1H, d, J=16.0 Hz), 6.98 (1H, d, J=8.9 Hz), 6.30 (1H, d, J=15.9 Hz), 3.80 (3H, s), 3.52 (2H, m), 3.45 (2H, m), 1.45 (9H, s); $^{13}$C NMR (CDCl$_3$) δ 166.9, 155.7, 145.8, 142.3, 134.1, 131.5, 127.1, 121.8, 115.4, 113.9, 79.5, 51.2, 42.7, 39.1, 27.9.

Intermediate 9

3-[4-(2-Amino-ethylamino)-3-nitro-phenyl]-acrylic acid methyl ester (IIIa2)

Method 1:
Remove Boc protecting group from (IIIa1) under acidic condition: 1) HCl/MeOH; 2) TFA/DCM.

Method 2:
To the ester (Ia, 2.47 g, 10.2 mmol) in dioxane (102 mL, 0.1 M) was added ethylenediamine (Merck. Product no. 8.00947, 2.04 mL, 30.6 mmol) followed by triethylamine (2.8 mL, 20.47 mmol). The resulting mixture was heated to 90° C. and stirred for 20 hours. The completion of reaction was confirmed by using HPLC (where the product IIIa2 t$_R$=1.6 min, starting material Ia t$_R$=3.1 min). Upon completion, solvent was removed and the crude was dissolved in DCM. The solution was washed with water, brine, dried over Na$_2$SO$_4$ and filtered. The filtrate after removal of the solvent gave the titled compound IIIa2. Yield=98%, LCMS m/z: 266 ([M+H]$^+$).

EXAMPLE 1

Preparation of 3-[1-(3-Dimethylamino-2,2-dimethyl-propyl)-2-(2,2-dimethyl-propyl)-1H-benzoimidazol-5-yl]-N-hydroxy-acrylamide (1)

The titled compound (1) was prepared according to Scheme 1 and II, by using appropriate starting materials.

Step 1:
To a pre-stirred solution of trans-4-chloro-3-nitrocinnamic acid (I, 11 g, 48 mmol) in dioxane (200 mL) was added triethylamine (20 mL, 126 mmol), followed by 3-dimethylamino-2,2-dimethyl-propylamine (20 mL, 143 mmol). The reaction mixture was allowed to stir at 100° C. for 1-2 days till all starting material was fully converted. Then, the solvent was removed under vacuum followed by the addition of H$_2$O (250 mL) to dissolve the residue. Conc. HCl was added till pH≈1 with orange precipitation. The suspension was filtered and residue was washed with H$_2$O several times to obtain (II) as orange solid (13 g, 84%). LCMS (ESI) m/z: 322 ([M+H]$^+$).

Step 2:
Compound (II, 13 g, 40.5 mmol) was dissolved in MeOH (250 mL) followed by the addition of conc. H$_2$SO$_4$ (5 mL). The reaction mixture was allowed to stir at 80° C. for 18 h. Solvent was removed under vacuum and H$_2$O (250 mL) was added to dissolve the residue. Na$_2$CO$_3$ was added till pH≈8-9, subsequently, MeOH was added and stirred for 1 hour. Then, the suspension was filtered under vacuo and the residue was washed with H$_2$O several times to obtain ester (III) as orange solid (10 g, 74%). LCMS (ESI) m/z: 336 ([M+H]$^+$).

Step 3:

To a stirred solution of ester (III, 1 equiv) and $SnCl_2 \cdot 2H_2O$ (5 equiv) in AcOH and MeOH (0.2 M, 1:9 mixture) was added 3,3-dimethyl butyraldehyde (1.5 equiv). The resulting mixture was heated to 45° C. with stirring. The progress of the reaction was monitor by LC/MS. When the reaction was completed, solvent was removed under reduced pressure at 30-35° C. To the resulting residue, 20 mL of water and 20 mL of ethyl acetate were added at room temperature, the pH value of the mixture was carefully adjusted to 9-10 by addition of conc. $NH_3 \cdot H_2O$. The mixture was stirred for half an hour, followed by centrifuge if necessary to separate the organic layer. The organic layer was collected. The aqueous phase and residue (oily-solid precipitate) were extracted another 3 times more with ethyl acetate as described above. The combined organic contents were dried over sodium sulphate, filtered and evaporated to dryness. The resulting oily residue was purified by flash column chromatography (isolated yield of cyclized product (VI) varies between 50-90%). LCMS (ESI) m/z: 386 ([M+H]$^+$).

Step 4:

To a stirred solution of ester (VI) and $NH_2OH \cdot HCl$ (10 equiv.) in MeOH (0.5M) was added NaOMe (20 equiv.) at −78° C. The reaction mixture was then allowed to warm up slowly to room temperature. The reaction was monitored by LC/MS and was completed in around 15 min. 1N HCl was then added slowly into the reaction mixture at 0° C. The desired product was separated by prep-HPLC and the fractions containing the desired product were freeze-dried. Product (VII) was obtained as TFA salt (isolated yield varies between 40-70%). HPLC purity at 254 nm: 100%, $t_R$=0.78 min. LCMS (ESI) m/z: 387 ([M+H]$^+$). $^1$H NMR (DMSO-d$_6$) δ 1.05 (15H, s), 2.91 (6H, s), 2.92 (2H, s), 3.32 (2H, bs), 4.35 (2H, s), 6.49 (1H, d, J=15.8 Hz), 7.56 (1H, d, J=9.0 Hz), 7.61 (1H, d, J=15.76 Hz), 7.83 (1H, d, J=9.0 Hz), 7.85 (1H, s), 9.22 (1H, bs), 10.72 (1H, bs); $^{13}$C NMR (DMSO-d$_6$) δ 162.6, 154.2, 138.0, 135.3 (br), 134.7, 131.5, 122.8, 119.2, 115.2, 114.0, 66.5, 51.1, 46.7, 38.4, 38.3, 33.6, 29.1, 22.8.

EXAMPLE 2

Preparation of 3-[1-(3-Dimethylamino-2,2-dimethyl-propyl)-2-isopropyl-1H-benzoimidazol-5-yl]-N-hydroxy-acrylamide (2)

The titled compound (2) was prepared according to the procedures described in Example 1, by using appropriate starting materials. HPLC purity at 254 nm: 100%, $t_R$=0.54 min. LCMS (ESI) m/z: 359 ([M+H]$^+$). $^1$H NMR (DMSO-d$_6$) δ 1.05 (6H, s), 1.40 (6H, d, J=6.36 Hz), 2.92 (6H, s), 3.36 (2H, s), 3.58 (1H, m, J=6.4 Hz), 4.44 (2H, s), 6.55 (1H, d, J=15.8 Hz), 7.63 (1H, d, J=15.8 Hz), 7.66 (1H, d, J=8.7 Hz), 7.95 (1H, d, J=8.7 Hz), 7.90 (1H, s), 9.71 (1H, bs), 10.80 (1H, bs).

EXAMPLE 3

Preparation of 3-[2-Butyl-1-(3-dimethylamino-2,2-dimethyl-propyl)-1H-benzoimidazol-5-yl]-N-hydroxy-acrylamide (3)

The titled compound (3) was prepared according to the procedures described in Example 1, by using appropriate starting materials. Yield: 74 mg as TFA salt. HPLC purity at 254 nm: 99.0%, $t_R$=0.89 min. LCMS (ESI) m/z: 373 ([M+H]$^+$). $^1$H NMR (CD$_3$OD) δ 7.99 (1H, d, J=8.8 Hz), 7.84 (1H, s), 7.72 (1H, d, J=8.7 Hz), 7.55 (1H, d, J=15.8 Hz), 6.53 (1H, d, J=15.7 Hz), 4.55 (2H, s), 3.43 (2H, s), 3.24 (2H, overlapped with CD2HOD), 3.00 (6H, s), 1.90 (2H, pentet, J=7.2 Hz), 1.49 (2H, m), 1.21 (6H, s), 0.98 (3H, t, J=7.3 Hz); $^{13}$C NMR (CD$_3$OD) δ 165.5 (br), 158.2, 139.8, 135.3, 135.1, 132.4, 126.4, 120.6 (br), 115.6, 114.3, 68.7, 53.5, 47.8 (Me×2), 39.5, 29.9, 27.2, 23.6 (Me×2), 23.3, 13.9.

EXAMPLE 4

Preparation of 3-[1-(3-Dimethylamino-2,2-dimethyl-propyl)-2-(2-methylsulfanyl-ethyl)-1H-benzoimidazol-5-yl]-N-hydroxy-acrylamide (4)

The titled compound (4) was prepared according to the procedures described in Example 1, by using appropriate starting materials. Yield: 17 mg as TFA salt. HPLC purity at 254 nm: 96.2%, $t_R$=0.75 min. LCMS (ESI) m/z: 391 ([M+H]$^+$). $^1$H NMR (CD$_3$OD) δ 8.02 (1H, d, J=8.3 Hz), 7.92 (1H, s), 7.80 (1H, d, J=8.7 Hz), 7.69 (1H, d, J=15.8 Hz), 6.60 (1H, d, J=15.8 Hz), 4.49 (2H, s), 3.50 (2H, t, J=7.2 Hz), 3.37 (2H, s), 3.03 (2H, t, J=7.2 Hz), 2.95 (6H, s), 2.18 (3H, s), 1.25 (6H, s); $^{13}$C NMR (CD$_3$OD) δ 163.7, 154.6, 138.2, 133.9, 132.8, 132.5, 124.1, 118.2, 113.3, 113.2, 66.7, 51.5, 45.9 (Me×2), 37.6, 29.9, 26.2, 21.7 (Me×2), 13.7.

EXAMPLE 5

Preparation of 3-[1-(3-Dimethylamino-2,2-dimethyl-propyl)-2-isobutyl-1H-benzoimidazol-5-yl]-N-hydroxy-acrylamide (6)

The titled compound (6) was prepared according to the procedures described in Example 1, by using appropriate starting materials. HPLC purity at 254 nm: 96.2%, $t_R$=0.82 min. LCMS (ESI) m/z: 373 ([M+H]$^+$). $^1$H NMR (DMSO-d$_6$): δ 10.80 (1H, s), 9.47 (1H, s), 7.93 (1H, s), 7.90 (1H, d, J=6.6 Hz), 7.64 (1H, d, J=7.4 Hz), 7.62 (1H, d, J=15.5 Hz), 6.54 (1H, d, J=15.8 Hz), 4.39 (2H, s), 3.33 (2H, s), 2.97 (2H, d, J=7.26 Hz), 2.92 (6H, s), 2.35 (1H, qn), 1.09 (6H, s), 0.97 (6H, d, J=6.6 Hz).

EXAMPLE 6

Preparation of 3-[1-(2-Diethylamino-ethyl)-2-isobutyl-1H-benzoimidazol-5-yl]-N-hydroxy-acrylamide (7)

The titled compound (7) was prepared according to the procedures described in Example 1, by using appropriate starting materials. HPLC purity at 254 nm: 99.0%, $t_R$=0.56 min. LCMS (ESI) m/z: 359 ([M+H]$^+$). $^1$H NMR (DMSO-d$_6$): δ 10.81 (1H, s), 10.13 (1H, s), 7.90 (1H, s), 7.81 (1H, d, J=8.5 Hz), 7.66 (1H, d, J=8.6 Hz), 7.61 (1H, d, J=15.8 Hz), 6.53 (1H, d, J=15.8 Hz), 4.72 (2H, t, J=7.8 Hz), 3.30 (2H, d), 2.93 (2H, d, J=7.2 Hz), 2.27 (1H, m), 1.24 (6H, t, J=7.2 Hz), 0.97 (6H, d, J=6.6 Hz) $^{13}$C NMR (DMSO-d$_6$) δ 162.7, 158.5, 158.2, 155.2, 138.4, 133.9, 131.0, 123.0, 118.6, 116.0, 111.6, 48.8, 46.8, 34.1, 27.1, 22.2, 8.5.

EXAMPLE 7

Preparation of 3-[2-Butyl-1-(2-diethylamino-ethyl)-1H-benzoimidazol-5-yl]-N-hydroxy-acrylamide (8)

The titled compound (8) was prepared according to the procedures described in Example 1, by using appropriate starting materials. Yield: 61 mg (20% in two steps) as TFA salt. HPLC purity at 254 nm: 98.1%, $t_R$=0.59 min. LCMS (ESI) m/z: 359 ([M+H]$^+$). $^1$H NMR (CD$_3$OD) δ 7.94 (1H, d, J=8.6 Hz), 7.85 (1H, s), 7.76 (1H, d, J=8.5 Hz), 7.50 (1H, d, J=15.7 Hz), 6.49 (1H, d, J=15.7 Hz), 4.96 (2H, overlapped with DHO, identified by COSY), 3.69 (2H, t-like, J=7.6 Hz), 3.44 (4H, q, J=7.6 Hz), 3.26 (2H, t, J=7.9 Hz), 1.94 (2H, pentet, J=7.5 Hz), 1.57 (2H, m), 1.40 (6H, t, J=7.2 Hz), 1.05 (3H, t, J=7.3 Hz); $^{13}$C NMR (CD$_3$OD) δ 165.5, 157.7, 140.0, 134.8, 134.0, 133.8, 126.5, 119.9, 115.1, 113.6, 50.2, 48.7 (2C), 40.5, 29.4, 26.6, 23.3, 13.9, 8.9 (2C). (TFA peak 163.4, 163.0, 162.7, 162.3; 122.3, 119.5, 116.6).

Dihydrochloride salt of 8 was prepared according to the procedures described in Example 50, Step 4 and 5, by using appropriate starting materials. $^1$H NMR (DMSO-d$_6$) δ 11.79 (brs, 1H), 10.92 (very br s, 1H), 8.18 (1H, d, J=8.6 Hz), 7.97 (1H, s), 7.79 (1H, d, J=8.6 Hz), 7.64 (1H, d, J=15.8 Hz), 6.65 (1H, d, J=15.8 Hz), 5.01 (2H, t-like, J=7.7 Hz), 3.48 (2H, m), 3.30-3.19 (6H, m), 1.87 (2H, pentet, J=7.8 Hz), 1.47 (2H, sextet, J=7.5 Hz), 1.29 (6H, t, J=7.2 Hz), 0.97 (3H, t, J=7.3 Hz); $^{13}$C NMR (DMSO-d$_6$) δ 162.3, 156.0, 137.3 (CH), 132.8, 132.3, 132.0 (br, identified by HMBC), 124.7 (CH), 120.2 (CH), 113.1 (2×CH), 48.2, 46.3, 39.0, 28.1, 25.0, 21.7, 13.6, 8.3.

EXAMPLE 8

Preparation of 3-[2-But-3-ynyl-1-(3-dimethylamino-2,2-dimethyl-propyl)-1H-benzoimidazol-5-yl]-N-hydroxy-acrylamide (9)

The titled compound (9) was prepared according to the procedures described in Example 1, by using appropriate starting materials. HPLC purity at 254 nm: 98.3%; t$_R$=0.52 min; LCMS (ESI) m/z: 369 ([M+H]$^+$). $^1$H NMR (DMSO-d$_6$) δ 9.49 (brs, 1H), 7.88-7.85 (m, 2H), 7.63-7.59 (m, 2H), 6.52 (d, J=15.79 Hz, 1H), 4.37 (s, 1H), 3.33 (s, 2H), 3.26 (t, J=7.24 Hz, 2H), 2.92 (s, 6H), 2.88 (t, J=2.54 Hz, 1H), 2.81 (dt, J=2.48, 7.70 Hz, 2H), 1.09 (s, 6H); $^{13}$C NMR (DMSO-d$_6$) δ 162.8, 155.3, 138.4, 138.0, 135.9, 130.5, 122.3, 118.4, 117.8, 116.4, 114.9, 112.9, 111.9, 82.8, 72.3, 66.9, 50.9, 46.7, 25.8, 22.8, 16.2.

EXAMPLE 9

Preparation of 3-[2-But-3-enyl-1-(3-dimethylamino-2,2-dimethyl-propyl)-1H-benzoimidazol-5-yl]-N-hydroxy-acrylamide (10)

The titled compound (10) was prepared according to the procedures described in Example 1, by using appropriate starting materials. HPLC purity at 254 nm: 99%; t$_R$=0.80 min; LCMS (ESI) m/z: 371 ([M+H]$^+$). $^1$H NMR (CD$_3$OD) δ 7.95 (d, J=8.8 Hz, 1H), 7.85 (s, 1H), 7.73 (d, J=8.8 Hz, 1H), 7.63 (d, J=15.8 Hz, 1H), 6.54 (d, J=15.8 Hz, 1H), 5.94-5.84 (m, 1H), 5.10 (dd, J=1.4, 17.1 Hz, 1H), 5.03 (dd, J=1.1, 10.2 Hz, 1H), 4.51 (s, 2H), 3.40 (s, 2H), 3.32 (t, J=7.6 Hz, 2H), 2.99 (s, 6H), 2.66 (q, J=7.5 Hz, 2H), 1.19 (s, 6H); $^{13}$C NMR (CD$_3$OD) δ 165.7, 157.6, 140.2, 136.3, 135.9, 134.7, 134.5, 125.9, 120.2, 117.9, 115.2, 103.6, 68.8, 53.4, 39.6, 32.0, 27.2, 23.7.

EXAMPLE 10

Preparation of 3-[2-But-3-enyl-1-(2-diethylamino-ethyl)-1H-benzoimidazol-5-yl]-N-hydroxy-acrylamide (11)

The titled compound (11) was prepared according to the procedures described in Example 1, by using appropriate starting materials. HPLC: 99.4%; t$_R$=0.52 min; LCMS (ESI) m/z: 357 ([M+H]$^+$ 1). $^1$H NMR (CD$_3$OD) δ 7.94 (d, J=8.7 Hz, 1H), 7.81 (s, 1H), 7.73 (d, J=8.3 Hz, 1H), 7.50 (d, J=15.87 Hz, 1H), 6.46 (d, J=15.8 Hz, 1H), 5.96-5.86 (m, 1H), 5.13 (dd, J=1.4, 17.1 Hz, 1H), 5.05 (dd, J=1.1, 10.2 Hz, 1H), 4.93 (t, J=7.9 Hz, 2H), 3.62-3.58 (m, 2H), 3.38-3.31 (m, 6H), 2.65 (q, J=7.6 Hz, 2H), 1.35-1.32 (m, 6H); $^{13}$C NMR (CD$_3$OD) δ 165.8, 157.0, 140.5, 136.6, 135.9, 134.6, 134.2, 126.1, 119.5, 117.7, 116.0, 113.3, 50.4, 40.4, 31.7, 26.7, 9.1.

EXAMPLE 11

Preparation of 3-[2-But-3-ynyl-1-(2-diethylamino-ethyl)-1H-benzoimidazol-5-yl]-N-hydroxy-acrylamide (12)

The titled compound (12) was prepared according to the procedures described in Example 1, by using appropriate starting materials. HPLC: 99.6%; t$_R$=0.37 min; LCMS (ESI) m/z: 355 ([M+H]$^+$). $^1$H NMR (CD$_3$OD) δ 7.82 (d, J=8.7 Hz, 1H), 7.68 (s, 1H), 7.58 (d, J=8.5 Hz, 1H), 7.31 (d, J=15.8 Hz, 1H), 6.31 (d, J=15.8 Hz, 1H), 4.87-4.79 (masked peaks), 3.54-3.50 (m, 2H), 3.37 (t, J=7.1 Hz, 2H), 3.24 (q, J=7.2 Hz, 4H), 2.73 (dt, J=2.4, 6.9 Hz, 2H), 2.30 (t, J=2.5 Hz, 1H), 1.21 (t, J=7.2 Hz, 6H); $^{13}$C NMR (CD$_3$OD) δ 165.9, 156.1, 140.9, 138.1, 135.2, 133.4, 125.6, 118.8, 117.0, 112.8, 82.4, 72.1, 50.6, 40.2, 26.7, 26.4, 17.3, 9.1.

EXAMPLE 12

Preparation of 3-[1-(3-Dimethylamino-2,2-dimethyl-propyl)-2-(3,3,3-trifluoro-propyl)-1H-benzoimidazol-5-yl]-N-hydroxy-acrylamide (13)

The titled compound (13) was prepared according to the procedures described in Example 1, by using appropriate starting materials. HPLC purity at 254 nm: 96.5%; t$_R$=0.80 min; LCMS (ESI) m/z: 413 ([M+H]$^+$).

EXAMPLE 13

Preparation of 3-[1-(2-Diethylamino-ethyl)-2-(3,3,3-trifluoro-propyl)-1H-benzoimidazol-5-yl]-N-hydroxy-acrylamide (14)

The titled compound (14) was prepared according to the procedures described in Example 1, by using appropriate starting materials. HPLC purity: 96.4%; t$_R$=1.37 min; LCMS (ESI) m/z: 399 ([M+H]$^+$). $^1$H NMR (DMSO-d$_6$) δ 1.25 (6H, t), 2.96 (2H, m), 3.31 (6H, m), 3.44 (2H, m), 4.72 (2H, m), 6.51 (1H, m), 7.51 (2H, m), 7.65 (1H, m), 7.83 (1H, m), 10.45 (1H, bs).

EXAMPLE 14

Preparation of 3-[1-(2-Diethylamino-ethyl)-2-ethoxymethyl-1H-benzoimidazol-5-yl]-N-hydroxy-acrylamide (15)

The titled compound (15) was prepared according to the procedures described in Example 1, by using appropriate starting materials. HPLC purity: 98.1%; t$_R$=0.48 min; LCMS (ESI) m/z: 361 ([M+H]$^+$).

EXAMPLE 15

Preparation of 3-[1-(3-Dimethylamino-2,2-dimethyl-propyl)-2-methyl-1H-benzoimidazol-5-yl]-N-hydroxy-acrylamide (16)

The titled compound (16) was prepared according to the procedures described in Example 1, by using appropriate starting materials. HPLC purity: 99.5%; $t_R$=0.30 min; LCMS (ESI) m/z: 331 ([M+H]$^+$). $^1$H NMR (DMSO-d$_6$) δ 1.13 (6H, s), 2.78 (2H, m), 2.89 (6H, s), 3.33 (2H, m), 4.42 (3H, s), 6.57 (1H, m), 7.57-7.69 (2H, m), 7.95 (2H, m), 9.68 (1H, bs), 10.81 (1H, bs).

EXAMPLE 16

Preparation of 3-[1-(2-Diethylamino-ethyl)-2-(2,2-dimethyl-propyl)-1H-benzoimidazol-5-yl]-N-hydroxy-acrylamide (17)

The titled compound (17) was prepared according to the procedures described in Example 1, by using appropriate starting materials. HPLC purity at 254 nm: 99.9%, $t_R$=0.95 min. LCMS (ESI) m/z: 373 ([M+H]$^+$). $^1$H NMR (CD$_3$OD) δ 7.85 (2H, t, J=8.3 Hz), 7.75 (1H, d, J=8.8 Hz), 7.61 (1H, d, J=15.8 Hz), 6.51 (1H, d, J=15.8 Hz), 4.93 (2H, t, J=6.1 Hz), 3.54 (2H, t, J=8.1 Hz), 3.31 (4H, qt, J=7.3 Hz), 3.10 (2H, s), 1.27 (6H, t, J=7.3 Hz), 1.06 (9H, s); $^{13}$C NMR (CD$_3$OD) δ 163.7, 153.3, 138.3, 133.1, 131.9, 124.5, 118.3, 117.1, 113.5, 111.8, 48.1, 39.1, 37.5, 32.9, 27.8, 7.1.

EXAMPLE 17

Preparation of N-Hydroxy-3-[1-(3-isopropylamino-propyl)-2-(3,3,3-trifluoro-propyl)-1H-benzoimidazol-5-yl]-acrylamide (18)

The titled compound (18) was prepared according to the procedures described in Example 1, by using appropriate starting materials. HPLC purity: 96.8%; $t_R$=0.72 min. LCMS (ESI) m/z: 399 ([M+H]$^+$). $^1$H NMR (DMSO-d$_6$) δ 1.18 (6H, d), 2.07 (2H, m), 2.95 (4H, m), 3.27 (3H, m), 4.43 (2H, m), 6.52 (1H, m), 7.55 (2H, m), 7.61 (1H, m), 7.84 (1H, m), 8.65 (2H, bs).

EXAMPLE 18

Preparation of 3-[2-(2,2-Dimethyl-propyl)-1-(2-isopropylamino-ethyl)-1H-benzoimidazol-5-yl]-N-hydroxy-acrylamide (19)

The titled compound (19) was prepared according to the procedures described in Example 1, by using appropriate starting materials. HPLC purity at 254 nm: 98.1%, $t_R$=0.86 min. LCMS (ESI) m/z: 359 ([M+H]$^+$). $^1$H NMR (CD$_3$OD) δ 7.86 (1H, d, J=8.6 Hz), 7.78 (1H, s), 7.73 (1H, d, J=8.5 Hz), 7.44 (1H, d, J=15.8 Hz), 6.45 (1H, d, J=15.4 Hz), 4.83 (2H, t, J=6.42 Hz), 3.52 (2H, t, J=6.6 Hz), 3.36 (1H, qt, J=6.5 Hz), 3.13 (2H, s), 1.26 (6H, d, J=6.2 Hz), 1.04 (9H, s); $^{13}$C NMR (CD$_3$OD) δ 161.2, 153.4, 138.3, 133.0, 124.4, 113.6, 112.0, 51.1, 41.8, 41.1, 37.3, 33.1, 27.8, 17.2.

EXAMPLE 19

Preparation of 3-[1-(2-Diisopropylamino-ethyl)-2-(2,2-dimethyl-propyl)-1H-benzoimidazol-5-yl]-N-hydroxy-acrylamide (20)

The titled compound (20) was prepared according to the procedures described in Example 1, by using appropriate starting materials. HPLC purity at 254 nm: 96.8%, $t_R$=0.94 min. LCMS (ESI) m/z: 400 ([M+H]$^+$). $^1$H NMR (CD$_3$OD) δ 7.86 (1H, s), 7.80 (1H, d, J=8.7 Hz), 7.76 (1H, d, J=8.6 Hz), 7.62 (1H, d, J=15.8 Hz), 6.52 (1H, d, J=16.0 Hz), 4.96 (2H, t, J=5.2 Hz), 3.84 (2H, m), 3.53 (2H, t, J=8.3 Hz), 3.06 (2H, s), 1.38 (12H, d, J=6.5 Hz), 1.05 (9H, s); $^{13}$C NMR (CD$_3$OD) δ 160.2, 153.1, 138.2, 133.2, 131.9, 124.6, 113.5, 111.8, 54.9, 423.0, 40.5, 37.7, 33.0, 27.8, 16.3.

EXAMPLE 20

Preparation of 3-[1-(2-Diisopropylamino-ethyl)-2-isobutyl-1H-benzoimidazol-5-yl]-N-hydroxy-acrylamide (21)

The titled compound (21) was prepared according to the procedures described in Example 1, by using appropriate starting materials. HPLC purity at 254 nm: 95.3%, $t_R$=0.76 min. LCMS (ESI) m/z: 387 ([M+H]$^+$). $^1$H NMR (CD$_3$OD) δ 7.85 (1H, s), 7.71 (2H, s), 7.66 (1H, d, J=15.8 Hz), 6.51 (1H, d, J=15.8 Hz), 4.75 (2H, t, J=7.2 Hz), 3.86 (2H, t, J=6.5 Hz), 3.50 (2H, t, J=8.6 Hz), 2.98 (2H, d, J=7.4 Hz), 2.26 (1H, m) 1.41 (12H, d, J=6.3 Hz), 1.06 (6H, d, J=6.6 Hz).

EXAMPLE 21

Preparation of 3-[1-(3-Dimethylamino-2,2-dimethyl-propyl)-2-hex-3-enyl-1H-benzoimidazol-5-yl]-N-hydroxy-acrylamide (22)

The titled compound (22) was prepared according to the procedures described in Example 1, by using appropriate starting materials. HPLC purity at 254 nm: 99.9%; $t_R$=1.24 min; LCMS (ESI) m/z: 399 ([M+H]$^+$). $^1$H NMR (CD$_3$OD) δ 8.22 (d, J=8.7 Hz, 1H), 8.11 (s, 1H), 7.96 (d, J=8.6 Hz, 1H), 7.81 (d, J=15.8 Hz, 1H), 6.68 (d, J=15.8 Hz, 1H), 5.69-5.59 (m, 2H), 4.79 (s, 2H), 3.66 (s, 2H), 3.55 (t, J=7.3 Hz, 2H), 3.24 (s, 6H), 2.91 (q, J=6.8 Hz, 2H), 2.21-2.11 (m, 2H), 1.44 (s, 6H), 1.02 (t, J=7.5 Hz, 3H); $^{13}$C NMR (CD$_3$OD) δ 165.7, 157.9, 140.2, 135.8, 134.6, 134.5, 126.1, 125.9, 120.1, 115.2, 114.6, 68.7, 533, 47.9, 39.6, 27.6, 25.9, 23.7, 21.4, 14.4.

EXAMPLE 22

Preparation of 3-[1-(3-Dimethylamino-2,2-dimethyl-propyl)-2-(2,4,4-trimethyl-pentyl)-1H-benzoimidazol-5-yl]-N-hydroxy-acrylamide (23)

The titled compound (23) was prepared according to the procedures described in Example 1, by using appropriate starting materials. HPLC purity at 254 nm: 98.6%; $t_R$=1.61 min; LCMS (ESI) m/z: 429 ([M+H]$^+$). $^1$H NMR (CD$_3$OD) δ 8.19 (d, J=8.8 Hz, 1H), 8.08 (s, 1H), 7.90 (d, J=8.8 Hz, 1H), 7.76 (d, J=15.7 Hz, 1H), 6.75 (d, J=15.8 Hz, 1H), 4.79 (s, 2H), 3.62 (s, 2H), 3.35-3.29 (m, 1H), 3.23 (s, 6H), 2.52 (brs, 2H), 1.50-1.45 (m, 2H), 1.36 (d, J=3.8 Hz, 6H), 1.12 (d, J=5.5 Hz, 3H), 1.02 (s, 6H); $^{13}$C NMR (CD$_3$OD) δ 165.6, 157.4, 139.9, 135.2, 135.1, 132.9, 126.4, 120.6, 115.7, 114.6, 68.6, 53.3, 51.4, 47.9, 39.7, 36.3, 31.9, 31.3, 30.2, 23.8, 22.3.

EXAMPLE 23

Preparation of 3-[2-Cyclohexyl-1-(3-dimethylamino-2,2-dimethyl-propyl)-1H-benzoimidazol-5-yl]-N-hydroxy-acrylamide (24)

The titled compound (24) was prepared according to the procedures described in Example 1, by using appropriate starting materials. HPLC purity at 254 nm: 99.9%; $t_R$=0.96 min; LCMS (ESI) m/z: 399 ([M+H]$^+$). $^1$H NMR (CD$_3$OD): δ 8.21 (d, J=8.8 Hz, 1H), 8.06 (s, 1H), 7.95 (d, J=8.8 Hz, 1H), 7.83 (d, J=15.8 Hz, 1H), 6.76 (d, J=15.8 Hz, 1H), 4.79 (s, 2H), 3.65 (s, 2H), 3.60-3.51 (m, 1H), 3.22 (s, 6H), 3.29-3.26 (m, 2H), 2.12-2.09 (m, 2H), 2.03-1.92 (m, 3H), 1.78-1.59 (m, 3H), 1.41 (s, 6H); $^{13}$C NMR (CD$_3$OD) δ 165.7, 161.3, 140.1, 135.4, 134.8, 134.0, 126.1, 120.3, 119.6, 116.7, 115.5, 114.9, 68.7, 53.1, 47.9, 39.2, 37.0, 32.4, 26.5, 26.3, 23.6.

EXAMPLE 24

Preparation of 3-[2-Bicyclo[2.2.1]hept-5-en-2-yl-1-(3-dimethylamino-2,2-dimethyl-propyl)-1H-benzoimidazol-5-yl]-N-hydroxy-acrylamide (25)

The titled compound (25) was prepared according to the procedures described in Example 1, by using appropriate starting materials. HPLC purity at 254 nm: 99.9%; $t_R$=0.91 min; LCMS (ESI) m/z: 409 ([M+H]$^+$).

EXAMPLE 25

Preparation of 3-[1-(2-Diethylamino-ethyl)-2-hex-3-enyl-1H-benzoimidazol-5-yl]-N-hydroxy-acrylamide (26)

The titled compound (26) was prepared according to the procedures described in Example 1, by using appropriate starting materials. HPLC: 99.9%; $t_R$=1.14 min; LCMS (ESI) m/z: 385 ([M+H]$^+$). $^1$H NMR (CD$_3$OD) δ 7.95 (d, J=8.6 Hz, 1H), 7.87 (s, 1H), 7.77 (d, J=8.5 Hz, 1H), 7.52 (d, J=15.8 Hz, 1H), 6.50 (d, J=15.8 Hz, 1H), 5.57-5.44 (m, 2H), 3.72-3.68 (m, 2H), 3.44 (q, J=7.2 Hz, 4H), 3.35-3.30 (masked peaks), 2.73 (q, J=7.1 Hz, 2H), 2.07-1.99 (m, 2H), 1.41 (t, J=7.2 Hz, 6H), 0.88 (t, J=7.5 Hz, 3H); $^{13}$C NMR (CD$_3$OD) δ 165.6, 157.2, 140.2, 135.9, 134.8, 134.6, 134.2, 126.4, 126.1, 119.8, 115.6, 113.5, 50.4, 40.5, 26.9, 25.4, 21.4, 14.4, 8.9.

EXAMPLE 26

Preparation of 3-[1-(2-Diisopropylamino-ethyl)-2-hex-3-enyl-1H-benzoimidazol-5-yl]-N-hydroxy-acrylamide (27)

The titled compound (27) was prepared according to the procedures described in Example 1, by using appropriate starting materials. HPLC: 99.9%; $t_R$=1.22 min; LCMS (ESI) m/z: 413 ([M+H]$^+$). $^1$H NMR (CD$_3$OD) δ 7.94-7.89 (m, 2H), 7.78 (d, J=8.7 Hz, 1H), 7.53 (d, J=15.8 Hz, 1H), 6.50 (d, J=15.8 Hz, 1H), 5.63-5.44 (m, 2H), 3.99-3.91 (m, 2H), 3.69-3.64 (m, 2H), 3.36-3.26 (masked peaks), 2.72 (q, J=7.2 Hz, 2H), 2.08-2.01 (m, 2H), 1.50 (d, J=6.5 Hz, 12H), 0.89 (t, J=7.5 Hz, 3H); $^{13}$C NMR (CD$_3$OD) δ 165.6, 157.0, 140.2, 135.9, 135.4, 134.5, 134.3, 126.6, 126.3, 126.2, 119.8, 115.8, 113.3, 56.9, 45.3, 41.9, 27.2, 25.5, 21.4, 18.2, 14.4.

EXAMPLE 27

Preparation of 3-[2-Hex-3-enyl-1-(2-isopropylamino-ethyl)-1H-benzoimidazol-5-yl]-N-hydroxy-acrylamide (28)

The titled compound (28) was prepared according to the procedures described in Example 1, by using appropriate starting materials. HPLC purity at 254 nm: 99.9%; $t_R$=1.12 min; LCMS (ESI) m/z: 371 ([M+H]$^+$). $^1$H NMR (CD$_3$OD) δ 8.00 (d, J=9.1 Hz, 1H), 7.77-7.75 (m, 2H), 7.17 (d, J=15.7 Hz, 1H), 6.34 (d, J=15.7 Hz, 1H), 5.57-5.42 (m, 2H), 4.92 (t, J=5.9 Hz, 2H), 3.72 (t, J=5.7 Hz, 2H), 3.54-3.48 (m, 1H), 3.39 (t, J=7.5 Hz, 2H), 2.72 (q, J=7.3 Hz, 2H), 2.06-1.99 (m, 2H), 1.39 (d, J=6.5 Hz, 6H), 0.87 (t, J=7.5 Hz, 3H).

EXAMPLE 28

Preparation of 3-[1-(2-Ethylamino-ethyl)-2-hex-3-enyl-1H-benzoimidazol-5-yl]-N-hydroxy-acrylamide (29)

The titled compound (29) was prepared according to the procedures described in Example 1, by using appropriate starting materials. HPLC purity at 254 nm: 99.9%; $t_R$=1.23 min; LCMS (ESI) m/z: 385 ([M+H]$^+$). $^1$H NMR (CD$_3$OD) δ 7.94 (d, J=8.6 Hz, 1H), 7.89 (s, 1H), 7.77 (d, J=8.4 Hz, 1H), 7.56 (d, J=15.8 Hz, 1H), 6.55 (d, J=15.7 Hz, 1H), 5.57-5.42 (m, 2H), 4.62 (t, J=7.5 Hz, 2H), 3.42-3.33 (m, 1H), 3.32-3.30 (masked peaks), 3.28-3.24 (m, 2H), 2.71 (q, J=7.2 Hz, 2H), 2.33 (brs, 2H), 2.03-1.94 (m, 2H), 1.36 (d, J=6.5 Hz, 6H), 0.84 (t, J=7.5 Hz, 3H); $^{13}$C NMR (CD$_3$OD) δ 165.6, 156.3, 139.9, 136.8, 136.2, 135.2, 133.8, 132.8, 126.7, 125.8, 120.4, 114.6, 114.1, 52.2, 43.5, 42.9, 27.2, 26.5, 25.5, 21.4, 19.2, 14.4.

EXAMPLE 29

Preparation of 3-[2-Hex-3-enyl-1-(3-isopropylamino-propyl)-1H-benzoimidazol-5-yl]-N-hydroxy-acrylamide (30)

The titled compound (30) was prepared according to the procedures described in Example 1, by using appropriate starting materials. HPLC purity at 254 nm: 99.9%; $t_R$=1.04 min; LCMS (ESI) m/z: 357 ([M+H]$^+$). $^1$H NMR (CD$_3$OD) δ 7.93 (d, J=8.4 Hz, 1H), 7.77-7.73 (m, 2H), 7.23 (d, J=15.7 Hz, 1H), 6.34 (d, J=15.7 Hz, 1H), 5.57-5.42 (m, 2H), 4.87 (masked peaks), 3.68 (brs, 2H), 3.35-3.30 (masked peaks), 3.22-3.17 (m, 2H), 2.72 (q, J=7.1 Hz, 2H), 1.35 (t, J=7.2 Hz, 3H), 0.88 (t, J=7.6 Hz, 3H); $^{13}$C NMR (CD$_3$OD) δ 165.6, 157.3, 140.5, 135.8, 134.9, 134.6, 134.2, 126.2, 126.1, 118.7, 115.9, 113.7, 113.6, 46.5, 45.0, 42.7, 26.4, 25.4, 21.4, 14.4, 11.4.

EXAMPLE 30

Preparation of 3-[1-(2-Diethylamino-ethyl)-2-hexyl-1H-benzoimidazol-5-yl]-N-hydroxy-acrylamide (31)

The titled compound (31) was prepared according to the procedures described in Example 1, by using appropriate starting materials. HPLC purity at 254 nm: 100%, $t_R$=1.31 min. LC-MS m/z: 387 ([M+H]$^+$). $^1$H NMR (DMSO-d$_6$) δ 0.88 (3H, t, J=7.0 Hz), 1.26 (6H, t, J=7.2 Hz), 1.34 (4H, m), 1.44 (2H, m), 1.85 (2H, m), 3.12 (2H, t, J=7.7 Hz), 3.31 (4H, m), 3.52 (2H, t, J=7.7 Hz), 4.81 (2H, t, J=7.7 Hz), 6.59 (1H, d, J=15.8 Hz), 7.63 (1H, d, J=15.8 Hz), 7.73 (1H, d, J=8.8 Hz), 7.93 (1H, d, J=8.8 Hz), 7.94 (1H, s).

EXAMPLE 31

Preparation of 3-[1-(3-isopropylamino-propyl)-2-(2,4,4-trimethyl-pentyl)-1H-benzoimidazol-5-yl]-N-hydroxy-acrylamide (32)

The titled compound (32) was prepared according to the procedures described in Example 1, by using appropriate starting materials. HPLC purity at 254 nm: HPLC: 97.5%, $t_R$=1.68 min. LC-MS m/z: 415 ([M+H]$^+$). $^1$H NMR (DMSO-d$_6$) δ 0.89 (9H, s), 0.98 (3H, d, J=6.6 Hz), 1.23 (6H, d, J=6.5 Hz), 2.08-2.29 (4H, m), 2.27 (1H, m), 2.98-3.12 (4H, m), 3.29 (1H, m), 4.53 (2H, t, J=7.4 Hz), 6.60 (1H, d, J=15.8 Hz), 7.65 (1H, d, J=15.8 Hz), 7.75 (1H, d, J=9.0 Hz), 7.96 (1H, d, J=9.0 Hz), 7.98 (1H, s), 8.75 (2H, bs).

EXAMPLE 32

Preparation of 3-[2-(2,2-Dimethyl-propyl)-1-(3-isopropylamino-propyl)-1H-benzoimidazol-5-yl]-N-hydroxy-acrylamide (33)

The titled compound (33) was prepared according to the procedures described in Example 1, by using appropriate starting materials. HPLC purity at 254 nm: 99%, $t_R$=1.01 min. LC-MS m/z: 375 ([M+H]$^+$). $^1$H NMR (DMSO-d$_6$) δ 0.98 (9H, s), 1.24 (6H, bs), 2.17 (2H, bs), 3.14 (4H, m), 3.28 (1H, bs), 4.53 (2H, bs), 6.65 (1H, d, J=15.5 Hz), 7.65 (1H, d, J=15.5 Hz), 7.81 (1H, d, J=7.4 Hz), 8.02 (1H, s), 8.03 (1H, d, J=7.4 Hz), 8.85 (2H, bs).

EXAMPLE 33

Preparation of 3-[1-(2-Diisopropylamino-ethyl)-2-(3,3,3-trifluoro-propyl)-1H-benzoimidazol-5-yl]-N-hydroxy-acrylamide (34)

The titled compound (34) was prepared according to the procedures described in Example 1, by using appropriate starting materials. HPLC: 97.5%; $t_R$=0.93 min. LCMS (ESI) m/z: 427 ([M+H]$^+$). $^1$H NMR (DMSO-d$_6$) δ1.35 (12H, m), 2.94 (2H, m), 3.24 (2H, m), 3.45 (2H, t), 3.80 (2H, m), 4.68 (2H, t), 6.48 (1H, m), 7.55 (3H, m), 7.85 (1H, m), 9.48 (1H, bs).

EXAMPLE 34

Preparation of N-Hydroxy-3-[2-isobutyl-1-(2-isopropylamino-ethyl)-1H-benzoimidazol-5-yl]-acrylamide (35)

The titled compound (35) was prepared according to the procedures described in Example 1, by using appropriate starting materials. HPLC purity at 254 nm: 98.3%, $t_R$=0.51 min. LCMS (ESI) m/z: 345 ([M+H]$^+$). $^1$H NMR (CD$_3$OD) δ 7.78 (1H, d, J=8.7 Hz), 7.76 (1H, s), 7.68 (1H, d, J=8.6 Hz), 7.46 (1H, d, J=15.8 Hz), 6.42 (1H, d, J=15.9 Hz), 4.70 (2H, t, J=7.4 Hz), 3.48 (2H, t, J=6.9 Hz), 3.37 (1H, m), 3.01 (2H, d, J=7.4 Hz), 2.21 (1H, m), 1.27 (6H, d, J=6.5 Hz), 1.00 (6H, d, J=6.6 Hz); $^{13}$C NMR (CD$_3$OD) δ 160.3, 155.3, 138.5, 134.1, 131.5, 124.2, 113.9, 111.4, 51.1, 42.0, 40.3, 33.4, 27.3, 20.6, 17.2.

EXAMPLE 35

Preparation of 3-[2-(2,2-Dimethyl-propyl)-1-(2-ethylamino-ethyl)-1H-benzoimidazol-5-yl]-N-hydroxy-acrylamide (36)

The titled compound (36) was prepared according to the procedures described in Example 1, by using appropriate starting materials. Yield: 74%. HPLC purity at 254 nm: 99.9%, $t_R$=0.71 min. LCMS (ESI) m/z: 345 ([M+H]$^+$). $^1$H NMR (CD$_3$OD) δ 7.81 (1H, d, J=8.6 Hz), 7.75 (1H, s), 7.69 (1H, d, J=8.5 Hz), 7.36 (1H, d, J=15.7 Hz), 6.40 (1H, d, J=15.3 Hz), 4.81 (2H, t, J=6.4 Hz), 3.51 (2H, t, J=6.3 Hz), 3.10 (2H, s), 3.06 (2H, qt, J=7.3 Hz), 1.23 (3H, t, J=7.2 Hz), 1.04 (9H, s); $^{13}$C NMR (CD$_3$OD) δ 161.0, 153.3, 138.5, 132.7, 132.2, 124.2, 117.5, 113.9, 111.9, 44.2, 43.0, 41.0, 37.4, 33.0, 27.9, 9.5.

EXAMPLE 36

Preparation of 3-[1-(2-Ethylamino-ethyl)-2-isobutyl-1H-benzoimidazol-5-yl]-N-hydroxy-acrylamide (37)

The titled compound (37) was prepared according to the procedures described in Example 1, by using appropriate starting materials. HPLC purity at 254 nm: 99.9%, $t_R$=0.40 min. LCMS (ESI) m/z: 331 ([M+H]$^+$). $^1$H NMR (CD$_3$OD) δ 7.81 (1H, d, J=8.6 Hz), 7.73 (1H, s), 7.67 (1H, d, J=8.2 Hz), 7.34 (1H, d, J=15.7 Hz), 6.36 (1H, d, J=15.7 Hz), 4.74 (2H, t, J=6.7 Hz), 3.54 (2H, t, J=6.5 Hz), 3.10 (2H, d, J=7.4 Hz), 3.06 (2H, d, J=9.5 Hz), 2.21 (1H, m), 1.23 (3H, t, J=7.3 Hz), 1.04 (6H, d, J=6.6 Hz); $^{13}$C NMR (CD$_3$OD) δ 163.7, 161.1, 154.8, 138.6, 133.2, 132.6, 132.4, 124.2, 117.2, 113.9, 111.6, 44.4, 43.0, 40.5, 33.4, 27.3, 20.6, 9.5.

EXAMPLE 37

Preparation of 3-[1-(2-Diisopropylamino-ethyl)-2-(2,4,4-trimethyl-pentyl)-1H-benzoimidazol-5-yl]-N-hydroxy-acrylamide (38)

The titled compound (38) was prepared according to the procedures described in Example 1, by using appropriate starting materials. HPLC: 99.0%; $t_R$=1.62 min; LCMS (ESI) m/z: 443 ([M+H]$^+$). $^1$H NMR (CD$_3$OD) δ 7.96-7.94 (m, 2H), 7.82 (d, J=8.7 Hz, 1H), 7.55 (d, J=15.8 Hz, 1H), 6.54 (d, J=15.8 Hz, 1H), 5.13-5.06 (masked peaks), 4.01-3.92 (m, 2H), 3.71-3.67 (m, 2H), 3.33-3.24 (masked peaks), 3.18-3.12 (m, 1H), 2.38-2.36 (m, 1H), 1.52 (s, 6H), 1.51 (s, 6H), 1.41-1.40 (m, 2H), 1.09 (d, J=6.6 Hz, 3H), 0.94 (s, 9H); $^{13}$C NMR (CD$_3$OD) δ 165.5, 156.5, 140.1, 134.8, 134.7, 134.0, 126.5, 120.0, 114.6, 113.6, 56.9, 51.7, 45.2, 42.0, 35.9, 31.9, 30.6, 30.2, 22.6, 18.3.

EXAMPLE 38

Preparation of N-Hydroxy-3-[1-(2-isopropylamino-ethyl)-2-(2,4,4-trimethyl-pentyl)-1H-benzoimidazol-5-yl]-acrylamide (39)

The titled compound (39) was prepared according to the procedures described in Example 1, by using appropriate starting materials. HPLC purity at 254 nm: 97.9%; $t_R$=1.49 min; LCMS (ESI) m/z: 401 ([M+H]$^+$). $^1$H NMR (CD$_3$OD) δ 7.98 (d, J=8.7 Hz, 1H), 7.79-7.76 (m, 2H), 7.24 (d, J=15.7 Hz, 1H), 6.39 (d, J=15.7 Hz, 1H), 4.97-4.89 (masked peaks), 3.70-3.66 (m, 2H), 3.53-3.47 (m, 1H), 3.34-3.28 (masked peaks), 3.22-3.15 (m, 1H), 2.31-2.29 (m, 1H), 1.39-1.38 (m, 9H), 1.07 (d, J=6.6 Hz, 3H), 0.9 (s, 9H); $^{13}$C NMR (CD$_3$OD) δ 165.5, 156.9, 140.5, 134.7, 134.4, 126.3, 118.9, 115.9, 113.8, 53.2, 51.5, 44.2, 42.8, 35.7, 31.9, 30.9, 30.2, 29.6, 19.1, 18.8.

EXAMPLE 39

Preparation of 3-[1-(2-Ethylamino-ethyl)-2-(2,4,4-trimethyl-pentyl)-1H-benzoimidazol-5-yl]-N-hydroxy-acrylamide (40)

The titled compound (40) was prepared according to the procedures described in Example 1, by using appropriate starting materials. HPLC purity at 254 nm: 100.0%; $t_R$=1.57 min; LCMS (ESI) m/z: 387 ([M+H]$^+$). $^1$H NMR (CD$_3$OD) δ 7.96 (d, J=8.6 Hz, 1H), 7.79 (s, 1H), 7.78-7.75 (d, J=8.7 Hz, 1H), 7.23 (d, J=15.7 Hz, 1H), 6.37 (d, J=15.7 Hz, 1H), 4.96-4.89 (masked peaks), 3.70-3.68 (m, 2H), 3.36-3.28 (masked peaks), 3.26-3.14 (m, 3H), 2.31-2.30 (m, 1H), 1.40-1.32 (m, 5H), 1.07 (d, J=6.6 Hz, 3H), 0.92 (s, 9H); $^{13}$C NMR (CD$_3$OD) δ 165.6, 156.9, 140.6, 134.9, 134.5, 134.2, 126.2, 118.7, 116.0, 113.7, 51.6, 46.5, 45.0, 42.7, 35.8, 31.9, 30.8, 30.2, 22.6, 11.4.

EXAMPLE 40

Preparation of 3-[1-(2-Diethylamino-ethyl)-2-(2,4,4-trimethyl-pentyl)-1H-benzoimidazol-5-yl]-N-hydroxy-acrylamide (41)

The titled compound (41) was prepared according to the procedures described in Example 1, by using appropriate starting materials. HPLC purity at 254 nm: 85.6%, $t_R$=1.55 min. LC-MS m/z: 415 ([M+H]$^+$). $^1$H NMR (CD$_3$OD) δ 7.91 (d, 2H, J=6.0 Hz), 7.80 (br, d, 1H, J=8.9 Hz), 7.68 (d, 2H, J=15.8 Hz), 6.58 (d, 1H, J=15.8 Hz), 4.96 (br, q, 2H), 3.64 (br, q, 2H), 3.43 (q, 4H, J=7.3 Hz), 1.40 (t, 8H), 1.09 (br, d, 4H, J=6.6 Hz), 0.94 (br, s, 10H); $^{13}$C NMR (CD$_3$OD) δ 156.8, 140.4, 135.8, 134.4, 134.3, 126.1, 115.8, 113.2, 119.7, 119.2, 51.6, 50.3, 40.3, 35.8, 31.9, 22.6, 9.0.

EXAMPLE 41

Preparation of 3-[1-(2-Diethylamino-ethyl)-2-propyl-1H-benzoimidazol-5-yl]-N-hydroxy-acrylamide (42)

The titled compound (42) was prepared according to the procedures described in Example 1, by using appropriate starting materials. HPLC purity at 254 nm: 99.0%, $t_R$=0.68 min. LC-MS (ESI) m/z: 345 ([M+H]$^+$). $^1$H NMR (CD$_3$OD) δ 8.15 (d, 2H, J=8.7 Hz), 7.68 (d, 1H, J=15.8 Hz), 6.63 (d, 1H, J=15.8 Hz), 5.08 (br, t, 2H), 3.70 (br, t, 2H), 3.44 (br, m, 4H), 3.35 (t, 2H), 2.03 (br, m, 2H), 1.44 (t, 6H, J=7.2 Hz), 1.20 (t, 3H); $^{13}$C NMR (CD$_3$OD) δ 165.5, 157.4, 139.8, 135.5, 133.5, 132.3, 120.7, 120.7, 114.5, 114.3, 40.8, 28.5, 21.0, 13.9, 9.1.

EXAMPLE 42

Preparation of 3-[1-(2-Diethylamino-ethyl)-2-(2-methylsulfanyl-ethyl)-1H-benzoimidazol-5-yl]-N-hydroxy-acrylamide (45)

The titled compound (45) was prepared according to the procedures described in Example 1, by using appropriate starting materials. Yield: 17 mg (in two steps) as TFA salt. HPLC purity at 254 nm: 80%, $t_R$=0.50 min. LCMS (ESI) m/z: 377 ([M+H]$^+$). $^1$H NMR (CD$_3$OD) δ 7.79 (1H, s), 7.77 (1H, d), 7.66 (1H, d, J=8.6 Hz), 7.54 (1H, d, J=15.8 Hz), 6.44 (1H, d, J=15.8 Hz), 4.83 (2H, masked by DHO, identified by COSY), 3.57 (2H, m), 3.41 (2H, t, J=7.1 Hz), 3.32 (4H), 3.01 (2H, t, J=7.1 Hz), 2.89 (3H, s), 1.30~1.25 (9H, overlapped t).

EXAMPLE 43

Preparation of 3-[2-Butyl-1-(2-isopropylamino-ethyl)-1H-benzoimidazol-5-yl]-N-hydroxy-acrylamide (46)

The titled compound (46) was prepared according to the procedures described in Example 1, by using appropriate starting materials. HPLC purity at 254 nm: 98.4%; $t_R$=1.56 min. LCMS m/z: 345 ([M+H]$^+$). $^1$H NMR (DMSO-d$_6$) δ 0.95 (3H, t), 1.22 (6H, m), 1.42 (2H, m), 1.80 (2H, m), 3.13 (2H, m), 3.41 (3H, t), 4.69 (2H, t), 6.58 (1H, m), 7.56 (1H, m), 7.73 (1H, m), 7.90 (2H, m), 9.14 (2H, bs).

Preparation of the Freebase of the Titled Compound:

To a pre-stirred solution of the methyl ester (1 eq) in dried methanol, NH$_2$OH.HCl (12 eq.) was added. The mixture was stirred in ice-water bath for about 10 min, followed by adding sodium methoxide solution (20 eq.). HPLC showed the reaction completed after 20 min, less than 1% of the acid was observed.

The above crude was treated with 1M of HCl until all the precipitate was dissolved (pH around 1-2). The pH value was carefully adjusted to around 7-8 using NaOH or NaHCO$_3$, the precipitate which was formed was collected by filtration. The solid was washed with water once. The above solid was suspended in methanol and water again and was treated with 6N HCl until all dissolved, the pH value was carefully adjusted to around 7-8 using NaOH and NaHCO$_3$. The precipitate, which was formed, was again collected by filtration; the freebase compound was obtained by drying in vacuo, the yield was around 80%-85%.

Preparation of the Hydrochloric Acid Salt of the Titled Compound:

The above freebase compound was suspended in methanol and water and was treated with 6N HCl (2.8 eq.). The solution became clear. After removing the methanol on a Rotary Evaporator, the hydrochloric acid salt was obtained by freeze-drying. It was further recrystallized from methanol (HPLC purity at 254 nm: >99%).

EXAMPLE 44

Preparation of 3-[2-Butyl-1-(3-isopropylamino-propyl)-1H-benzoimidazol-5-yl]-N-hydroxy-acrylamide (47)

The titled compound (47) was prepared according to the procedures described in Example 1, by using appropriate starting materials. HPLC purity at 254 nm: 98.2%; $t_R$=1.72 min. LCMS (ESI) m/z: 359 ([MH]$^+$). $^1$H NMR (DMSO-d$_6$) δ 0.95 (3H, t), 1.22 (6H, m), 1.45 (2H, m), 1.82 (2H, m), 2.14 (2H, m), 3.17 (4H, m), 3.28 (1H, m), 4.52 (2H, t), 6.62 (1H, m), 7.57 (1H, m), 7.72 (1H, m), 7.89 (2H, m), 8.80 (2H, bs).

EXAMPLE 45

Preparation of 3-[1-(1-Benzyl-piperidin-4-yl)-2-butyl-1H-benzoimidazol-5-yl]-N-hydroxy-acrylamide (48)

The titled compound (48) was prepared according to the procedures described in Example 1, by using appropriate starting materials. HPLC purity at 254 nm: 96.7%, $t_R$=1.35 min. LC-MS m/z: 433 ([M+H]$^+$). $^1$H NMR (DMSO-d$_6$) δ 0.94 (3H, s), 1.41 (2H, m), 1.77 (2H, m), 2.19 (2H, m), 2.99-3.10 (2H, m), 3.24 (4H, m), 3.68 (2H, m), 4.38 (2H, s), 5.01 (1H, m), 6.65 (1H, d, J=15.8 Hz), 7.47-7.49 (3H, m), 7.61 (1H, d, J=15.8 Hz), 7.69 (3H, m), 7.97 (1H, s), 8.60 (1H, d, J=8.8 Hz), 10.35 (2H, s), 11.95 (1H, s).

EXAMPLE 46

Preparation of 3-[2-Butyl-1-(2-ethylamino-ethyl)-1H-benzoimidazol-5-yl]-N-hydroxy-acrylamide (44)

The titled compound (44) was prepared according to the procedures described in Example 1, by using appropriate starting materials. HPLC purity at 254 nm: 98%; LC-MS m/z: 331 ([M+H]$^+$). $^1$H NMR (DMSO-d$_6$) δ 10.88 (br s, 1H), 9.12 (br s, 2H), 7.93 (s, 1H), 7.87 (d, 1H, J=8.4 Hz), 7.71 (d, 1H, J=8.3 Hz), 7.62 (d, 1H, J=15.7 Hz), 6.59 (d, 1H, J=15.6 Hz), 4.67 (t-like, 2H), 3.42 (br s, 2H), 3.08 (q, 2H, J=7.7 Hz, Pr—CH$_2$), 3.05 (br s, 2H), 1.81 (m, 2H), 1.45 (m, 2H), 1.18 (t, 3H, J=7.1 Hz), 0.95 (t, 3H, J=7.0 Hz); $^{13}$C NMR (DMSO-d$_6$) δ 162.6, 156.2, 138.0, 135.0, 133.5, 131.6, 123.5, 119.2, 114.8, 112.1, 44.5, 42.4, 40.6, 28.2, 25.2, 21.7, 13.5, 10.8.

EXAMPLE 47

Preparation of 3-[2-But-3-enyl-1-(2-ethylamino-ethyl)-1H-benzoimidazol-5-yl]-N-hydroxy-acrylamide (49)

The titled compound (49) was prepared according to the procedures described in Example 1, by using appropriate starting materials. HPLC: 99.0%; t$_R$=1.61 min; LCMS m/z: 329 ([M+H]$^+$). $^1$H NMR (CD$_3$OD) δ 7.85 (d, J=8.5 Hz, 1H), 7.78 (s, 1H), 7.72 (d, J=8.5 Hz, 1H), 7.38 (d, J=15.7 Hz, 1H), 6.40 (d, J=15.5 Hz, 1H), 6.02-5.92 (m, 1H), 5.19 (dd, J=17.1, 1.3 Hz, 1H), 5.12 (dd, J=10.2, 0.9 Hz, 1H), 4.80 (t, J=6.4 Hz, 2H), 3.62 (t, J=6.2 Hz, 2H), 3.22-3.16 (m, 2H), 2.71 (q, J=7.2 Hz, 2H), 1.35 (t, J=7.2 Hz, 3H); $^{13}$C NMR (CD$_3$OD) δ 178.3, 157.1, 140.7, 136.5, 133.9, 125.9, 118.8, 117.6, 116.2, 113.2, 101.5, 67.6, 46.4, 44.9, 42.4, 31.6, 26.7, 20.7, 11.4.

EXAMPLE 48

Preparation of 3-[2-Hexyl-1-(2-isopropylamino-ethyl)-1H-benzoimidazol-5-yl]-N-hydroxy-acrylamide (50)

The titled compound (50) was prepared according to the procedures described in Example 1, by using appropriate starting materials. HPLC purity at 254 nm: 94.4%, t$_R$=1.32 min. LCMS (ESI) m/z: 373 ([M+H]$^+$). $^1$H NMR (CD$_3$OD) δ 7.80 (1H, d, J=8.5 Hz), 7.74 (1H, s), 7.64 (1H, d, J=9.0 Hz), 7.50 (1H, d, J=13.6 Hz), 6.42 (1H, d, J=15.8 Hz), 4.65 (2H, d, J=6.6 Hz), 3.48 (2H, d, J=6.6 Hz), 3.38 (1H, qt, J=6.5 Hz), 3.13 (2H, t, J=5.9 Hz) 1.82 (2H, t, J=6.7 Hz), 1.44 (2H, t, J=7.0 Hz) 1.29 (7H, m) 0.84 (6H, d, J=7.0 Hz).

EXAMPLE 49

Preparation of 3-[1-(2-Dimethylamino-ethyl)-2-(2,4,4-trimethyl-pentyl)-1H-benzoimidazol-5-yl]-N-hydroxy-acrylamide (51)

The titled compound (51) was prepared according to the procedures described in Example 1, by using appropriate starting materials. HPLC purity at 254 nm: 100%, t$_R$=1.49 min. LC-MS m/z: 331 ([M+H]$^+$). $^1$H NMR (DMSO-d$_6$) δ 0.85 (9H, s), 1.03 (2H, d, J=6.4 Hz), 1.34 (2H, m), 2.27 (1H, m), 3.00 (6H, s), 3.24-3.27 (4H, m), 4.79 (3H, m), 6.53 (1H, d, J=15.72 Hz), 7.62 (1H, d, J=15.7 Hz), 7.75 (1H, d, J=8.4 Hz), 7.86 (1H, s), 7.87 (1H, d, J=8.4 Hz).

EXAMPLE 50

Preparation of 3-[1-(2-Ethylamino-ethyl)-2-hexyl-1H-benzoimidazol-5-yl]-N-hydroxy-acrylamide (52)

The titled compound (52) was prepared according to the procedures described in Example 1, by using appropriate starting materials. The modified or detailed procedures were described as below.

Step 3:

To a stirred solution of 3-[4-(2-ethylamino-ethylamino)-3-nitro-phenyl]-acrylic acid methyl ester (8.174 g, 27.87 mmol) and heptaldehyde (4.85 g, 42.47 mmol, 1.52 eq) in AcOH and MeOH (1:9 v/v, 300 mL) was added SnCl$_2$.2H$_2$O (31.45 g, 139.4 mmol, 5 eq) in portions. The resulting mixture was heated to 40° C. with stirring. The progress of the reaction was monitor by LC/MS. When the reaction was completed, solvent was removed under reduced pressure below 40° C. The resultant residue was diluted with EtOAc (50 mL) then basified (pH>10) with saturated aqueous Na$_2$CO$_3$ and extracted with dichloromethane (×3). Filtration may be needed to remove the white precipitates or suspension derived from Tin in order to get clearly separated layers. The organic extracts were combined, dried (Na$_2$SO$_4$), filtered, and evaporated to dryness. The resulting oily residue was purified by flash column chromatography (silica, φ67×65 mm, solvent MeOH/DCM gradient from 0 to 10%). 3-[1-(2-ethylamino-ethyl)-2-hexyl-1H-benzoimidazol-5-yl]-acrylic acid methyl ester was obtained as yellow solid (4.445 g, 44.6%). HPLC purity at 254 nm: 98.8%, t$_R$=1.71 min. LCMS (ESI) m/z: 358 ([M+H]$^+$). $^1$H NMR (CDCl$_3$) δ 7.88 (1H, d, J=1.2 Hz), 7.83 (1H, d, J=16.0 Hz), 7.43 (1H, dd, J=8.4, 1.4 Hz), 7.33 (1H, d, J=8.4 Hz), 6.43 (1H, d, J=15.9 Hz), 4.22 (2H, t, J=6.6 Hz), 3.80 (3H, s), 3.01 (2H, t, J=6.6 Hz), 2.89 (2H, t, J=7.9 Hz), 2.65 (2H, q, J=7.1 Hz), 1.91 (2H, pentet, J=7.8 Hz), 1.46 (2H, m), 1.35 (4H, m), 1.07 (3H, t, J=7.1 Hz), 0.90 (3H, t, J=7.0 Hz). The solid could be recrystallized from Hexanes-ether to give a white or pale yellow solid with HPLC purity at 254 nm: 99.2%.

In another experiment starting with 2.725 g of 3-[4-(2-ethylamino-ethylamino)-3-nitro-phenyl]-acrylic acid methyl ester, the titled compound was obtained in 52.8% yield (1.753 g).

Step 4:

To a solution of 3-[1-(2-ethylamino-ethyl)-2-hexyl-1H-benzoimidazol-5-yl]-acrylic acid methyl ester (4.428 g, 12.39 mmol) and NH$_2$OH.HCl (8.66 g, 124.7 mmol) in dry MeOH (50 mL) which was stirred and cooled in a dry-ice acetone bath, added NaOMe solution in MeOH (25%, 4.37 M, 55 mL, 240 mmol). The reaction mixture was then stirred at room temperature. The progress of reaction was monitored by LC/MS (usually reaction completed within 30~90 min) and quenched by adding 6N HCl (40 mL). The mixture (HPLC purity at 254 nm=94.6%) was added Milli-Q water, adjusted pH ~8 by 1N NaOH and evaporated to remove the organic solvent. The resultant residue was washed with Milli-Q water (×3) and re-dissolved in MeOH-DCM, the solution was filtered and diluted with Milli-Q water. The suspension was evaporated to remove the organic solvent and the resultant residue was washed with Milli-Q water (×2). The free base of the titled compound was obtained (HPLC purity at 254 nm=98%). The free base could be recrystallized from MeOH-Ethyl acetate to give a white or pale yellow solid.

Step 5: Hydrochloric Acid Salt Formation.

The above freebase was dissolved in MeOH and excess 6N HCl (final pH<2) and the clear solution was evaporated to dryness and then diluted with MeOH, co-evaporated with PhMe (×1) and EtOAc (×2). The solid was recrystallized from MeOH-EtOAc to give a white or pale yellow solid (3.298 g, 61.7%). HPLC purity at 254 nm: 98.4~99.6%, t$_R$=1.23 min.

LCMS (ESI) m/z: 359 ([M+H]$^+$). $^1$H NMR (CD$_3$OD) δ 9.33 (residual NH), 8.03 (1H, d, J=8.3 Hz), 7.77 (1H, s), 7.73 (1H, d, J=8.2 Hz), 7.16 (1H, d, J=15.7 Hz), 6.34 (1H, d, J=15.7 Hz), 4.88 (2H, overlapped with DHO, identified by COSY), 3.63 (2H, br t like), 3.32 (2H, d, J=7.9 Hz), 3.15 (2H, q, J=7.1), 1.94 (2H, pentet, J=7.1), 1.53 (2H, pentet, J=6.7 Hz), 1.42-1.31 (4H, m), 1.33 (3H, t, J=7.1 Hz), 0.88 (3H, t, J=7.0 Hz); $^{13}$C NMR (CD$_3$OD) δ 163.4, 155.8, 138.1, 133.0, 132.0, 130.3, 125.1, 117.4, 112.8, 112.5, 44.5, 43.2, 41.1, 30.5, 28.0, 25.3, 25.2, 21.6, 12.4, 9.6. Anal. (C$_{20}$H$_{30}$N$_4$O$_2$.2HCl) Cl: calcd, 16.44. found, 16.00.

EXAMPLE 51

Preparation of N-Hydroxy-3-[1-(2-isopropylamino-ethyl)-2-(3,3,3-trifluoro-propyl)-1H-benzoimidazol-5-yl]-acrylamide (53)

The titled compound (53) was prepared according to the procedures described in Example 1, by using appropriate starting materials. HPLC: 98.1%; t$_R$=0.63 min. LC-MS m/z: 385 ([M+H]$^+$).

EXAMPLE 52

Preparation of 3-[1-(2-Dimethylamino-ethyl)-2-hex-3-enyl-1H-benzoimidazol-5-yl]-N-hydroxy-acrylamide (54)

The titled compound (54) was prepared according to the procedures described in Example 1, by using appropriate starting materials. HPLC purity at 254 nm: 99.9%, t$_R$=0.96 min. LCMS (ESI) m/z: 357 ([M+H]$^+$). $^1$H NMR (CD$_3$OD) δ 7.87 (1H, d, J=8.6 Hz), 7.80 (1H, d, J=8.8 Hz), 7.72 (1H, d, J=8.3 Hz), 7.49 (1H, d, J=15.8 Hz), 6.44 (1H, d, J=15.8 Hz), 5.44 (1H, m), 5.38 (1H, m), 4.84 (2H, t, J=6.1 Hz), 3.61 (2H, t, J=7.7 Hz), 3.20 (2H, t, J=4.2 Hz) 2.97 (6H, s), 2.61 (4H, qt, J=7.1 Hz), 1.93 (2H, qn, J=7.7 Hz), 0.78 (3H, t, J=7.5 Hz); $^{13}$C NMR (CD$_3$OD) δ 163.6, 160.0, 155.1, 138.1, 134.1, 133.1, 131.9, 131.6, 124.7, 123.9, 118.2, 117.2, 114.3, 113.1, 111.8, 53.2, 42.1, 38.8, 24.8, 23.3, 19.4, 12.4.

EXAMPLE 53

Preparation of 3-[1-(2-Amino-ethyl)-2-(2,4,4-trim-ethyl-pentyl)-1H-benzoimidazol-5-yl]-N-hydroxy-acrylamide (55)

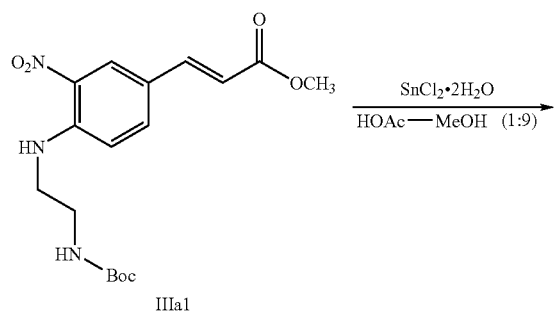

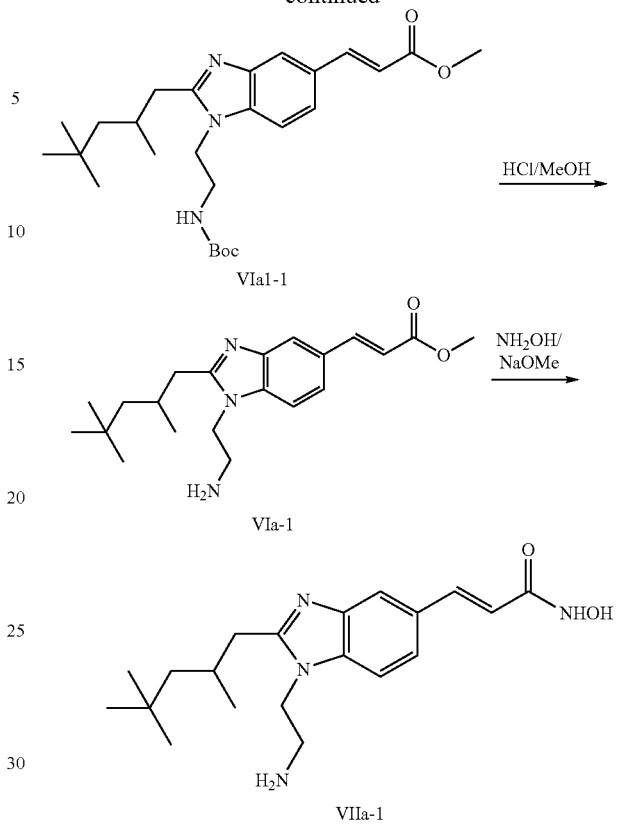

Step 1:
To a stirred solution of 3-[4-(2-tert-Butoxycarbonylamino-ethylamino)-3-nitro-phenyl]-acrylic acid methyl ester (IIIa1, 65.2 mg, 0.178 mmol) and 3,5,5-trimethylhexanal (45 μL, 0.26 mmol) in a mixed solvent of AcOH-MeOH (1:9 v/v, 2 mL) and DCM (1 mL) was added SnCl$_2$.2H$_2$O (184 mg, 0.815 mmol). The resulting mixture was heated to 40° C. with stirring overnight. The solvent was removed under reduced pressure and the resultant residue was added saturated aqueous Na$_2$CO$_3$ and extracted with EtOAc (×3). The extracts gave the crude (VIa1-1, 91 mg) with HPLC purity at 254 nm: 49.3%, t$_R$=3.02 min and 7.9%, t$_R$=1.97 min (de-Boc product). LCMS (ESI) m/z: 458 ([M+H]$^+$) and 358 ([M+H]$^+$, de-Boc product).

Step 2:
The above crude (VIa1-1) was dissolved in MeOH (4 mL) and 6N HCl (1 mL) and heated at 70° C. for 30 min. The solution was evaporated to dryness and co-evaporated with PhMe (×2) and MeOH (×1). The residue (crude VIa-1, 81.9 mg) was spilt to two parts (43.4 mg, equal to 0.0945 mmol of IIIa1, and 38.5 mg equal to 0.0839 mmol of IIIa1).

Step 3:
The titled compound (55) was prepared according to the Step 4 described in Example 1, by using crude (VIa-1, 38.5 mg). VIIa-1 was obtained as TFA salt (2.3 mg, 4.7% from IIIa1). HPLC purity at 254 nm: 92.7%, t$_R$=1.46 min. LCMS (ESI) m/z: 359 ([M+H]$^+$). $^1$H NMR (CD$_3$OD) δ 7.81 (1H, s), 7.70 (1H, d, J=8.6 Hz), 7.65 (1H, d, J=8.4 Hz), 7.59 (1H, d, J=15.8 Hz), 6.47 (1H, brd, J=14.6 Hz), 4.63 (2H, t, J=5.4 Hz), 3.38 (2H, t, J=6.5 Hz), 3.02 (1H, dd, J=15.5, 6.5 Hz), 2.90 (1H, dd, J=15.3, 8.6 Hz), 2.20 (1H, brs or m), 1.33 (1H, dd, J=14.1, 3.4 Hz), 1.25 (1H, dd, J=14.0, 6.6 Hz), 0.98 (3H, d, J=6.2 Hz), 0.83 (9H, s).

EXAMPLE 54

Preparation of 3-[1-(2-Amino-ethyl)-2-(2-methoxy-nonyl)-1H-benzoimidazol-5-yl]-N-hydroxy-acrylamide (56)

The titled compound (56) was prepared according to the procedures described in Example 53, by using appropriate starting materials. HPLC purity at 254 nm: 91.8%, $t_R$=1.93 min. LCMS (ESI) m/z: 403 ([M+H]$^+$). $^1$H NMR (CD$_3$OD) δ some identified peaks: 7.81 (1H, s), 7.70~7.58 (3H, m), 6.46 (1H, br d, J=14.4 Hz), 4.62 (2H, m), 3.69 (1H, br s or m), 3.38 (2H, t, J=7.3 Hz), 1.67 (1H, m), 1.56 (1H, m), 1.50-1.20 (10H, m), 0.82 (3H, t, J=6.2 Hz).

EXAMPLE 55

Preparation of 3-[2-Butyl-1-(2-dimethylamino-ethyl)-1H-benzoimidazol-5-yl]-N-hydroxy-acrylamide (57)

The titled compound (57) was prepared according to the procedures described in Example 1, by using appropriate starting materials. HPLC purity at 254 nm: 100%, $t_R$=0.42 min. LC-MS m/z: 331 ([M+H]$^+$). $^1$H NMR (DMSO-d$_6$) δ 0.97 (3H, t, J=7.3 Hz), 1.49 (3H, m), 1.83 (2H, m), 3.09 (2H, t, J=7.72 Hz), 3.54 (2H, t, J=7.6 Hz), 4.74 (2H, t, J=7.6 Hz), 6.57 (1H, d, J=15.7 Hz), 7.62 (1H, d, J=15.7 Hz), 7.71 (1H, d, J=8.6 Hz), 7.93 (1H, d, J=8.6 Hz), 7.97 (1H, s), 10.68 (2H, bs).

EXAMPLE 56

Preparation of 3-[2-Hexyl-1-(2-dimethylamino-ethyl)-1H-benzoimidazol-5-yl]-N-hydroxy-acrylamide (58)

The titled compound (58) was prepared according to the procedures described in Example 1, by using appropriate starting materials. HPLC purity at 254 nm: 100%, $t_R$=0.42 min. LC-MS m/z: 359 ([M+H]$^+$). $^1$H NMR (DMSO-d$_6$) δ 0.89 (3H, t, J=6.9 Hz), 1.28-1.54 (6H, m), 1.85 (2H, m), 2.92 (6H, s), 3.09 (2H, t, J=7.6 Hz), 3.51 (2H, t, J=7.8 Hz), 4.76 (2H, t, J=7.8 Hz), 6.57 (1H, d, J=15.8 Hz), 7.63 (1H, d, J=15.8 Hz), 7.70 (1H, d, J=8.6 Hz), 7.90 (1H, d, J=8.6 Hz), 7.91 (1H, s), 10.68 (2H, bs).

EXAMPLE 57

Preparation of 3-{1-(2-Diethylamino-ethyl)-2-[2-(2,2-dimethyl-propionylamino)-ethyl]-1H-benzoimidazol-5-yl}-N-hydroxy-acrylamide (61)

The titled compound (61) was prepared according to the procedures described below, Steps 1 & 2 were performed as in Scheme I:

Step 3:

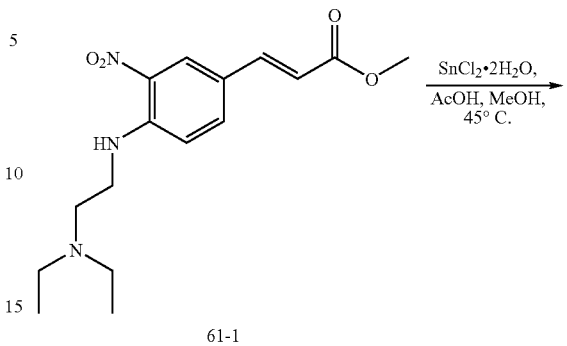

61-1

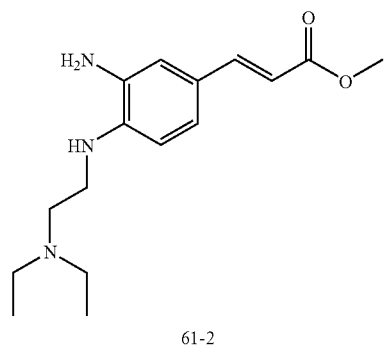

61-2

To a pre-stirred solution of 3-[4-(2-diethylamino-ethylamino)-3-nitro-phenyl]-acrylic acid methyl ester (61-1, 280 mg, 1.0 mmol) in glacial acetic acid (5 mL), tin chloride was added (1.18 g, 10.0 mmol). The resulting solution was heated to 45° C. for 17 hours and then cooled to room temperature. The solvent was removed under vacuum. Water (20 mL) and dichloromethane (20 mL) was added to the residue and stirred for 30 minutes. The organic layer was dried (MgSO$_4$), filtered and concentrated to an oily residue. 100 mL diethyl ether was added and stirred for 4 hours. The product 3-[3-amino-4-(2-diethylamino-ethylamino)-phenyl]-acrylic acid methyl ester was obtained in 54.9% yield (207.6 mg). LCMS m/z: 292 ([M+H]$^+$).

Step 4

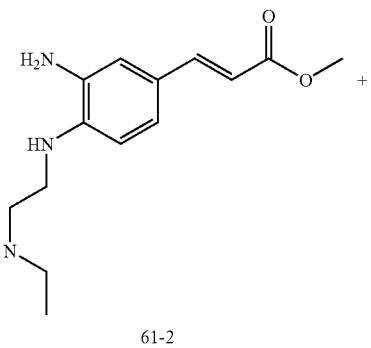

61-2

-continued

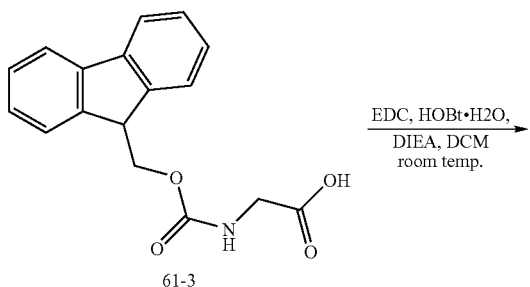

61-3

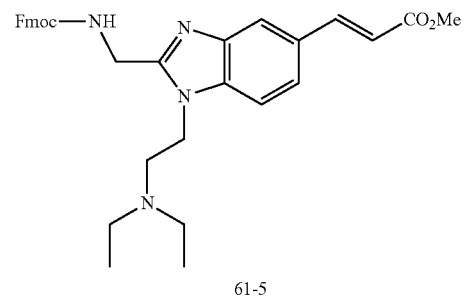

61-5

Glacial acetic acid (8.9 mL) was added into 3-[3-amino-4-(2-diethylamino-ethylamino)-phenyl]-acrylic acid methyl ester (61-4, 2.54 g, 4.46 mmol) and the reaction mixture was stirred at 70° C. for 14 h. When the reaction has completed, the mixture was concentrated in vacuo. Saturated sodium hydrogencarbonate (20 mL) was added and dichloromethane (3×20 mL) was used to extract the aqueous layer. The combined organic contents were dried in sodium sulphate before being filtered and concentrated in vacuo. The product 3-{1-(2-dethylamino-ethyl)-2-[(9H-fluoren-9-ylmethoxycarbonylamino)-methyl]-1H-benzoimidazol-5-yl}-acrylic acid methyl ester (61-5) was obtained in 66.1% (1.62 g). LCMS m/z: 553 ([M+H]$^+$).

Step 6

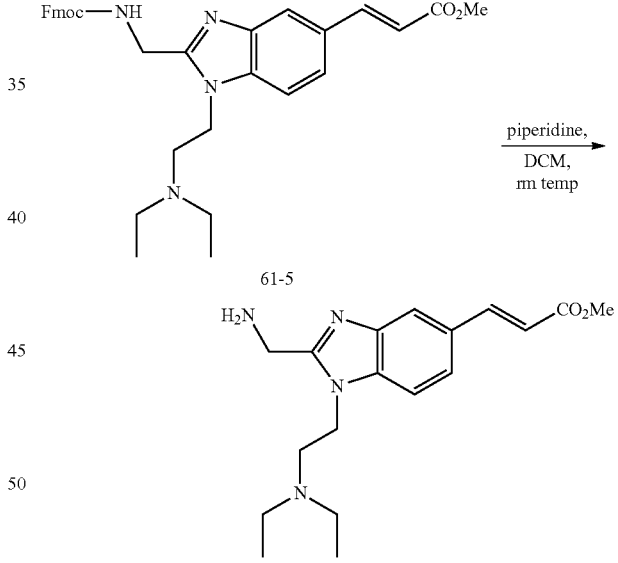

To a pre-stirred solution of 3-[3-amino-4-(2-diethylamino-ethylamino)-phenyl]-acrylic acid methyl ester (61-2, 1.93 g, 6.65 mmol) and dichloromethane (13.3 mL) was added a cocktail solution of N-(3-dimethylaminopropyl)-N'-ethylcarbodiimide hydrochloride (2.55 g, 13.31 mmol), 1-hydroxybenzotriazole hydrate (2.04 g, 13.31 mmol), N,N-diisopropylethylamine (2.20 mL, 13.31 mmol) and dichloromethane (26.6 mL). After stirring for 0.5 h, Fmoc-Gly-OH (61-3, 2.97 g, 9.98 mmol) was added. When the starting material has fully reacted, ethyl acetate (100 mL) was added to dilute the mixture. The organic contents were washed with saturated sodium hydrogencarbonate (2×25 mL) and brine (2×25 mL), before drying in sodium sulphate. The mixture was then filtered and concentrated in vacuo. The product 3-[3-amino-4-(2-diethylamino-ethylamino)-phenyl]-acrylic acid methyl ester was obtained in 67.3% yield (2.54 g). LCMS m/z: 571 ([M+H]$^+$).

Step 5

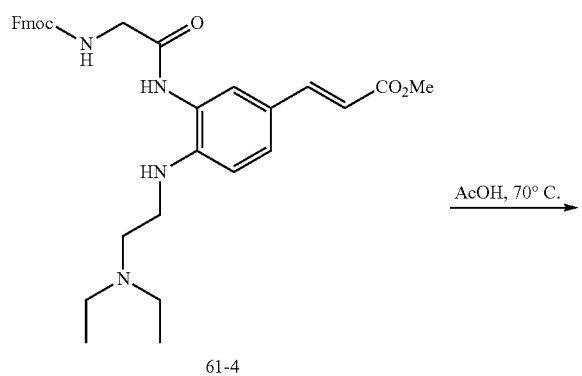

61-4

To a pre-stirred solution of 3-{1-(2-dethylamino-ethyl)-2-[(9H-fluoren-9-ylmethoxycarbonylamino)-methyl]-1H-benzoimidazol-5-yl}-acrylic acid methyl ester (61-5, 1.62 g, 2.94 mmol) and dichloromethane (8.90 mL) was added piperidine (1.45 mL, 14.69 mmol). When the reaction has completed, the mixture was concentrated in vacuo. The desired product was separated by reverse phase preparative HPLC. After lyopholyzation, 0.52 g (53.6%) of 3-[2-aminomethyl-1-(2-diethylamino-ethyl)-1H-benzoimidazol-5-yl]-acrylic acid methyl ester was obtained as powder. LCMS m/z: 331 ([M+H]$^+$).

Step 7

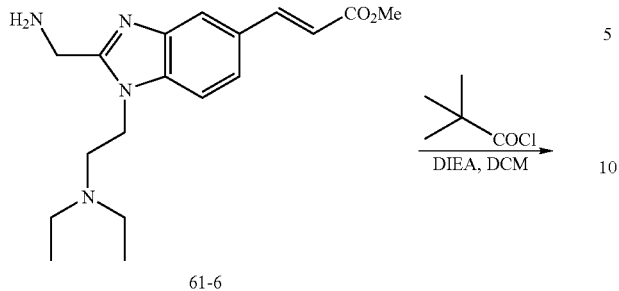

To a pre-stirred solution of 3-[2-aminomethyl-1-(2-diethylamino-ethyl)-1H-benzoimidazol-5-yl]-acrylic acid methyl ester (61-6, 0.10 g, 0.23 mmol), N,N-diisopropylethylamine (97 µL, 0.58 mmol) and dichloromethane (1.17 mL) was added 2,2-dimethyl-propionyl chloride (34.6 µL, 0.28 mmol) and the resulting reaction mixture was stirred at room temperature for 1 h. When the reaction has completed, ethyl acetate (20 mL) was added to dilute the mixture. The organic contents were washed with saturated sodium hydrogencarbonate (2×20 mL) and brine (2×20 mL), before drying in Na$_2$SO$_4$. The mixture was filtered and concentrated in vacuo. The product 3-{1-(2-diethylamino-ethyl)-2-[(2,2-dimethyl-propionylamino)-methyl]-1H-benzoimidazol-5-yl}-acrylic acid methyl ester (61-7) was obtained in 76.6% (74.1 mg). LCMS m/z: 415 ([M+H]$^+$).

Step 8

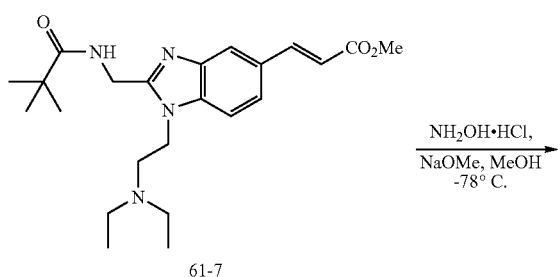

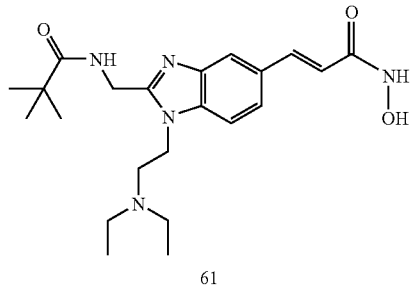

To a stirred solution of 3-{1-(2-diethylamino-ethyl)-2-[(2,2-dimethyl-propionylamino)-methyl]-1H-benzoimidazol-5-yl}-acrylic acid methyl ester (61-7, 73.8 mg, 0.18 mmol) and hydroxylamine hydrochloride (124 mg, 1.78 mmol) in MeOH (0.3 mL) was added sodium methoxide (30% in methanol) (0.8 mL, 3.6 mmol) at −78° C. The reaction mixture was then allowed to warm up slowly to room temperature. The reaction was monitored by LC/MS and was completed in around 15 min. 1N HCl was then added slowly into the reaction mixture at 0° C. The desired product was separated by reverse phase preparative HPLC. After lyopholyzation, 22.2 mg (24.3%) of 3-{1-(2-diethylamino-ethyl)-2-[(2,2-dimethyl-propionylamino)-methyl]-1H-benzoimidazol-5-yl}-N-hydroxy-acrylamide was obtained as powder. HPLC purity: 99.5%, t$_R$=0.94 min. LCMS m/z: 416 ([M+H]$^+$). $^1$H NMR (CD$_3$OD) δ 7.89 (s, 1H), 7.84 (d, J=8.5 Hz, 1H), 7.73 (d, J=8.4 Hz, 1H), 7.55 (d, J=15.8 Hz, 1H), 6.53 (d, J=15.8 Hz, 1H), 4.98 (t, J=7.3 Hz, 2H), 4.73 (s, 2H), 3.75 (t, J=7.5 Hz, 2H), 3.42 (q, J=7.2 Hz, 4H), 1.37 (t, J=7.3 Hz, 6H), 1.22 (s, 9H); $^{13}$C NMR (CD$_3$OD) δ 182.5, 168.9, 162.2, 161.9, 154.8, 140.8, 137.9, 135.0, 133.9, 126.0, 119.3, 117.1, 112.9, 50.9, 40.5, 39.7, 36.7, 27.6, 9.1.

EXAMPLE 58

Preparation of N-{2-[1-(2-Diethylamino-ethyl)-5-(2-hydroxycarbamoyl-vinyl)-1H-benzoimidazol-2-yl]-ethyl}-3,3-dimethyl-butyramide (59)

The titled compound (59) was prepared according to the procedures described in Example 57, by using appropriate starting materials. HPLC purity at 254 nm: 94.0%; t$_R$=0.99 min. LC-MS m/z: 444 ([M+H]$^+$).

EXAMPLE 59

Preparation of N-[1-(2-Diethylamino-ethyl)-5-(2-hydroxycarbamoyl-vinyl)-1H-benzoimidazol-2-ylmethyl]-butyramide (62)

The titled compound (62) was prepared according to the procedures described in Example 57, by using appropriate starting materials. HPLC purity at 254 nm: 85.1%; t$_R$=0.58 min; LCMS m/z: 402 ([M+H]$^+$). $^1$H NMR (CD$_3$OD) δ 7.88-7.56 (m, 2H), 7.73 (s, 1H), 7.60 (d, J=15.8 Hz, 1H), 6.51 (d, J=15.8 Hz, 1H), 4.99-4.79 (m, masked peaks), 4.81 (s, 2H), 3.74 (t, J=7.8 Hz, 2H), 3.46-3.41 (m, 4H), 2.31 (t, J=7.4 Hz, 2H), 1.39 (t, J=7.2 Hz, 6H), 0.95 (t, J=7.4 Hz, 3H); $^{13}$C NMR (CD$_3$OD) δ117.1, 165.9, 154.6, 140.9, 129.6, 128.4, 127.3, 125.9, 118.6, 112.8, 111.5, 50.7, 40.4, 38.4, 36.4, 19.9, 14.0, 9.0.

EXAMPLE 60

Preparation of 3-[2-(3,3-Dimethyl-butyl)-1-(2-ethylamino-ethyl)-1H-benzoimidazol-5-yl]-N-hydroxy-acrylamide (63)

The titled compound (63) was prepared according to the procedures described in Example 1, by using appropriate starting materials. HPLC: 99.0%; $t_R$=0.93 min; LCMS m/z: 359 ([M+H]$^+$). $^1$H NMR (CD$_3$OD) δ 7.5 (d, J=8.4 Hz, 1H), 7.75-7.74 (m, 2H), 7.16 (d, J=15.7 Hz, 1H), 6.31 (d, J=15.7 Hz, 1H), 4.89 (brs, 2H), 3.72 (brs, 2H), 3.29-3.18 (m, 4H), 1.90-1.86 (m, 2H), 1.35 (t, J=7.1 Hz, 3H), 1.09 (s, 9H); $^{13}$C NMR (CD$_3$OD) δ 165.7, 158.4, 140.4, 134.9, 134.5, 134.2, 126.2, 122.5, 119.2, 115.6, 113.4, 55.3, 44.0, 40.8, 40.7, 31.3, 29.3, 22.9.

EXAMPLE 61

Preparation of 3-[1-(2-Dimethylamino-ethyl)-2-(3,3-dimethyl-butyl)-1H-benzoimidazol-5-yl]-N-hydroxy-acrylamide (64)

The titled compound (64) was prepared according to the procedures described in Example 1, by using appropriate starting materials. HPLC: 99.0%; $t_R$=0.83 min; LCMS m/z: 359 ([M+H]$^+$). $^1$H NMR (CD$_3$OD) δ7.94 (d, J=7.8 Hz, 1H), 7.81 (s, 1H), 7.73 (d, J=7.9 Hz, 1H), 7.42 (d, J=15.7 Hz, 1H), 6.64 (d, J=15.7 Hz, 1H), 4.93 (brs, 2H), 3.76 (brs, 2H), 3.22 (t, J=7.7 Hz, 2H), 3.09 (s, 6H), 1.91-1.87 (m, 2H), 1.08 (s, 9H); $^{13}$C NMR (CD$_3$OD) δ 165.4, 158.4, 140.2, 134.5, 134.2, 133.2, 126.5, 118.8, 115.3, 113.9, 46.4, 45.1, 42.9, 40.6, 31.3, 29.2, 22.9, 11.4.

EXAMPLE 62

Preparation of 3-[1-(2-Dimethylamino-ethyl)-2-pentyl-1H-benzoimidazol-5-yl]-N-hydroxy-acrylamide (65)

The titled compound (65) was prepared according to the procedures described in Example 1, by using appropriate starting materials. HPLC purity at 254 nm: 98.5%; $t_R$=0.78 min. LCMS m/z: 345 ([M+H]$^+$). $^1$H NMR (DMSO-d$_6$) δ 0.89 (3H, m), 1.38 (4H, m), 1.83 (2H, m), 2.93 (6H, s), 3.04 (2H, m), 3.50 (2H, t), 4.70 (2H, m), 6.55 (1H, d), 7.57 (1H, d), 7.61 (1H, m), 7.81 (2H, m), 10.42 (1H, bs).

EXAMPLE 63

Preparation of 3-[1-(2-Dimethylamino-ethyl)-2-(2,2,2-trifluoro-ethyl)-1H-benzoimidazol-5-yl]-N-hydroxy-acrylamide (64)

The titled compound (64) was prepared according to the procedures described in Example 1, by using appropriate starting materials. HPLC purity at 254 nm: 91.1%; $t_R$=0.68 min. LCMS m/z: 357 ([M+H]$^+$).

EXAMPLE 64

Preparation of 3-[1-(2-Ethylamino-ethyl)-2-pentyl-1H-benzoimidazol-5-yl]-N-hydroxy-acrylamide (68)

The titled compound (68) was prepared according to the procedures described in Example 1, by using appropriate starting materials. HPLC purity at 254 nm: 98.4%; $t_R$=0.87 min. LCMS m/z: 345 ([M+H]$^+$).

EXAMPLE 65

Preparation of N-Hydroxy-3-[1-(2-isopropylamino-ethyl)-2-pentyl-1H-benzoimidazol-5-yl]-acrylamide (71)

The titled compound (71) was prepared according to the procedures described in Example 1, by using appropriate starting materials. HPLC purity at 254 nm: 97.4%; $t_R$=0.95 min. LCMS m/z: 359 ([M+H]$^+$). $^1$H NMR (DMSO-d$_6$) δ 0.89 (3H, m), 1.22 (6H, d), 1.38 (4H, m), 1.82 (2H, m), 2.99 (3H, m), 4.56 (2H, m), 6.51 (1H, d), 7.59 (2H, d), 7.64 (1H, m), 7.88 (1H, m), 8.74 (2H, bs).

EXAMPLE 66

Preparation of 3-[2-Hexyl-1-(2-methylamino-ethyl)-1H-benzoimidazol-5-yl]-N-hydroxy-acrylamide (74)

The titled compound (74) was prepared according to the procedures described in Example 1, by using appropriate starting materials. HPLC purity at 254 nm: 96.0%, $t_R$=1.12 min. LCMS m/z: 345 ([M+H]$^+$). $^1$H NMR (CD$_3$OD) δ 7.76 (2H, s), 7.70 (1H, d, J=8.6 Hz). 7.50 (1H, d, J=15.7 Hz), 6.43 (1H, d, J=15.7 Hz), 4.81 (2H, d, J=5.7 Hz), 3.49 (2H, bs), 3.15 (2H, dt, J=4.8 Hz), 2.71 (3H, s), 1.85 (2H, qn, J=5.1 Hz), 1.46 (2H, m), 1.33 (4H, m), 0.85 (3H, t, J=7.1 Hz); $^{13}$C NMR (CD$_3$OD) δ 163.7, 157.8, 138.5, 132.7, 124.2, 117.6, 113.7, 111.2, 40.2, 32.2, 30.5, 28.0, 25.6, 25.1, 21.6, 12.3.

EXAMPLE 67

Preparation of N-Hydroxy-3-[1-(2-methylamino-ethyl)-2-pentyl-1H-benzoimidazol-5-yl]-acrylamide (75)

The titled compound (75) was prepared according to the procedures described in Example 1, by using appropriate starting materials. HPLC purity at 254 nm: 97.8%; $t_R$=0.80 min. LCMS m/z: 331 ([M+H]$^+$). $^1$H NMR (DMSO-d$_6$) δ 0.89 (3H, m), 1.38 (4H, m), 1.84 (2H, m), 2.51 (3H, s), 3.14 (2H, m), 3.38 (2H, t), 4.70 (2H, m), 6.57 (1H, d), 7.62 (1H, d), 7.73 (1H, m), 7.96 (2H, m), 9.13 (2H, s).

EXAMPLE 68

Preparation of 3-(2-Butyl-1-pyrrolidin-3-yl-1H-benzoimidazol-5-yl)-N-hydroxy-acrylamide (69)

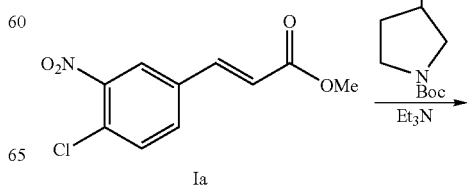

Ia

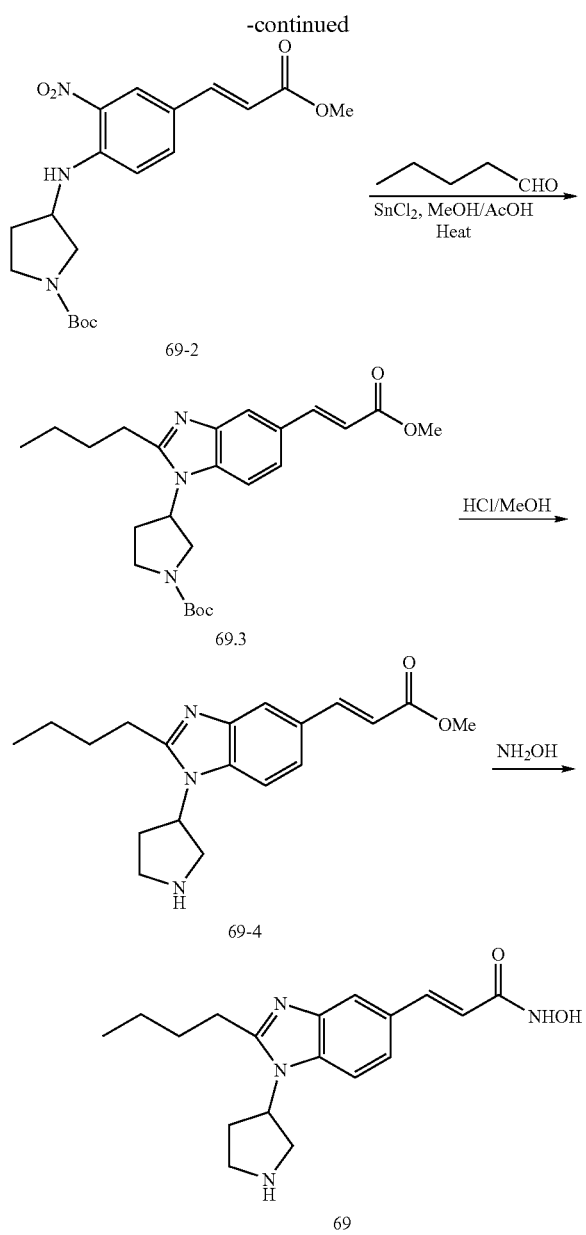

Step 1.

To a solution of methyl trans-4-Chloro-3-nitrocinnamate (Ia, 4.8 g, 20 mmol) in triethyl amine (5.5 mL, 40 mmol) was added 3-Amino-pyrrolidine-1-carboxylic acid tert-butyl ester (11.2 g, 60 mmol), the resulting mixture was then heated to 100° C. for 8 hours, then another portion of methyl trans-4-Chloro-3-nitrocinnamate (4.8 g, 20 mmol) and triethyl amine (5.5 mL, 40 mmol) was added, the resulting mixture was allowed to stir overnight at 100° C., then reaction was quenched by adding 200 mL of DCM and 80 mL of 1M HCl solution. After separation of DCM layer, the aqueous solution was extracted with DCM one more time, and combined with previous DCM solution, which was then washed with brine, dried over sodium sulfate, then filtered through silica gel short column, and rinsed with ethyl acetate and hexanes mixture (2:1) until the orange color band was completely rinsed down. After removal of solvent under reduced pressure, the residue 69-2 was obtained (around 80% of yield in most of cases) as orange solid, which is pure enough (95% purity from HPLC) for next step. LC-MS m/z: 292 ([M-Boc+H]$^+$).

Step 2.

To a solution of compound 69-2 (7.84 g, 20.0 mmol) in 100 mL of MeOH and AcOH mixture (1:9) was added corresponding aldehyde (3.0 mL, 30.0 mmol) and tin chloride (22.6 g, 100 mmol), the resulting mixture was stirred at 42° C. for 24 hrs. Then the mixture was diluted using ethyl acetate (300 mL) at room temperature, and was then quenched with sat. sodium carbonate (30 mL). The resulting mixture was stirred for additional 1 hour, then organic layer was decanted to another conic flask. Solid left in reaction flask was suspension with another portion of ethyl acetate (300 mL), which was then decanted and combined with previous portion of ethyl acetate and was then filtered through silica gel short column and rinsed with ethyl acetate, after removal of filtrate under reduced pressure, the residue was pure enough for next step and also could be purified on column (hexanes: EtOAc=1:2) to give a pale-yellow solid 69-3 (3.8 g, 44%). LC-MS m/z: 456 ([M+H]$^+$).

Step 3.

To a flask charged with compound 69-3 (456 mg, 1 mmol) was added 1.25 M HCl in MeOH (4 mL), the resulting mixture was then heated to reflux for 2 hours, which was then evaporated to dryness under reduced pressure to give compound 4 as HCl salt, which is pure enough for next step without any purification. LC-MS m/z: 356 ([M+H]$^+$).

Step 4.

To a solution of above crude 69-4 (around 0.16 mmol) product in MeOH (0.5 mL) was added a pre-prepared NH$_2$OH stock solution (2.0 M, 2 mL). The resulting mixture was stirred at room temperature for 2 hrs. After quenching with TFA (0.4 mL), the resulting mixture was subjected to HPLC purification to afford 25 mg of 3-(2-Butyl-1-pyrrolidin-3-yl-1H-benzoimidazol-5-yl)-N-hydroxy-acrylamide. HPLC purity: 98%; LC-MS m/z: 329 ([M+H]$^+$). $^1$H NMR (CD$_3$OD) δ 0.95 (3H, t, J=7.2 Hz), 1.46 (2H, m), 1.77 (2H, m), 2.52-2.82 (2H, m), 3.10-3.17 (2H, m), 3.48 (1H, m), 3.80 (2H, m), 5.55 (1H, m), 6.48 (1H, d, J=16.0 Hz), 7.58 (1H, d, J=16.0 Hz), 7.67 (1H, d, J=8.0 Hz), 7.78-7.92 (2H, m).

EXAMPLE 69

Preparation of 3-(2-Butyl-1-piperidin-4-yl-1H-benzoimidazol-5-yl)-N-hydroxy-acrylamide (70)

The titled compound (70) was prepared according to the procedures described in Example 78, by using appropriate starting materials. HPLC purity: 98%; LCMS m/z: 343 ([M+H]$^+$). $^1$H NMR (CD$_3$OD) δ 0.96 (3H, t, J=7.2 Hz), 1.46 (2H, m), 1.79 (2H, m), 2.21 (2H, m), 2.82 (2H, m), 3.10-3.17 (2H, m), 3.26 (1H, m), 3.60 (2H, m), 4.96 (1H, m), 6.49 (1H, d, J=15.8 Hz), 7.60 (1H, d, J=15.8 Hz), 7.66 (1H, d, J=8.0 Hz), 7.82 (1H, s) (1H, d, J=8.0 Hz).

EXAMPLE 70

Preparation of 3-(2-Hexyl-1-pyrrolidin-3-yl-1H-benzoimidazol-5-yl)-N-hydroxy-acrylamide (80)

The titled compound (80) was prepared according to the procedures described in Example 68, by using appropriate starting materials. HPLC purity: 98%; LCMS m/z: 357 ([M+H]$^+$). $^1$H NMR (CD$_3$OD) δ 0.84 (3H, t, J=7.2 Hz), 1.22-1.38 (4H, m), 1.44 (2H, m), 1.81 (2H, m), 2.52-2.82 (2H, m), 3.10-3.17 (2H, m), 3.48 (1H, m), 3.80 (2H, m), 5.56 (1H, m), 6.48 (1H, d, J=15.8 Hz), 7.56 (1H, d, J=15.8 Hz), 7.65 (1H, d, J=9.2 Hz), 7.84 (1H, s), 7.90 (1H, d, J=9.2 Hz).

EXAMPLE 71

Preparation of 3-[2-Butyl-1-(1-methyl-pyrrolidin-3-yl)-1H-benzoimidazol-5-yl]-N-hydroxy-acrylamide (81)

The titled compound (81) was prepared according to the procedures described in Example 68, by using 69-4 via reductive amination to introduce a methyl group. HPLC purity: 98%; LCMS m/z: 343 ([M+H]$^+$). $^1$H NMR (CD$_3$OD) δ 0.99 (3H, t, J=7.2 Hz), 1.52 (2H, m), 1.83 (2H, m), 2.65-2.92 (2H, m), 3.09 (3H, s), 3.15-3.25 (2H, m), 3.58 (1H, br.), 3.90 (2H, m), 5.73 (1H, m), 6.51 (1H, d, J=16.0 Hz), 7.58 (1H, d, J=16.0 Hz), 7.69 (1H, d, J=8.0 Hz), 7.88 (1H, s), 8.00 (1H, d, J=9.2 Hz).

EXAMPLE 72

Preparation of 3-(2-Hexyl-1-piperidin-3-yl-1H-benzoimidazol-5-yl)-N-hydroxy-acrylamide (82)

The titled compound (82) was prepared according to the procedures described in Example 68, by using appropriate starting materials. HPLC purity: 97%; LCMS m/z: 343 ([M+H]$^+$). $^1$H NMR (CD$_3$OD) δ 0.99 (3H, t, J=7.2 Hz), 1.52 (2H, m), 1.84 (2H, m), 2.04 (1H, m), 2.20 (2H, m), 2.61 (1H, m), 3.12-3.22 (2H, m), 3.49 (1H, m), 3.67 (1H, m), 3.78 (1H, t, J=12.0 Hz), 4.98 (1H, m), 6.53 (1H, d, J=15.8 Hz), 7.63 (1H, d, J=15.8 Hz), 7.70 (1H, d, J=9.2 Hz), 7.86 (1H, s), 8.06 (1H, d, J=8.8 Hz).

EXAMPLE 73

Preparation of 3-(2-Butyl-1-piperidin-3-yl-1H-benzoimidazol-5-yl)-N-hydroxy-acrylamide (83)

The titled compound (83) was prepared according to the procedures described in Example 68, by using appropriate starting materials. HPLC purity: 97%; LCMS m/z: 371 ([M+H]$^+$). $^1$H NMR (CD$_3$OD) δ 0.88 (3H, t, J=7.2 Hz), 1.22-1.42 (4H, m), 1.47 (2H, m), 1.84 (2H, m), 2.04 (1H, m), 2.20 (2H, m), 2.62 (1H, m), 3.12-3.22 (2H, m), 3.48 (1H, m), 3.68 (1H, m), 3.78 (1H, t, J=12.0 Hz), 5.01 (1H, m), 6.53 (1H, d, J=15.8 Hz), 7.62 (1H, d, J=15.8 Hz), 7.70 (1H, d, J=9.2 Hz), 7.86 (1H, s), 8.06 (1H, d, J=8.8 Hz).

EXAMPLE 74

Preparation of (E)-N-hydroxy-3-(1-(1-methylpiperidin-3-yl)-2-pentyl-1H-benzo[d]imidazol-5-yl)acrylamide (86)

The titled compound (86) was prepared according to the procedures described in Example 71, by using appropriate starting materials. HPLC purity: 99.3%, t$_R$=1.06 min; LCMS m/z: 371 ([M+H]$^+$). $^1$H NMR (CD$_3$OD) δ 8.18 (d, J=7.9 Hz, 1H), 7.92 (s, 1H), 7.77 (d, J=8.1 Hz, 1H), 7.61 (d, J=15.7 Hz, 1H), 6.58 (d, J=15.7 Hz, 1H), 5.21 (brs, 1H), 3.69 (brs, 2H), 3.69-3.66 (m, 1H), 3.37-3.27 (masked peaks), 3.03 (s, 3H), 2.66 (brs, 1H), 2.29-2.22 (m, 3H), 1.94-1.90 (m, 2H), 1.54-0.94 (m, 4H), 0.96 (t, J=7.1 Hz, 3H); $^{13}$C NMR (CD$_3$OD) δ165.6, 157.6, 139.9, 134.6, 134.1, 132.5, 126.3, 120.4, 115.5, 115.2, 54.9, 54.4, 53.3, 44.1, 32.4, 27.5, 27.3, 26.8, 23.2, 23.1, 14.2.

EXAMPLE 75

Preparation of (E)-3-(2-hexyl-1-(1-(2-hydroxyethyl) piperidin-3-yl)-1H-benzo[d]imidazol-5-yl)-N-hydroxyacrylamide (90)

The titled compound (90) was prepared according to the procedures described in Example 68, by using appropriate starting materials and alkylation of the piperidine with 2-bromoethanol. LCMS m/z: 415 ([M+H]$^+$).

EXAMPLE 76

Preparation of N-Hydroxy-3-[1-(1-pentyl-piperidin-3-yl)-1H-benzoimidazol-5-yl]-acrylamide (94)

The titled compound (94) was prepared according to the procedures described in Example 68, by using appropriate starting materials (formic acid for benzimidazole ring formation and reductive amination of the piperidine with pentanal). HPLC purity: 95%; LC-MS m/z: 357 ([M+H]$^+$). $^1$H NMR (CD$_3$OD) δ 9.04 (s, 1H), 7.94 (brs, 2H), 7.78 (d, 1H, J=8.2 Hz), 7.70 (d, 1H, J=15.7 Hz), 6.57 (d, 1H, J=15.9 Hz), 5.14-5.10 (m, 1H), 3.85 (dd, 2H, J=88.0, 9.0 Hz), 3.48-3.13 (m, 4H), 2.43-2.12 (m, 4H), 1.94-1.80 (m, 2H), 1.39-1.29 (m, 4H), 0.94 (t, 3H, J=6.8 Hz).

EXAMPLE 77

Preparation of N-Hydroxy-3-[1-(1-phenethyl-piperidin-3-yl)-1H-benzoimidazol-5-yl]-acrylamide (96)

The titled compound (96) was prepared according to the procedures described in Example 76, by using appropriate starting materials. HPLC purity: 98.6%; LC-MS m/z: 391 ([M+H]$^+$). $^1$H NMR (CD$_3$OD) δ 8.93 (s, 1H), 7.95 (s, 1H), 7.91 (d, 1H, J=8.5 Hz), 7.76 (d, 1H, J=8.5 Hz), 7.70 (d, 1H, J=15.8 Hz), 7.35-7.24 (m, 6H), 6.56 (d, 1H, J=15.7 Hz), 5.10 (t, 1H, J=11.4 Hz), 3.91 (dd, 2H), 3.55-3.45 (m, 2H), 3.15-3.11 (m, 2H), 2.46-2.13 (m, 6H).

EXAMPLE 78

Preparation of N-Hydroxy-3-{1-[1-(3-phenyl-propyl)-piperidin-3-yl]-1H-benzoimidazol-5-yl}-acrylamide (97)

The titled compound (97) was prepared according to the procedures described in Example 76, by using appropriate starting materials. HPLC purity: 94.5%; LC-MS: 405 ([M+H]$^+$) $^1$H NMR (CD$_3$OD) δ 8.68 (s, 1H), 7.94 (s, 1H), 7.80 (d, 1H, J=8.4 Hz), 7.71 (d, 1H, J=15.7 Hz), 7.69 (d, 1H, J=8.2 Hz), 7.31-7.17 (m, 6H), 6.54 (d, 1H, J=15.6 Hz), 3.71 (dd, 2H, J=66 Hz, 10.9 Hz), 3.48-3.40 (m, 1H), 3.13-3.05 (m, 2H), 2.73 (t, 2H, J=7.4 Hz), 2.38-2.04 (m, 8H).

EXAMPLE 79

Preparation of 3-{1-[1-(3,3-Dimethyl-butyl)-pyrrolidin-3-yl]-1H-benzoimidazol-5-yl}-N-hydroxy-acrylamide (99)

The titled compound (99) was prepared according to the procedures described in Example 76, by using appropriate starting materials. HPLC purity: 91.9%; t$_R$=1.10 min. LC-MS m/z: 357 ([MH]$^+$). $^1$H NMR (DMSO-d$_6$) δ 0.91 (9H, s), 1.52

(4H, m), 3.09 (1H, m), 3.29 (6H, m), 6.52 (1H, d), 7.43 (2H, m), 7.62 (1H, m), 7.80 (1H, m), 8.82 (1H, s), 10.25 (1H, bs).

EXAMPLE 80

Preparation of 3-{1-[2-(Ethyl-methyl-amino)-ethyl]-2-pentyl-1H-benzoimidazol-5-yl}-N-hydroxy-acrylamide (79)

The titled compound (79) was prepared according to the procedures described in Example 1, by using appropriate starting materials. HPLC purity: 99%; $t_R$=0.68 min. LC-MS m/z: 359 ([M+H]$^+$). $^1$H NMR (DMSO-d$_6$) δ 0.89 (3H, m), 1.23 (3H, m), 1.38 (4H, m), 1.84 (2H, m), 2.92 (3H, s), 3.10 (2H, m), 3.28 (2H, m), 3.52 (2H, m), 4.77 (2H, m), 6.58 (1H, d), 7.61 (1H, d), 7.71 (1H, m), 7.92 (2H, m), 10.48 (1H, bs).

EXAMPLE 81

Preparation of 3-{2-Butyl-1-[2-(ethyl-methyl-amino)-ethyl]-1H-benzoimidazol-5-yl}-N-hydroxy-acrylamide (85)

The titled compound (85) was prepared according to the procedures described in Example 1, by using appropriate starting materials. HPLC purity: 95.8%; $t_R$=1.04 min. LC-MS m/z: 345 ([M+H]$^+$). $^1$H NMR (DMSO-d$_6$) δ 0.95 (3H, m), 1.25 (3H, m), 1.46 (2H, m), 1.81 (2H, m), 2.92 (3H, s), 3.13 (2H, m), 3.27 (2H, m), 3.54 (2H, m), 4.80 (2H, m), 6.60 (1H, d), 7.62 (1H, d), 7.75 (1H, m), 7.92 (2H, m), 10.59 (1H, bs).

EXAMPLE 82

Preparation of 3-(2-Butyl-1-{2-[ethyl-(3-hydroxy-propyl)-amino]-ethyl}-1H-benzoimidazol-5-yl)-N-hydroxy-acrylamide (91)

The titled compound (91) was prepared according to the procedures described in Example 1, by using appropriate starting materials. HPLC purity: 93.5%; $t_R$=0.50 min. LC-MS (m/z): 389 ([MH]$^+$). $^1$H NMR (DMSO-d$_6$) δ 0.94 (3H, m), 1.25 (3H, m), 1.46 (2H, m), 1.83 (4H, m), 3.04 (2H, m), 3.31 (4H, m), 3.50 (4H, m), 4.72 (2H, m), 6.54 (1H, d), 7.61 (1H, m), 7.69 (1H, m), 7.80 (1H, m), 7.90 (1H, m), 10.20 (1H, bs).

EXAMPLE 83

Preparation of 3-(1-{2-[Ethyl-(3-hydroxy-propyl)-amino]-ethyl}-2-pentyl-1H-benzoimidazol-5-yl)-N-hydroxy-acrylamide (92)

The titled compound (92) was prepared according to the procedures described in Example 1, by using appropriate starting materials. HPLC purity: 93.5%; $t_R$=0.50 min. LC-MS (m/z): 389 ([M+H]$^+$) $^1$H NMR (DMSO-d$_6$) δ 0.94 (3H, m), 1.25 (3H, m), 1.46 (2H, m), 1.83 (4H, m), 3.04 (2H, m), 3.31 (4H, m), 3.50 (4H, m), 4.72 (2H, m), 6.54 (1H, d), 7.61 (1H, m), 7.69 (1H, m), 7.80 (1H, m), 7.90 (1H, m), 10.20 (1H, bs).

EXAMPLE 84

Preparation of 3-{1-[2-(Butyl-ethyl-amino)-ethyl]-1H-benzoimidazol-5-yl}-N-hydroxy-acrylamide (95)

The titled compound (95) was prepared according to the procedures described in Example 76, by using appropriate starting materials. HPLC purity: 99.9%; LC-MS m/z: 331 ([M+H]$^+$). $^1$H NMR (CD$_3$OD) δ 9.29 (s, 1H), 7.99-7.95 (m, 2H), 7.82 (d, 1H, J=8.5 Hz), 7.56 (d, 1H, J=15.6 Hz), 6.53 (d, 1H, J=15.5 Hz), 5.0-4.95 (m, 2H), 3.86-3.78 (m, 2H), 3.42 (dd, 2H, J=13.3, 7.1 Hz), 3.28-3.26 (m, 2H), 1.74-1.71 (m, 2H), 1.43 (qt, 2H, J=7.4, 3.8 Hz), 1.38 (t, 3H, J=7.2 Hz), 1.00 (t, 3H, J=7.3 Hz).

EXAMPLE 85

Preparation of 3-[2-(4-Cyano-butyl)-1-(2-diethylamino-ethyl)-1H-benzoimidazol-5-yl]-N-hydroxy-acrylamide (101)

The titled compound (101) was prepared according to the procedures described in Example 57, by using appropriate starting materials. HPLC purity at 254 nm: 99.9%. LC-MS (ESI) m/z: 384 ([M+H]$^+$). $^1$H NMR (CD$_3$OD) δ 7.78 (1H, s) 7.76 (1H, d, J=8.5 Hz), 7.63 (1H, d, J=16.9 Hz), 7.58 (1H, d. J=5.1 Hz), 6.44 (1H, d, J=15.3 Hz), 4.70 (2H, in water peak), 3.50 (2H, t, J=7.6 Hz), 3.32 (4H, qt, J=7.3 Hz), 3.07 (2H, t, J=8.0 Hz), 2.50 (2H, t, J=7.0 Hz), 1.99 (2H, q, J=7.5 Hz), 1.78 (2H, q, J=7.3 Hz), 1.29 (6H, t, J=7.3 Hz).

EXAMPLE 86

Preparation of 3-{1-[2-(Butyl-isopropyl-amino)-ethyl]-1H-benzoimidazol-5-yl}-N-hydroxy-acrylamide (108)

The titled compound (108) was prepared according to the procedures described in Example 76, by using appropriate starting materials. HPLC purity: 98.8%; $t_R$=1.33 min. LC-MS m/z: 345 ([M+H]$^+$). $^1$H NMR (DMSO-d$_6$) δ 0.90 (3H, m), 1.25 (6H, d), 1.35 (2H, m), 1.64 (2H, m), 3.09 (2H, m), 3.51 (1H, m), 3.73 (2H, m), 4.74 (2H, m), 6.52 (1H, d), 7.53 (2H, m), 7.64 (1H, m), 7.80 (1H, m), 8.62 (1H, m), 9.40 (1H, bs), 10.72 (1H, bs).

EXAMPLE 87

Preparation of N-Hydroxy-3-{1-[2-(isopropyl-pentyl-amino)-ethyl]-1H-benzoimidazol-5-yl}-acrylamide (109)

The titled compound (109) was prepared according to the procedures described in Example 76, by using appropriate starting materials. LC-MS m/z: 359 ([M+H]$^+$). $^1$H NMR (DMSO-d$_6$) δ 0.88 (3H, t), 1.25 (10H, m), 1.64 (2H, m), 3.12 (2H, m), 3.51 (1H, b), 3.60 (1H, b), 3.73 (1H, b), 4.74 (2H, t), 6.51 (1H, d), 7.59 (1H, s), 7.63 (1H, d), 7.80 (1H, d), 7.93 (1H, s), 8.65 (1H, s), 9.46 (1H, b).

EXAMPLE 88

Preparation of 3-[2-(5-Cyano-pentyl)-1-(2-diethylamino-ethyl)-1H-benzoimidazol-5-yl]-N-hydroxy-acrylamide (110)

The titled compound (110) was prepared according to the procedures described in Example 57, by using appropriate starting materials. HPLC purity at 254 nm: 95.4%. LC-MS (ESI) m/z: 347 ([M+H]$^+$). $^1$H NMR (CD$_3$OD) δ 7.96 (1H, d, J=8.5 Hz), 7.90 (1H, s) 7.81 (1H, d, J=8.5 Hz), 7.59 (1H, d. J=15.6 Hz), 6.55 (1H, d, J=15.5 Hz), 4.96 (2H, t, J=7.3 Hz), 3.69 (2H, t, J=7.1 Hz), 3.44 (4H, qt, J=7.2 Hz), 3.31 (2H, embedded in MeOD peak), 2.51 (2H, t, J=6.9 Hz), 2.05-1.98 (2H, m), 1.78 (2H, m, J=7.4 Hz), 1.70 (2H, m, J=6.4 Hz), 1.41 (3H, t, J=7.2 Hz).

EXAMPLE 89

Preparation of 3-(1-{2-[(3,3-Dimethyl-butyl)-ethyl-amino]-ethyl}-1H-benzoimidazol-5-yl)-N-hydroxy-acrylamide (111)

The titled compound (111) was prepared according to the procedures described in Example 76, by using appropriate starting materials. TFA salt. HPLC purity: 97.7%; LC-MS m/z: 359 ([M+H]$^+$). $^1$H NMR (CD$_3$OD) δ 9.10 (s, 1H), 7.89 (d, 1H, J=8.9 Hz), 7.88 (s, 1H), 7.74 (d, 1H, J=8.6 Hz), 7.51 (d, 1H, J=15.7 Hz), 6.46 (d, 1H, J=15.7 Hz), 4.98-4.93 (m, 2H), 3.77-3.75 (m, 2H), 3.38 (dd, 2H, J=13.3, 7.2 Hz), 3.22-3.18 (m, 2H), 1.60-1.59 (m, 2H), 1.33 (t, 3H, J=7.1 Hz), 0.91 (s, 9H).

HCl salt. $^1$H NMR (DMSO-d$_6$) δ 9.90 (bs, 1H), 8.65 (s, 1H), 7.93 (s, 1H), 7.82 (d, 1H, J=8.5 Hz), 7.64 (d, 1H, J=8.1 Hz), 7.61 (d, 1H, J=15.6 Hz), 7.52 (d, 1H, J=15.8 Hz), 4.76-4.72 (t, 2H, J=7.0), 3.65-3.60 (m, 2H), 3.32-3.24 (m, 2H), 3.17-3.08 (m, 2H), 1.52-1.47 (m, 2H), 1.22 (t, 3H, J=7.2 Hz), 0.87 (s, 9 Hz).

EXAMPLE 90

Preparation of 3-{1-[2-(Ethyl-propyl-amino)-ethyl]-1H-benzoimidazol-5-yl}-N-hydroxy-acrylamide (112)

The titled compound (112) was prepared according to the procedures described in Example 76, by using appropriate starting materials. HPLC purity: 98.1%; LC-MS m/z: 315 ([M+H]$^+$). $^1$H NMR (CD$_3$OD) δ 9.43 (s, 1H), 7.99 (d, 1H, J=8.5 Hz), 7.93 (s, 1H), 7.82 (d, 1H, J=8.5 Hz), 7.53 (d, 1H, J=15.7 Hz), 6.50 (d, 1H, J=15.5 Hz), 5.00-4.96 (m, 2H), 3.78 (t, 2H, J=6.1 Hz), 3.37 (dd, 2H, J=14.2, 7.2 Hz), 3.22-3.19 (m, 2H), 1.75 (qt, 2H, J=7.5 Hz), 1.33 (t, 3H, J=7.2 Hz), 0.99 (t, 3H, J=7.3 Hz).

EXAMPLE 91

Preparation of N-Hydroxy-3-(1-{2-[isopropyl-(2-methyl-pentyl)-amino]-ethyl}-1H-benzoimidazol-5-yl)-acrylamide (113)

The titled compound (113) was prepared according to the procedures described in Example 76, by using appropriate starting materials. LC-MS m/z: 373-[(M+H)$^+$]]. $^1$H NMR (DMSO-d$_6$) δ 0.86-0.97 (7H, m), 1.14-1.28 (12H, m), 4.70 (2H, b), 6.49 (1H, d), 7.58-7.62 (2H, m), 7.73 (1H, d), 7.91 (1H, s), 8.48 (1H, s).

EXAMPLE 92

Preparation of 3-{1-[2-(Ethyl-hexyl-amino)-ethyl]-2-methyl-1H-benzoimidazol-5-yl}-N-hydroxy-acrylamide (116)

The titled compound (116) was prepared according to the procedures described in Example 57, by using appropriate starting materials. HPLC purity at 254 nm: 98.2%, t$_R$=1.27 min. LC-MS (ESI) m/z: 373 ([M+H]$^+$). $^1$H NMR (CD$_3$OD) δ 7.85 (1H, s), 7.78 (1H, d, J=8.4 Hz), 7.70 (1H, d, J=8.7 Hz), 7.15 (1H, d, J=15.9 Hz), 6.53 (1H, d, J=15.9 Hz), 4.81 (2H), 3.63 (2H, t, J=7.7 Hz), 3.41 (2H, qt, J=7.2 Hz), 3.29 (2H), 2.82 (3H, s), 1.74 (2H, m), 1.37 (11H, m), 0.93 (3H, t, J=6.9 Hz).

EXAMPLE 93

Preparation of 3-{1-[2-(Butyl-ethyl-amino)-ethyl]-2-trifluoromethyl-1H-benzoimidazol-5-yl}-N-hydroxy-acrylamide (117)

The titled compound (117) was prepared according to the procedures described in Example 57, by using appropriate starting materials. HPLC purity at 254 nm: 97.3%, t$_R$=1.50 min. LC-MS (ESI) m/z: 399 ([M+H]$^+$). $^1$H NMR (CD$_3$OD) δ 7.95 (1H, s), 7.70 (2H, s), 7.62 (1H, d, J=15.9 Hz), 6.46 (1H, d, J=15.8 Hz), 5.24 (2H), 3.50 (2H, t, J=8.8 Hz), 3.31 (2H, qt, J=7.2 Hz), 3.17 (2H), 1.63 (2H, m), 1.35 (2H, qt, J=7.5 Hz), 1.29 (3H, t, J=7.2 Hz), 0.92 (3H, t, J=7.4 Hz).

EXAMPLE 94

Preparation of 3-{1-[2-(Ethyl-hexyl-amino)-ethyl]-2-trifluoromethyl-1H-benzoimidazol-5-yl}-N-hydroxy-acrylamide (118)

The titled compound (118) was prepared according to the procedures described in Example 57, by using appropriate starting materials. HPLC purity at 254 nm: 94.6%, t$_R$=2.07 min. LC-MS (ESI) m/z: 427 ([M+H]$^+$). $^1$H NMR (CD$_3$OD) δ 8.04 (1H, s), 7.80 (2H, s), 7.72 (1H, d, J=15.8 Hz), 6.56 (1H, d, J=15.6 Hz), 4.85 (2H), 3.61 (2H, t, J=8.5 Hz), 3.42 (2H, qt, J=7.2 Hz), 3.26 (2H), 1.75 (2H, m), 1.39 (9H, m, J=7.5 Hz), 0.93 (3H, t, J=7.0 Hz).

EXAMPLE 95

Preparation of 3-[1-(2-Dipropylamino-ethyl)-1H-benzoimidazol-5-yl]-N-hydroxy-acrylamide (120)

The titled compound (120) was prepared according to the procedures described in Example 76, by using appropriate starting materials. HPLC purity: 100%. LC-MS m/z: 331 ([M+H]$^+$). $^1$H NMR (DMSO-d$_6$) δ 0.86 (6H, d), 1.64 (4H, m), 3.09 (4H, m), 3.60 (2H, m), 4.76 (2H, m), 6.53 (1H, d), 7.55 (2H, m), 7.65 (1H, m), 7.88 (1H, m), 8.75 (1H, m), 9.93 (1H, bs).

EXAMPLE 96

Preparation of N-Hydroxy-3-(1-{2-[isopropyl-(3-methyl-butyl)-amino]-ethyl}-1H-benzoimidazol-5-yl)-acrylamide (121)

The titled compound (121) was prepared according to the procedures described in Example 76, by using appropriate starting materials. HPLC purity: 98.7%; t$_R$=1.02 min. LC-MS (m/z): 358 ([M+H]$^+$). $^1$H NMR (DMSO-d$_6$) δ 0.88 (6H, d), 1.28 (6H, m), 1.59 (3H, m), 3.10 (3H, m), 3.68 (2H, m), 4.71 (2H, m), 6.50 (1H, d), 7.50 (2H, m), 7.59 (1H, m), 7.63 (1H, m), 8.52 (1H, m), 9.50 (1H, bs), 10.70 (1H, bs).

EXAMPLE 97

Preparation of 3-(1-{2-[(3,3-Dimethyl-butyl)-methyl-amino]-ethyl}-1H-benzoimidazol-5-yl)-N-hydroxy-acrylamide (122)

The titled compound (122) was prepared according to the procedures described in Example 76, by using appropriate starting materials. HPLC purity at 254 nm: 97.8%; $t_R$=0.93 min. LC-MS m/z: 345 ([M+H]$^+$). $^1$H NMR (DMSO-d$_6$) δ 0.84 (9H, s), 1.52 (2H, m), 2.90 (3H, s), 3.17 (2H, m), 3.68 (2H, m), 4.80 (2H, m), 6.58 (1H, d), 7.59 (2H, m), 7.86 (1H, m), 7.90 (1H, m), 8.82 (1H, m), 10.10 (1H, bs).

EXAMPLE 98

Preparation of 3-(1-{2-[(2-Ethyl-butyl)-methyl-amino]-ethyl}-1H-benzoimidazol-5-yl)-N-hydroxy-acrylamide (123)

The titled compound (123) was prepared according to the procedures described in Example 76, by using appropriate starting materials. HPLC purity at 254 nm: 97.7%; $t_R$=0.87 min. LC-MS m/z: 345 ([M+H]$^+$). $^1$H NMR (DMSO-d$_6$) δ 0.81 (6H, m), 1.29 (4H, m), 1.69 (1H, m), 2.89 (3H, s), 3.08 (2H, m), 3.59 (2H, m), 4.77 (2H, m), 6.53 (1H, d), 7.52 (2H, m), 7.86 (1H, m), 7.94 (1H, m), 8.80 (1H, m), 9.54 (1H, bs).

EXAMPLE 99

Preparation of 3-{1-[2-(3,3-Dimethyl-butylamino)-ethyl]-1H-benzoimidazol-5-yl}-N-hydroxy-acrylamide (126)

The titled compound (126) was prepared according to the procedures described in Example 76, by using appropriate starting materials. HPLC purity: 100%; $t_R$=1.01 min. LC-MS m/z: 331 ([M+H]$^+$). $^1$H NMR (DMSO-d$_6$) δ 0.88 (9H, s), 1.44 (2H, m), 2.92 (2H, m), 3.50 (2H, m), 4.66 (2H, m), 6.54 (1H, d), 7.58 (2H, m), 7.82 (1H, m), 7.90 (1H, m), 8.74 (1H, m).

EXAMPLE 100

Preparation of N-Hydroxy-3-{1-[2-(methyl-pent-4-enyl-amino)-ethyl]-1H-benzoimidazol-5-yl}-acrylamide (127)

The titled compound (127) was prepared according to the procedures described in Example 76, by using appropriate starting materials. HPLC purity: 100%; $t_R$=0.92 min. LC-MS m/z: 329 ([M+H]$^+$). $^1$H NMR (DMSO-d$_6$) δ 1.17 (2H, m), 2.06 (2H, m), 2.90 (3H, s), 3.10 (2H, m), 3.65 (2H, m), 4.80 (2H, m), 5.03 (2H, m), 5.75 (1H, m), 6.57 (1H, d), 7.60 (1H, d), 7.69 (1H, m), 7.90 (1H, m), 7.97 (1H, m), 8.92 (1H, m), 10.29 (1H, bs).

EXAMPLE 101

Preparation of 3-(1-{2-[(3,3-Dimethyl-butyl)-propyl-amino]-ethyl}-1H-benzoimidazol-5-yl)-N-hydroxy-acrylamide (128)

The titled compound (128) was prepared according to the procedures described in Example 76, by using appropriate starting materials. HPLC purity: 99.0%; $t_R$≈1.18 min. LC-MS m/z: 373 ([M+H]$^+$). $^1$H NMR (DMSO-d$_6$) δ 0.88 (12H, m), 1.51 (2H, m), 1.64 (2H, m), 3.10 (4H, m), 3.63 (2H, m), 4.76 (2H, m), 6.54 (1H, d), 7.65 (2H, m), 7.80 (1H, m), 7.94 (1H, m), 8.83 (1H, m), 9.93 (1H, bs).

EXAMPLE 102

Preparation of 3-{1-[2-(3,3-Dimethyl-butylamino)-ethyl]-2-propyl-1H-benzoimidazol-5-yl}-N-hydroxy-acrylamide (130)

Step 1: Cyclization

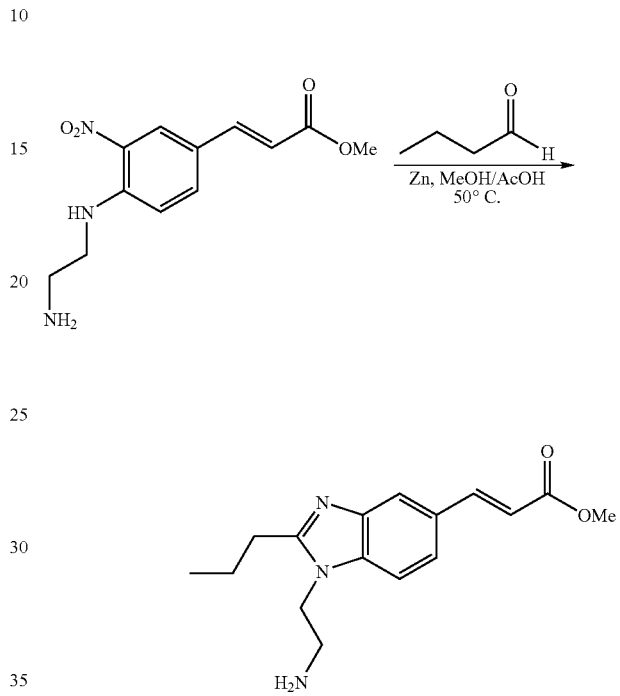

To the starting material (IIIa2, 3.34 g, 12.6 mmol) in 20% AcOH in MeOH (33 mL, 0.2 M) was added butyraldehyde (1.7 mL, 18.9 mmol) followed by zinc powder (4.12 g, 63 mmol). The resulting mixture was heat up to 50° C. and stirred at this temperature for 30 minutes. The completion of reaction was monitored by HPLC and LCMS. The solvent was then evaporated to dryness and the crude was dissolved with ethyl acetate, subsequently saturated aqueous sodium carbonate was added till pH=9 and the mixture was centrifuged spin at 9000 rpm for 10 min. The liquid was decanted and solid was rinsed with ethyl acetate (sonicated). The liquid was extracted with ethyl acetate and then purified by flash chromatography (silica, 3% MeOH in DCM) to give 3-[1-(2-Amino-ethyl)-2-propyl-1H-benzoimidazol-5-yl]-acrylic acid methyl ester. Yield=25%, LC-MS m/z: 288 ([M+H]$^+$).

Step 2: Reductive-Amination

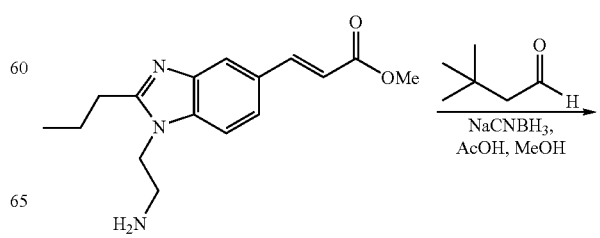

-continued

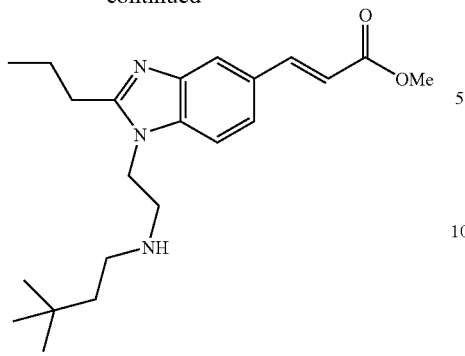

To 3-[1-(2-Amino-ethyl)-2-propyl-1H-benzoimidazol-5-yl]-acrylic acid methyl ester (1.2 g, 4.2 mmol) in MeOH (40 mL) was added 3,3-Dimethyl-butyraldehyde (0.524 mL, 4.2 mmol). The resulting mixture was stirred at rt for 2 hours prior to the addition of acetic acid (2 mL) and sodium cyanoborohydride (0.395 g, 6.3 mmol) and the reaction was stirred at rt for another 30 minutes. Solvent was removed and the residual was dissolved in DCM upon which was washed with aqueous sodium bicarbonate, water and brine. The is combined organic layer, after workup, was purified by flash chromatography (silica, 4% MeOH in DCM). LC-MS m/z: 372 ([M+H]$^+$).
Step 3: Hydroxamic Acid Formation.

The titled compound (130) was prepared according to the procedures described in Example 1 (Step 4), by using appropriate starting materials.
TFA salt of 130: HPLC purity: 99.9%; LC-MS m/z: 373 ([M+H]$^+$). $^1$H NMR (CD$_3$OD) δ 7.89 (d, 1H, J=8.6 Hz), 7.81 (s, 1H), 7.76 (d, 1H, J=8.6 Hz), 7.44 (d, 1H, J=15.7 Hz), 6.44 (d, 1H, J=15.7 Hz), 4.81 (t, 2H, J=7.0 Hz), 3.65 (t, 2H, J=6.4 Hz), 3.23-3.19 (m, 2H), 3.16-3.12 (m, 2H), 2.01-1.94 (m, 2H), 1.65-1.61 (m, 2H), 1.16 (t, 3H, 7.3 Hz), 0.96 (s, 9H). Dihydrochloride salt of 130 was prepared according to the procedures described in Example 50, Step 4 and 5, by using appropriate starting materials. HPLC purity: 98.1%; LC-MS m/z: 373 ([M+H]$^+$). $^1$H NMR (DMSO-d$_6$) δ 10.89 (1H, br s), 9.77 (2H, b, —NH$_2^+$—), 8.12 (1H, d, J=8.6 Hz), 7.97 (1H, s), 7.78 (1H, d, J=8.5 Hz), 7.64 (1H, d, J=15.8 Hz), 6.64 (1H, d, J=15.8 Hz), 4.88 (2H, t, J=5.8 Hz), 3.41 (2H, m), 3.26 (2H, t, J=7.6 Hz), 2.91 (2H, m), 1.90 (2H, sextet, J=7.6 Hz), 1.56 (2H, m), 1.05 (3H, t, J=7.3 Hz), 0.88 (9H, s); $^{13}$C NMR (DMSO-d$_6$) δ 162.4, 155.9, 137.4 (CH), 132.8, 132.4, 131.8 (br), 124.6 (CH), 120.2 (CH), 113.2 (CH), 113.0 (CH), 44.9, 44.0, 41.1, 38.6, 29.4 (Cq), 28.9, 27.1, 19.9, 13.5.

EXAMPLE 103

Preparation of 3-[1-[2-(3,3-Dimethyl-butylamino)-ethyl]-2-(2,2-dimethyl-propyl)-1H-benzoimidazol-5-yl]-N-hydroxy-acrylamide (131)

The titled compound (131) was prepared according to the procedures described in Example 102, by using appropriate starting materials. HPLC purity: 92%; LC-MS m/z: 401 ([M+H]$^+$). $^1$H NMR (CD$_3$OD) δ 7.89 (s, 1H), 7.85 (d, 1H, J=8.5 Hz), 7.77 (d, 1H, J=108.7 Hz), 7.63 (d, 1H, J=15.8 Hz), 6.55 (d, 1H, J=15.7 Hz), 4.91-4.81 (m, 2H), 3.58 (t, 2H, J=6.5 Hz), 3.13-3.08 (m, 4H), 1.63-1.58 (m, 2H), 1.13 (s, 9H), 0.96 (s, 9H).

EXAMPLE 104

Preparation of 3-[1-{2-[Bis-(3,3-dimethyl-butyl)-amino]-ethyl}-2-(2,2-dimethyl-propyl)-1H-benzoimidazol-5-yl]-N-hydroxy-acrylamide (132)

The titled compound (132) was prepared according to the procedures described in Example 102, by using appropriate starting materials. HPLC purity: 96%; LC-MS m/z: 485 ([M+H]$^+$). $^1$H NMR (CD$_3$OD) δ 7.93 (s, 1H), 7.88 (d, 1H, J=8.5 Hz), 7.80 (d, 1H, J=8.7 Hz), 7.72 (d, 1H, J=15.8 Hz), 6.59 (d, 1H, J=15.8 Hz), 5.00 (t, 2H, J=6.5 Hz), 3.67 (t, 2H, J=7.5 Hz), 3.13-3.08 (m, 2H), 1.68-1.64 (m, 4H), 1.14 (s, 9H), 0.96 (s, 18H).

EXAMPLE 105

Preparation of 3-{1-[2-(2,2-Dimethyl-propylamino)-ethyl]-1H-benzoimidazol-5-yl}-N-hydroxy-acrylamide (133)

The titled compound (133) was prepared according to the procedures described in Example 76, by using appropriate starting materials. HPLC purity: 99.9%; LC-MS m/z: 317 ([M+H]$^+$). $^1$H NMR (CD$_3$OD) δ8.82 (s, 1H), 7.94 (s, 1H), 7.83 (d, 1H, J=8.5 Hz), 7.75 (d, 1H, J=8.7 Hz), 7.66 (d, 1H, J=15.8 Hz), 6.53 (d, 1H, J=15.8 Hz), 4.92-4.78 (m, 2H), 3.64 (t, 2H, J=7.0 Hz), 2.98 (s, 2H), 1.09 (s, 9H).

EXAMPLE 106

Preparation of 3-(1-{2-[(2,2-Dimethyl-propyl)-propyl-amino]-ethyl}-1H-benzoimidazol-5-yl)-N-hydroxy-acrylamide (134)

The titled compound (134) was prepared according to the procedures described in Example 76, by using appropriate starting materials. HPLC purity: 99.9%; LCMS m/z: 359 ([M+H]$^+$). $^1$H NMR (CD$_3$OD) δ 9.07 (s, 1H), 7.95 (s, 1H), 7.92 (d, 1H, J=8.7 Hz), 7.78 (d, 1H, J=8.4 Hz), 7.66 (d, 1H, J=15.8 Hz), 6.56 (d, 1H, J=15.8 Hz), 4.99-4.97 (m, 2H), 3.74 (t, 2H=7.0 Hz), 3.32-3.20 (m, 4H), 1.85-1.82 (m, 2H), 1.03 (s, 9H), 0.92 (t, 3H, J=7.1 Hz).

EXAMPLE 107

Preparation of 3-{1-[2-(3,3-Dimethyl-butylamino)-ethyl]-2-ethyl-1H-benzoimidazol-5-yl}-N-hydroxy-acrylamide (135)

The titled compound (135) was prepared according to the procedures described in Example 102, by using appropriate starting materials. HPLC purity: 94.3%; LCMS m/z: 359 ([M+H]$^+$). $^1$H NMR (CD$_3$OD) δ 7.69 (d, 1H, J=8.0 Hz), 7.54 (s, 1H), 7.53 (d, 1H, J=109.8 Hz), 6.89 (d, 1H, J=16.1 Hz), 6.08 (d, 1H, J=15.7 Hz), 4.80-4.70 (m, 2H), 3.55-3.45 (m, 2H), 3.20-3.19 (m, 2H), 2.95-2.90 (m, 2H), 1.56-1.52 (m, 2H), 1.42 (t, 3H, 7.4 Hz), 0.81 (s, 9H).

EXAMPLE 108

Preparation of 3-[1-(2-Diethylamino-ethyl)-2-propylamino-1H-benzoimidazol-5-yl]-N-hydroxy-acrylamide (105)

The titled compound (105) was made according to the following synthetic scheme.

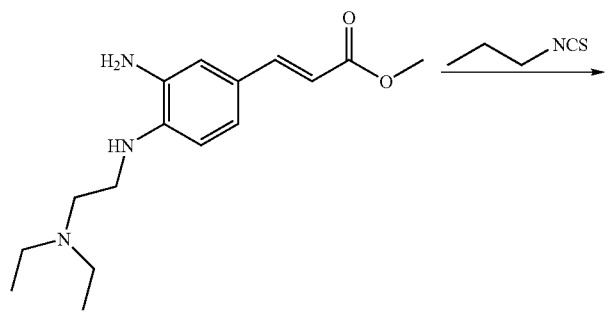

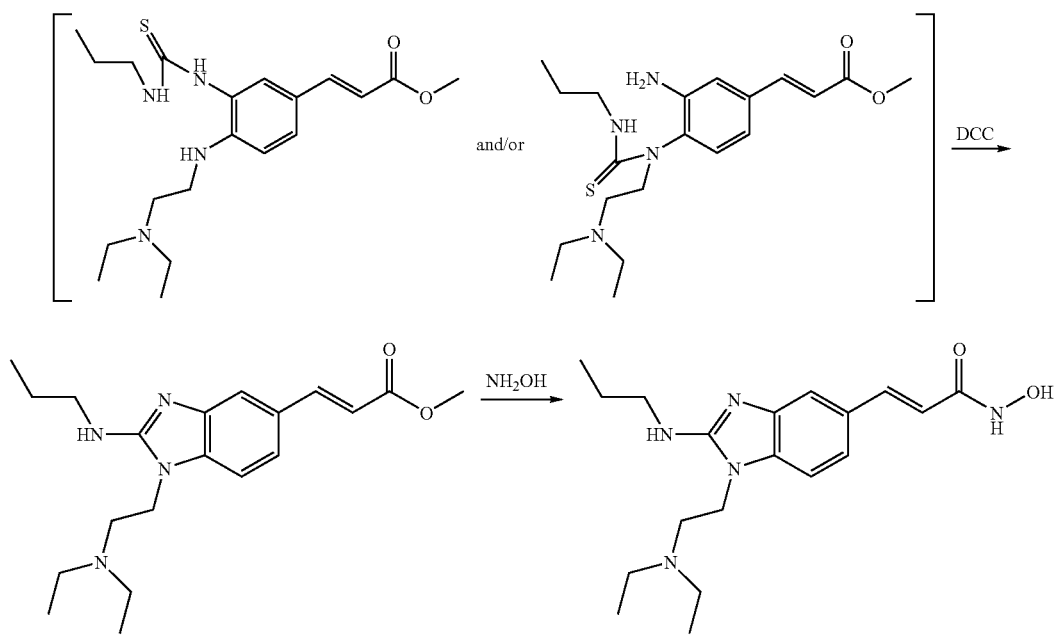

HPLC purity: 100%. ¹H-NMR (DMSO-d₆) δ 0.97 (3H, t, J=7.32 Hz), 1.22 (6H, m), 1.68 (2H, m), 3.09-3.60 (10H, m), 6.47 (1H, d, J=15.80 Hz), 7.52-7.64 (4H, m), 9.03 (2H, bs), 10.10 (1H, s), 10.81 (1H, s).

EXAMPLE 109

Preparation of 3-[1-(3-Dimethylamino-2,2-dimethyl-propyl)-2-propylamino-1H-benzoimidazol-5-yl]-N-hydroxy-acrylamide (115)

The titled compound (115) was made by using method analogous to compound (105). HPLC purity: 97%. ¹H-NMR (DMSO-d₆) δ 0.97 (3H, t, J=7.28), 1.15 (6H, s), 1.69 (2H, m, J=7.28 Hz), 2.89 (6H, s), 3.28 (2H, s), 3.42 (2H, m), 4.15 (2H, s), 6.47 (2H, d, J=15.80), 7.49-7.75 (4H, m), 8.94 (1H, bs), 9.42 (1H, bs), 10.81 (1H, bs), 13.44 (1H, bs).

EXAMPLE 110

Preparation of 3-(1-{2-[(3,3-Dimethyl-butyl)-methyl-amino]-ethyl}-2-propyl-1H-benzoimidazol-5-yl)-N-hydroxy-acrylamide (136)

The titled compound (136) was prepared by reacting of 3-{1-[2-(3,3-dimethyl-butylamino)-ethyl]-2-propyl-1H-benzoimidazol-5-yl}-N-hydroxy-acrylamide (130) with formaldehyde (10 eq.) and NaBH₃CN (3 eq.) in MeOH. TFA salt of 136: HPLC purity at 254 nm, 99.8%; LCMS (ESI) m/z: 387 ([M+H]⁺). ¹H NMR (CD₃OD) δ 7.85 (1H, d, J=8.5 Hz), 7.84 (1H, s), 7.74 (1H, d, J=8.3 Hz), 7.63 (1H, d, J=15.8 Hz), 6.52 (1H, d, J=15.5 Hz), 4.81 (2H, m), 3.62 (2H, br t-like), 3.20 (2H, m), 3.13 (2H, t, J=7.3 Hz), 3.01 (3H, s), 1.93 (2H, m), 1.63 (2H, m), 1.10 (3H, t, J=7.2 Hz), 0.93 (9H, s).

EXAMPLE 111

Preparation of 3-(1-{2-[(3,3-Dimethyl-butyl)-(2,2,2-trifluoro-ethyl)-amino]-ethyl}-1H-benzoimidazol-5-yl)-N-hydroxy-acrylamide (137)

The titled compound (137) was prepared as TFA salt according to the procedures described as below.

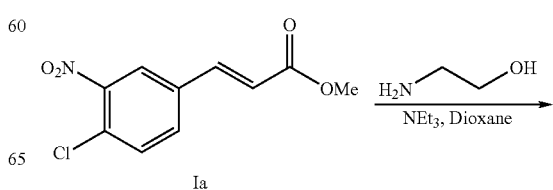

-continued

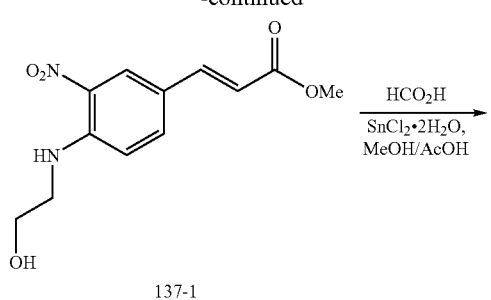

137-1

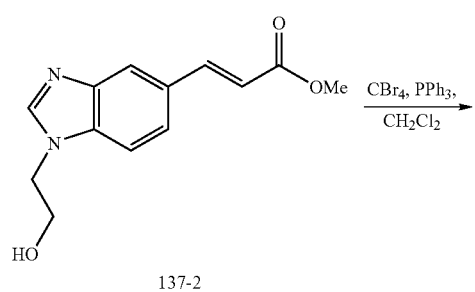

137-2

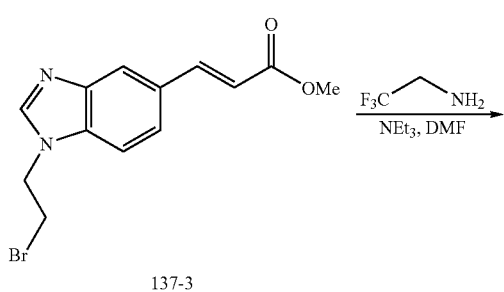

137-3

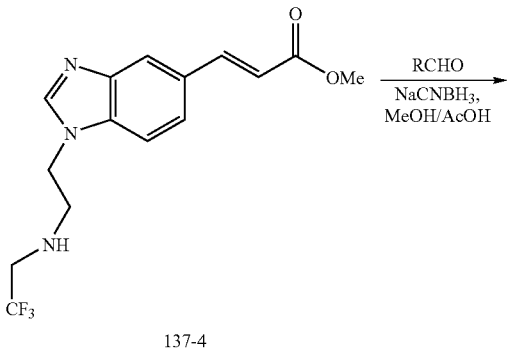

137-4

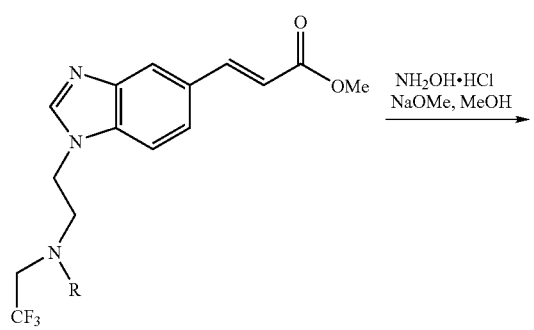

137-5: R = 3,3-dimethyl-Bu
138-5: R = n-Bu

-continued

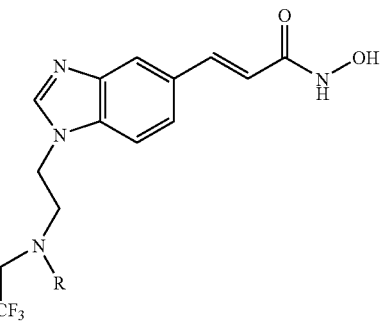

137: R = 3,3-dimethyl-Bu
138: R = n-Bu

Step 1

To a solution of 3-(4-chloro-3-nitro-phenyl)-acrylic acid methyl ester (Ia, 3 g, 12 mmol) in dioxane (100 mL) was added 2-aminoethanol (2.2 mL, 37 mmol) and triethylamine (3.4 mL, 25 mmol). The reaction mixture was heated at 90° C. for 48 hours where all the starting material has been converted to the product. Solvent was evaporated resulting in compound 137-1. The solid was washed with water (×3) and dried over $Na_2SO_4$. Yield: 88%. Purity at 254 nm: 98%, $t_R$=2.4 min. LCMS m/z: 267 ([M+H]$^+$).

Step 2

To a solution of 3-[4-(2-hydroxy-ethylamino)-3-nitro-phenyl]-acrylic acid methyl ester (137-1, 0.200 g, 0.75 mmol) in MeOH (3.7 mL) was added $HCO_2H$ (0.226 mL, 6 mmol) and $SnCl_2.2H_2O$ (0.982 g, 3.7 mmol). The reaction mixture was allowed to stir at 50° C. for 16 hours. Solvent was removed and the residue was basified and then extracted with ethyl acetate. The unpurified crude was used for the next step. LCMS m/z: 247 ([M+H]$^+$).

Step 3

To a solution of crude 3-[1-(2-hydroxy-ethyl)-1H-benzoimidazol-5-yl]-acrylic acid methyl ester (137-2, 0.120 g, 0.49 mmol) in $CH_2Cl_2$ (3.5 mL) was added $PPh_3$ (0.383 g, 1.46 mmol) and $CBr_4$ (0.485 g, 1.46 mmol). The reaction mixture was stirred at room temperature for 30 minutes and then washed with water (×2) and brine (×1), dried over $Na_2SO_4$ and concentrated. Compound 137-3 was purified by reverse phase preparative HPLC. Yield: 80%. Purity at 254 nm: 99.9%, $t_R$=1.2 min. LCMS m/z: 309/311 ([M+H]$^+$).

Step 4

To a solution of 3-[1-(2-bromo-ethyl)-1H-benzoimidazol-5-yl]-acrylic acid methyl ester (137-3, 72 mg, 0.23 mmol) in anhydrous N,N-dimethylformamide (2.5 mL) in a 4 mL vial was added 2,2,2-trifluoroethylamine (185 μl, 2.32 mmol) and triethylamine (321 μl, 2.32 mmol). The reaction mixture was stirred at 80° C. for 16 hours. Ethyl acetate and water was added to the reaction mixture. The aqueous layer was extracted with ethyl acetate (×2). Then, the combined organic layer was washed with water (×1) and brine (×1). The unpurified crude was used for the next step of reaction. LCMS m/z: 328 ([M+H]$^+$).

Step 5

The above crude 3-{1-[2-(2,2,2-trifluoroethylamino)ethyl]-1H-benzoimidazol-5-yl}-acrylic acid methyl ester (137-4) was dissolved in MeOH (2 mL) and AcOH (0.5 mL). Then, 3,3-dimethylbutyraldehyde (42 μl, 0.336 mmol) was added and the resulting mixture was stirred for 2 hours prior to the addition of NaCNBH$_3$ (21 mg, 0.336 mmol). The reaction mixture was stirred for 30 minutes. Solvent was removed and the residue was re-dissolved in CH$_2$Cl$_2$ and washed with sat. NaHCO$_3$ (×2), water (×2) and brine (×1). The crude 137-5: LCMS m/z: 412 ([M+H]$^+$).

Step 6

The crude 137-5 was then converted to the tilted compound (137) as TFA salt according to the procedures described in Example 1. HPLC purity at 254 nm: 99.9%, t$_R$=2.4 min. LCMS m/z: 413 ([M+H]$^+$). $^1$H NMR (CD$_3$OD) δ 0.79 (9H, s), 1.04-1.08 (2H, m), 2.60-2.64 (2H, m), 3.11 (2H, t, J=5.4 Hz), 3.20 (2H, q, J=9.7 Hz), 4.54 (2H, t, J=5.3 Hz), 6.61 (1H, d, J=15.7 Hz), 7.74 (1H, d, J=15.7 Hz), 7.85-7.96 (2H, m), 7.99 (1H, s), 9.11 (1H, s).

EXAMPLE 112

Preparation of 3-(1-{2-[Butyl-(2,2,2-trifluoro-ethyl)-amino]-ethyl}-1H-benzoimidazol-5-yl)-N-hydroxy-acrylamide (138)

The titled compound (138) was prepared according to the procedures described in Example 111, by using appropriate starting materials.

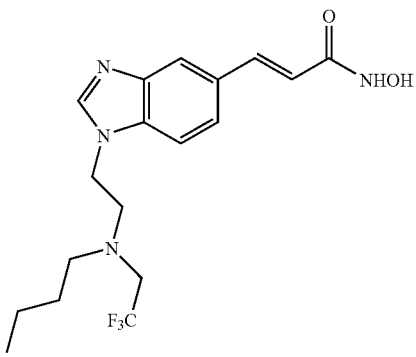

HPLC purity at 254 nm: 99.9%, t$_R$=2.8 min. LCMS m/z: 385 ([M+H]$^+$). $^1$H NMR (CD$_3$OD) δ 0.79 (3H, t, J=7.2 Hz), 1.15-1.24 (4H, m), 2.64 (2H, t, J=6.9 Hz), 3.12 (2H, t, J=5.5 Hz), 3.20 (2H, q, J=9.7 Hz), 4.55 (2H, t, J=5.4 Hz), 6.60 (1H, d, J=15.7 Hz), 7.74 (1H, d, J=15.8 Hz), 7.83-7.92 (2H, m), 7.98 (1H, s), 9.07 (1H, s).

The following compounds are representative examples prepared by methods disclosed or analogous to those disclosed in above Examples 1-112:

| Compound | Structure | m/z [M + H]$^+$ | NAME |
|---|---|---|---|
| 1 | 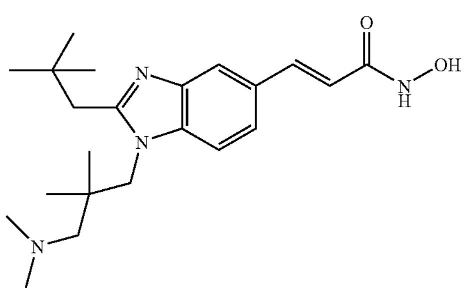 | 387 | 3-[1-(3-Dimethylamino-2,2-dimethyl-propyl)-2-(2,2-dimethyl-propyl)-1H-benzoimidazol-5-yl]-N-hydroxy-acrylamide |
| 2 | 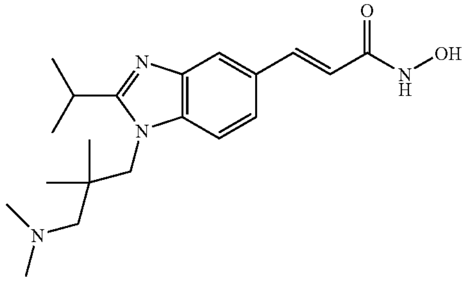 | 359 | 3-[1-(3-Dimethylamino-2,2-dimethyl-propyl)-2-isopropyl-1H-benzoimidazol-5-yl]-N-hydroxy-acrylamide |

| Compound | Structure | m/z [M + H]+ | NAME |
|---|---|---|---|
| 3 | 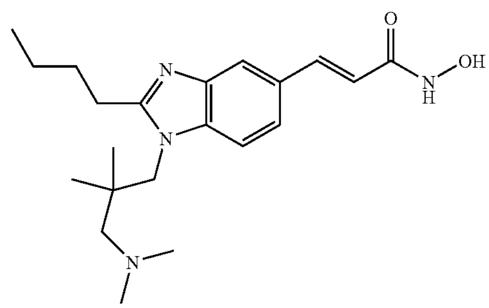 | 373 | 3-[2-Butyl-1-(3-dimethylamino-2,2-dimethyl-propyl)-1H-benzoimidazol-5-yl]-N-hydroxy-acrylamide |
| 4 | 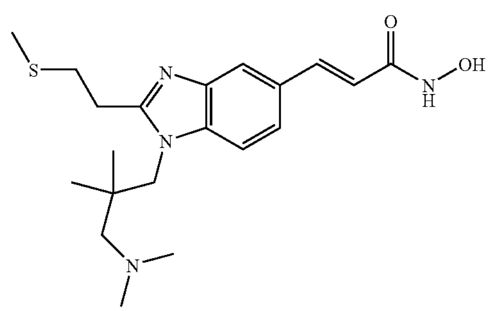 | 391 | 3-[1-(3-Dimethylamino-2,2-dimethyl-propyl)-2-(2-methylsulfanyl-ethyl)-1H-benzoimidazol-5-yl]-N-hydroxy-acrylamide |
| 5 | 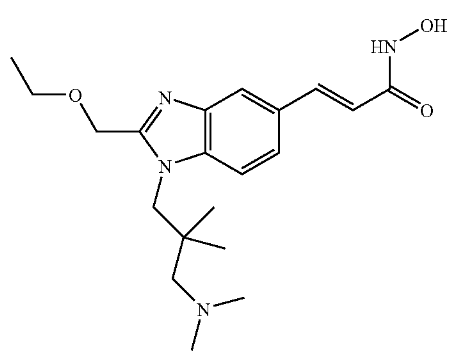 | 375 | 3-[1-(3-Dimethylamino-2,2-dimethyl-propyl)-2-ethoxymethyl-1H-benzoimidazol-5-yl]-N-hydroxy-acrylamide |
| 6 | 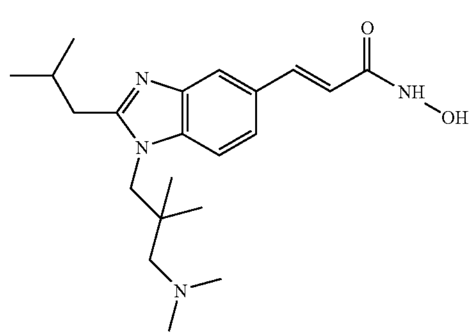 | 373 | 3-[1-(3-Dimethylamino-2,2-dimethyl-propyl)-2-isobutyl-1H-benzoimidazol-5-yl]-N-hydroxy-acryl |

-continued

| Compound | Structure | m/z [M + H]⁺ | NAME |
|---|---|---|---|
| 7 | 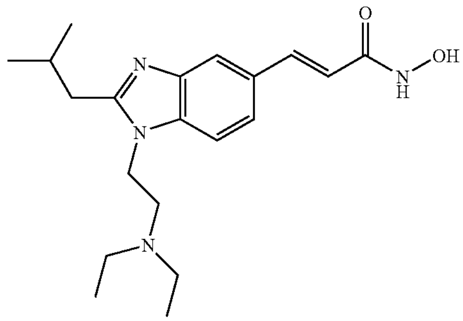 | 359 | 3-[1-(2-Diethylamino-ethyl)-2-isobutyl-1H-benzoimidazol-5-yl]-N-hydroxy-acrylamide |
| 8 | 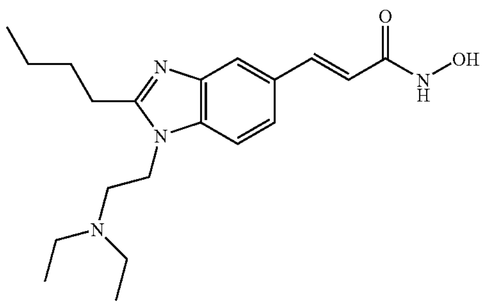 | 359 | 3-[2-Butyl-1-(2-diethylamino-ethyl)-1H-benzoimidazol-5-yl]-N-hydroxy-acrylamide |
| 9 | 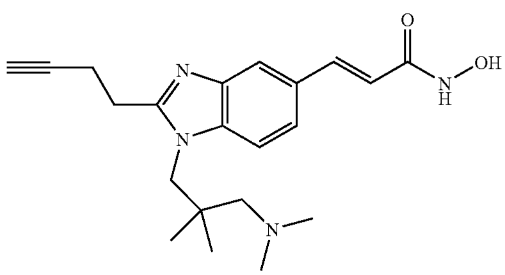 | 369 | 3-[2-But-3-ynyl-1-(3-dimethylamino-2,2-dimethyl-propyl)-1H-benzoimidazol-5-yl]-N-hydroxy-acrylamide |
| 10 | 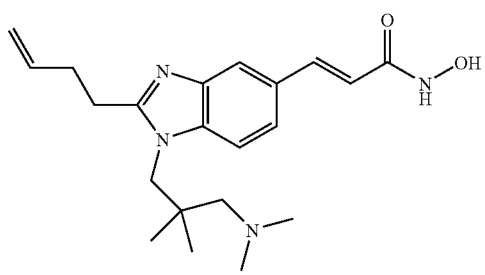 | 371 | 3-[2-But-3-enyl-1-(3-dimethylamino-2,2-dimethyl-propyl)-1H-benzoimidazol-5-yl]-N-hydroxy-acrylamide |
| 11 | 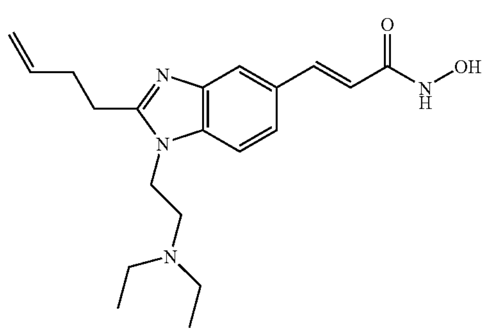 | 357 | 3-[2-But-3-enyl-1-(2-diethylamino-ethyl)-1H-benzoimidazol-5-yl]-N-hydroxy-acrylamide |

| Compound | Structure | m/z [M + H]+ | NAME |
|---|---|---|---|
| 12 | 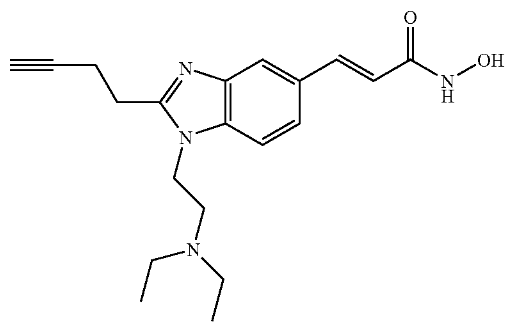 | 355 | 3-[2-But-3-ynyl-1-(2-diethylamino-ethyl)-1H-benzoimidazol-5-yl]-N-hydroxy-acrylamide |
| 13 | 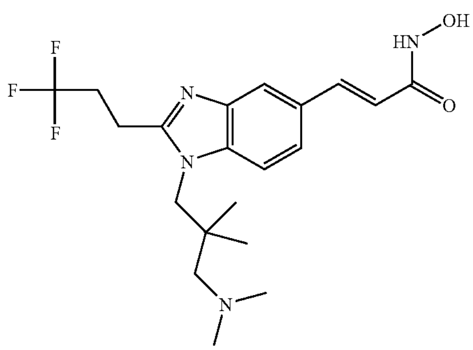 | 413 | 3-[1-(3-Dimethylamino-2,2-dimethyl-propyl)-2-(3,3,3-trifluoro-propyl)-1H-benzoimidazol-5-yl]-N-hydroxy-acrylamide |
| 14 | 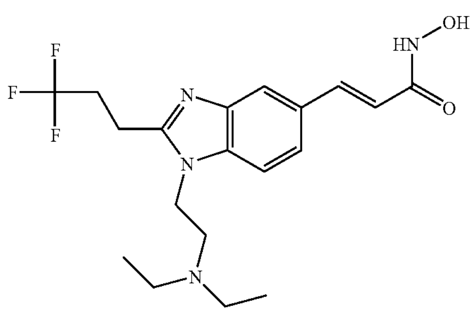 | 399 | 3-[1-(2-Diethylamino-ethyl)-2-(3,3,3-trifluoro-propyl)-1H-benzoimidazol-5-yl]-N-hydroxy-acrylamide |
| 15 | 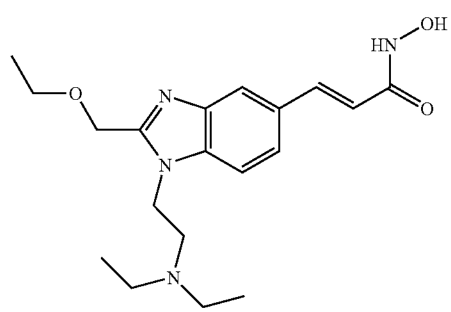 | 361 | 3-[1-(2-Diethylamino-ethyl)-2-ethoxymethyl-1H-benzoimidazol-5-yl]-N-hydroxy-acrylamide |

-continued

| Compound | Structure | m/z [M + H]+ | NAME |
|---|---|---|---|
| 16 | 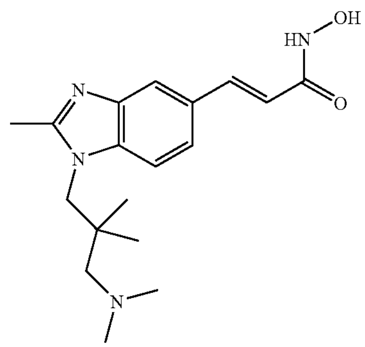 | 331 | 3-[1-(3-Dimethylamino-2,2-dimethyl-propyl)-2-methyl-1H-benzoimidazol-5-yl]-N-hydroxy-acrylamide |
| 17 | 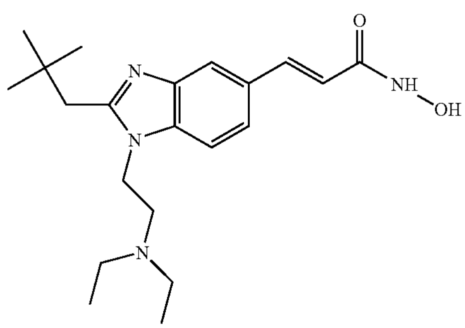 | 373 | 3-[1-(2-Diethylamino-ethyl)-2-(2,2-dimethyl-propyl)-1H-benzoimidazol-5-yl]-N-hydroxy-acrylaide |
| 18 | 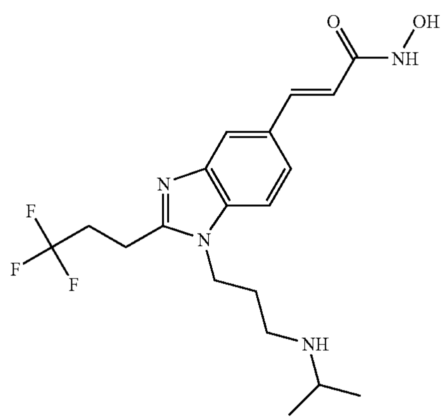 | 399 | N-Hydroxy-3-[1-(3-isopropylamino-propyl)-2-(3,3,3-trifluoro-propyl)-1H-benzoimidazol-5-yl]-acrylamide |
| 19 | 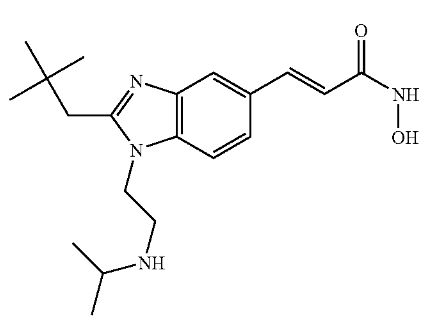 | 359 | 3-[2-(2,2-Dimethyl-propyl)-1-(2-isopropylamimo-ethyl)-1H-benzoimidazol-5-yl]-N-hydroxy-acrylamide |

| Compound | Structure | m/z [M + H]+ | NAME |
|---|---|---|---|
| 20 | 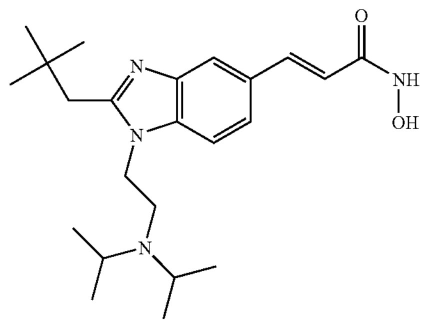 | 401 | 3-[1-(2-Diisopropylamino-ethyl)-2-(2,2-dimethyl-propyl)-1H-benzoimidazol-5-yl]-N-hydroxy-acrylamide |
| 21 | 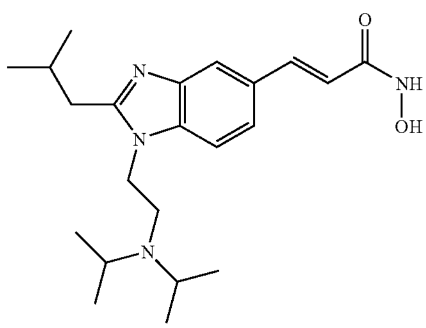 | 387 | 3-[1-(2-Diisopropylamino-ethyl)-2-isobutyl-1H-benzoimidazol-5-yl]-N-hydroxy-acrylamide |
| 22 | 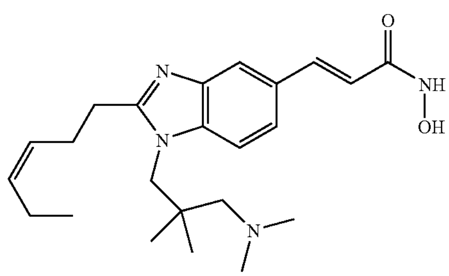 | 399 | 3-[1-(3-Dimethylamino-2,2-dimethyl-propyl)-2-hex-3-enyl-1H-benzoimidazol-5-yl]-N-hydroxy-acrylamide |
| 23 | 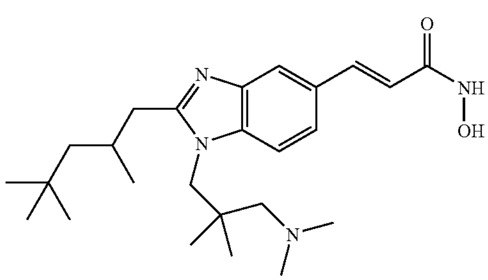 | 429 | 3-[1-(3-Dimethylamino-2,2-dimethyl-propyl)-2-(2,4,4-trimethyl-pentyl)-1H-benzoimidazol-5-yl]-N-hydroxy-acrylamide |
| 24 | 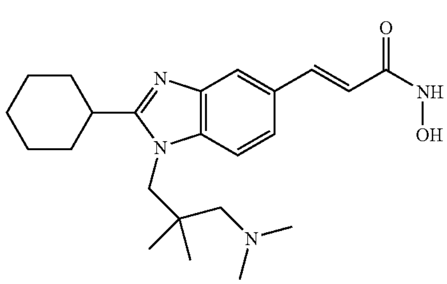 | 399 | 3-[2-Cyclohexyl-1-(3-dimethylamino-2,2-dimethyl-propyl)-1H-benzoimidazol-5-yl]-N-hydroxy-acrylamide |

-continued

| Compound | Structure | m/z [M + H]⁺ | NAME |
|---|---|---|---|
| 25 | 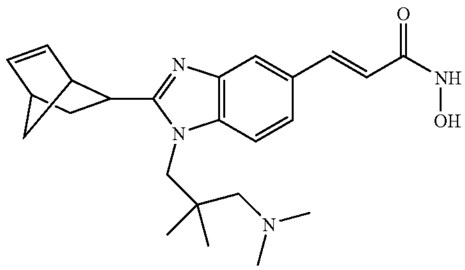 | 409 | 3-[2-Bicyclo[2.2.1]hept-5-en-2-yl-1-(3-dimethylamino-2,2-dimethyl-propyl)-1H-benzoimidazol-5-yl]-N-hydroxy-acrylamide |
| 26 | 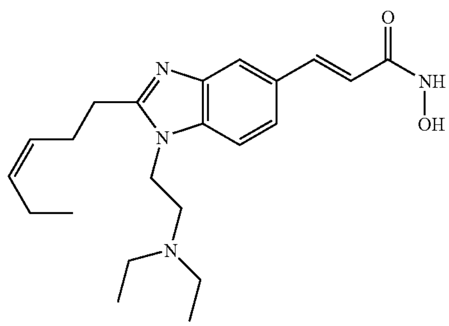 | 385 | 3-[1-(2-Diethylamino-ethyl)-2-hex-3-enyl-1H-benzoimidazol-5-yl]-N-hydroxy-acrylamide |
| 27 | 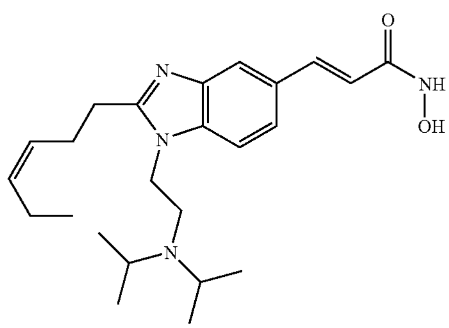 | 413 | 3-[1-(2-Diisopropylamino-ethyl)-2-hex-3-enyl-1H-benzoimidazol-5-yl]-N-hydroxy-acrylamide |
| 28 | 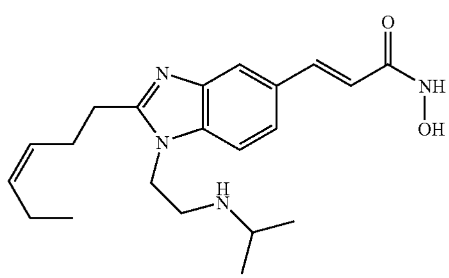 | 371 | 3-[2-Hex-3-enyl-1-(2-isopropylamino-ethyl)-1H-benzoimidazol-5-yl]-N-hydroxy-acrylamide |
| 29 | 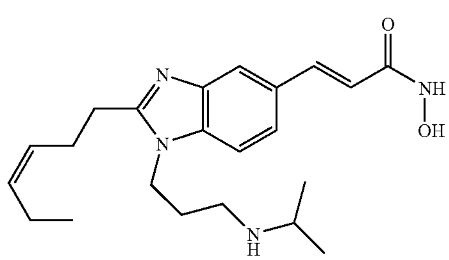 | 385 | 3-[2-Hex-3-enyl-1-(3-isopropylamino-propyl)-1H-benzoimidazol-5-yl]-N-hydroxy-acrylamide |

-continued

| Compound | Structure | m/z [M + H]+ | NAME |
|---|---|---|---|
| 30 | 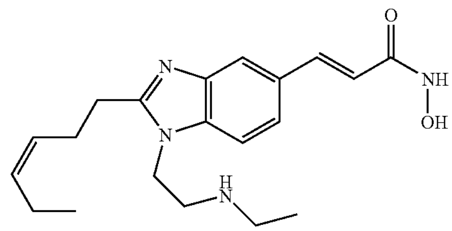 | 357 | 3-[1-(2-Ethylamino-ethyl)-2-hex-3-enyl-1H-benzoimidazol-5-yl]-N-hydroxy-acrylamide |
| 31 | 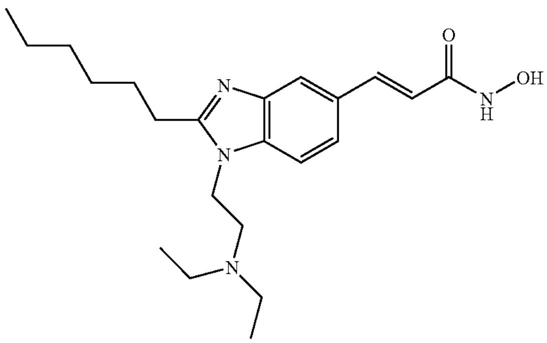 | 387 | 3-[1-(2-Diethylamino-ethyl)-2-hexyl-1H-benzoimidazol-5-yl]-N-hydroxy-acrylamide |
| 32 | 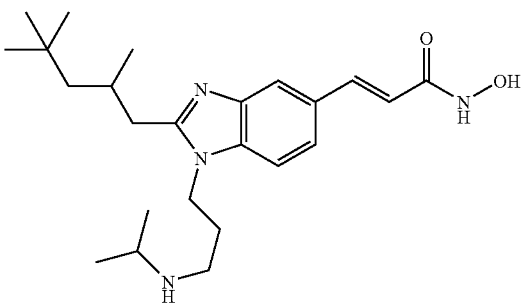 | 415 | N-Hydroxy-3-[1-(3-isopropylamino-propyl)-2-(2,4,4-trimethyl-pentyl)-1H-benzoimidazol-5-yl]-acrylamide |
| 33 | 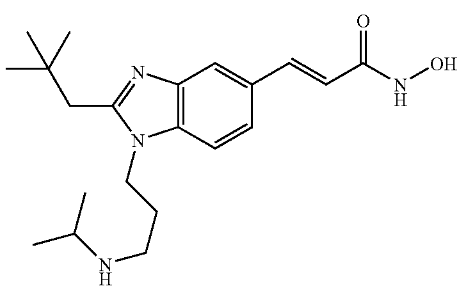 | 373 | 3-[2-(2,2-Dimethyl-propyl)-1-(3-isopropylamino-propyl)-1H-benzoimidazol-5-yl]-N-hydroxy-acrylamide |
| 34 | 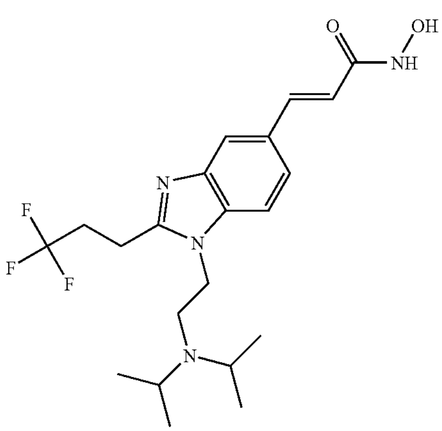 | 427 | 3-[1-(2-Diisopropylamino-ethyl)-2-(3,3,3-trifluoro-propyl)-1H-benzoimidazol-5-yl]-N-hydroxy-acrylamide |

| Compound | Structure | m/z [M + H]+ | NAME |
|---|---|---|---|
| 35 | 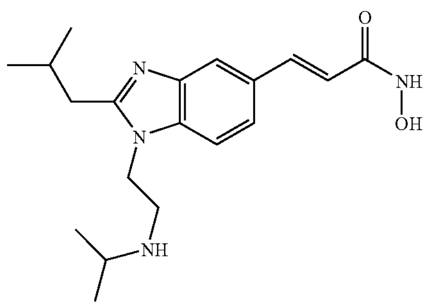 | 345 | N-Hydroxy-3-[2-isobutyl-1-(2-isopropylamino-ethyl)-1H-benzoimidazol-5-yl]-acrylamide |
| 36 | 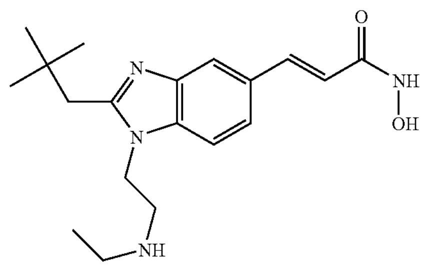 | 345 | 3-[2-(2,2-Dimethyl-propyl)-1-(2-ethylamimo-ethyl)-1H-benzoimidazol-5-yl]-N-hydroxy-acrylamide |
| 37 | 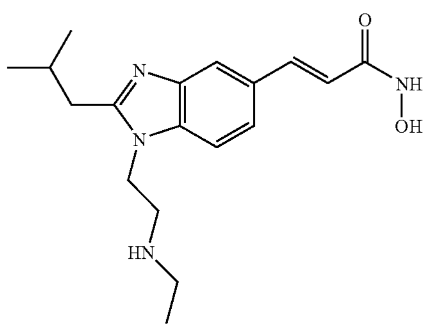 | 331 | 3-[1-(2-Ethylamino-ethyl)-2-isobutyl-1H-benzoimidazol-5-yl]-N-hydroxy-acrylamide |
| 38 | 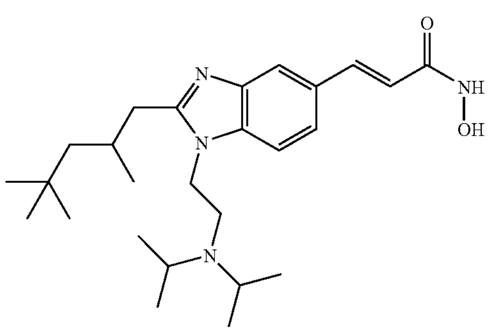 | 443 | 3-[1-(2-Diisopropylamino-ethyl)-2-(2,4,4-trimethyl-pentyl)-1H-benzoimidazol-5-yl]-N-hydroxy-acrylamide |
| 39 | 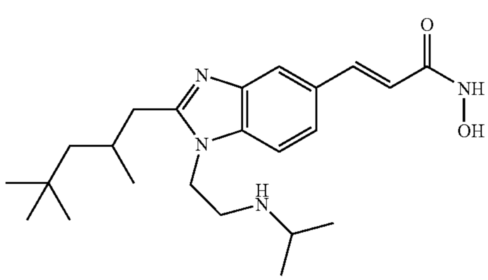 | 401 | N-Hydroxy-3-[1-(2-isopropylamino-ethyl)-2-(2,4,4-trimethyl-pentyl)-1H-benzoimidazol-5-yl]-acrylamide |

| Compound | Structure | m/z [M + H]+ | NAME |
|---|---|---|---|
| 40 | 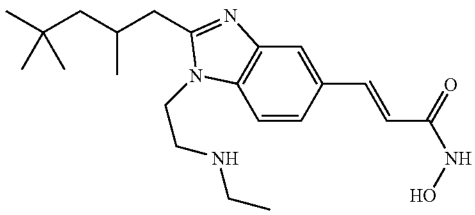 | 387 | 3-[1-(2-Ethylamino-ethyl)-2-(2,4,4-trimethyl-pentyl)-1H-benzoimidazol-5-yl]-N-hdroxy-acrylamide |
| 41 | 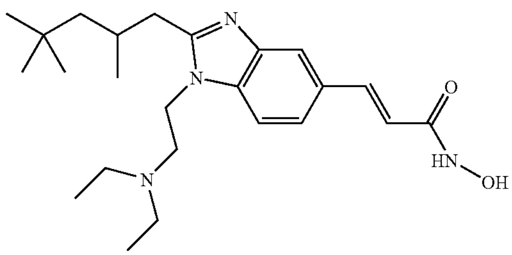 | 415 | 3-[1-(2-Diethylamino-ethyl)-2-(2,4,4-trimethyl-pentyl)-1H-benzoimidazol-5-yl]-N-hydroxy-acrylamide |
| 42 | 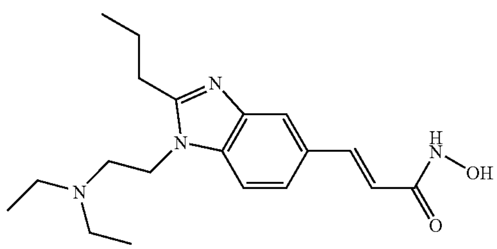 | 345 | 3-[1-(2-Diethylamino-ethyl)-2-propyl-1H-benzoimidazol-5-yl]-N-hydroxy-acrylamide |
| 43 | 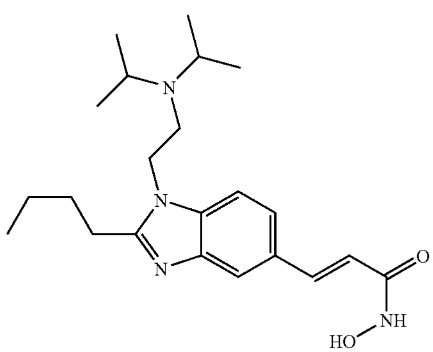 | 387 | 3-[2-Butyl-1-(2-diisopropylamimo-ethyl)-1H-benzoimidazol-5-yl]-N-hydroxy-acrylmide |
| 44 | 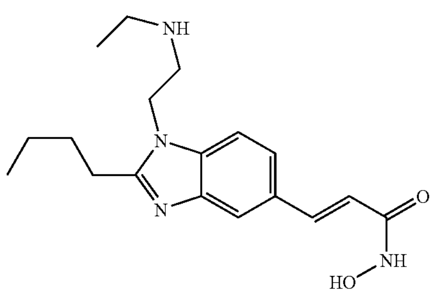 | 331 | 3-[2-Butyl-1-(2-ethylamino-ethyl)-1H-benzoimidazol-5-yl]-N-hydroxy-acrylamide |

-continued

| Compound | Structure | m/z [M + H]+ | NAME |
|---|---|---|---|
| 45 | 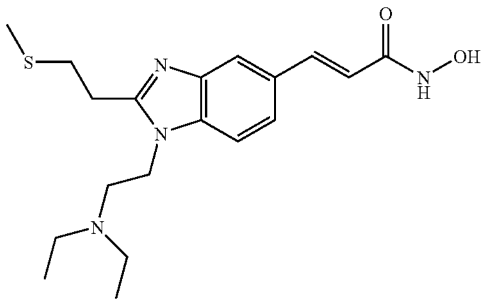 | 377 | 3-[1-(2-Diethylamino-ethyl)-2-(2-methylsulfanyl-ethyl)-1H-benzoimidazol-5-yl]-N-hydroxy-acrylamide |
| 46 | 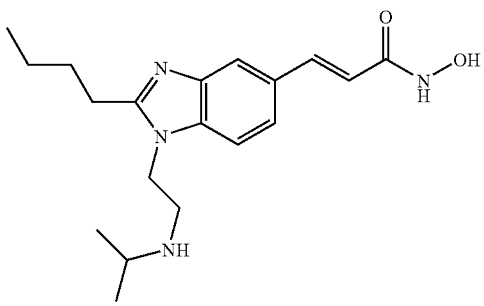 | 345 | 3-[2-Butyl-1-(2-isopropylamino-ethyl)-1H-benzoimidazol-5-yl]-N-hydroxy-acrylamide |
| 47 | 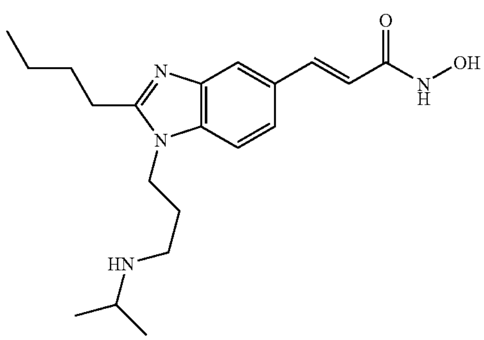 | 359 | 3-[2-Butyl-1-(3-isopropylamino-propyl)-1H-benzoimidazol-5-yl]-N-hydroxy-acrylamie |
| 48 | 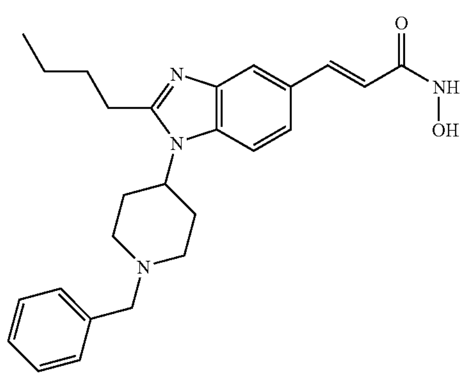 | 433 | 3-[1-(1-Benzyl-piperidin-4-yl)-2-butyl-1H-benzoimidazol-5-yl]-N-hydroxy-acrylamide |

-continued

| Compound | Structure | m/z [M + H]+ | NAME |
|---|---|---|---|
| 49 | 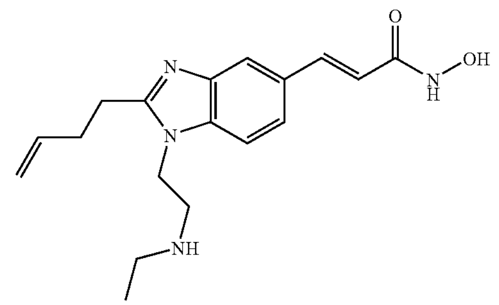 | 329 | 3-[2-But-3-enyl-1-(2-ethylamino-ethyl)-1H-benzoimidazol-5-yl]-N-hydroxy-acrylamide |
| 50 | 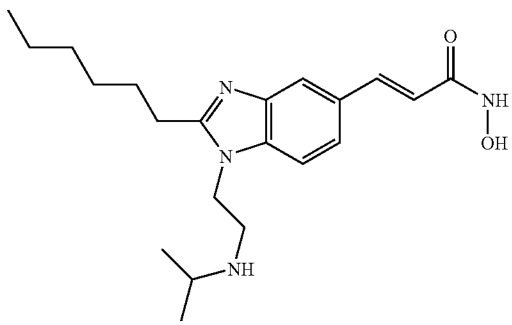 | 373 | 3-[2-Hexyl-1-(2-isopropylamino-ethyl)-1H-benzoimidazol-5-yl]-N-hydroxy-acrylamide |
| 51 | 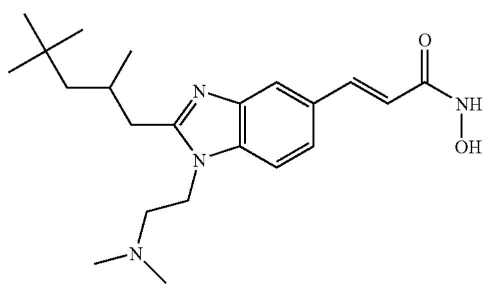 | 387 | 3-[1-(2-Dimethylamino-ethyl)-2-(2,4,4-trimethyl-pentyl)-1H-benzoimidazol-5-yl]-N-hydroxy-acrylamide |
| 52 | 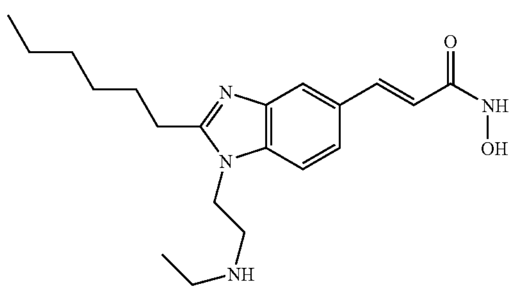 | 359 | 3-[1-(2-Ethylamino-ethyl)-2-hexyl-1H-benzoimidazol-5-yl]-N-hydroxy-acrylamide |
| 53 | 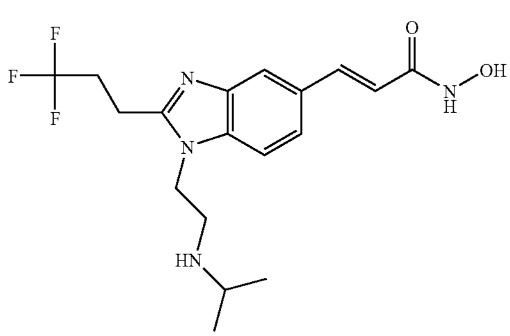 | 385 | N-Hydroxy-3-[1-(2-isopropylamino-ethyl)-2-(3,3,3-trifluoro-propyl)-1H-benzoimidazol-5-yl]-acrylamide |

-continued

| Compound | Structure | m/z [M + H]+ | NAME |
|---|---|---|---|
| 54 | 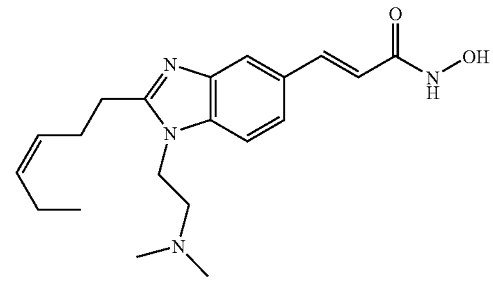 | 357 | 3-[1-(2-Dimethylamino-ethyl)-2-hex-3-enyl-1H-benzoimidazol-5-yl]-N-hydroxy-acrylamide |
| 55 | 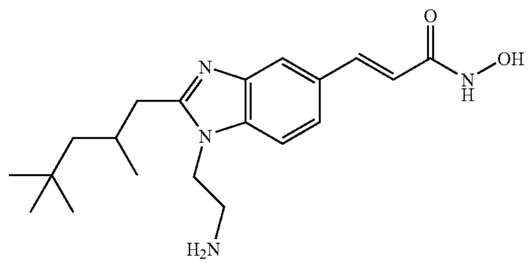 | 359 | 3-[1-(2-Amino-ethyl)-2-(2,4,4-trimethyl-pentyl)-1H-benzoimidazol-5-yl]-N-hydroxy-acrylamide |
| 56 | 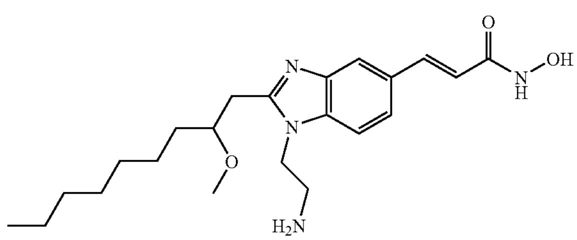 | 403 | 3-[1-(2-Amino-ethyl)-2-(2-methoxy-nonyl)-1H-benzoimidazol-5-yl]-N-hydroxy-acrylamide |
| 57 | 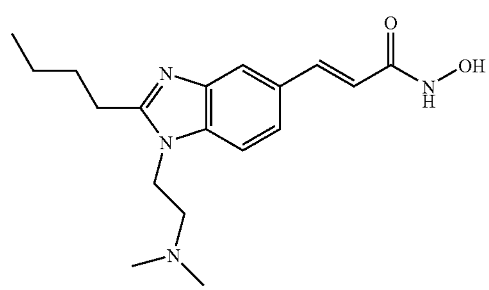 | 331 | 3-[2-Butyl-1-(2-dimethylamino-ethyl)-1H-benzoimidazol-5-yl]-N-hydroxy-acrylamide |
| 58 | 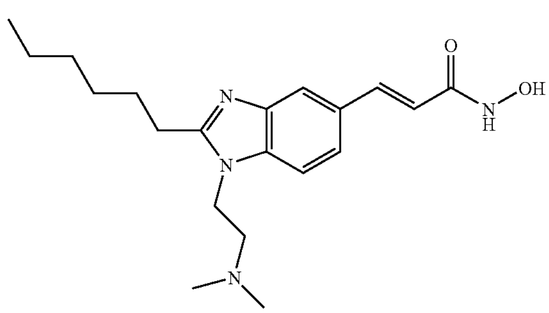 | 359 | 3-[1-(2-Dimethylamino-ethyl)-2-hexyl-1H-benzoimidazol-5-yl]-N-hydroxy-acrylamide |

| Compound | Structure | m/z [M + H]+ | NAME |
|---|---|---|---|
| 59 | 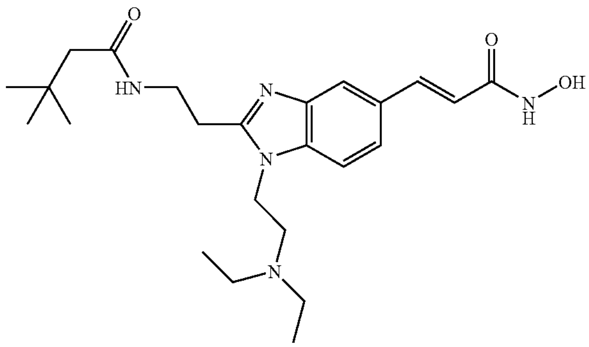 | 444 | N-{2-[1-(2-Diethylamino-ethyl)-5-(2-hydroxycarbamoyl-vinyl)-1H-benzoimidazol-2-yl]-ethyl}-3,3-dimethyl-butyramide |
| 60 | 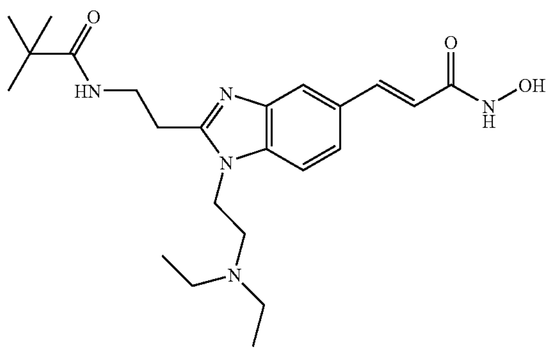 | 430 | 3-{1-(2-Diethylamino-ethyl)-2-[2-(2,2-dimethyl-propionylamino)-ethyl]-1H-benzoimidazol-5-yl}-N-hydroxy-acrylamie |
| 61 | 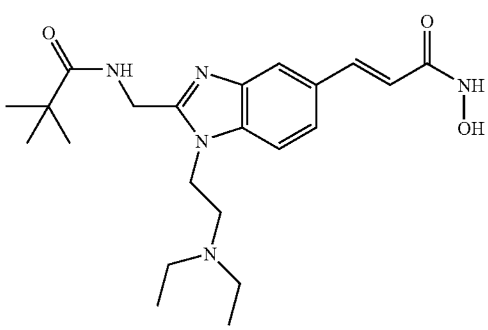 | 416 | 3-{1-(2-Diethylamino-ethyl)-2-[(2,2-dimethyl-propionylamino)-methyl]-1H-benzoimidazol-5-yl}-N-hydroxy-acrylamide |
| 62 | 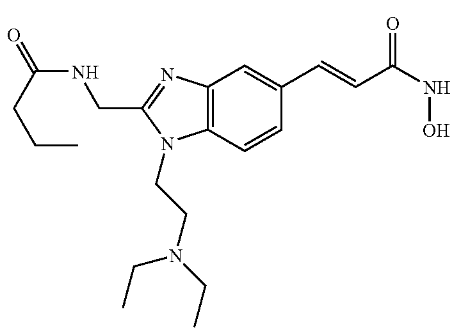 | 402 | N-[1-(2-Diethylamino-ethyl)-5-(2-hydroxycarbamoyl-vinyl)-1H-benzoimidazol-2-ylmethyl]-butyramide |

-continued

| Compound | Structure | m/z [M + H]+ | NAME |
|---|---|---|---|
| 63 | 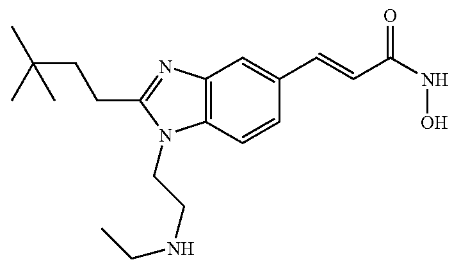 | 359 | 3-[1-(2-ethylamino-ethyl)-2-(3,3-dimethyl-butyl)-1H-benzoimidazol-5-yl]-N-hydroxy-acrylamide |
| 64 | 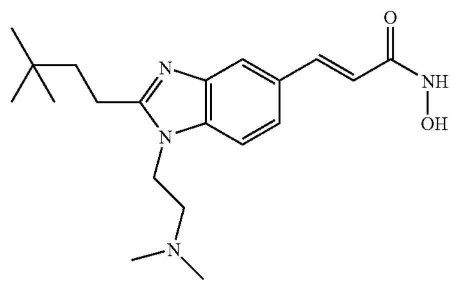 | 359 | 3-[2-(3,3-Dimethyl-butyl)-1-(2-Dimethylamino-ethyl)-1H-benzoimidazol-5-yl]-N-hydroxy-acrylamide |
| 65 | 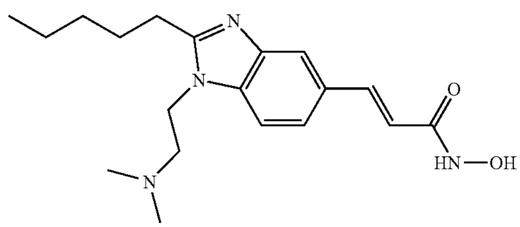 | 345 | 3-[1-(2-Dimethylamino-ethyl)-2-pentyl-1H-benzoimidazol-5-yl]-N-hydroxy-acrylamide |
| 66 | 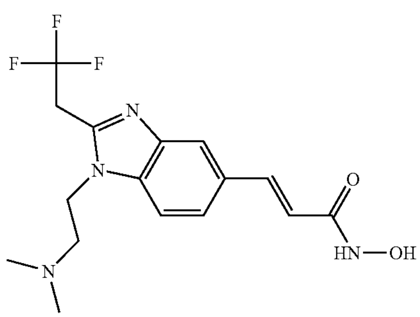 | 357 | 3-[1-(2-Dimethylamino-ethyl)-2-(2,2,2-trifluoro-ethyl)-1H-benzoimidazol-5-yl]-N-hydroxy-acrylamide |
| 67 | 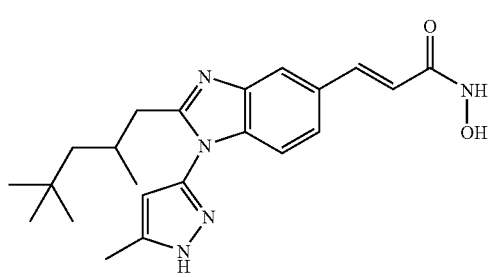 | 396 | N-Hydroxy-3-[1-(5-methyl-1H-pyrazol-3-yl)-2-(2,4,4-trimethyl-pentyl)-1H-benzoimidazol-5-yl]-acrylamide |

-continued

| Compound | Structure | m/z [M + H]⁺ | NAME |
|---|---|---|---|
| 68 | 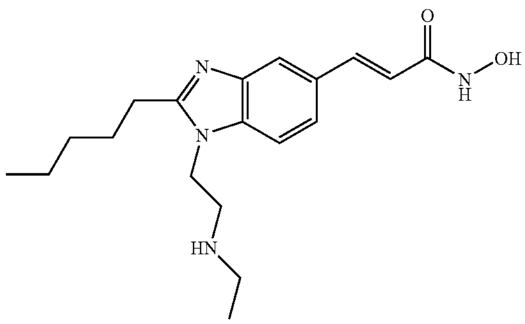 | 345 | 3-[1-(2-Ethylamino-ethyl)-2-pentyl-1H-benzoimidazol-5-yl]-N-hydroxy-acrylamide |
| 69 | 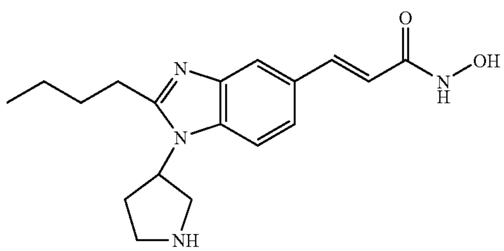 | 329 | 3-(2-Butyl-1-pyrrolidin-3-yl-1H-benzoimidazol-5-yl)-N-hydroxy-acrylamide |
| 70 | 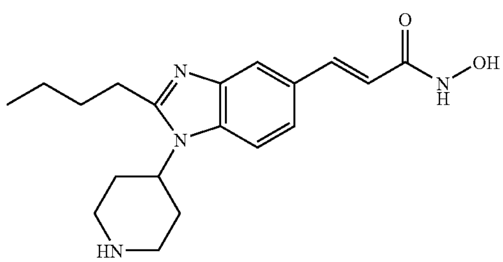 | 343 | 3-(2-Butyl-1-piperidin-4-yl-1H-benzoimidazol-5-yl)-N-hydroxy-acrylamide |
| 71 | 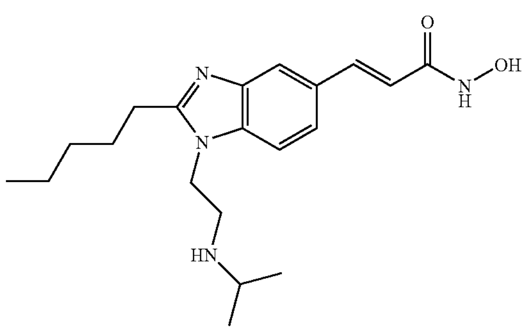 | 359 | N-Hydroxy-3-[1-(2-isopropylamino-ethyl)-2-pentyl-1H-benzoimidazol-5-yl]-acrylamide |
| 72 | 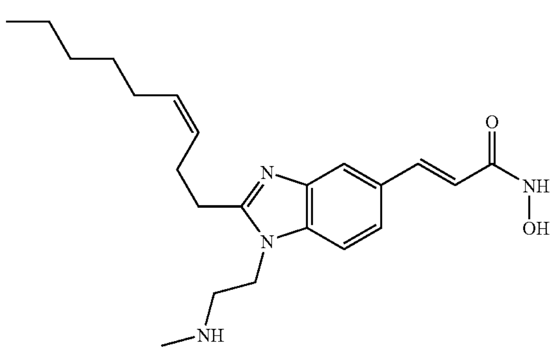 | 385 | N-Hydroxy-3-[1-(2-methylamino-ethyl)-2-non-3-enyl-1H-benzoimidazol-5-yl]-acrylamide |

| Compound | Structure | m/z [M + H]+ | NAME |
|---|---|---|---|
| 73 | 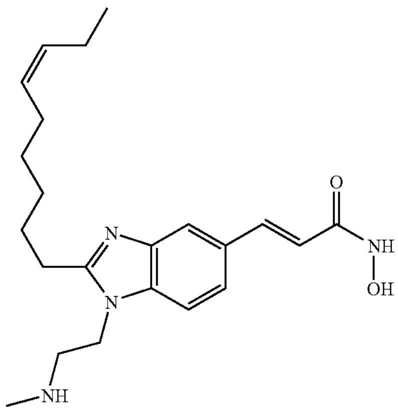 | 385 | N-Hydroxy-3-[1-(2-methylamino-ethyl)-2-non-6-enyl-1H-benzoimidazol-5-yl]-acrylamide |
| 74 | 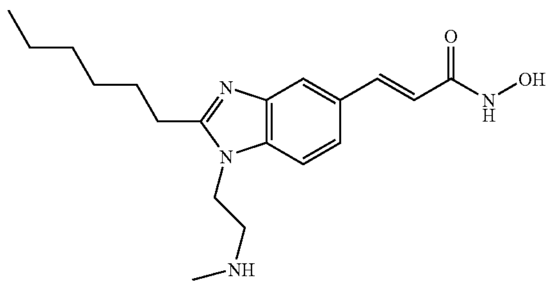 | 345 | 3-[2-Hexyl-1-(2-methylamino-ethyl)-1H-benzoimidazol-5-yl]-N-hydroxy-acrylamide |
| 75 | 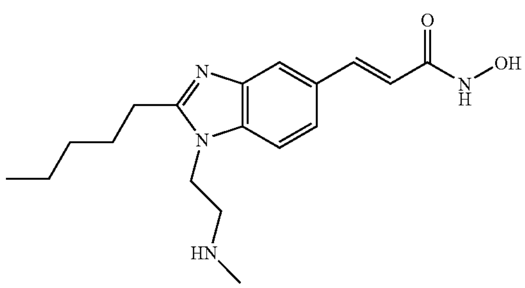 | 331 | N-Hydroxy-3-[1-(2-methylamino-ethyl)-2-pentyl-1H-benzoimidazol-5-yl]-acrylamide |
| 76 | 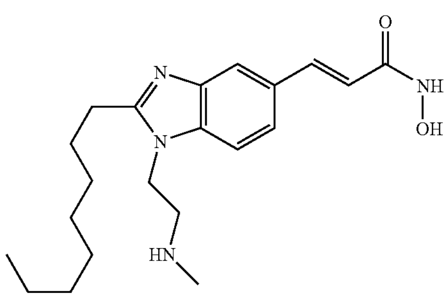 | 373 | N-Hydroxy-3-[1-(2-methylamino-ethyl)-2-octyl-1H-benzoimidazol-5-yl]-acrylamide |
| 77 | 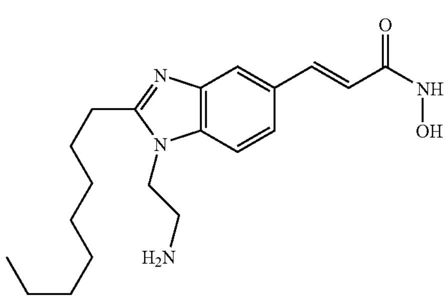 | 359 | 3-[1-(2-Amino-ethyl)-2-octyl-1H-benzoimidazol-5-yl]-N-hydroxy-acr |

-continued

| Compound | Structure | m/z [M + H]+ | NAME |
|---|---|---|---|
| 78 | 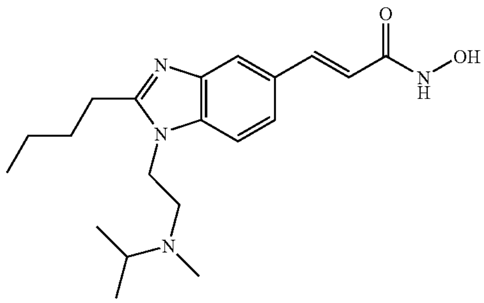 | 359 | 3-{2-Butyl-1-[2-(isopropyl-methyl-amino)-ethyl]-1H-benzoimidazol-5-yl}-N-hydroxy-acrylamide |
| 79 | 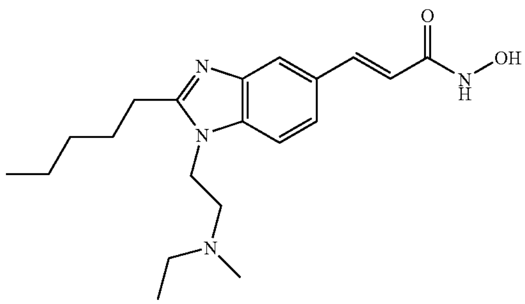 | 359 | 3-{1-[2-(Ethyl-methyl-amino)-ethyl]-2-pentyl-1H-benzoimidazol-5-yl}-N-hydroxy-acrylamide |
| 80 | 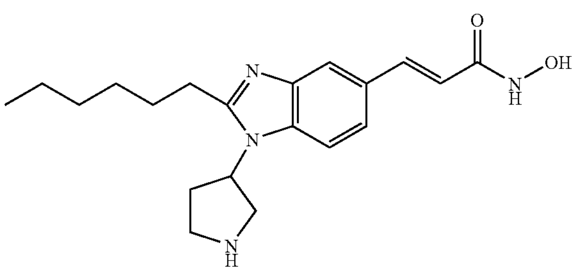 | 357 | 3-(2-Hexyl-1-pyrrolidin-3-yl-1H-benzoimidazol-5-yl)-N-hydroxy-acrylamide |
| 81 | 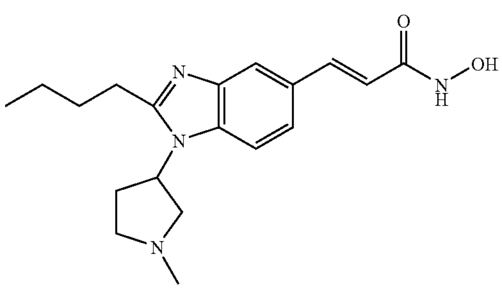 | 343 | 3-[2-Butyl-1-(1-methyl-pyrrolidin-3-yl)-1H-benzoimidazol-5-yl]-N-hydroxy-acrylamide |
| 82 | 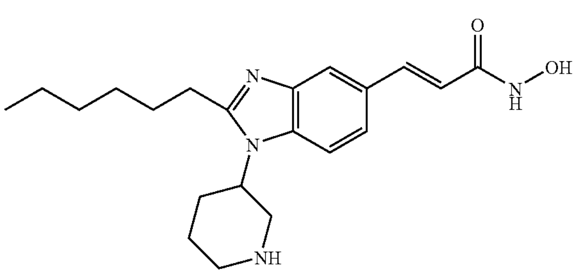 | 371 | 3-(2-Hexyl-1-piperidin-3-yl-1H-benzoimidazol-5-yl)-N-hydroxy-acrylamide |

| Compound | Structure | m/z [M + H]+ | NAME |
|---|---|---|---|
| 83 | 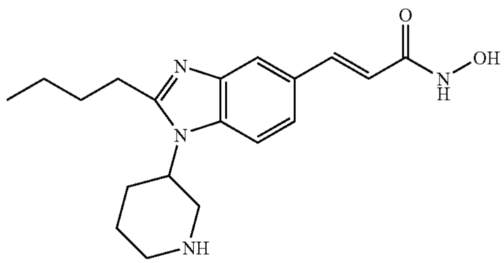 | 343 | 3-(2-Butyl-1-piperidin-3-yl-1H-benzoimidazol-5-yl)-N-hydroxy-acrylamide |
| 84 | 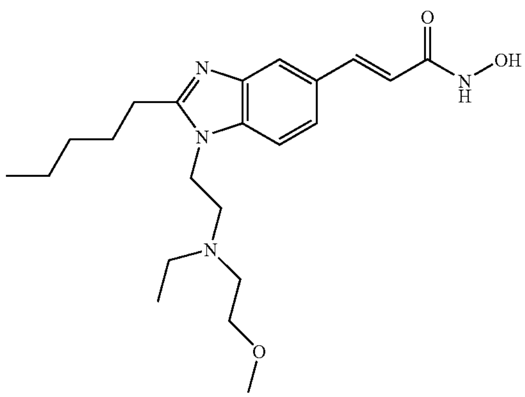 | 403 | 3-(1-{2-[Ethyl-(2-methoxy-ethyl)-amino]-ethyl}-2-pentyl-1H-benzoimidazol-5-yl)-N-hydroxy-acrylamide |
| 85 | 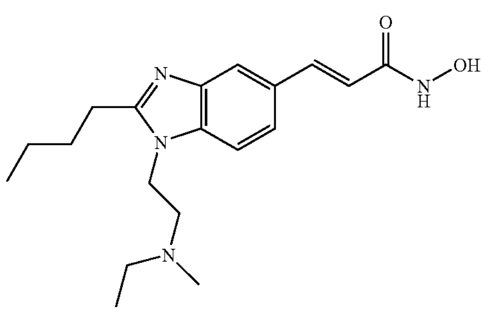 | 345 | 3-{2-Butyl-1-[2-(ethyl-methyl-amino)-ethyl]-1H-benzoimidazol-5-yl}-N-hydroxy-acrylamide |
| 86 | 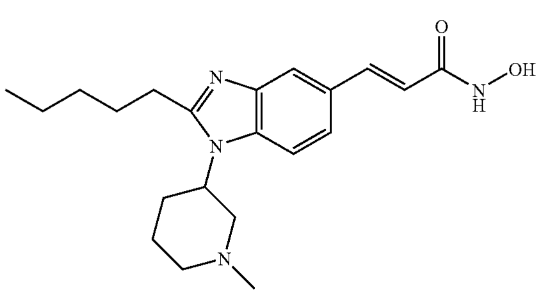 | 371 | N-Hydroxy-3-[1-(1-methyl-piperidin-3-yl)-2-pentyl-1H-benzoimidazol-5-yl]-acrylamide |

-continued

| Compound | Structure | m/z [M + H]+ | NAME |
|---|---|---|---|
| 87 | 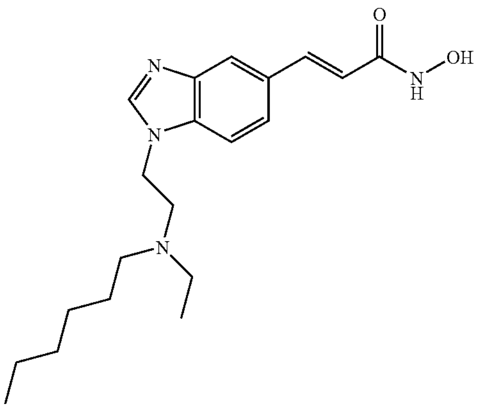 | 359 | 3-{1-[2-(Ethyl-hexyl-amino)-ethyl]-1H-benzoimidazol-5-yl}-N-hydroxy-acrylamide |
| 88 | 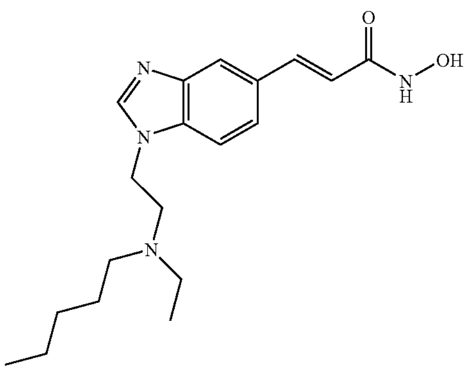 | 345 | 3-{1-[2-(Ethyl-pentyl-amino)-ethyl]-1H-benzoimidazol-5-yl}-N-hydroxy-acrylamide |
| 89 | 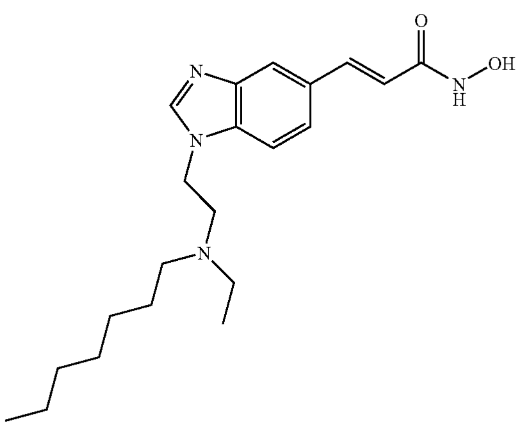 | 373 | 3-{1-[2-(Ethyl-heptyl-amino)-ethyl]-1H-benzoimidazol-5-yl}-N-hydroxy-acrylamide |
| 90 | 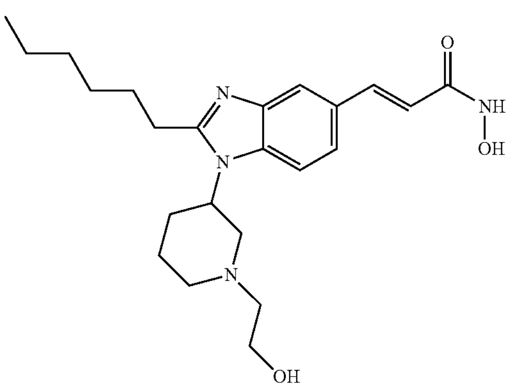 | 415 | 3-{2-Hexyl-1-[1-(2-hydroxy-ethyl)-piperidin-3-yl]-1H-benzoimidazol-5-yl}-N-hydroxy-acrylamide |

-continued

| Compound | Structure | m/z [M + H]+ | NAME |
|---|---|---|---|
| 91 | 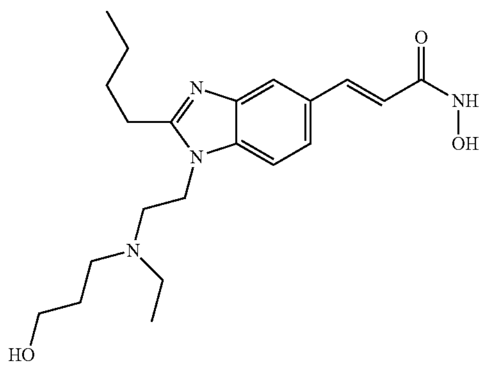 | 389 | 3-(2-Butyl-1-{2-[ethyl-(3-hydroxy-propyl)-amino]-ethyl}-1H-benzoimidazol-5-yl)-N-hydroxy-acrylamide |
| 92 | 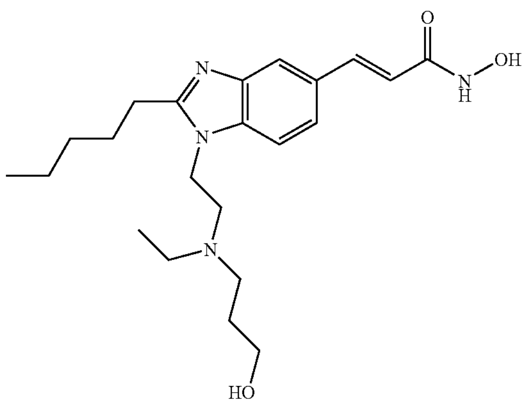 | 403 | 3-(1-{2-[Ethyl-(3-hydroxy-propyl)-amino]-ethyl}-2-pentyl-1H-benzoimidazol-5-yl)-N-hydroxy-acrylamide |
| 93 | 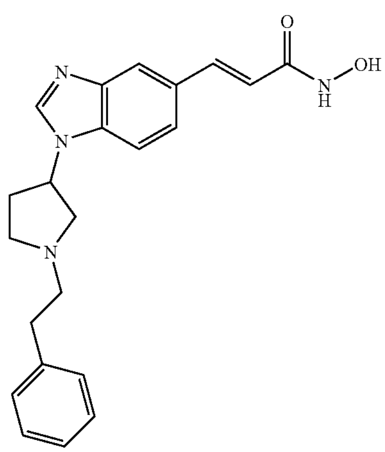 | 377 | (E)-N-hydroxy-3-(1-(1-phenethylpyrrolidin-3-yl)-1H-benzo[d]imidazol-5-yl)acrylamide |
| 94 | 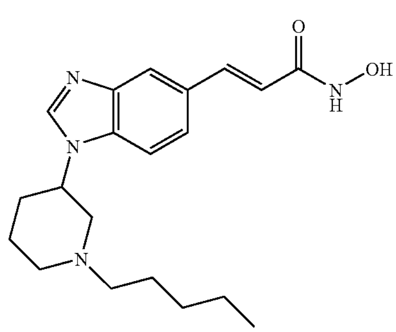 | 357 | (E)-N-hydroxy-3-(1-(1-pentylpiperidin-3-yl)-1H-benzo[d]imidazol-5-yl)acrylamide |

| Compound | Structure | m/z [M + H]+ | NAME |
|---|---|---|---|
| 95 | 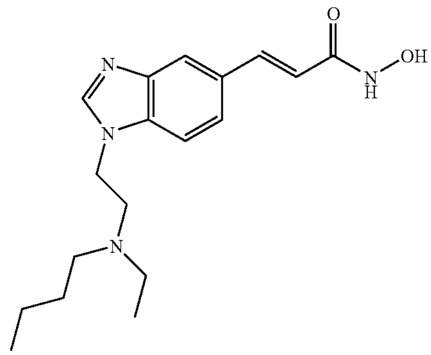 | 331 | 3-{1-[2-(Butyl-ethyl-amino)-ethyl]-1H-benzoimidazol-5-yl}-N-hydroxy-acrylamide |
| 96 | 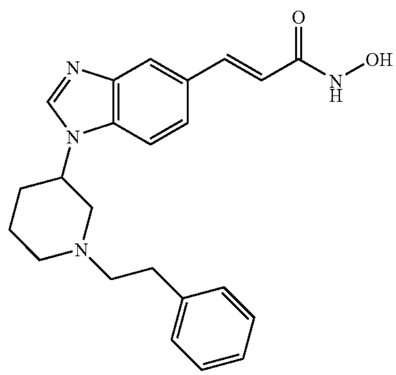 | 391 | (E)-N-hydroxy-3-(1-(1-phenethylpiperidin-3-yl)-1H-benzo[d]imidazol-5-yl)acrylamide |
| 97 | 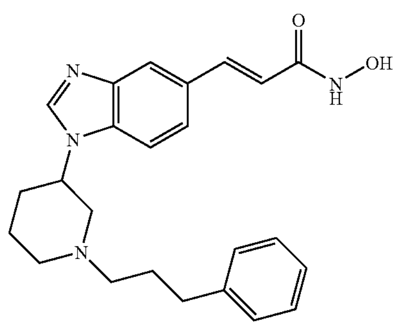 | 405 | (E)-N-hydroxy-3-(1-(1-(3-phenylpropyl)piperidin-3-yl)-1H-benzo[d]imidazol-5-yl)acrylamide |
| 98 | 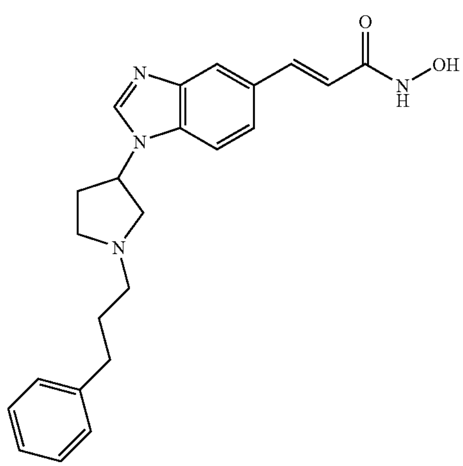 | 391 | (E)-N-hydroxy-3-(1-(1-(3-phenylpropyl)pyrrolidin-3-yl)-1H-benzo[d]imidazol-5-yl)acrylamide |

-continued

| Compound | Structure | m/z [M + H]+ | NAME |
|---|---|---|---|
| 99 | 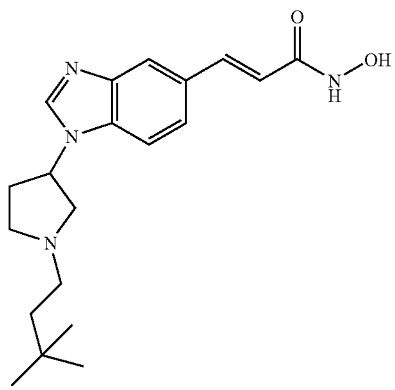 | 357 | 3-{1-[1-(3,3-Dimethyl-butyl)-pyrrolidin-3-yl]-1H-benzoimidazol-5-yl}-N-hydroxy-acrylamide |
| 100 | 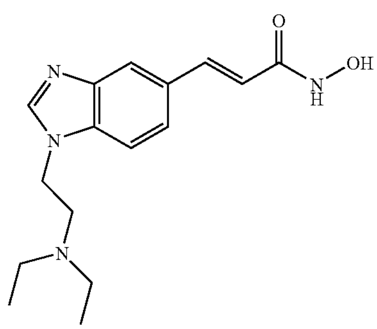 | 303 | (E)-3-(1-(2-(diethylamino)ethyl)-1H-benzo[d]imidazol-5-yl)-N-hydroxyacrylamide |
| 101 | 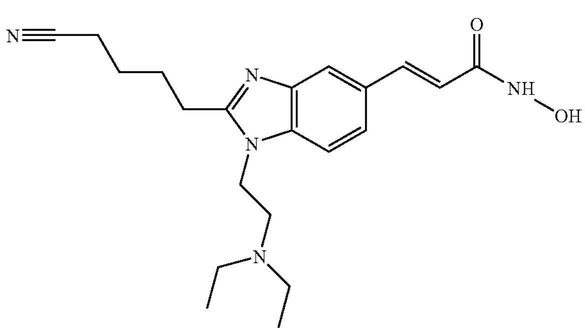 | 384 | 3-[2-(4-Cyano-butyl)-1-(2-diethylamino-ethyl)-1H-benzoimidazol-5-yl]-N-hydroxyacrylamide |
| 102 | 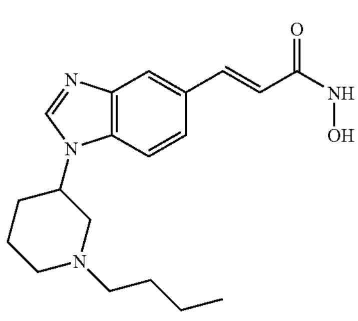 | 343 | (E)-3-(1-(1-butylpiperidin-3-yl)-1H-benzo[d]imidazol-5-yl)-N-hydroxyacrylamide |

-continued
| Compound | Structure | m/z [M + H]+ | NAME |
|---|---|---|---|
| 103 | 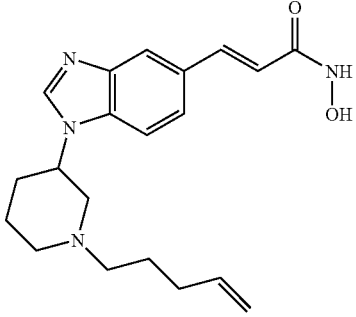 | 355 | (E)-N-hydroxy-3-(1-(1-(pent-4-enyl)piperidin-3-yl)-1H-benzo[d]imidazol-5-yl)acrylamide |
| 104 | 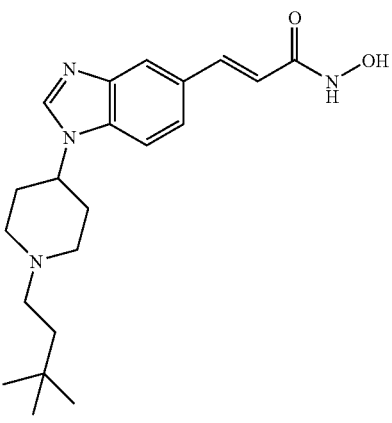 | 371 | (E)-3-(1-(1-(3,3-dimethylbutyl)piperidin-4-yl)-1H-benzo[d]imidazol-5-yl)-N-hydroxyacrylamide |
| 105 | 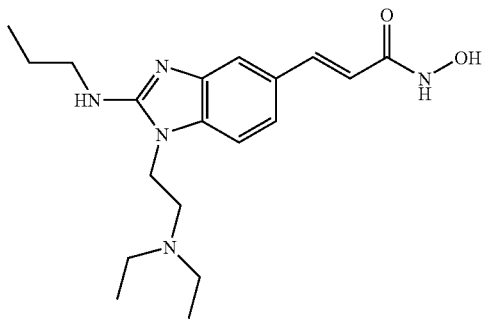 | 360 | 3-[1-(2-Diethylamino-ethyl)-2-propylamino-1H-benzoimidazol-5-yl]-N-hydroxy-acrylamide |
| 107 | 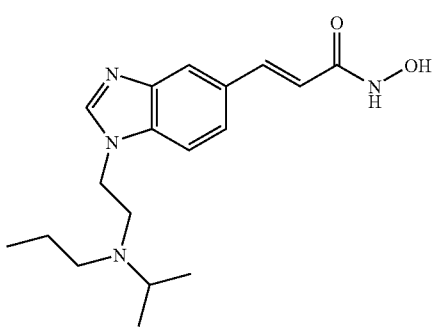 | 331 | (E)-N-hydroxy-3-(1-(2-(isopropyl(propyl)amino)ethyl)-1H-benzo[d]imidazol-5-yl)acrylamide |

-continued

| Compound | Structure | m/z [M + H]+ | NAME |
|---|---|---|---|
| 108 | 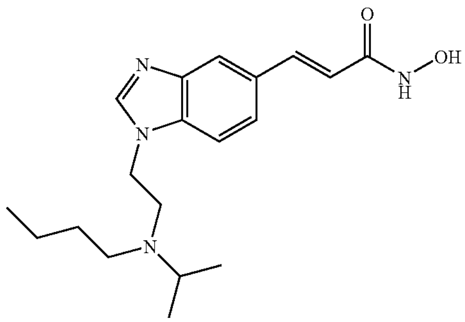 | 345 | 3-{1-[2-(Butyl-isopropyl-amino)-ethyl]-1H-benzoimidazol-5-yl}-N-hydroxy-acrylamide |
| 109 | 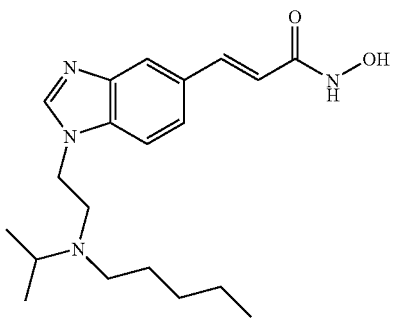 | 359 | N-Hydroxy-3-{1-[2-(isopropyl-pentyl-amino)-ethyl]-1H-benzoimidazol-5-yl}-acrylamide |
| 110 | 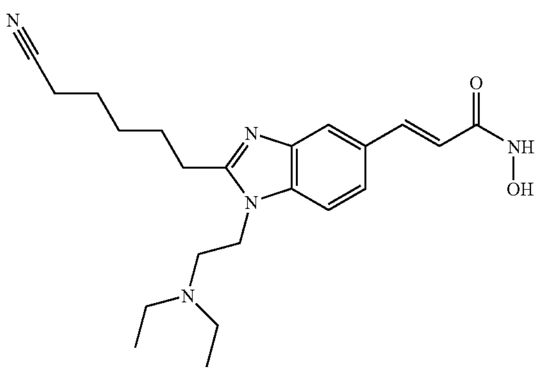 | 398 | 3-[2-(5-Cyano-pentyl)-1-(2-diethylamino-ethyl)-1H-benzoimidazol-5-yl]-N-hydroxy-acrlamide |
| 111 | 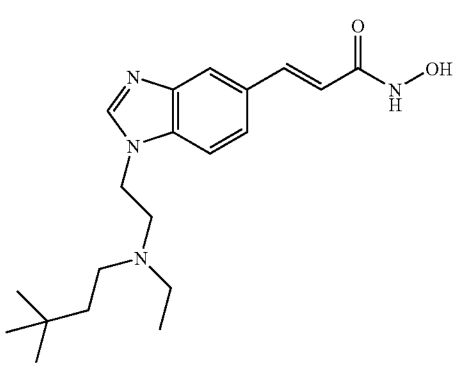 | 359 | 3-(1-{2-[(3,3-Dimethyl-butyl)-ethyl-amino]-ethyl}-1H-benzoimidazol-5-yl)-N-hydroxy-acrylamide |

-continued

| Compound | Structure | m/z [M + H]+ | NAME |
|---|---|---|---|
| 112 | 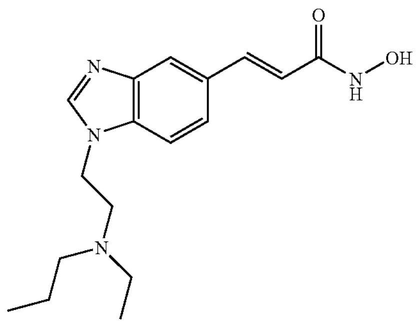 | 317 | 3-{1-[2-(Ethyl-propyl-amino)-ethyl]-1H-benzoimidazol-5-yl}-N-hydroxy-acrylamide |
| 113 | 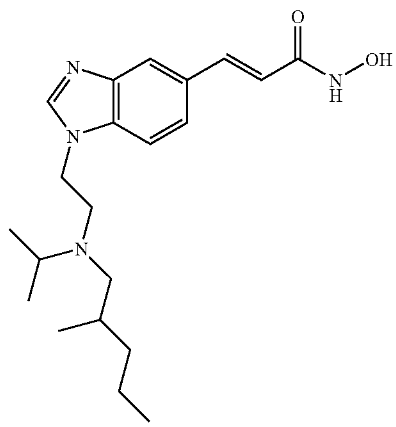 | 373 | N-Hydroxy-3-(1-{2-[isopropyl-(2-methyl-pentyl)-amino]-ethyl}-1H-benzoimidazol-5-yl)-acrylamide |
| 114 | 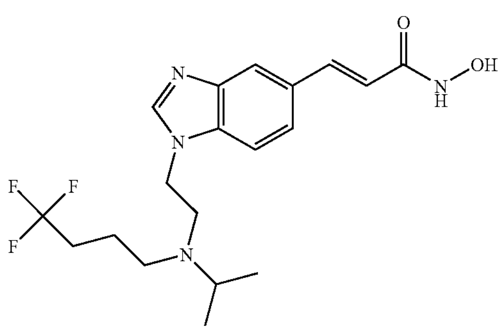 | 399 | (E)-N-hydroxy-3-(1-(2-(isopropyl(4,4,4-trifluorobutyl)amino)ethyl)-1H-benzo[d]imidazol-5-yl)acrylamide |
| 115 | 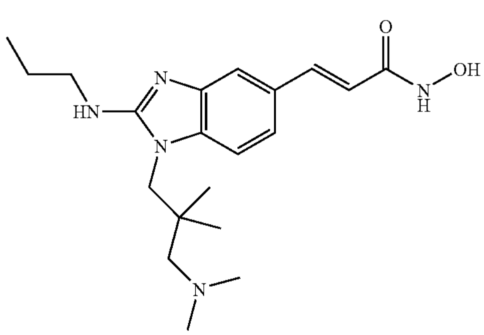 | 374 | 3-[1-(3-Dimethylamino-2,2-dimethyl-propyl)-2-propylamino-1H-benzoimidazol-5-yl]-N-hydroxy-acr |

| Compound | Structure | m/z [M + H]+ | NAME |
|---|---|---|---|
| 116 | 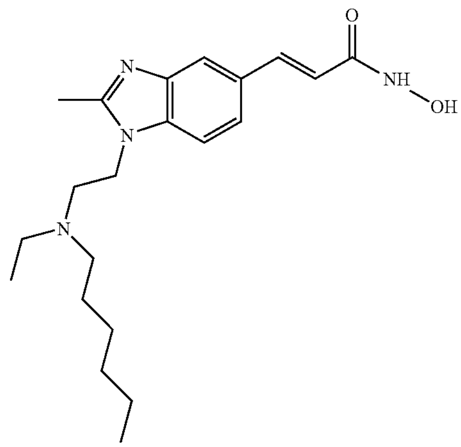 | 373 | 3-{1-[2-(Ethyl-hexyl-amino)-ethyl]-2-methyl-1H-benzoimidazol-5-yl}-N-hydroxy-acrylamide |
| 117 | 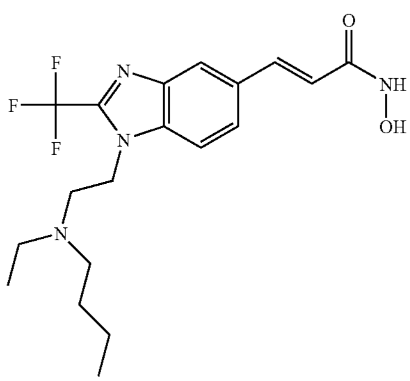 | 399 | 3-{1-[2-(Butyl-ethyl-amino)-ethyl]-2-trifluoromethyl-1H-benzoimidazol-5-yl}-N-hydroxy-acrylamide |
| 118 | 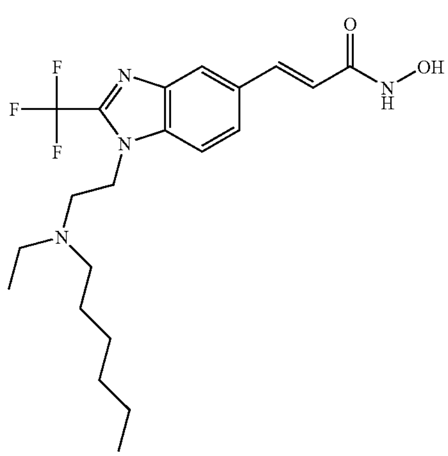 | 427 | 3-{1-[2-(Ethyl-hexyl-amino)-ethyl]-2-trifluoromethyl-1H-benzoimidazol-5-yl}-N-hydroxy-acrylamide |

-continued

| Compound | Structure | m/z [M + H]+ | NAME |
|---|---|---|---|
| 119 | 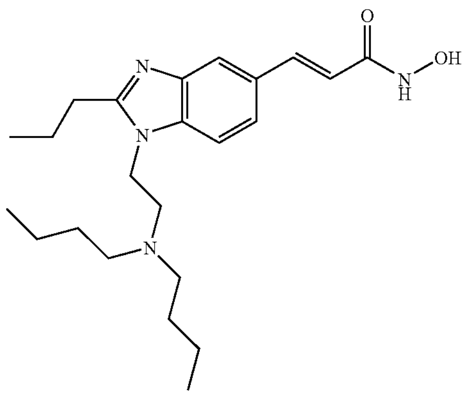 | 401 | (E)-3-(1-(2-(dibutylamino)ethyl)-2-propyl-1H-benzo[d]imidazol-5-yl)-N-hydroxyacrylamide |
| 120 | 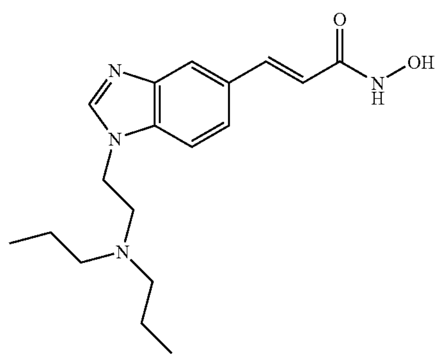 | 331 | 3-[1-(2-Dipropylamino-ethyl)-1H-benzoimidazol-5-yl]-N-hydroxy-acrylame |
| 121 | 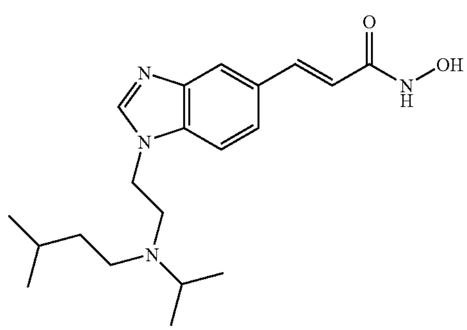 | 359 | N-Hydroxy-3-(1-{2-[isopropyl-(3-methyl-butyl)-amino]-ethyl}-1H-benzoimidazol-5-yl)-acramide |
| 122 | 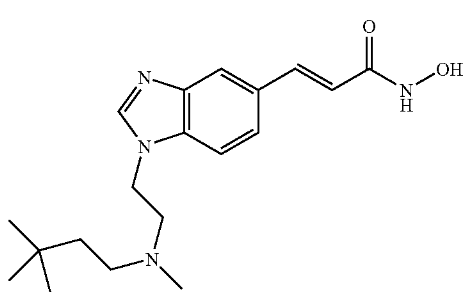 | 345 | 3-(1-{2-[(3,3-Dimethyl-butyl)-methyl-amino]-ethyl}-1H-benzoimidazol-5-yl)-N-hydroxy-acrylamide |

| Compound | Structure | m/z [M + H]+ | NAME |
|---|---|---|---|
| 123 | 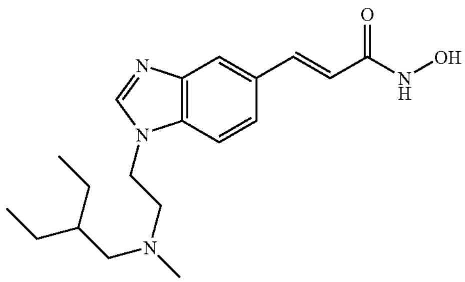 | 345 | 3-(1-{2-[(2-Ethyl-butyl)-methyl-amino]-ethyl}-1H-benzoimidazol-5-yl)-N-hydroxy-acrylamide |
| 124 | 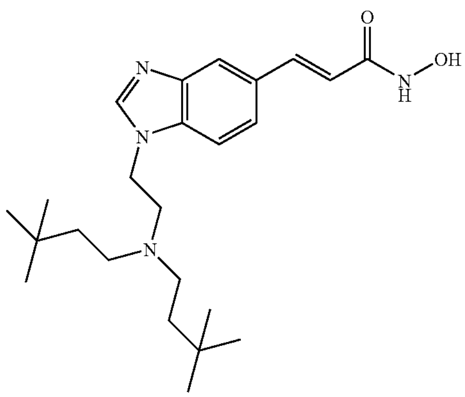 | 415 | (E)-3-(1-(2-(bis(3,3-dimethylbutyl)amino)ethyl)-1H-benzo[d]imidazol-5-yl)-N-hydroxyacrylamide |
| 125 | 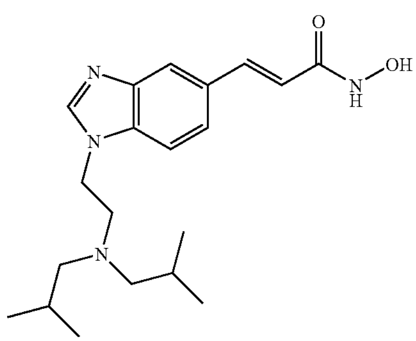 | 359 | (E)-3-(1-(2-(diisobutylamino)ethyl)-1H-benzo[d]imidazol-5-yl)-N-hydroxyacrylamide |
| 126 | 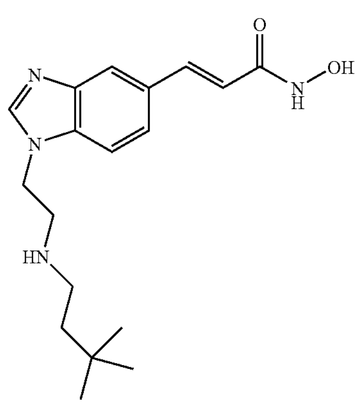 | 331 | 3-{1-[2-(3,3-Dimethyl-butylamino)-ethyl]-1H-benzoimidazol-5-yl}-N-hydroxy-acrylamide |

-continued

| Compound | Structure | m/z [M + H]+ | NAME |
|---|---|---|---|
| 127 | 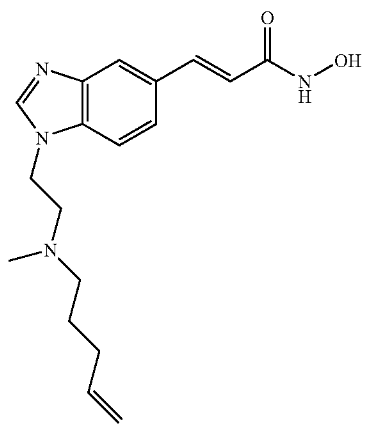 | 329 | N-Hydroxy-3-{1-[2-(methyl-pent-4-enyl-amino)-ethyl]-1H-benzoimidazol-5-yl}-acrylamide |
| 128 | 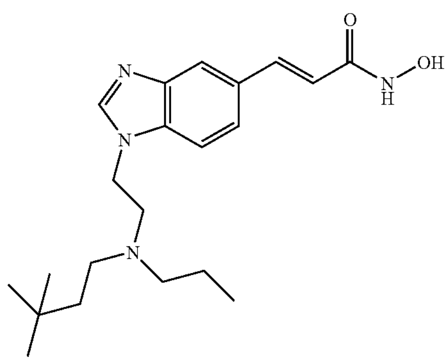 | 373 | 3-(1-{2-[(3,3-Dimethyl-butyl)-propyl-amino]-ethyl}-1H-benzoimidazol-5-yl)-N-hydroxy-acrylamide |
| 129 | 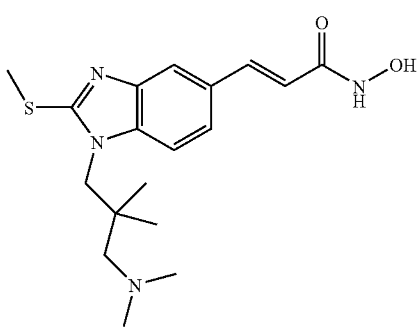 | 363 | 3-[1-(3-Dimethylamino-2,2-dimethyl-propyl)-2-methylsulfanyl-1H-benzoimidazol-5-yl]-N-hydroxy-acrylamide |
| 130 | 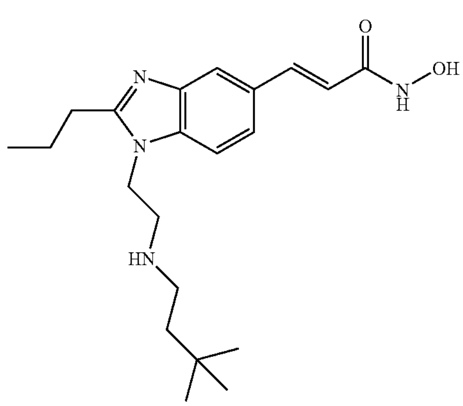 | 373 | 3-{1-[2-(3,3-Dimethyl-butylamino)-ethyl]-2-propyl-1H-benzoimidazol-5-yl}-N-hydroxy-acrylamide |

-continued

| Compound | Structure | m/z [M + H]+ | NAME |
|---|---|---|---|
| 131 | 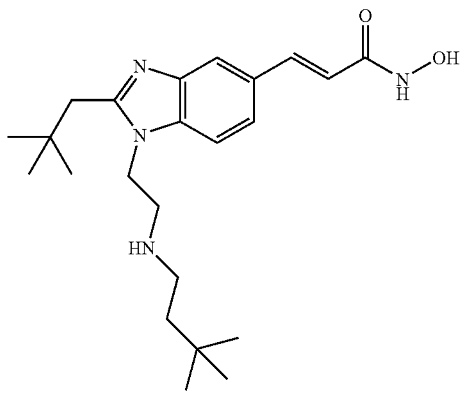 | 401 | 3-[1-[2-(3,3-Dimethyl-butylamino)-ethyl]-2-(2,2-dimethyl-propyl)-1H-benzoimidazol-5-yl]-N-hydroxy-acrylamide |
| 132 | 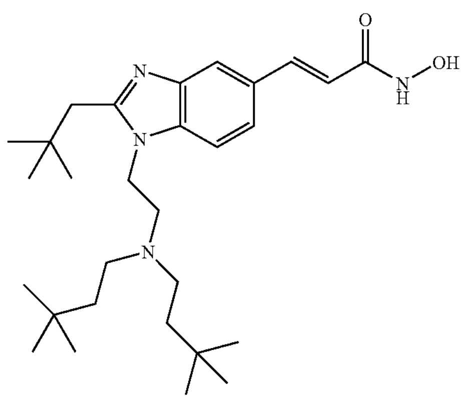 | 485 | 3-[1-{2-[Bis-(3,3-dimethyl-butyl)amino]-ethyl}-2-(2,2-dimethyl-propyl)-1H-benzoimidazol-5-yl]-N-hydroxy-acrylamide |
| 133 | 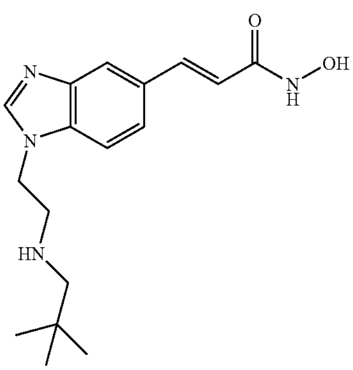 | 317 | 3-{1-[2-(2,2-Dimethyl-propylamino)-ethyl]-1H-benzoimidazol-5-yl}-N-hydroxy-acrylamide |
| 134 | 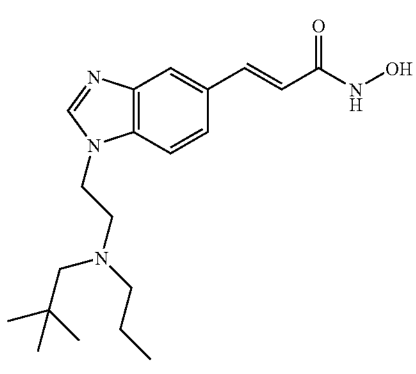 | 359 | 3-(1-{2-[(2,2-Dimethyl-propyl)-propyl-amino]-ethyl}-1H-benzoimidazol-5-yl)-N-hydroxy-acrylamide |

-continued

| Compound | Structure | m/z [M + H]+ | NAME |
|---|---|---|---|
| 135 | 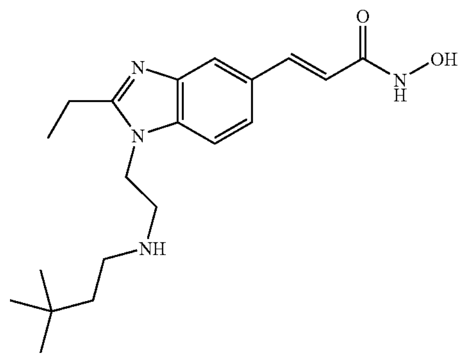 | 359 | 3-{1-[2-(3,3-Dimethyl-butylamino)-ethyl]-2-ethyl-1H-benzoimidazol-5-yl}-N-hydroxy-acrylamide |
| 136 | 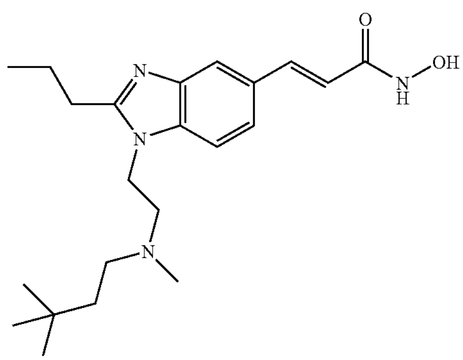 | 387 | 3-(1-{2-[(3,3-Dimethyl-butyl)-methyl-amino]-ethyl}-2-propyl-1H-benzoimidazol-5-yl)-N-hydroxy-acrylamide |
| 137 | 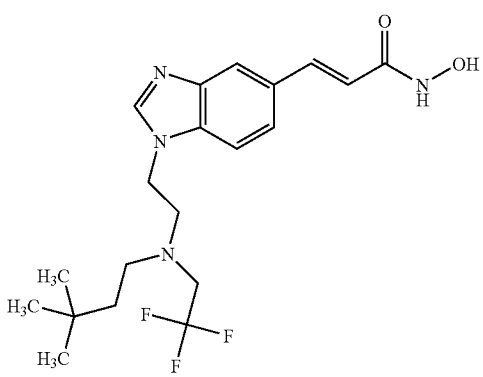 | 413 | 3-(1-{2-[(3,3-Dimethyl-butyl)-(2,2,2-trifluoro-ethyl)-amino]-ethyl}-1H-benzoimidazol-5-yl)-N-hydroxy-acrylamide |
| 138 | 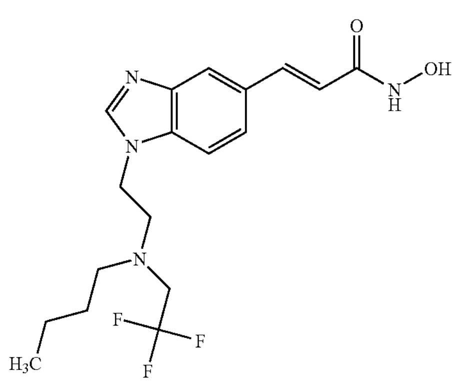 | 385 | 3-(1-{2-[Butyl-(2,2,2-trifluoro-ethyl)-amino]-ethyl}-1H-benzoimidazol-5-yl)-N-hydroxy-acrylamide |

Biological Testing and Enzyme Assays
Recombinant GST-HDAC1 Protein Expression and Purification Human cDNA library was prepared using cultured SW620 cells. Amplification of human HDAC1 coding region from this cDNA library was cloned separately into the baculovirus expression pDEST20 vector (GATEWAY Cloning Technology, Invitrogen Pte Ltd). The pDEST20-HDAC1 construct was confirmed by DNA sequencing. Recombinant baculovirus was prepared using the Bac-To-Bac method following the manufacturer's instruction (Invitrogen Pte Ltd). Baculovirus titer was determined by plaque assay to be about $10^8$ PFU/ml.

Expression of GST-HDAC1 was done by infecting SF9 cells (Invitrogen Pte Ltd) with pDEST20-HDAC1 baculovirus at MOI=1 for 48 h. Soluble cell lysate was incubated with pre-equilibrated Glutathione Sepharose 4B beads (Amersham) at 4° C. for 2 h. The beads were washed with PBS buffer for 3 times. The GST-HDAC1 protein was eluted by elution buffer containing 50 mM Tris, pH8.0, 150 mM NaCl, 1% Triton X-100 and 10 mM or 20 mM reduced Glutathione. The purified GST-HDAC1 protein was dialyzed with HDAC storage buffer containing 10 mM Tris, pH7.5, 100 mM NaCl and 3 mM $MgCl_2$. 20% Glycerol was added to purified GST-HDAC1 protein before storage at −80° C.

In Vitro HDAC Assay for Determination of IC50 Values

The assay has been carried out in 96 well format and the BIOMOL fluorescent-based HDAC activity assay has been applied. The reaction composed of assay buffer, containing 25 mM Tris pH 7.5, 137 mM NaCl, 2.7 mM KCl, 1 mM $MgCl_2$, 1 mg/ml BSA, tested compounds, an appropriate concentration of HDAC1 enzyme, 500 uM Flur de lys generic substrate for HDAC1 enzyme and subsequently was incubated at room temperature for 2 h. Flur de lys Developer was added and the reaction was incubated for 10 min. Briefly, deacetylation of the substrate sensitizes it to the developer, which then generates a fluorophore. The fluorophore is excited with 360 nm light and the emitted light (460 nm) is detected on a fluorometric plate reader (Tecan Ultra Microplate detection system, Tecan Group Ltd.).

The analytical software, Prism 4.0 (GraphPad Software Inc) has been used to generate $IC_{50}$ from a series of data. $IC_{50}$ is defined as the concentration of compound required for 50% inhibition of HDAC enzyme activity.

The HDAC enzyme inhibition results of representative compounds are shown in Table 1 (unit is micromolar).

TABLE 1

HDAC1 enzyme activity $IC_{50}$ (unit is micromolar).

| Compound | $IC_{50}$ (μM) |
|---|---|
| 1 | 0.042 |
| 2 | 0.38 |
| 3 | 0.15 |
| 4 | 0.12 |
| 5 | 0.17 |
| 6 | 0.18 |
| 7 | 0.091 |
| 8 | 0.052 |
| 9 | 0.21 |
| 10 | 0.14 |
| 11 | 0.070 |
| 12 | 0.064 |
| 13 | 0.42 |
| 14 | 0.077 |
| 15 | 0.085 |
| 17 | 0.13 |
| 19 | 0.064 |
| 20 | 0.26 |

TABLE 1-continued

HDAC1 enzyme activity $IC_{50}$ (unit is micromolar).

| Compound | $IC_{50}$ (μM) |
|---|---|
| 21 | 0.38 |
| 22 | 0.064 |
| 23 | 0.045 |
| 24 | 0.51 |
| 25 | 0.23 |
| 26 | 0.040 |
| 27 | 0.23 |
| 28 | 0.021 |
| 29 | 0.13 |
| 30 | 0.021 |
| 31 | 0.045 |
| 32 | 0.060 |
| 33 | 0.23 |
| 34 | 0.88 |
| 35 | 0.082 |
| 36 | 0.096 |
| 37 | 0.091 |
| 38 | 0.56 |
| 39 | 0.024 |
| 40 | 0.027 |
| 41 | 0.062 |
| 42 | 0.15 |
| 43 | 0.33 |
| 44 | 0.054 |
| 45 | 0.053 |
| 46 | 0.049 |
| 47 | 0.21 |
| 48 | 0.43 |
| 49 | 0.11 |
| 50 | 0.036 |
| 51 | 0.066 |
| 52 | 0.025 |
| 53 | 0.10 |
| 54 | 0.048 |
| 55 | 0.037 |
| 56 | 0.029 |
| 57 | 0.090 |
| 58 | 0.030 |
| 59 | 0.077 |
| 60 | 0.10 |
| 61 | 0.070 |
| 62 | 0.054 |
| 63 | 0.051 |
| 64 | 0.10 |
| 65 | 0.078 |
| 66 | 0.34 |
| 68 | 0.034 |
| 70 | 0.068 |
| 71 | 0.040 |
| 72 | 0.017 |
| 73 | 0.026 |
| 74 | 0.028 |
| 75 | 0.050 |
| 76 | 0.018 |
| 77 | 0.026 |
| 78 | 0.044 |
| 79 | 0.040 |
| 80 | 0.040 |
| 81 | 0.12 |
| 82 | 0.10 |
| 83 | 0.19 |
| 84 | 0.063 |
| 85 | 0.11 |
| 86 | 0.16 |
| 87 | 0.10 |
| 88 | 0.047 |
| 89 | 0.080 |
| 90 | 0.51 |
| 91 | 0.060 |
| 92 | 0.050 |
| 93 | 0.23 |
| 94 | 0.064 |
| 95 | 0.052 |
| 96 | 0.080 |
| 97 | 0.10 |
| 98 | 0.32 |

TABLE 1-continued

HDAC1 enzyme activity IC$_{50}$ (unit is micromolar).

| Compound | IC$_{50}$ (μM) |
|---|---|
| 99 | 0.12 |
| 100 | 0.19 |
| 101 | 0.08 |
| 102 | 0.54 |
| 103 | 0.10 |
| 104 | 0.41 |
| 105 | 0.13 |
| 107 | 0.074 |
| 108 | 0.043 |
| 109 | 0.048 |
| 110 | 0.044 |
| 111 | 0.029 |
| 112 | 0.12 |
| 113 | 0.016 |
| 114 | 0.063 |
| 116 | 0.10 |
| 117 | 0.19 |
| 118 | 0.48 |
| 119 | 0.18 |
| 120 | 0.11 |
| 121 | 0.079 |
| 122 | 0.037 |
| 123 | 0.027 |
| 124 | 0.085 |
| 125 | 0.16 |
| 126 | 0.042 |
| 127 | 0.078 |
| 128 | 0.031 |
| 129 | 0.77 |
| 130 | 0.036 |
| 131 | 0.066 |
| 133 | 0.072 |
| 134 | 0.22 |
| 135 | 0.074 |
| 136 | 0.053 |
| 137 | 0.093 |
| 138 | 0.10 |

Cell-Based Proliferation Assay for Determination of GI$_{50}$ Values

Human colon cancer cell lines (Colo205, HCT116), Ovarian cancer cell line (A2780), Hepatoma cell line (HEP3B), Prostate cancer cell line (PC3) were obtained from ATCC or ECACC. Colo205 cells were cultivated in RPMI 1640 containing 2 mM L-Glutamine, 5% FBS, 1.0 mM Na Pyruvate, 1 U/ml of penicillin and 1 μg of streptomycin. HCT116 cells were cultivated in McCoy's containing RPMI 1640 containing 2 mM L-Glutamine, 5% FBS, 1 U/ml of penicillin and 1 μg of streptomycin. A2780 cells were cultivated in RPMI 1640 containing 2 mM L-Glutamine, 5% FBS, 1 U/ml of penicillin and 1 μg of streptomycin. HEP3B cells were cultivated in EMEM containing 2 mM L-glutamine, 5% FBS, 1% non essential amino acid, 1 mM Na Pyruvate, 1 U/ml of penicillin and 1 μg of streptomycin. PC3 cells were cultivated in F12K, 2 mM L-glutamine, 5% FBS, 1 U/ml of penicillin and 1 μg of streptomycin. PC3, Colo205, and HCT116 cells were seeded in 96-wells plate at 1000, 5000 and 6000 cells per well respectively. A2780 and HEP3B cells were seeded in 96-wells plate at 4000 cells per well respectively. The plates were incubated at 37° C., 5% CO$_2$, for 24 h. Cells were treated with compounds at various concentrations for 96 h. Cell growth was then monitored using CyQUANT® cell proliferation assay (Invitrogen Pte Ltd). Dose response curves were plotted to determine GI$_{50}$ values for the compounds using XL-fit (ID Business Solution, Emeryville, Calif.). GI$_{50}$ is defined as the concentration of compound required for 50% inhibition of cell growth.

The cellular or growth inhibition activity results of representative compounds are shown in Table 2 and 3. The data indicated that the compounds of this invention are active in the inhibition of tumour cell growth.

TABLE 2

Cellular or Growth Inhibition Activity in Colo205 cells (unit is micromolar)

| Compound | GI$_{50}$ (μM) |
|---|---|
| 1 | 0.50 |
| 2 | 2.12 |
| 3 | 2.22 |
| 4 | 2.62 |
| 5 | 2.58 |
| 6 | 2.69 |
| 7 | 0.81 |
| 8 | 0.56 |
| 9 | 1.87 |
| 10 | 1.77 |
| 11 | 0.48 |
| 12 | 0.51 |
| 13 | 5.5 |
| 14 | 0.63 |
| 15 | 1.50 |
| 17 | 1.19 |
| 19 | 0.53 |
| 20 | 2.66 |
| 21 | 2.51 |
| 22 | 0.75 |
| 23 | 0.19 |
| 24 | 2.99 |
| 25 | 2.38 |
| 26 | 0.37 |
| 27 | 1.42 |
| 28 | 0.18 |
| 29 | 1.92 |
| 30 | 0.31 |
| 31 | 0.42 |
| 32 | 0.74 |
| 33 | 2.11 |
| 34 | 4.4 |
| 35 | 0.66 |
| 36 | 0.86 |
| 37 | 1.09 |
| 38 | 1.94 |
| 39 | 0.23 |
| 40 | 0.16 |
| 41 | 0.92 |
| 42 | 0.98 |
| 43 | 1.86 |
| 44 | 0.87 |
| 45 | 0.54 |
| 46 | 0.48 |
| 47 | 3.6 |
| 48 | 0.78 |
| 49 | 1.75 |
| 50 | 0.17 |
| 51 | 0.26 |
| 52 | 0.21 |
| 53 | 1.05 |
| 54 | 0.46 |
| 55 | 0.91 |
| 56 | 0.90 |
| 57 | 0.65 |
| 58 | 0.38 |
| 59 | 2.28 |
| 60 | 2.48 |
| 61 | 1.32 |
| 62 | 2.60 |
| 63 | 0.54 |
| 64 | 0.73 |
| 65 | 0.56 |
| 66 | 8.8 |
| 68 | 0.52 |
| 70 | 7.0 |
| 71 | 0.24 |
| 72 | 0.16 |
| 73 | 0.23 |
| 74 | 0.55 |
| 75 | 1.20 |

TABLE 2-continued

Cellular or Growth Inhibition Activity in Colo205 cells (unit is micromolar)

| Compound | GI$_{50}$ (µM) |
|---|---|
| 76 | 0.29 |
| 77 | 0.67 |
| 78 | 0.54 |
| 79 | 0.45 |
| 80 | 1.37 |
| 81 | 1.00 |
| 82 | 1.23 |
| 83 | 4.9 |
| 84 | 1.03 |
| 85 | 1.52 |
| 86 | 2.08 |
| 87 | 1.07 |
| 88 | 0.55 |
| 89 | 0.87 |
| 90 | 8.1 |
| 91 | 2.40 |
| 92 | 1.82 |
| 93 | 2.14 |
| 94 | 0.60 |
| 95 | 0.57 |
| 96 | 0.70 |
| 97 | 0.67 |
| 99 | 1.89 |
| 100 | 2.25 |
| 101 | 2.44 |
| 102 | 2.08 |
| 103 | 0.48 |
| 104 | 1.99 |
| 105 | 1.77 |
| 107 | 0.63 |
| 108 | 0.44 |
| 109 | 0.49 |
| 110 | 1.74 |
| 111 | 0.21 |
| 112 | 0.88 |
| 113 | 0.61 |
| 114 | 0.72 |
| 116 | 0.70 |
| 117 | 1.80 |
| 118 | 1.88 |
| 119 | 0.77 |
| 120 | 0.49 |
| 121 | 0.49 |
| 122 | 0.15 |
| 123 | 0.15 |
| 124 | 0.54 |
| 125 | 0.68 |
| 126 | 0.42 |
| 127 | 0.34 |
| 128 | 0.14 |
| 129 | 3.9 |
| 130 | 0.15 |
| 131 | 0.33 |
| 133 | 0.56 |
| 134 | 2.30 |
| 135 | 0.26 |
| 136 | 0.39 |
| 137 | 1.97 |
| 138 | 1.96 |

TABLE 3

Cellular or Growth Inhibition Activity in Various Cancer Cell Lines

| Compound | Cell lines | | | |
|---|---|---|---|---|
| | HCT116 | A2780 | PC3 | HEP3B |
| 1 | ++ | +++ | +++ | ++ |
| 7 | + | + | ++ | |
| 8 | ++ | ++ | +++ | + |
| 22 | + | +++ | +++ | |
| 23 | ++ | +++ | +++ | |
| 30 | ++ | +++ | +++ | |
| 40 | +++ | +++ | +++ | |
| 44 | + | ++ | +++ | |
| 46 | +++ | +++ | +++ | ++ |
| 50 | +++ | +++ | +++ | |
| 52 | +++ | +++ | +++ | |
| 58 | +++ | +++ | +++ | +++ |
| 71 | +++ | +++ | +++ | |
| 111 | | | | +++ |
| 130 | +++ | +++ | +++ | |

("+++" for GI$_{50}$ < 0.5 µM, "++" for GI$_{50}$ between 0.5 and 1.0 µM, "+" for GI$_{50}$ between 1.0 µM to 5.0 µM)

Histone H3 Acetylation Assay

A hallmark of histone deacetylase (HDAC) inhibition is the increase in the acetylation level of histones. Histone acetylation, including H3, H4 and H2A can be detected by immunoblotting (western-blot). Colo205 cells, approximately 5×10$^5$ cells, were seeded in the previously described medium, cultivated for 24 h and subsequently treated with HDAC inhibitory agents and a positive control at a final concentration of 10 µM. After 24 h, cells were harvested and lysed according to the instruction from Sigma Mammalian Cell Lysis Kit. The protein concentration was quantified using BCA method (Sigma Pte Ltd). The protein lysate was separated using 4-12% bis-tris SDS-PAGE gel (Invitrogen Pte Ltd) and was transferred onto PVDF membrane (BioRad Pte Ltd). The membrane was probed using primary antibody specific for acetylated histone H3 (Upstate Pte Ltd). The detection antibody, goat anti rabbit antibody conjugated with HRP was used according to the manufacturing instruction (Pierce Pte Ltd). After removing the detection antibody from the membrane, an enhanced chemiluminescent substrate for detection of HRP (Pierce Pte Ltd) was added onto the membrane. After removing the substrate, the membrane was exposed to an X-ray film (Kodak) for 1 sec-20 mins. The X-ray film was developed using the X-ray film processor. The density of each band observed on the developed film could be qualitatively analyzed using UVP Bioimaging software (UVP, Inc, Upland, Calif.). The values were then normalized against the density of actin in the corresponding samples to obtain the expression of the protein.

The results of immuno-blotting assay using acetylated histone H3 antibody are shown in Table 4 for representative compounds of this invention.

TABLE 4

| Compound | Histone Acetylation activities (Histone-3) |
|---|---|
| 1 | Active |
| 2 | Active |
| 3 | Active |
| 7 | Active |
| 8 | Active |
| 11 | Active |
| 12 | Active |
| 14 | Active |
| 17 | Active |
| 19 | Active |
| 22 | Active |

TABLE 4-continued

| Compound | Histone Acetylation activities (Histone-3) |
|---|---|
| 26 | Active |
| 28 | Active |
| 30 | Active |
| 32 | Active |
| 35 | Active |
| 36 | Active |
| 37 | Active |
| 39 | Active |
| 40 | Active |
| 41 | Active |
| 42 | Active |
| 44 | Active |
| 45 | Active |
| 46 | Active |
| 48 | Active |
| 49 | Active |
| 50 | Active |
| 52 | Active |
| 55 | Active |
| 58 | Active |
| 63 | Active |
| 65 | Active |
| 68 | Active |
| 71 | Active |
| 74 | Active |
| 130 | Active |

These data demonstrate that compounds of this invention inhibit histone deacetylases, thereby resulting in the accumulation of acetylated histones such as H3.

Measurement of Microsomal Stability

Metabolic stability measurements in the in vitro using liver microsomes aids in the prediction of the in vivo hepatic clearance and the compound stability towards phase I biotransformation reactions mediated by P450 isozymes.

Pooled human liver microsome (HLM was purchased from BD Gentest (BD BioSciences). The incubations consisted of test compound (5 µM) or control compound (Verapamil), NADPH-generating system solution A (25 mM NADP$^+$, 66 mM glucose-6-phosphate, 66 mM MgCl$_2$ in H$_2$O), NADPH-generating system solution B (40 U/ml glucose-6-phosphate dehydrogenase in 5 mM sodium citrate) and 1.0 mg/ml microsomal protein, respectively, in 100 mM potassium phosphate buffer (pH 7.4). Samples were incubated for 0, 5, 15, 30, 45, 60 min. Reaction was terminated with ice-cold 80% acetonitrile and 20% DMSO. Samples were subsequently centrifuged at 4° C. for 15 min at 2,000 rpm. 100 µL of the supernatant was transferred to the LC-MS Plate for analysis. Before quantitative analysis, the compound was tuned in LC/MS machine to get the optimized MS condition. Liquid chromatography was performed on a Luna C18 column (Phenomenex U.S.A, Torrance, Calif.) (2×50 mm, 5 µM). % of the compound remaining (by area) at each time point is calculated with respect to time 0 min. Plot % remaining against time (min) to obtain the curve and use the Prism software to obtain the $t_{1/2}$. These are demonstrated in table 5.

TABLE 5

| Compound | $t_{1/2}$ (min) |
|---|---|
| 1 | >30 |
| 2 | >30 |
| 8 | >30 |
| 11 | >30 |
| 12 | >30 |
| 14 | >30 |
| 19 | >30 |
| 35 | >30 |
| 40 | >30 |
| 44 | >30 |
| 46 | >30 |
| 52 | >30 |
| 58 | >30 |
| 63 | >30 |
| 68 | >30 |
| 71 | >30 |
| 74 | >30 |
| 78 | >30 |
| 80 | >30 |
| 88 | >30 |
| 108 | >30 |
| 130 | >30 |

The measured in vitro $t_{1/2}$>30 mins for the above compounds signifies that the contribution towards the clearance of the compound due to metabolism is expected to be low in the in vivo situation and thus help in yielding longer half-life and increased exposure of the compounds.

The above results demonstrated the compounds of formula (I) were metabolically stable in human liver microsome assay. Together with the appropriate physicochemical properties, e.g., molecular weight, log P and high solubility, the above compounds could exhibit adequate pharmacological exposure and effect to the body when administrated intravenously or especially orally.

In Vivo Pharmacokinetic (PK) Studies

Compound was dissolved in appropriate solution (saline or DMA and Cremaphor in saline) at 1 mg/ml for intravenous (IV) administration, or in 0.5% methyl cellulose, 0.1% Tween 80 in water at 5 mg/ml for oral administration. Mice were randomized according to body weight, grouped three per time point. Mice were administered single IV dose (10 mg/kg) via tail vein, or single oral dose (50 mg/kg) via gavage. At pre-defined time points (predose, 5 or 10, 30 min, 1, 2, 4, 8, and 24 h), one group of mice was sacrificed by overdose CO$_2$ and blood samples were collected by cardiac puncture. The blood samples were centrifuged immediately for 10 min at 3000 rpm to separate plasma, and plasma was kept frozen at −80° C. until analysis by LC/MS/MS. Before sample analysis, the method was developed for LC/MS/MS assay. The method was validated for signal-response of the calibration standards, auto-sampler stability for ~15 hours intra-day and inter-day calibration curve using eight calibration standards excluding the blank plasma. QC samples at three different concentrations in triplicates were prepared to determine the accuracy and precision. The extracted QC samples were compared to unextracted samples to determine the extraction efficiency of the analyte. LLOQ was determined by using triplicate samples of 1 ng/mL and 2 ng/mL to obtain accuracy and precision at the low end. Samples were analysed using the validated method. Data was analyzed by the non-compartmental model using WinNolin 4.0 software (Pharsight, Mountain View, Calif., USA). The mean values for the plasma compound concentration-time profiles were used in mouse PK study.

The PK parameter $AUC_{0-last}$ providing the information on the overall exposure of the drug in vivo is one of the key PK/PD parameters that helps in predicting the efficacy of an anti-cancer compound. The higher the AUC value, the better will be the in vivo efficacy of the compound at similar in vitro potency. Pharmacokinetic data of selected compounds in Table 5 were shown in Table 6 below.

TABLE 6

Representative pharmacokinetic data [compounds were in hydrochloric acid salt form (2HCl), dosed at 50 mg/kg, p.o.]

| Compound | $AUC_{0\text{-}last}$ (ng · h/ml) |
|---|---|
| 1 | 1868 |
| 8 | 1836 |
| 130 | 1050 |

The data in Table 6 further demonstrated that compounds with high metabolic stability as shown by representative compounds in Table 5 together with the appropriate physicochemical properties, e.g., molecular weight, log P, and high solubility, were able to yield adequate pharmacological exposure and effect in the animal when administrated orally.

In Vivo Antineoplastic (or Anti-Tumor) Effect of HDAC Inhibiting Agents:

The efficacy of the compounds of the invention can then be determined using in vivo animal xenograft studies. The animal xenograft model is one of the most commonly used in vivo cancer models.

In these studies Female athymic nude mice (Harlan), 12-14 weeks of age would be implanted subcutaneously in the flank with $5 \times 10^6$ cells of HCT116 human colon tumor cells, or with $5 \times 10^6$ cells of A2780 human ovarian tumor cells, or with $5 \times 10^6$ cells of PC3 prostate cancer cells. When the tumor reaches the size 100 mm$^3$, the xenograft nude mice would be paired-match into various treatment groups. The selected HDAC inhibitors would be dissolved in appropriate vehicles and administered to xenograft nude mice intraperitoneally, intravenously or orally daily for 14-21 days. The dosing volume will be 0.01 ml/g body weight. Paclitaxol, used as positive control, will be prepared for intravenous administration in an appropriate vehicle. The dosing volume for Paclitaxol will be 0.01 ml/g body weight. Tumor volume will be calculated every second day or twice-a-week of post injection using the formula: Volume (mm$^3$)=(w$^2$×l)/2, where w=width and l=length in mm of an HCT116, or A2780, or PC3 tumor. Compounds of this invention that are tested would show significant reduction in tumor volume relative to controls treated with vehicle only. Acetylated histone relative to vehicle treated control group when measured shall be accumulated. The result will therefore indicate that compounds of this invention are efficacious in treating a proliferative disorder/disease such as cancer.

The details of specific embodiments described in this invention are not to be construed as limitations. Various equivalents and modifications may be made without departing from the essence and scope of this invention, and it is understood that such equivalent embodiments are part of this invention.

What is claimed is:

1. A compound of the formula (I):

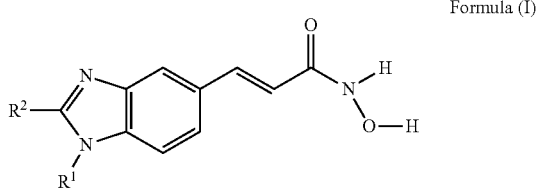

Formula (I)

wherein
R$^1$ is a group of formula:

R$^2$ is selected from the group consisting of: alkyl which may be unsubstituted or substituted with F, cyano, C$_2$-C$_6$alkenyl, or C$_2$-C$_6$alkynyl, and heteroalkyl which may be unsubstituted or substituted by =O;

each R$^{20}$, R$^{21}$, R$^{22}$, R$^{23}$, R$^{24}$ and R$^{25}$ is independently selected from the group consisting of: H and methyl;

each R$^{26}$ and R$^{27}$ is independently selected from the group consisting of H, hydroxylalkyl and alkyl;

m, n and o are integers independently selected from the group consisting of 0, 1, 2, 3 and 4;

or a pharmaceutically acceptable salt or prodrug thereof.

2. A compound according to claim 1 wherein the sum of m+n+o is an integer selected from the group consisting of 0, 1, 2, 3 and 4.

3. A compound according to claim 2 wherein the sum of m+n+o is 2 or 3.

4. A compound according to claim 3 wherein R$^1$ is selected from the group consisting of:
—(CR$^{20}$R$^{21}$)$_2$—NR$^{26}$R$^{27}$;
—(CR$^{22}$R$^{23}$)$_2$—NR$^{26}$R$^{27}$;
—(CR$^{24}$R$^{25}$)$_2$—NR$^{26}$R$^{27}$;
—(CR$^{20}$R$^{21}$)—(CR$^{22}$R$^{23}$)—NR$^{26}$R$^{27}$;
—(CR$^{20}$R$^{21}$)(CR$^{24}$R$^{25}$)—NR$^{26}$R$^{27}$;
—(CR$^{22}$R$^{23}$)—(CR$^{24}$R$^{25}$)—NR$^{26}$R$^{27}$;
—(CR$^{20}$R$^{21}$)$_3$—NR$^{26}$R$^{27}$;
—(CR$^{22}$R$^{23}$)$_3$—NR$^{26}$R$^{27}$;
—(CR$^{24}$R$^{25}$)$_3$—NR$^{26}$R$^{27}$;
—(CR$^{20}$R$^{21}$)$_2$—(CR$^{22}$R$^{23}$)—NR$^{26}$R$^{27}$;
—(CR$^{20}$R$^{21}$)$_2$—(CR$^{24}$R$^{25}$)—NR$^{26}$R$^{27}$;
—(CR$^{20}$R$^{21}$)—(CR$^{22}$R$^{23}$)$_2$—NR$^{26}$R$^{27}$;
—(CR$^{22}$R$^{23}$)$_2$—(CR$^{24}$R$^{25}$)—NR$^{26}$R$^{27}$;
—(CR$^{20}$R$^{21}$)—(CR$^{24}$R$^{25}$)$_2$—NR$^{26}$R$^{27}$;
—(CR$^{22}$R$^{23}$)—(CR$^{24}$R$^{25}$)$_2$—NR$^{26}$R$^{27}$; and
—(CR$^{20}$R$^{21}$)—(CR$^{22}$R$^{23}$)—(CR$^{24}$R$^{25}$)—NR$^{26}$R$^{27}$.

5. A compound according to claim 4 wherein the compound is selected from the group consisting of:

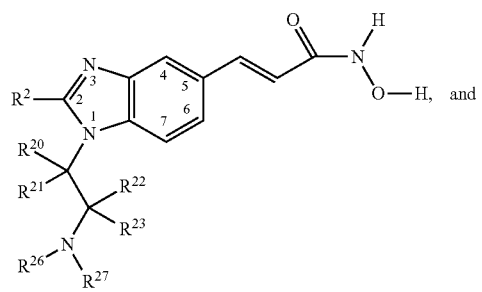

and

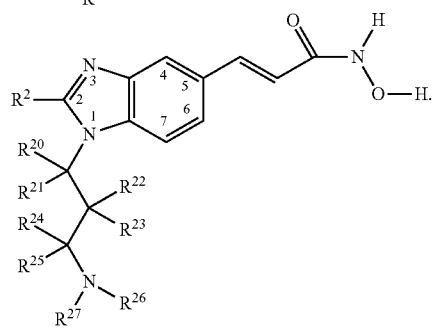

6. A compound according to claim 5 wherein $R^{26}$ and $R^{27}$ are independently selected from the group consisting of: H and alkyl.

7. A compound according to claim 6 wherein $R^{26}$ and $R^{27}$ are independently selected from the group consisting of H, methyl, ethyl, isopropyl, propyl, butyl, isobutyl, pentyl, hexyl and heptyl.

8. A compound according to claim 1 wherein $R^1$ is a group of formula:

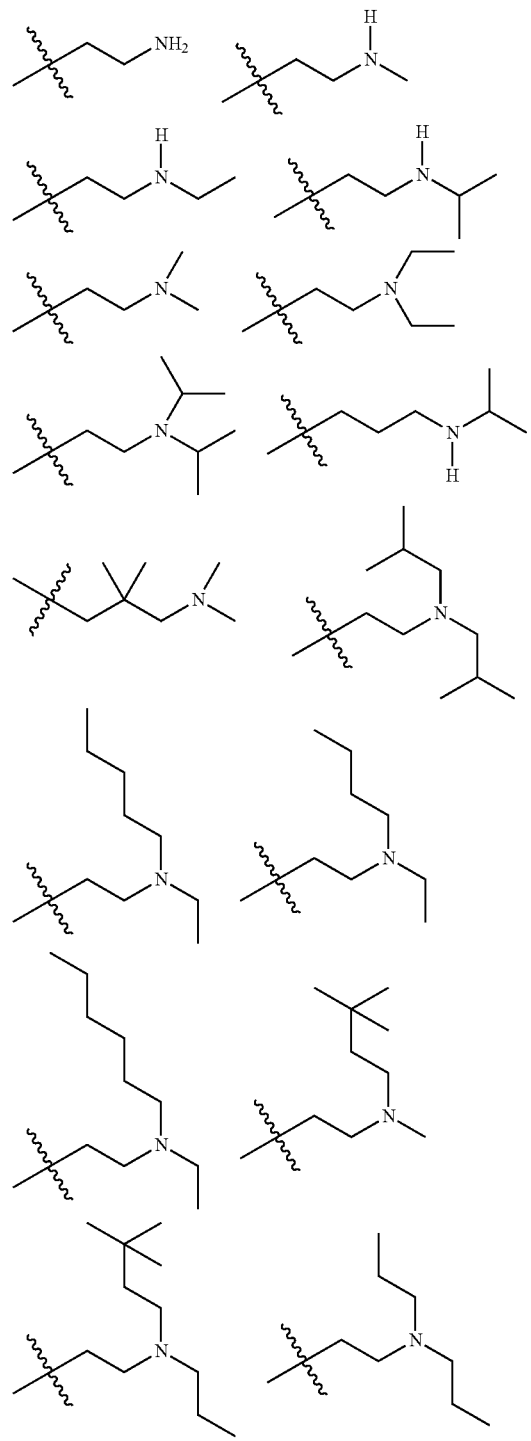

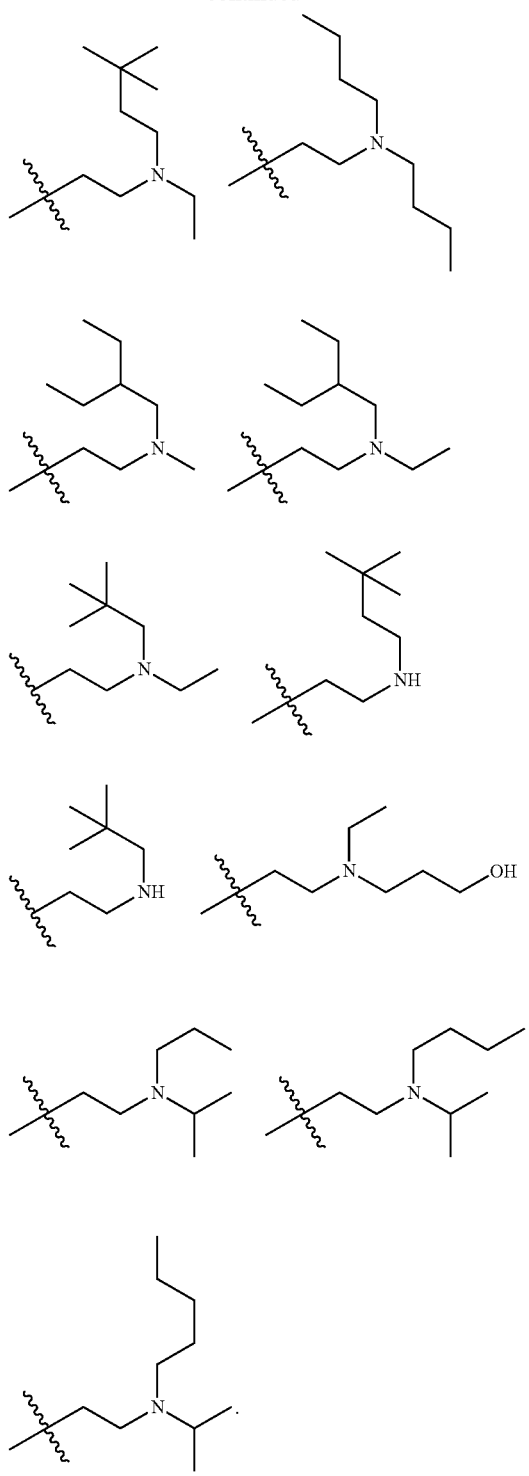

9. A compound according to claim 1 wherein $R^2$ is selected from the group consisting of ethyl, 1-methyl-ethyl, 2,2,2-trifluoroethyl, propyl, 2-methyl-propyl, 2,2-dimethyl-propyl, 3,3,3-trifluoro-propyl, butyl, 3,3-dimethyl-butyl, pentyl, 2,4,4-trimethyl-pentyl, hexyl and octyl.

10. The compound of claim 1 wherein the compound is selected from compounds, and their pharmaceutically acceptable salts, selected from the group consisting of

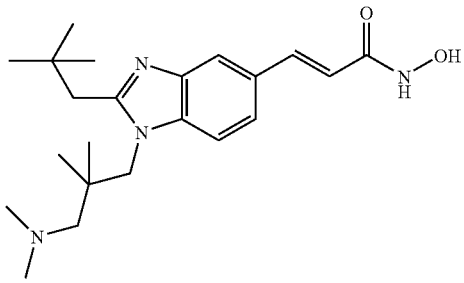

3-[1-(3-Dimethylamino-2,2-dimethyl-propyl)-2-(2,2-dimethyl-propyl)-1H-benzoimidazol-5-yl]-N-hydroxy-acrylamide

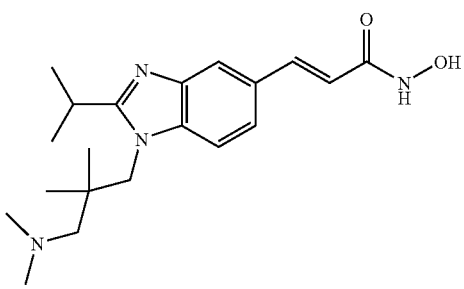

3-[1-(3-Dimethylamino-2,2-dimethyl-propyl)-2-isopropyl-1H-benzoimidazol-5-yl]-N-hydroxy-acrylamide

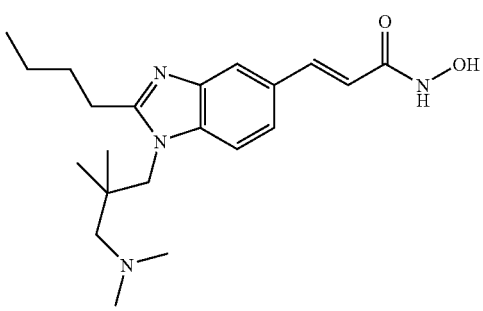

3-[2-Butyl-1-(3-dimethylamino-2,2-dimethyl-propyl)-1H-benzoimidazol-5-yl]-N-hydroxy-acrylamide

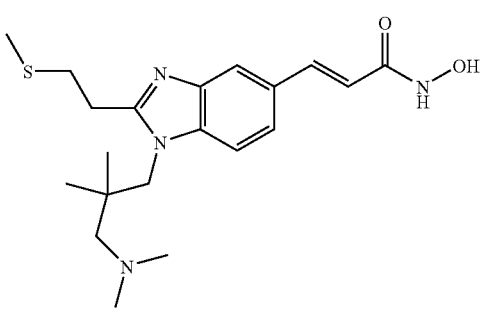

3-[1-(3-Dimethylamino-2,2-dimethyl-propyl)-2-(2-methylsulfanyl-ethyl)-1H-benzoimidazol-5-yl]-N-hydroxy-acrylamide

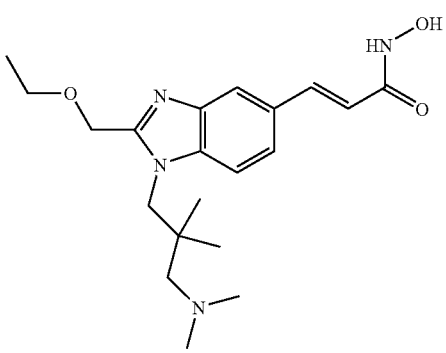

3-[1-(3-Dimethylamino-2,2-dimethyl-propyl)-2-ethoxymethyl-1H-benzoimidazol-5-yl]-N-hydroxy-acrylamide

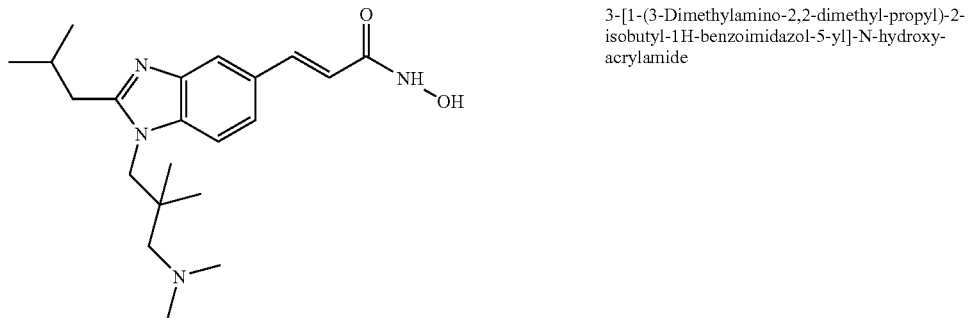

3-[1-(3-Dimethylamino-2,2-dimethyl-propyl)-2-isobutyl-1H-benzoimidazol-5-yl]-N-hydroxy-acrylamide

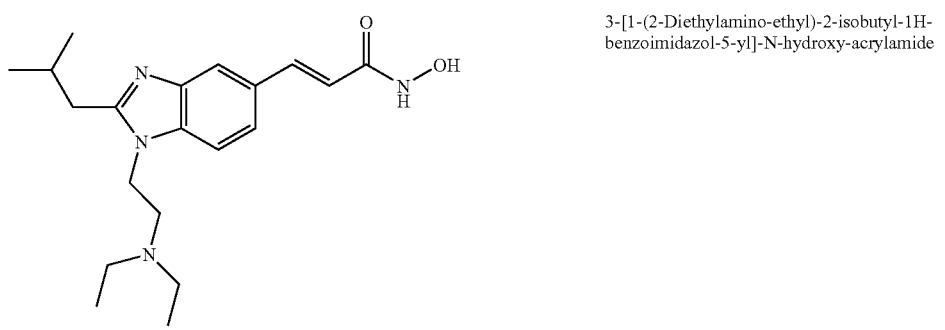

3-[1-(2-Diethylamino-ethyl)-2-isobutyl-1H-benzoimidazol-5-yl]-N-hydroxy-acrylamide

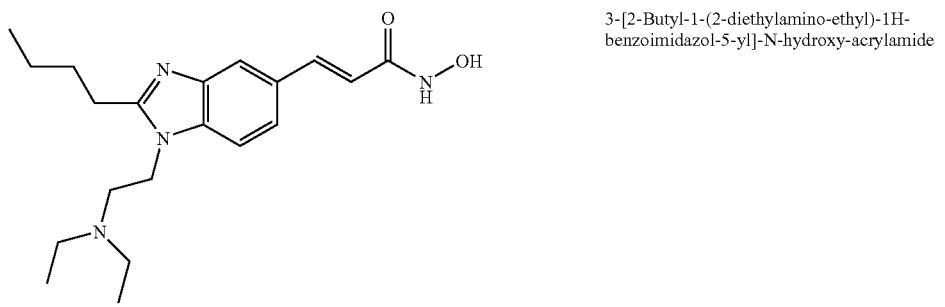

3-[2-Butyl-1-(2-diethylamino-ethyl)-1H-benzoimidazol-5-yl]-N-hydroxy-acrylamide

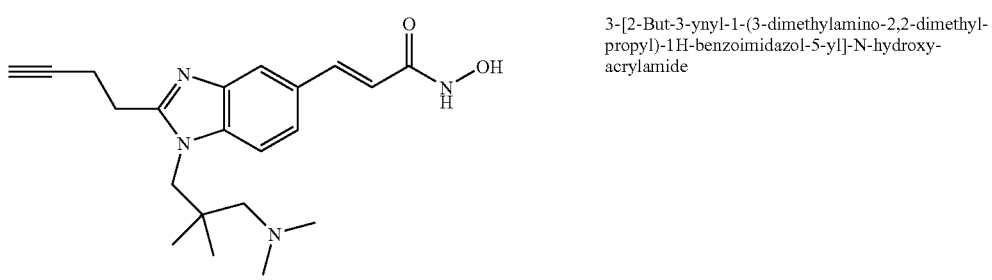

3-[2-But-3-ynyl-1-(3-dimethylamino-2,2-dimethyl-propyl)-1H-benzoimidazol-5-yl]-N-hydroxy-acrylamide

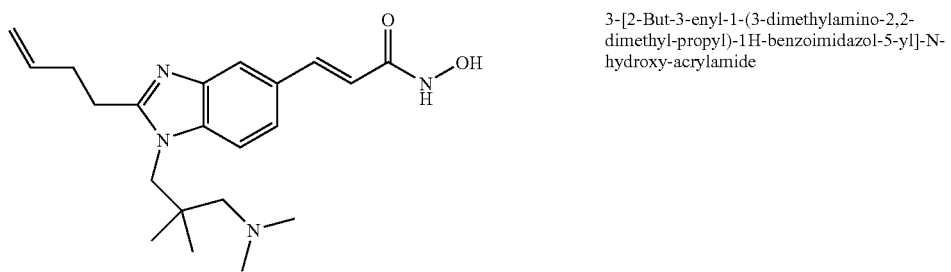

3-[2-But-3-enyl-1-(3-dimethylamino-2,2-dimethyl-propyl)-1H-benzoimidazol-5-yl]-N-hydroxy-acrylamide

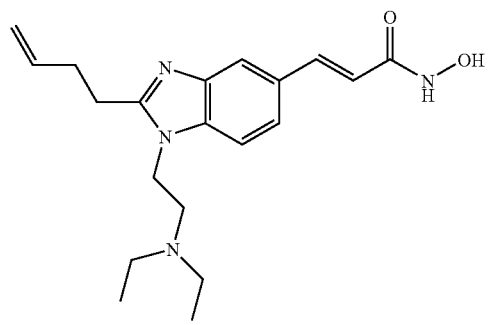
3-[2-But-3-enyl-1-(2-diethylamino-ethyl)-1H-benzoimidazol-5-yl]-N-hydroxy-acrylamide

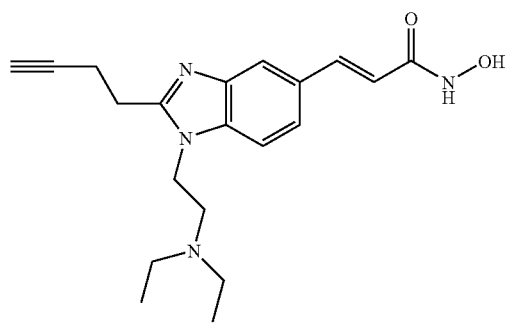
3-[2-But-3-ynyl-1-(2-diethylamino-ethyl)-1H-benzoimidazol-5-yl]-N-hydroxy-acrylamide

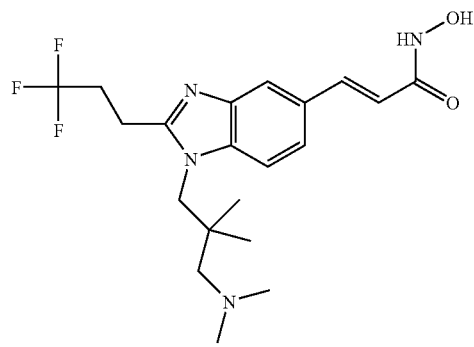
3-[1-(3-Dimethylamino-2,2-dimethyl-propyl)-2-(3,3,3-trifluoro-propyl)-1H-benzoimidazol-5-yl]-N-hydroxy-acrylamide

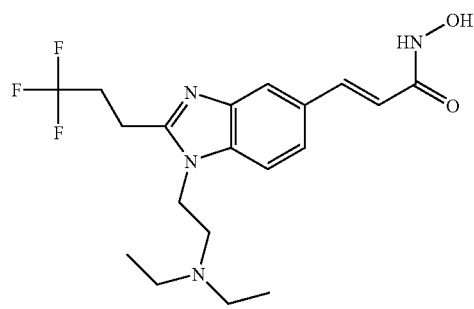
3-[1-(2-Diethylamino-ethyl)-2-(3,3,3-trifluoro-propyl)-1H-benzoimidazol-5-yl]-N-hydroxy-acrylamide

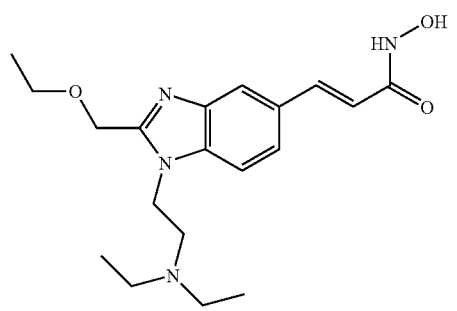
3-[1-(2-Diethylamino-ethyl)-2-ethoxymethyl-1H-benzoimidazol-5-yl]-N-hydroxy-acrylamide

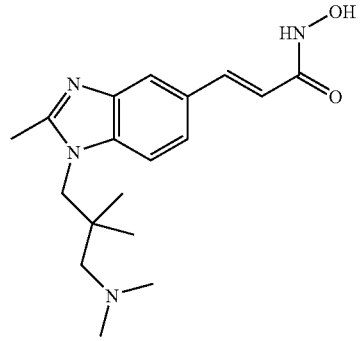
3-[1-(3-Dimethylamino-2,2-dimethyl-propyl)-2-methyl-1H-benzoimidazol-5-yl]-N-hydroxy-acrylamide
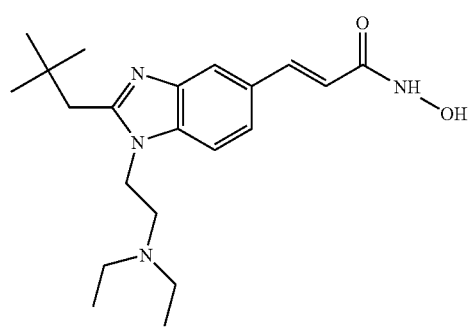
3-[1-(2-Diethylamino-ethyl)-2-(2,2-dimethyl-propyl)-1H-benzoimidazol-5-yl]-N-hydroxy-acrylamide
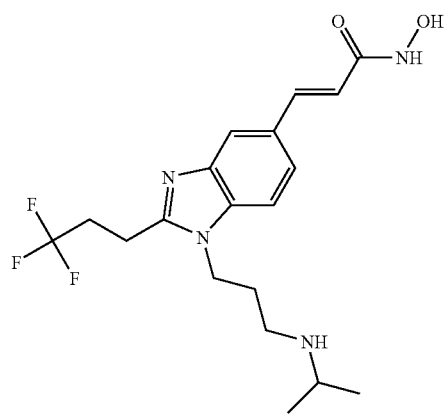
N-Hydroxy-3-[1-(3-isopropylamino-propyl)-2-(3,3,3-trifluoro-propyl)-1H-benzoimidazol-5-yl]-acrylaide
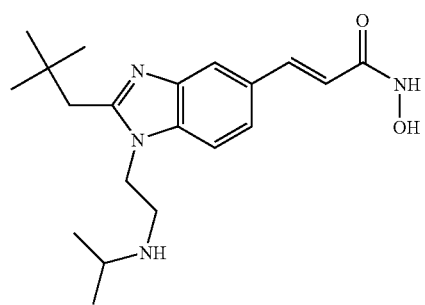
3-[2-(2,2-Dimethyl-propyl)-1-(2-isopropylamino-ethyl)-1H-benzoimidazol-5-yl]-N-hydroxy-acrylamide

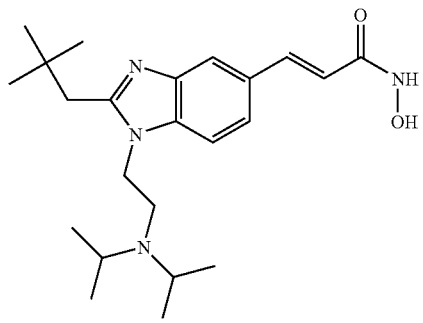 3-[1-(2-Diisopropylamino-ethyl)-2-(2,2-dimethyl-propyl)-1H-benzoimidazol-5-yl]-N-hydroxy-acrylamide

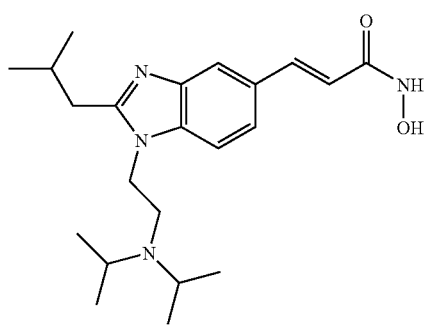 3-[1-(2-Diisopropylamino-ethyl)-2-isobutyl-1H-benzoimidazol-5-yl]-N-hydroxy-acrylamide

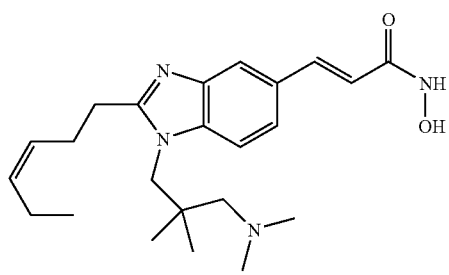 3-[1-(3-Dimethylamino-2,2-dimethyl-propyl)-2-hex-3-enyl-1H-benzoimidazol-5-yl]-N-hydroxy-acrylamide

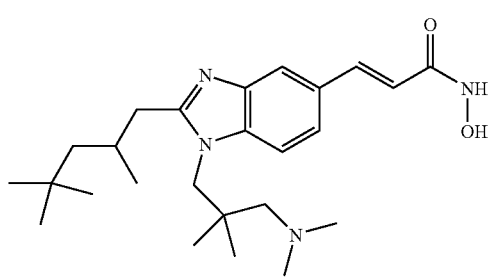 3-[1-(3-Dimethylamino-2,2-dimethyl-propyl)-2-(2,4,4-trimethyl-pentyl)-1H-benzoimidazol-5-yl]-N-hydroxy-acrylamide

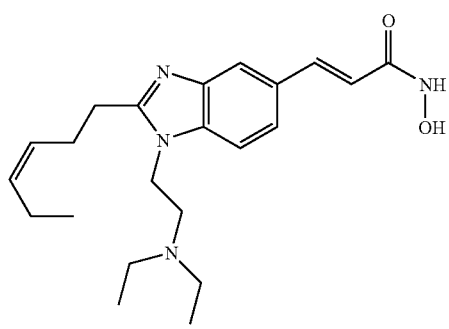 3-[1-(2-Diethylamino-ethyl)-2-hex-3-enyl-1H-benzoimidazol-5-yl]-N-hydroxy-acrylamide

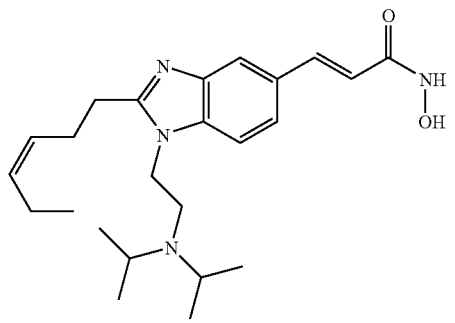
3-[1-(2-Diisopropylamino-ethyl)-2-hex-3-enyl-1H-benzoimidazol-5-yl]-N-hydroxy-acrylamide
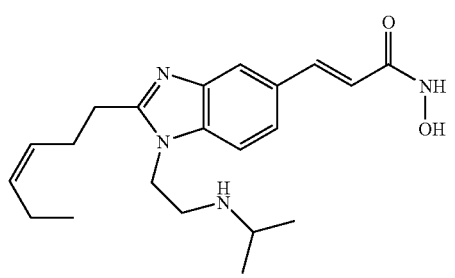
3-[2-Hex-3-enyl-1-(2-isopropylamino-ethyl)-1H-benzoimidazol-5-yl]-N-hydroxy-acrylamide
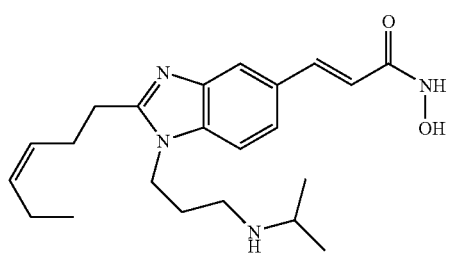
3-[2-Hex-3-enyl-1-(3-isopropylamino-propyl)-1H-benzoimidazol-5-yl]-N-hydroxy-acrylamide
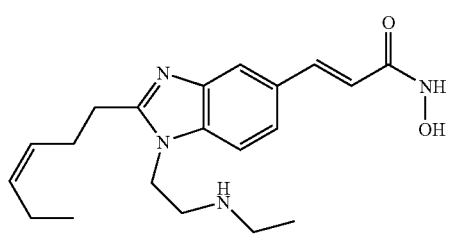
3-[1-(2-Ethylamino-ethyl)-2-hex-3-enyl-1H-benzoimidazol-5-yl]-N-hydroxy-acrylamide
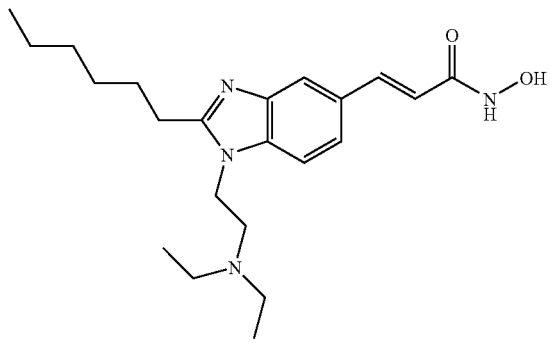
3-[1-(2-Diethylamino-ethyl)-2-hexyl-1H-benzoimidazol-5-yl]-N-hydro

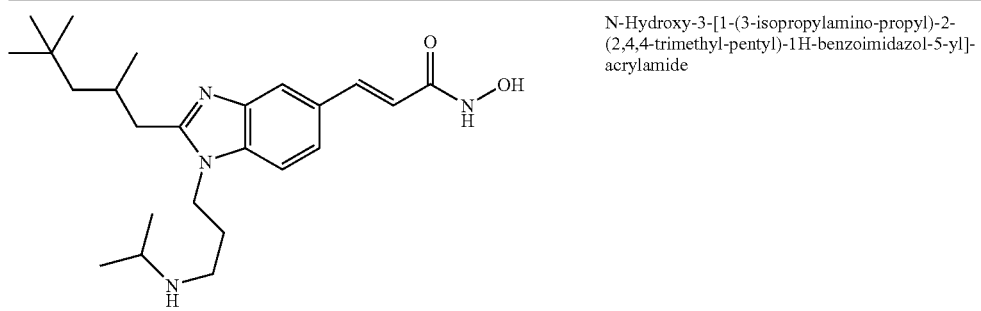
N-Hydroxy-3-[1-(3-isopropylamino-propyl)-2-(2,4,4-trimethyl-pentyl)-1H-benzoimidazol-5-yl]-acrylamide

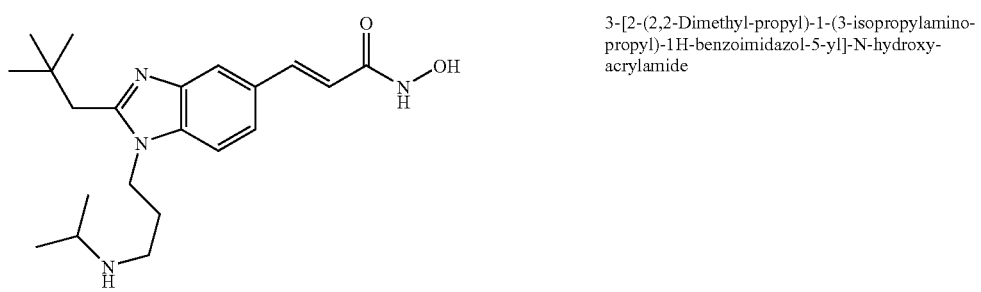
3-[2-(2,2-Dimethyl-propyl)-1-(3-isopropylamino-propyl)-1H-benzoimidazol-5-yl]-N-hydroxy-acrylamide

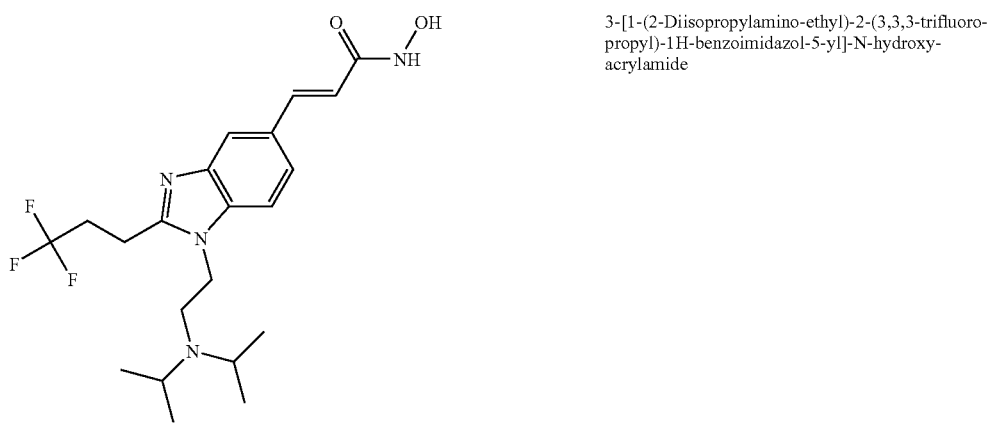
3-[1-(2-Diisopropylamino-ethyl)-2-(3,3,3-trifluoro-propyl)-1H-benzoimidazol-5-yl]-N-hydroxy-acrylamide

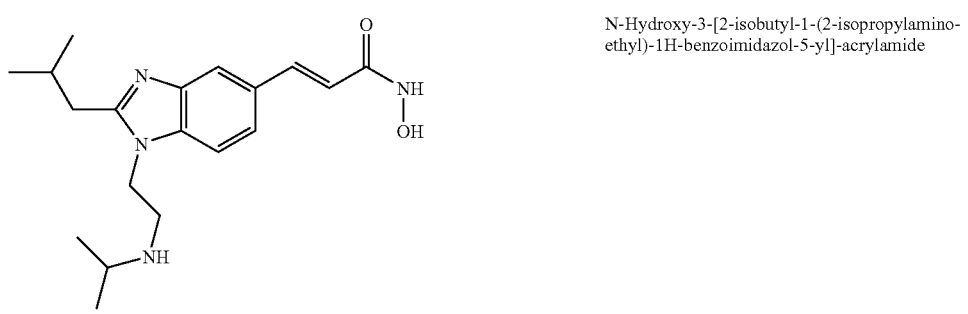
N-Hydroxy-3-[2-isobutyl-1-(2-isopropylamino-ethyl)-1H-benzoimidazol-5-yl]-acrylamide

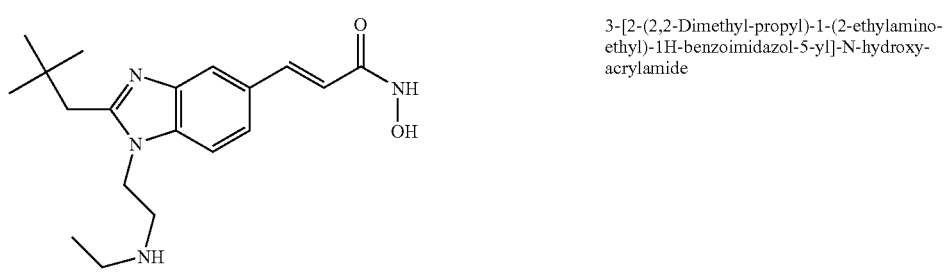
3-[2-(2,2-Dimethyl-propyl)-1-(2-ethylamino-ethyl)-1H-benzoimidazol-5-yl]-N-hydroxy-acrylamide

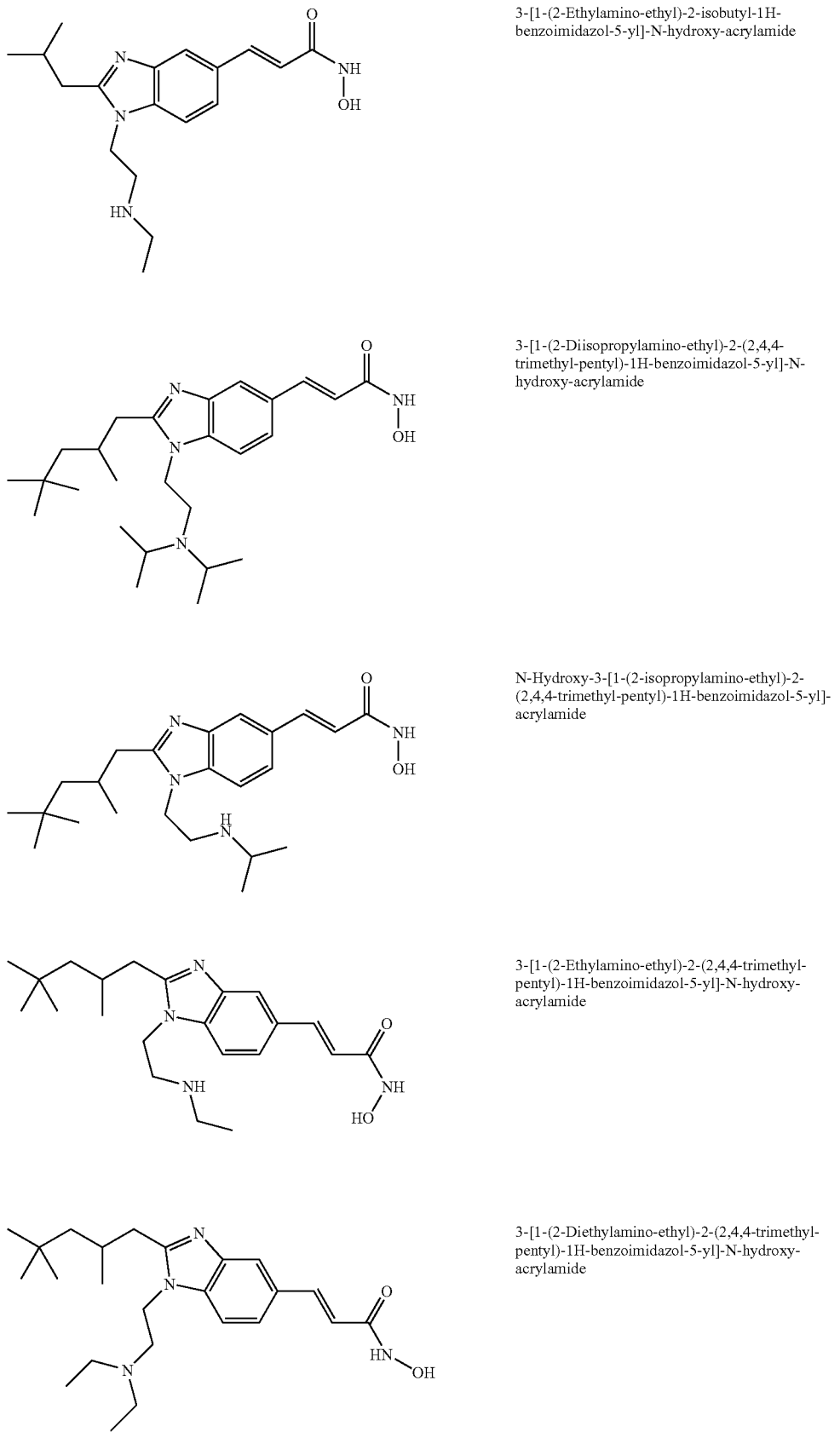

3-[1-(2-Ethylamino-ethyl)-2-isobutyl-1H-benzoimidazol-5-yl]-N-hydroxy-acrylamide 3-[1-(2-Diisopropylamino-ethyl)-2-(2,4,4-trimethyl-pentyl)-1H-benzoimidazol-5-yl]-N-hydroxy-acrylamide N-Hydroxy-3-[1-(2-isopropylamino-ethyl)-2-(2,4,4-trimethyl-pentyl)-1H-benzoimidazol-5-yl]-acrylamide 3-[1-(2-Ethylamino-ethyl)-2-(2,4,4-trimethyl-pentyl)-1H-benzoimidazol-5-yl]-N-hydroxy-acrylamide 3-[1-(2-Diethylamino-ethyl)-2-(2,4,4-trimethyl-pentyl)-1H-benzoimidazol-5-yl]-N-hydroxy-acrylamide

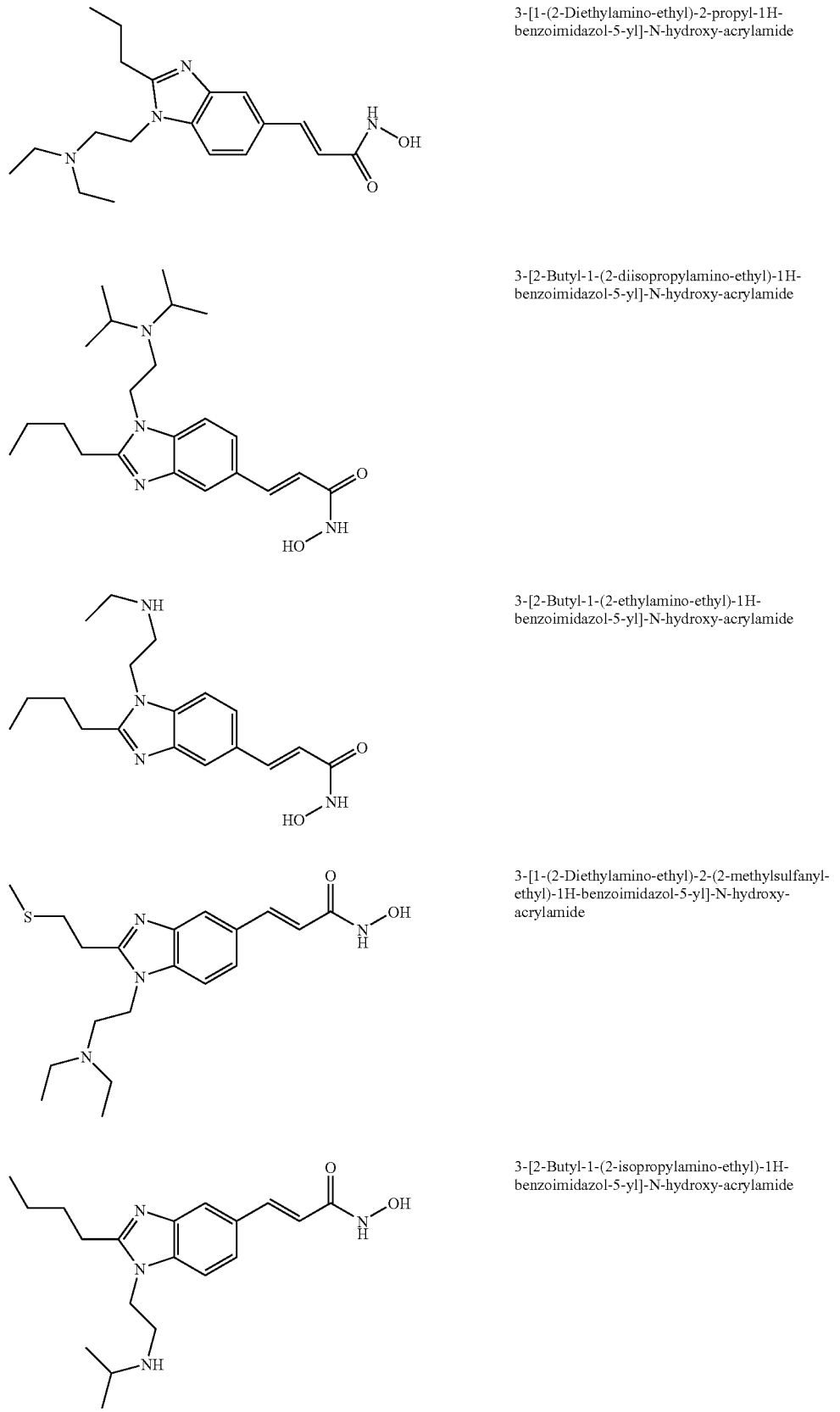
3-[1-(2-Diethylamino-ethyl)-2-propyl-1H-benzoimidazol-5-yl]-N-hydroxy-acrylamide
3-[2-Butyl-1-(2-diisopropylamino-ethyl)-1H-benzoimidazol-5-yl]-N-hydroxy-acrylamide
3-[2-Butyl-1-(2-ethylamino-ethyl)-1H-benzoimidazol-5-yl]-N-hydroxy-acrylamide
3-[1-(2-Diethylamino-ethyl)-2-(2-methylsulfanyl-ethyl)-1H-benzoimidazol-5-yl]-N-hydroxy-acrylamide
3-[2-Butyl-1-(2-isopropylamino-ethyl)-1H-benzoimidazol-5-yl]-N-hydroxy-acrylamide

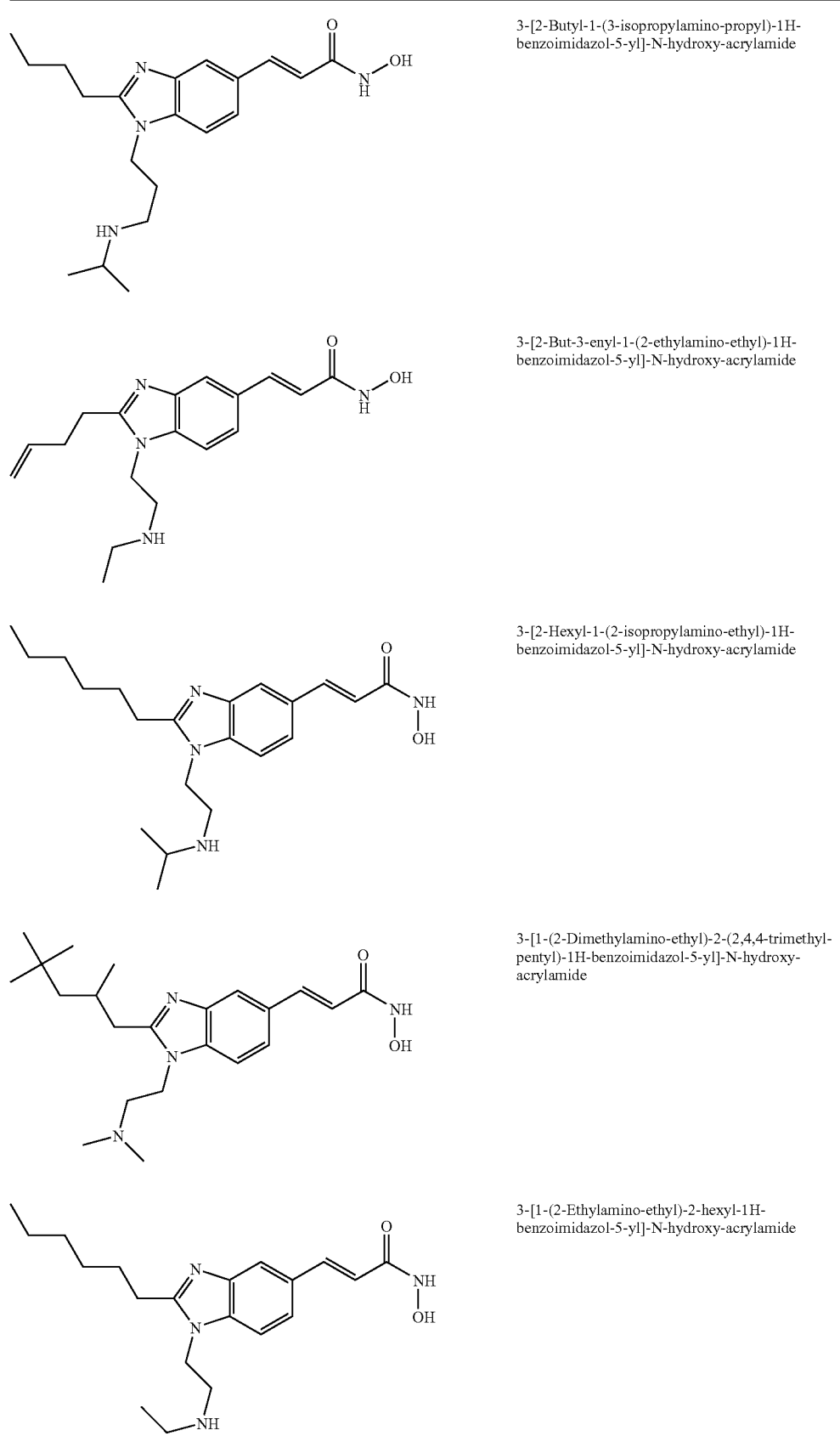
3-[2-Butyl-1-(3-isopropylamino-propyl)-1H-benzoimidazol-5-yl]-N-hydroxy-acrylamide
3-[2-But-3-enyl-1-(2-ethylamino-ethyl)-1H-benzoimidazol-5-yl]-N-hydroxy-acrylamide
3-[2-Hexyl-1-(2-isopropylamino-ethyl)-1H-benzoimidazol-5-yl]-N-hydroxy-acrylamide
3-[1-(2-Dimethylamino-ethyl)-2-(2,4,4-trimethyl-pentyl)-1H-benzoimidazol-5-yl]-N-hydroxy-acrylamide
3-[1-(2-Ethylamino-ethyl)-2-hexyl-1H-benzoimidazol-5-yl]-N-hydroxy-acrylamide

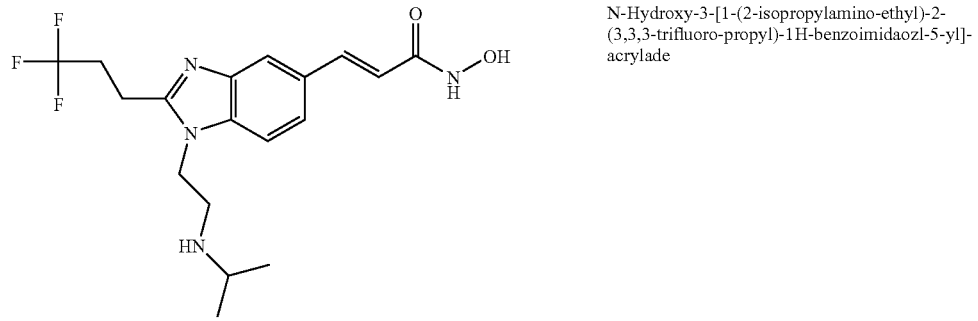
N-Hydroxy-3-[1-(2-isopropylamino-ethyl)-2-(3,3,3-trifluoro-propyl)-1H-benzoimidaozl-5-yl]-acrylade
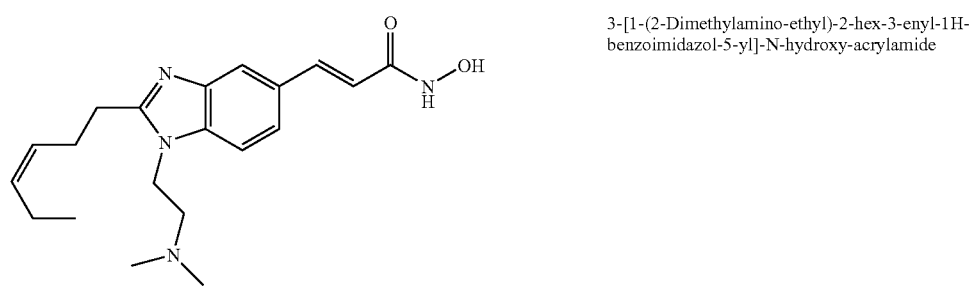
3-[1-(2-Dimethylamino-ethyl)-2-hex-3-enyl-1H-benzoimidazol-5-yl]-N-hydroxy-acrylamide
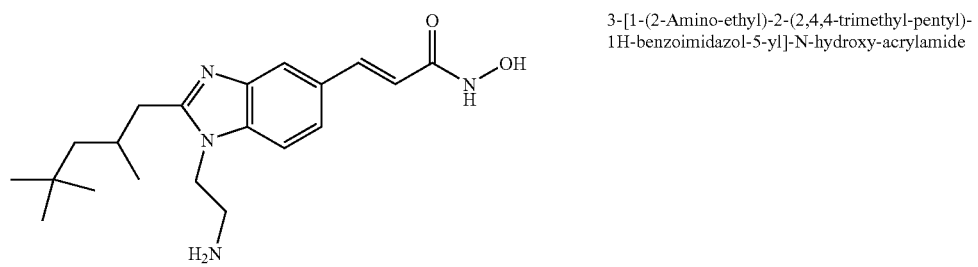
3-[1-(2-Amino-ethyl)-2-(2,4,4-trimethyl-pentyl)-1H-benzoimidazol-5-yl]-N-hydroxy-acrylamide
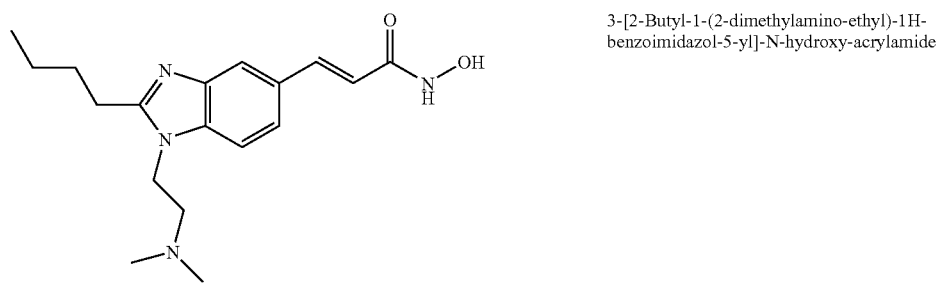
3-[2-Butyl-1-(2-dimethylamino-ethyl)-1H-benzoimidazol-5-yl]-N-hydroxy-acrylamide
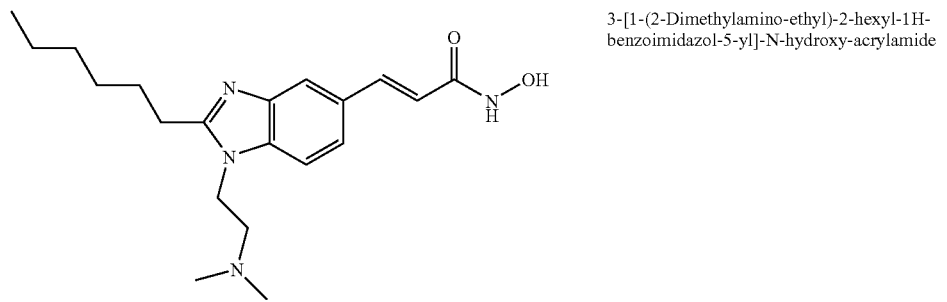
3-[1-(2-Dimethylamino-ethyl)-2-hexyl-1H-benzoimidazol-5-yl]-N-hydroxy-acrylamide

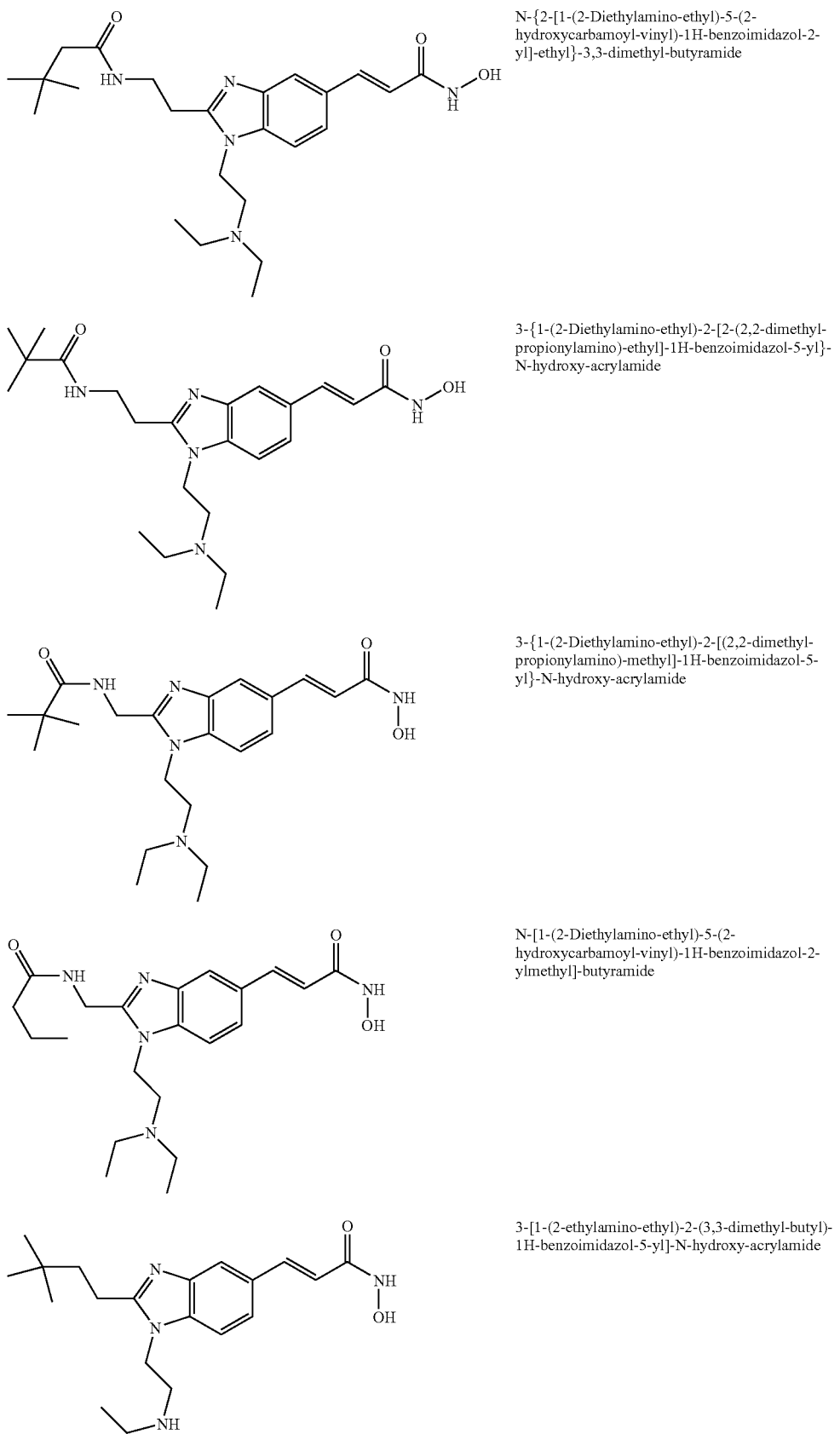

N-{2-[1-(2-Diethylamino-ethyl)-5-(2-hydroxycarbamoyl-vinyl)-1H-benzoimidazol-2-yl]-ethyl}-3,3-dimethyl-butyramide 3-{1-(2-Diethylamino-ethyl)-2-[2-(2,2-dimethyl-propionylamino)-ethyl]-1H-benzoimidazol-5-yl}-N-hydroxy-acrylamide 3-{1-(2-Diethylamino-ethyl)-2-[(2,2-dimethyl-propionylamino)-methyl]-1H-benzoimidazol-5-yl}-N-hydroxy-acrylamide N-[1-(2-Diethylamino-ethyl)-5-(2-hydroxycarbamoyl-vinyl)-1H-benzoimidazol-2-ylmethyl]-butyramide 3-[1-(2-ethylamino-ethyl)-2-(3,3-dimethyl-butyl)-1H-benzoimidazol-5-yl]-N-hydroxy-acrylamide

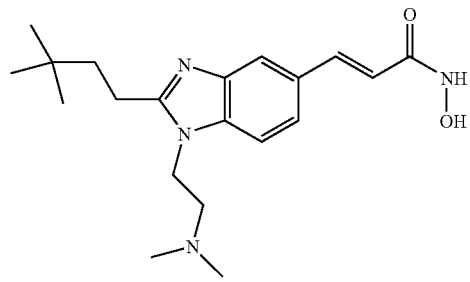

3-[2-(3,3-Dimethyl-butyl)-1-(2-Dimethylamino-ethyl)-1H-benzoimidazol-5-yl]-N-hydroxy-acrylamide

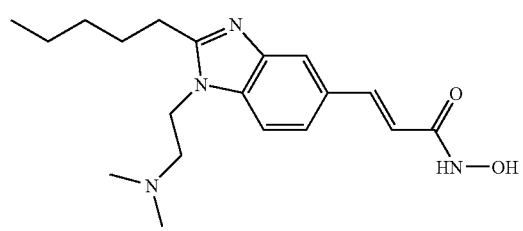

3-[1-(2-Dimethylamino-ethyl)-2-pentyl-1H-benzoimidazol-5-yl]-N-hydroxy-acrylamide

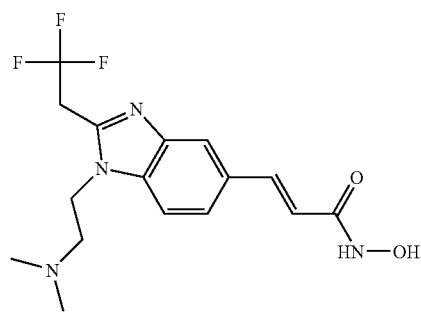

3-[1-(2-Dimethylamino-ethyl)-2-(2,2,2-trifluoro-ethyl)-1H-benzoimidazol-5-yl]-N-hydroxy-acrylamide

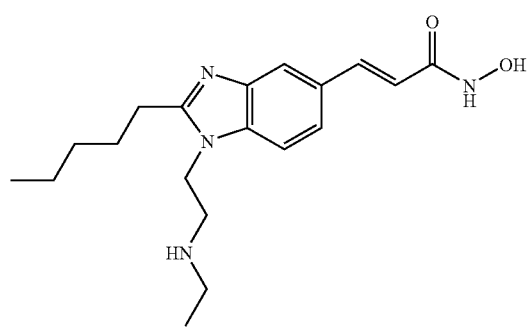

3-[1-(2-Ethylamino-ethyl)-2-pentyl-1H-benzoimidazol-5-yl]-N-hydroxy-acrylamide

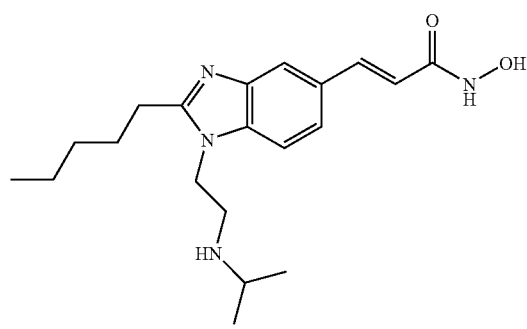

N-Hydroxy-3-[1-(2-isopropylamino-ethyl)-2-pentyl-1H-benzoimidazol-5-yl]-acrylamide

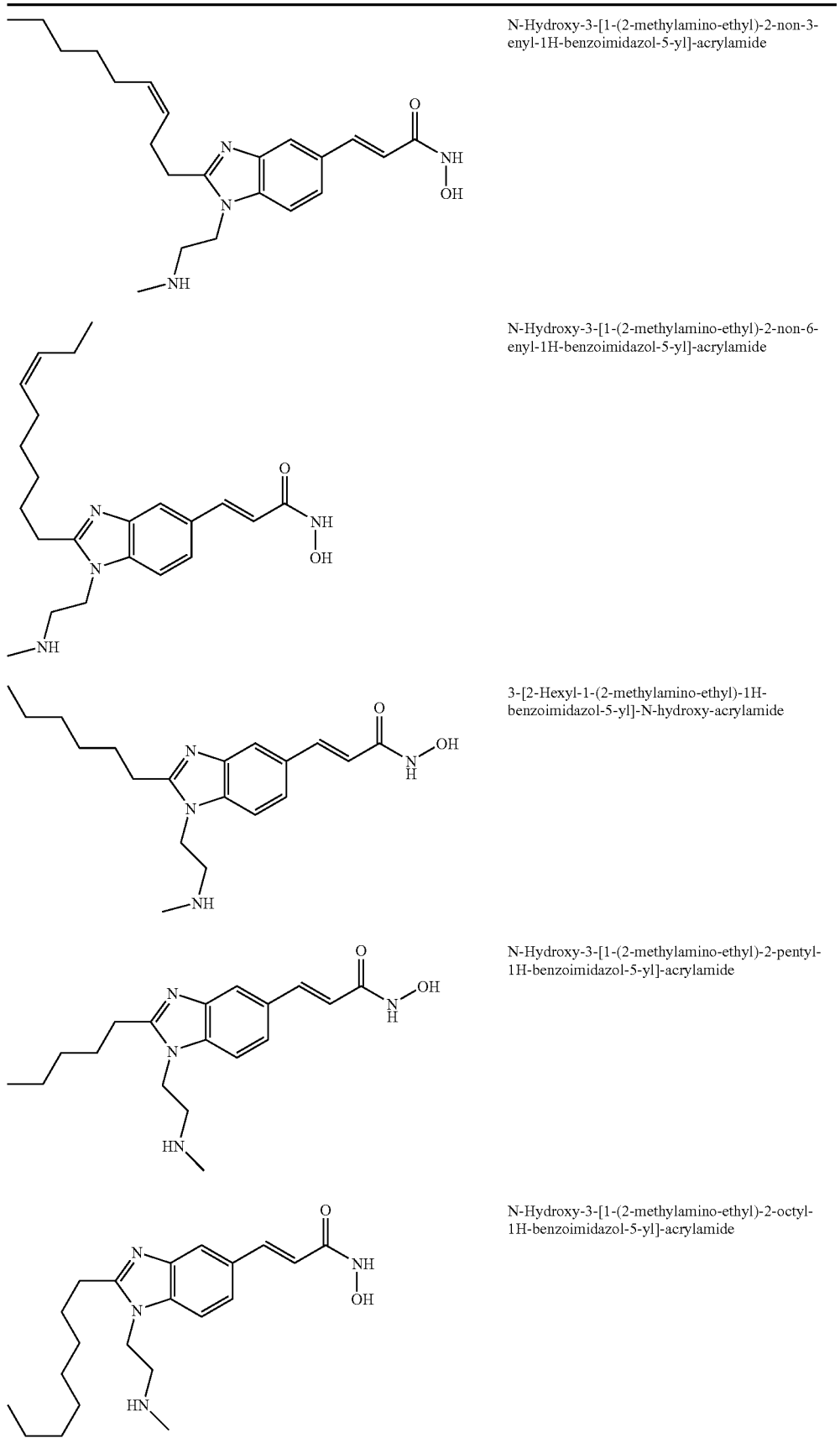
N-Hydroxy-3-[1-(2-methylamino-ethyl)-2-non-3-enyl-1H-benzoimidazol-5-yl]-acrylamide
N-Hydroxy-3-[1-(2-methylamino-ethyl)-2-non-6-enyl-1H-benzoimidazol-5-yl]-acrylamide
3-[2-Hexyl-1-(2-methylamino-ethyl)-1H-benzoimidazol-5-yl]-N-hydroxy-acrylamide
N-Hydroxy-3-[1-(2-methylamino-ethyl)-2-pentyl-1H-benzoimidazol-5-yl]-acrylamide
N-Hydroxy-3-[1-(2-methylamino-ethyl)-2-octyl-1H-benzoimidazol-5-yl]-acrylamide

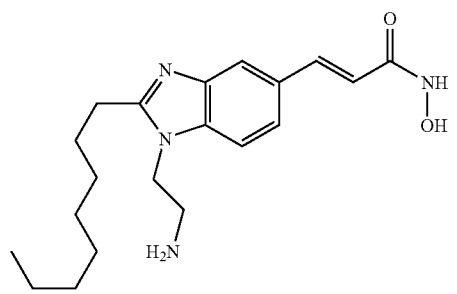
3-[1-(2-Amino-ethyl)-2-octyl-1H-benzoimidazol-5-yl]-N-hydroxy-acrylamide

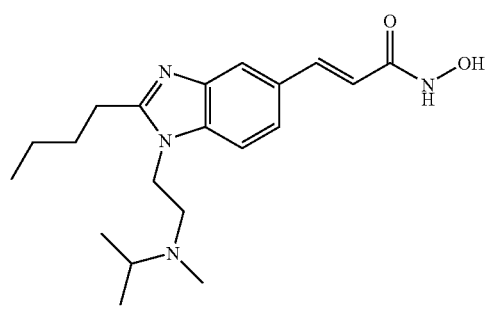
3-{2-Butyl-1-[2-(isopropyl-methyl-amino)-ethyl]-1H-benzoimidazol-5-yl}-N-hydroxy-acrylamide

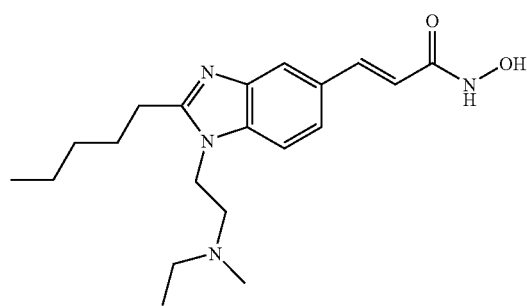
3-{1-[2-(Ethyl-methyl-amino)-ethyl]-2-pentyl-1H-benzoimidazol-5-yl}-N-hydroxy-acrylamide

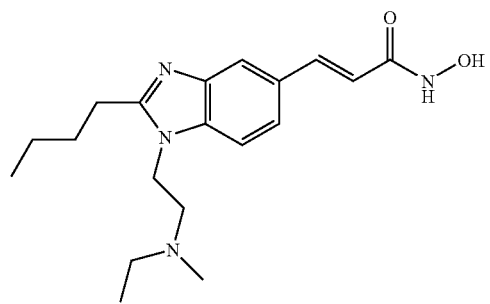
3-{2-Butyl-1-[2-(ethyl-methyl-amino)-ethyl]-1H-benzoimidazol-5-yl}-N-hydroxy-acrylamide

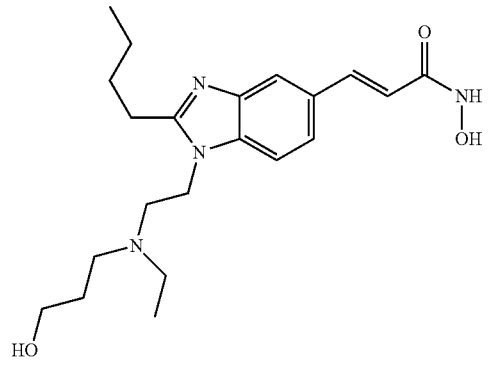
3-(2-Butyl-1-{2-[ethyl-(3-hydroxy-propyl)-amino]-ethyl}-1H-benzoimidazol-5-yl)-N-hydroxy-acrylamide.

11. A pharmaceutical composition including a compound according to claim 1 and a pharmaceutically acceptable diluent, excipient or carrier.

12. A method of treating colon cancer in a patient, wherein the method includes the administration of a therapeutically effective amount of a compound according to claim 1 to the patient.

13. A method of synthesizing compounds of formula I as defined in claim 1

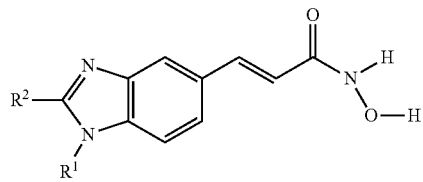

wherein $R^1$ and $R^2$ are as defined in claim 1, the method including
(a) providing a compound of the formula (A1):

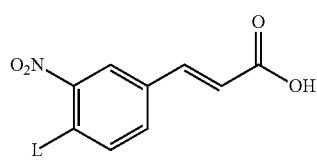

wherein L is a leaving group,
(b) protecting the carboxyl group to produce a compound of the formula (A2):

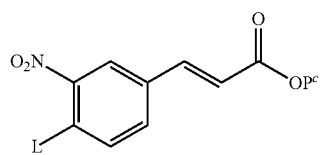

wherein L is a leaving group and $P^c$ is a carboxyl protecting group,
(c) displacing the leaving group with an amine of formula $R^1NH_2$ to produce a compound of the formula:

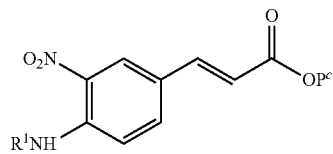

wherein $R^1$ is as defined in claim 1 or a protected form thereof, and $P^c$ is a carboxyl protecting group
(d) optionally reacting the compound to further functionalise $R^1$
(e) reducing the nitro group;
(f) reacting the reduced product with a compound of formula $R^2CO_2H$ or a compound of formula $R^2CHO$ and cyclising the product thus produced to produce a compound of the formula (A4):

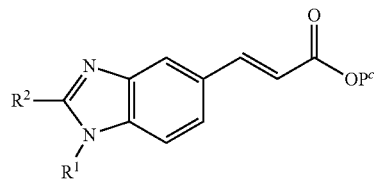

wherein $R^1$ and $R^2$ are as defined in claim 1 or protected forms thereof, and $P^c$ is a carboxyl protecting group
(g) converting the compound to a compound of formula I;
wherein (d) can be carried out after any one of (c) (e) or (f) and further wherein (e) and (f) can be carried out sequentially or simultaneously.

14. A methd of synthesizing compounds of formula I as defined in claim 1

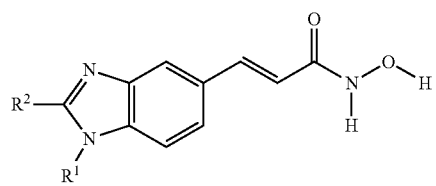

wherein $R^1$ and $R^2$ are as defined in claim 1, the method including:
(a) providing an aldehyde of the formula (B1)

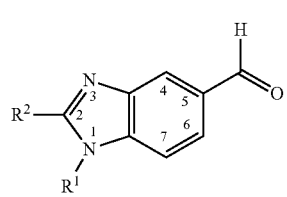

wherein $R^1$ and $R^2$ are as defined in claim 1,
(b) subjecting the aldehyde to reaction with an appropriately substituted olefination agent to produce a compound of formula (B2)

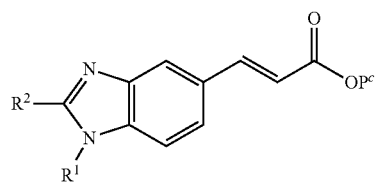

wherein $R^1$ and $R^2$ are as defined in claim 1, and $P^c$ is H or a carboxyl protecting group
(c) converting the compound to a compound of formula I.

15. A method according to claim 14 wherein (a) includes:

(a1) providing a compound of the formula (B3):

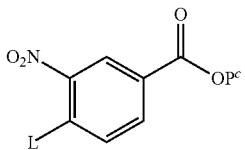

(B3)

wherein L is a leaving group and $P^c$ is a carboxyl protecting group, (a2) displacing the leaving group with an amine of formula R to produce a compound of the formula (B4):

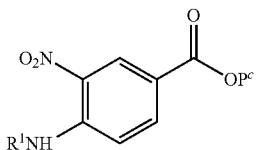

(B4)

wherein $R^1$ is as defined in claim 1 or a protected form thereof, and $P^c$ is a carboxyl protecting group (a3) optionally reacting the compound to further functionalise $R^1$ (a4) reducing the nitro group;

(a5) reacting the reduced product with a compound of formula $R^2CO_2H$ or a compound of formula $R^2CHO$ and cyclising the product thus produced to produce a compound of the formula (B5):

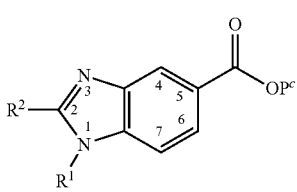

(B5)

wherein $R^1$ and $R^2$ are as defined in claim 1 or protected forms thereof, and $P^c$ is a carboxyl protecting group (a6) converting the protected carboxyl group to the corresponding aldehyde;

wherein (a3) can be carried out after any one of (a2), (a4), (a5) or (a6) and further wherein (a4) and (a5) may be carried out sequentially or simultaneously.

16. A method of synthesizing compounds of formula I as defined in claim 1

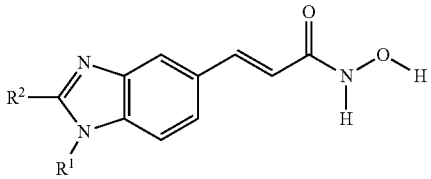

wherein $R^1$ and $R^2$, are as defined in claim 1, the method including:

(a) providing a compound of the formula (C1)

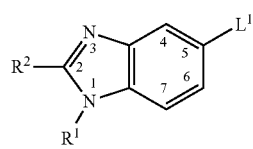

(C1)

wherein $R^1$ and $R^2$ are as defined in claim 1 or protected forms thereof, and $L^1$ is a leaving group (b) converting the compound in (a) to a compound of formula (C2);

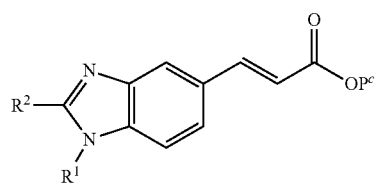

(C2)

wherein $R^1$ and $R^2$ are as defined in claim 1 or protected forms thereof, and $P^c$ is H or a carboxyl protecting group (c) converting the compound to a compound of formula I.

17. A method according to claim 16 wherein (a) includes:

(a1) providing a compound of the formula (C3):

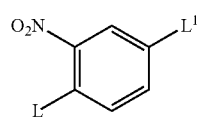

(C3)

wherein L and $L^1$ are leaving groups, (a2) displacing the leaving group (L) with an amine of formula $R^1NH_2$ to produce a compound of the formula (C4):

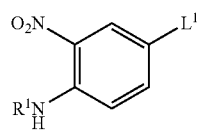

(C4)

wherein $R^1$ is as defined in claim 1 or a protected form thereof, and $L^1$ is a leaving group;

(a3) optionally reacting the compound to further functionalise $R^1$ (a4) reducing the nitro group;

(a5) reacting the reduced product with a compound of formula R²CO₂H or a compound of formula R²CHO and cyclising the product thus produced to produce a compound of the formula (C1):

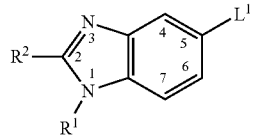
(C1)

wherein (a3) can be carried out after any one of (a2), (a4) or (a5) and further wherein (a4) and (a5) may be carried out sequentially or simultaneously.

18. A method according to claim 13 wherein the compound produced has the formula:

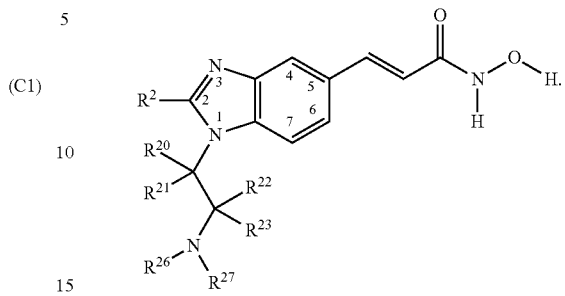

19. A Compound according to claim 1 selected from the group consisting of:

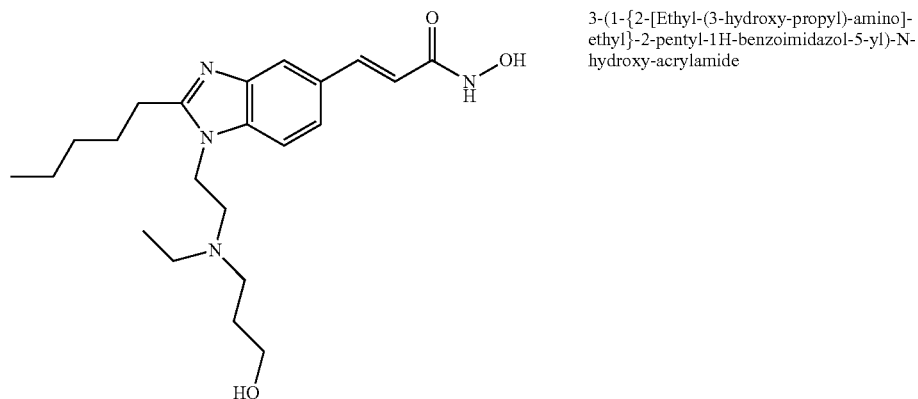

3-(1-{2-[Ethyl-(3-hydroxy-propyl)-amino]-ethyl}-2-pentyl-1H-benzoimidazol-5-yl)-N-hydroxy-acrylamide

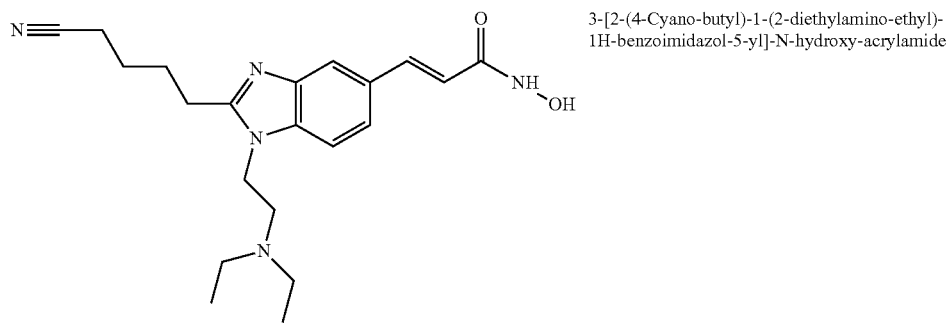

3-[2-(4-Cyano-butyl)-1-(2-diethylamino-ethyl)-1H-benzoimidazol-5-yl]-N-hydroxy-acrylamide

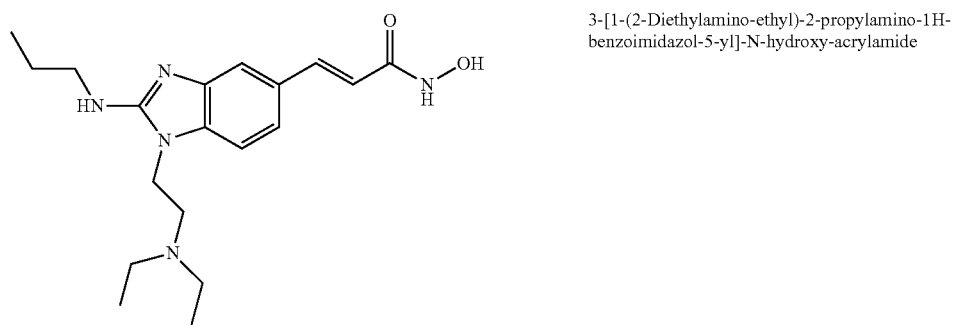

3-[1-(2-Diethylamino-ethyl)-2-propylamino-1H-benzoimidazol-5-yl]-N-hydroxy-acrylamide

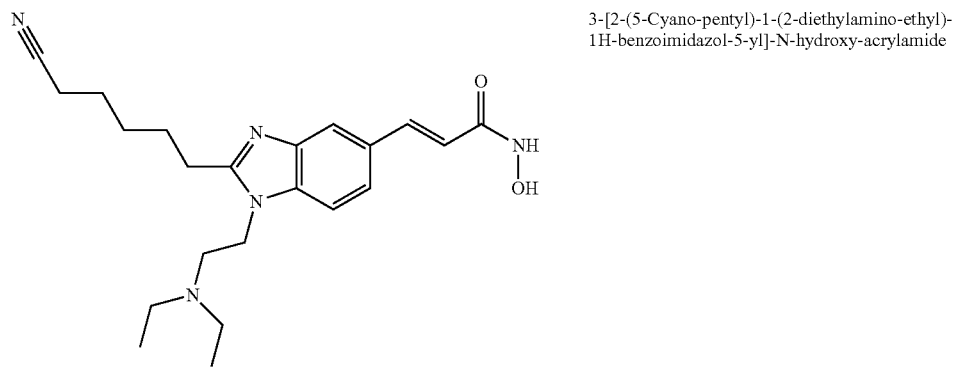
3-[2-(5-Cyano-pentyl)-1-(2-diethylamino-ethyl)-1H-benzoimidazol-5-yl]-N-hydroxy-acrylamide
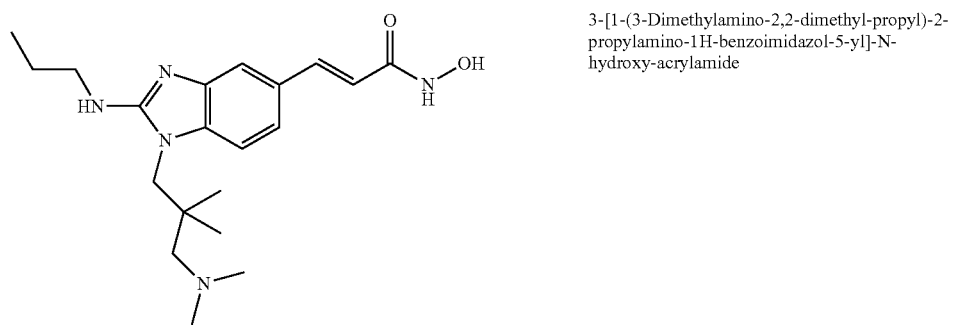
3-[1-(3-Dimethylamino-2,2-dimethyl-propyl)-2-propylamino-1H-benzoimidazol-5-yl]-N-hydroxy-acrylamide
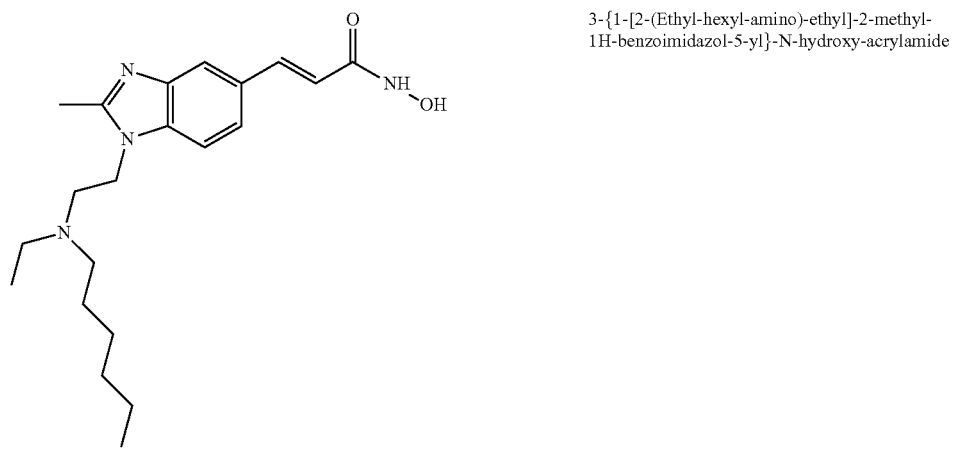
3-{1-[2-(Ethyl-hexyl-amino)-ethyl]-2-methyl-1H-benzoimidazol-5-yl}-N-hydroxy-acrylamide
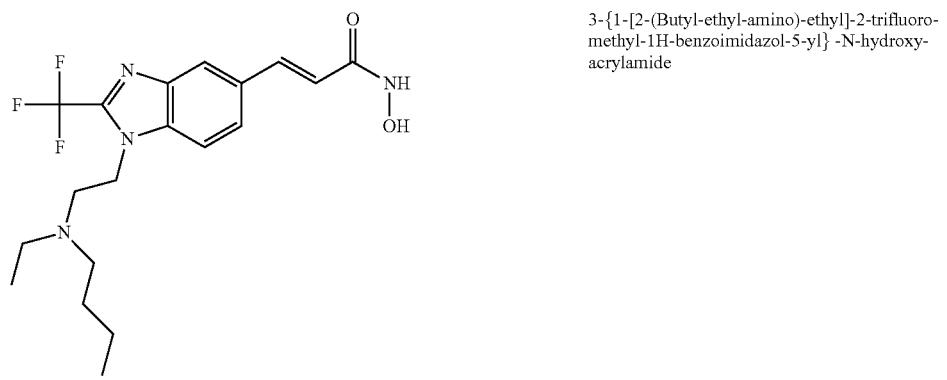
3-{1-[2-(Butyl-ethyl-amino)-ethyl]-2-trifluoro-methyl-1H-benzoimidazol-5-yl}-N-hydroxy-acrylamide

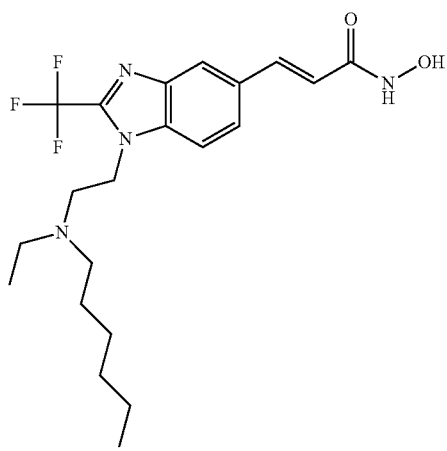
3-{1-[2-(Ethyl-hexyl-amino)-ethyl]-2-trifluoro-methyl-1H-benzoimidazol-5-yl}-N-hydroxy-acrylamide
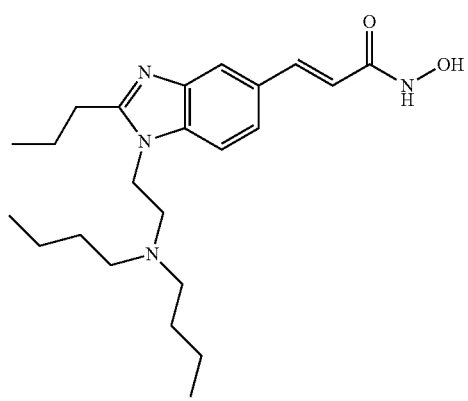
(E)-3-(1-(2-(dibutylamino)ethyl)-2-propyl-1H-benzo[d]imidazol-5-yl)-N-hydroxyacrylamide
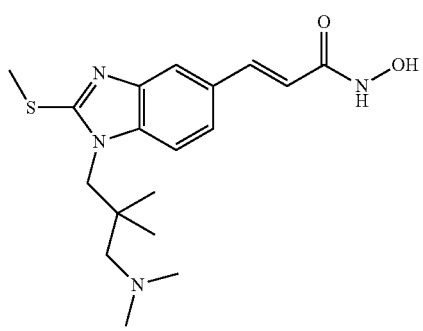
3-[1-(3-Dimethylamino-2,2-dimethyl-propyl)-2-methylsulfanyl-1H-benzoimidazol-5-yl]-N-hydroxy-acrylamide
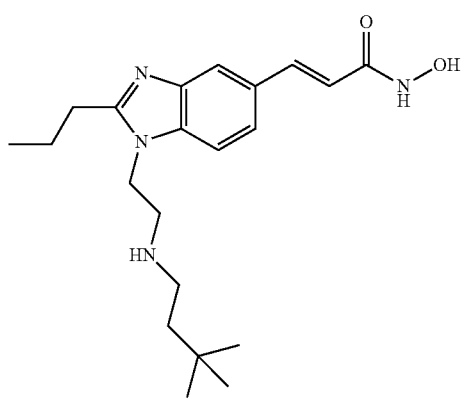
3-{1-[2-(3,3-Dimethyl-butylamino)-ethyl]-2-propyl-1H-benzoimidazol-5-yl}-N-hydroxy-acrylamide

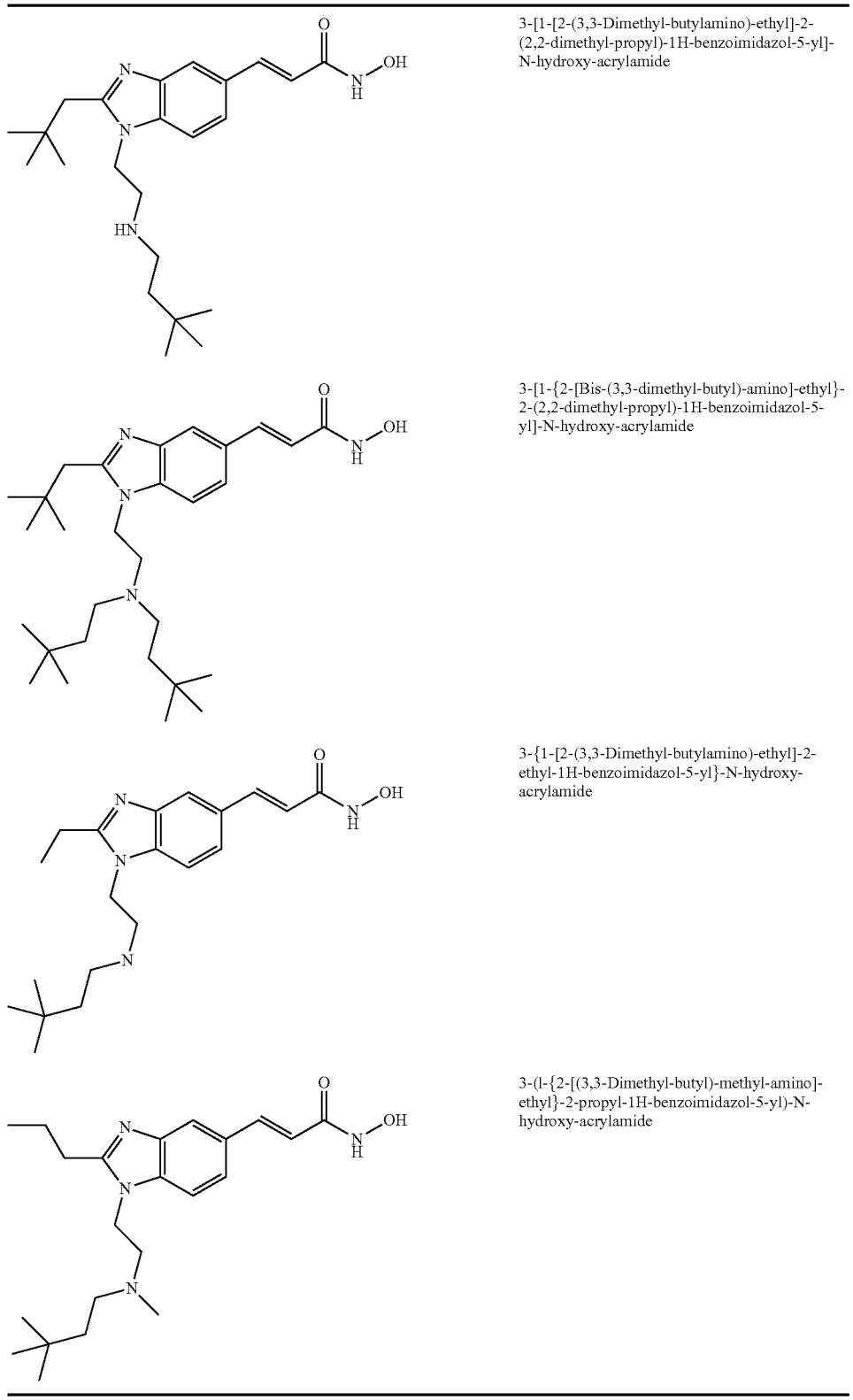
3-[1-[2-(3,3-Dimethyl-butylamino)-ethyl]-2-(2,2-dimethyl-propyl)-1H-benzoimidazol-5-yl]-N-hydroxy-acrylamide
3-[1-{2-[Bis-(3,3-dimethyl-butyl)-amino]-ethyl}-2-(2,2-dimethyl-propyl)-1H-benzoimidazol-5-yl]-N-hydroxy-acrylamide
3-{1-[2-(3,3-Dimethyl-butylamino)-ethyl]-2-ethyl-1H-benzoimidazol-5-yl}-N-hydroxy-acrylamide
3-(l-{2-[(3,3-Dimethyl-butyl)-methyl-amino]-ethyl}-2-propyl-1H-benzoimidazol-5-yl)-N-hydroxy-acrylamide
* * * * *